United States Patent [19]

(12) United States Patent
Ellison

(10) Patent No.: US 11,298,062 B2
(45) Date of Patent: Apr. 12, 2022

(54) MULTI-PURPOSE INTERACTIVE COGNITIVE PLATFORM

(71) Applicant: CONFLU3NCE LTD, Jerusalem (IL)

(72) Inventor: Tami Robyn Ellison, Jerusalem (IL)

(73) Assignee: Conflu3nce LTD, Jerusalem (IL)

( * ) Notice: Subject to any disclaimer, the term of this patent is extended or adjusted under 35 U.S.C. 154(b) by 100 days.

(21) Appl. No.: 16/752,138

(22) Filed: Jan. 24, 2020

(65) Prior Publication Data

US 2020/0253527 A1 Aug. 13, 2020

Related U.S. Application Data

(63) Continuation-in-part of application No. 16/550,022, filed on Aug. 23, 2019, which is a (Continued)

(51) Int. Cl.
*G16H 50/30* (2018.01)
*A61B 5/16* (2006.01)
*G16H 20/70* (2018.01)

(52) U.S. Cl.
CPC .............. *A61B 5/165* (2013.01); *A61B 5/168* (2013.01); *G16H 20/70* (2018.01); *G16H 50/30* (2018.01)

(58) Field of Classification Search
CPC .............. G06T 11/00; G06T 11/60; G06T 2207/20221; G06T 2207/30242; G06T 7/13; G06T 7/136; G06T 7/174; G06T 7/90; G06T 7/0002; G06T 7/11; G06T 2207/20132; G06T 2207/30168; G06T 3/4038; G06T 5/50; G16H 50/20; G16H 50/30; G16H 10/20; G16H 20/70; (Continued)

(56) References Cited

U.S. PATENT DOCUMENTS 6,102,846 A * 8/2000 Patton ................... A61B 5/486
600/26
8,690,325 B1 * 4/2014 Straus .................. A61B 5/0002
351/200

(Continued)

*Primary Examiner* — Ian L Lemieux
(74) *Attorney, Agent, or Firm* — David Lewis

(57) ABSTRACT

An interactive multi-purpose interactive cognitive platform is provided that uses image-based interactivities and may use enriched visual stimuli for diagnoses, treatment, and to evaluate and assess the progress and/or treatment of cognitive diseases and/or conditions with cognitive impacts. The platform may be used for performance enhancement training. The platform may include a graphical user interface. The platform is designed to cooperatively engage multiple cognitive domains using interactivities-embedded assessments. The images and image sets may involve the application of Gestalt principles for assessments and may be personalized address individual user preferences. The multi-purpose interactive cognitive platform may be used to produce diagnostics and/or treatment plans for specific cognitive conditions and diseases with a cognitive component. The multi-purpose interactive cognitive platform may be used for gaming, stress reduction, mindfulness, skills development, training, and/or performance enhancement for those without cognitive problems and/or for those interested in maintaining their cognitive health.

53 Claims, 38 Drawing Sheets

Related U.S. Application Data continuation-in-part of application No. 16/427,305, filed on May 30, 2019, now Pat. No. 11,158,060, which is a continuation-in-part of application No. 16/262,884, filed on Jan. 30, 2019, now Pat. No. 11,176,675, and a continuation-in-part of application No. 15/884,565, filed on Jan. 31, 2018, now Pat. No. 10,582,189, said application No. 16/262,884 is a continuation-in-part of application No. 15/884,565, filed on Jan. 31, 2018, now Pat. No. 10,582,189, said application No. 16/550,022 is a continuation-in-part of application No. 15/884,565, filed on Jan. 31, 2018, now Pat. No. 10,582,189.

(60) Provisional application No. 62/721,665, filed on Aug. 23, 2018, provisional application No. 62/626,208, filed on Feb. 5, 2018, provisional application No. 62/499,655, filed on Feb. 1, 2017.

(58) Field of Classification Search
CPC ........... H04N 13/261; H04N 2213/003; H04N 2213/006; A61B 5/01; A61B 5/0205; A61B 5/024; A61B 5/0263; A61B 5/055; A61B 5/11; A61B 5/1116; A61B 5/165; A61B 5/168; A61B 5/369; A61B 5/4082; A61B 5/4088; A61B 5/486; A61B 5/6802; A61B 5/686; A61B 5/7264; G06F 21/316; G06F 21/36; G06F 21/40; G06F 2221/2133; G06F 3/011; G06F 3/0482; G06K 9/00

See application file for complete search history.

(56) References Cited

U.S. PATENT DOCUMENTS

| | | | |
|---|---|---|---|
| 10,188,337 B1* | 1/2019 | Charvat | G16H 10/20 |
| 2010/0191156 A1* | 7/2010 | Sakamoto | A61B 5/165 |
| | | | 600/595 |
| 2015/0164402 A1* | 6/2015 | Smith | A61B 5/1114 |
| | | | 600/595 |
| 2015/0350730 A1* | 12/2015 | el Kaliouby | A61B 5/165 |
| | | | 725/12 |
| 2016/0278682 A1* | 9/2016 | Khaligh-Razavi | G16H 50/20 |
| 2017/0251985 A1* | 9/2017 | Howard | A61B 5/165 |
| 2018/0103886 A1* | 4/2018 | Landau | A61B 5/4064 |
| 2019/0150819 A1* | 5/2019 | Charvat | G16H 10/20 |
| 2019/0175090 A1* | 6/2019 | Reiner | G16H 50/20 |
| 2019/0254581 A1* | 8/2019 | Papathomas | G16H 50/50 |
| 2019/0385711 A1* | 12/2019 | Shriberg | G10L 25/66 |
| 2020/0151439 A1* | 5/2020 | Johnson | G16H 30/20 |
| 2020/0383621 A1* | 12/2020 | Cuestas Rodriguez | A61B 5/7435 |
| 2020/0388178 A1* | 12/2020 | Barbuto | G16H 50/20 |
| 2021/0110894 A1* | 4/2021 | Shriberg | G09B 19/00 |
| 2021/0110895 A1* | 4/2021 | Shriberg | A61B 5/164 |
| 2021/0192351 A1* | 6/2021 | Zakariaie | A61B 3/0041 |
| 2021/0224601 A1* | 7/2021 | Chen | G06N 3/08 |

* cited by examiner

Table 1

| | D1<br>M | D2<br>A | D3<br>VS | D4<br>EF | D5<br>SM | D6<br>L | A2 | A3 | A4 | A6 |
|---|---|---|---|---|---|---|---|---|---|---|
| MIT 4/8 (+0.0) A1 | 2.00 | 5.00 | 5.00 | 5.00 | 3.00 | 3.00 | 23 | 3.833 | 0.1667 | 0.1663 |
| A5 | .0870 | .2170 | .2170 | .2170 | .1300 | .1300 | | | | |

FIG. 4B

Table 2

| | D1<br>M | D2<br>A | D3<br>VS | D4<br>EF | D5<br>SM | D6<br>L | A2 | A3 | A4 | A6 |
|---|---|---|---|---|---|---|---|---|---|---|
| MIT 2/4 (-0.25) A1 | 1.75 | 4.75 | 4.75 | 4.75 | 2.75 | 2.75 | 21.5 | 3.583 | 0.1666 | 0.1663 |
| A5 | .0810 | .2210 | .2210 | .2210 | .1280 | .1280 | | | | |
| MIT 4/8 (+0.0) A1 | 2.00 | 5.00 | 5.00 | 5.00 | 3.00 | 3.00 | 23.0 | 3.830 | | 0.1665 |
| A5 | .0870 | .2170 | .2170 | .2170 | .1300 | .1300 | | | | |
| MIT 6/12 (+0.25) A1 | 2.25 | 5.25 | 5.25 | 5.25 | 3.25 | 3.25 | 24.5 | 4.083 | 0.1667 | 0.1667 |
| A5 | .0920 | .2140 | .2140 | .2140 | .1330 | .1330 | | | | |
| MIT 10/20 (+0.75) A1 | 2.75 | 5.75 | 5.75 | 5.75 | 3.75 | 3.75 | 27.5 | 4.583 | 0.1666 | 0.1665 |
| A5 | .1000 | .2090 | .2090 | .2090 | .1360 | .1360 | | | | |

FIG. 4C

Table 3

| | D1 | D2 | D3 | D4 | D5 | D6 | | | | |
|---|---|---|---|---|---|---|---|---|---|---|
| | M | A | VS | EF | SM | L | A2 | A3 | A4 | A6 |
| MIT 2/4 (-0.75) Moderate to Severe Alzheimer's disease | | | | | | | | | | |
| A1 | 1.00 | 4.00 | 4.00 | 4.00 | 2.00 | 2.00 | 17.0 | 2.833 | 0.1666 | |
| A5 | .0588 | .2353 | .2353 | .2353 | .1176 | .1176 | | | | 0.1666 |
| MIT 2/4 (-0.50) Moderate Alzheimer's disease | | | | | | | | | | |
| A1 | 1.25 | 4.25 | 4.25 | 4.25 | 2.25 | 2.25 | 18.5 | 3.083 | 0.1666 | |
| A5 | .0676 | .2297 | .2297 | .2297 | .1216 | .1216 | | | | 0.1666 |
| MIT 2/4 (-0.25) Progressive MCI | | | | | | | | | | |
| A1 | 1.50 | 4.50 | 4.50 | 4.50 | 2.50 | 2.50 | 20.0 | 3.333 | 0.1666 | |
| A5 | .0750 | .2250 | .2250 | .2250 | .1250 | .1250 | | | | 0.1667 |
| MIT 2/4 (-0.15) Mild Cognitive Impairment (MCI) | | | | | | | | | | |
| A1 | 1.60 | 4.60 | 4.60 | 4.60 | 2.60 | 2.60 | 20.6 | 3.433 | 0.1667 | |
| A5 | .1000 | .2090 | .2090 | .2090 | .1360 | .1360 | | | | 0.1665 |
| MIT 2/4 (0.00) (older adult, age 60-70) | | | | | | | | | | |
| A1 | 1.75 | 4.75 | 4.75 | 4.75 | 2.75 | 2.75 | 21.5 | 3.583 | 0.1666 | |
| A5 | .0810 | .2210 | .2210 | .2210 | .1280 | .1280 | | | | 0.1667 |

FIG. 4D

| IX Set | | D1 M | D2 A | D3 VS | D4 EF | D5 SM | D6 L | A2 | A3 | A4 | A6 |
|---|---|---|---|---|---|---|---|---|---|---|---|
| IX1 | MIT 4/8 MatchIT! 2-image composite 4 sections from each image: match 4 parts | | | | | | | | | | |
| | A1 | 2.00 | 5.00 | 5.00 | 5.00 | 3.00 | 3.00 | 23.0 | 3.83 | 0.1665 | |
| | A5 | .087 | .217 | .217 | .217 | .130 | .130 | | | | 0.1663 |
| IX2 | CON 10IP Construct interactivity 2-image: 5 sections per image | | | | | | | | | | |
| | A1 | 3.00 | 3.00 | 5.00 | 5.00 | 4.00 | 3.00 | 23.0 | 3.83 | 0.1665 | |
| | A5 | .130 | .130 | .217 | .217 | .174 | .130 | | | | 0.1663 |
| IX3 | MP 5x5 Missing Pieces interactivity 5x5 grid, 5 pieces to place | | | | | | | | | | |
| | A1 | 5.00 | 5.00 | 6.00 | 5.00 | 5.00 | 2.00 | 28.0 | 4.67 | 0.1668 | |
| | A5 | .178 | .178 | .214 | .178 | .178 | .071 | | | | 0.1662 |
| IX4 | OID$_{sp}$ Object Identification interactivity; identify 5-7 objects in a single image with recall at a specified time | | | | | | | | | | |
| | A1 | 4.50 | 3.00 | 2.00 | 2.00 | 3.00 | 5.00 | 19.5 | 3.25 | 0.1665 | |
| | A5 | .250 | .154 | .103 | .103 | .154 | .256 | | | | 0.1667 |
| IX5 | DD Dimensional Descriptors interactivity; describe 5-7 object/elements in each image in a 2-image composite | | | | | | | | | | |
| | A1 | 5.00 | 6.00 | 4.00 | 3.00 | 3.00 | 6.00 | 27.0 | 4.50 | 0.1667 | |
| | A5 | .185 | .222 | .148 | .111 | .111 | .222 | | | | 0.1665 |

FIG. 4E(1)/Table 4A

| IX-Set | D1 | D2 | D3 | D4 | D5 | D6 | A9 | A10 | A11 |
|---|---|---|---|---|---|---|---|---|---|
| A7 | 19.5 | 22.0 | 22.0 | 20.0 | 18.0 | 19.0 | 23.4 | 3.90 | 0.1667 |
| A8 | 4.0 | 4.4 | 3.6 | 4.0 | 3.6 | 3.8 | | | |

FIG. 4E(2)/Table 4B

Table 5

| Attention | | |
|---|---|---|
| | Divided Attention | Visual Attention |
| | Sustained Attention | Choice Decision-based Reaction Time |
| | Selective Attention | Distractibility (Distraction/Flankers) |
| Visual Spatial | | |
| | Perception | Global Visual-Spatial Cognition |
| | Spatial Perception | Scanning |
| | Visual Problem-Solving | |
| Executive Function | | |
| | Judgment | Dis-inhibition/Impulsivity |
| | Decision-making | Reasoning |
| | Problem-solving | |
| Memory | | |
| | Short-term | Visual |
| | Long-term | Verbal |
| | Working | Episodic |
| Language | | |
| | Comprehension | Verbal Fluency – categorical |
| | Expression | Verbal Fluency – phonemic |
| Sensorimotor | | |
| | Constructional Praxis | Processing Speed |
| | Mental Rotation Praxis | Visual Scanning |
| | Cognitive Flexibility | |

FIG. 4F

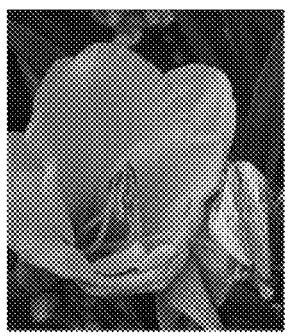
FIG. 6B     FIG. 6C     FIG. 6D
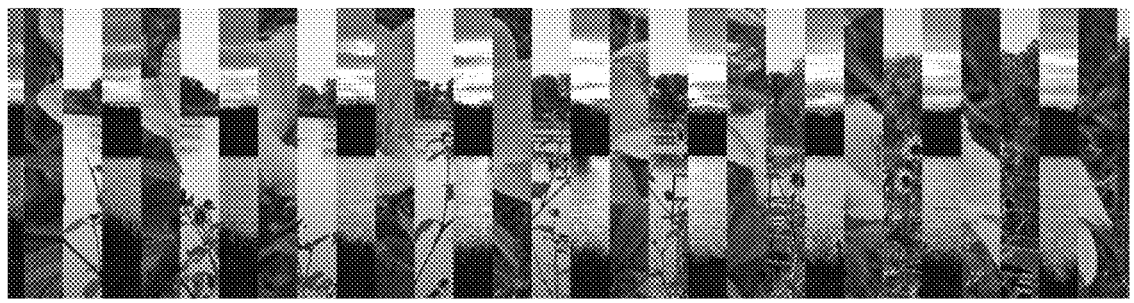
FIG. 6E Table 6

| Ambiguity Factor | Range | Formula | | |
|---|---|---|---|---|
| Contig Number ($AF_1$) | 0-6 | Sobel or Differential Edge counts using color and thresholded images. Compare b/w area counts | | |
| Color Block ($AF_2$) | 1.0-6.0 | Sequential color extraction using reduced 2-6 color images, quadrant based identification of dominant colors (total, Q1-A4, top, bottom, right, left) | | |
| Linearity ($AF_3$) | -1.0 to +1.0 | $C_{linearity} = C_A + C_D$ where $C_A$ is the angularity across the contiguity and $C_D$ is a break in the contiguity | | |
| Continuity ($AF_4$) | -1.0 to +1.0 | $C_{cont} = C_{VD} + C_{CE}$ | | |
| Color Block Depth (100) ($AF_5$) | 0.25 to 1.0 | define color block distribution (see rules table) | | |
| Spatial Color-Contig ($AF_6$) | -2.0 to +2.0 | compare contig # to color block # | | |
| Ambiguity Value (CR) ($\sum AF_1...AF_6$)/6 | | 0.75 to 2.25 | | |
| Ambiguity Saliency Value ($AF_1 + AF_2 + AF_3 + AF_4$) | -0.75 to 15 | 3.5 - 3.75 | | |
| Color Block$_{DEPTH}$ = $CBD_{100}/CBD_{66}$ | | | | |
| Aesthetic Value ($V_{AES} = 1/(CBD_{100})(CB_{DEPTH}))$ | 0.1 to 16 | 1.25 - 2.5 | | |
| Switch Capacity $CF_{(Q)} = V_{AES} + CR$ | -2.0 to 6.75 | 3-image, c#2 $\sum CF_{(Q)} = 5-10$ | 2-image, c#2 $\sum CF_{(Q)} = 3.5-7$ | 2-image, c#=0 $\sum CF_{(Q)} = 0-2$ |
| Compositing Factor $CF_{(CR)} = CF_{(Q)} - 0.25$ | -2.0 to 6.50 | 1.667 - 3.333 | 1.75 - 3.5 | 0 - 1 |

FIG. 19B

Table 7

| AF₄ Rules Table: Contiguity Continuity Range (-1.0 to +1.0) Vertical Disruptor and Irregular Edge | |
|---|---|
| *If* | *Then* |
| an image has at least one contiguity which is continuous across the entire width of the image (75-100% +/-3%) | Assign a value of 1.0 |
| the contiguity is continuous across 50-75% +/-3% of the image | Assign a value of 0 |
| the contiguity is <50% or if contiguity # is 0 | Assign a value of -1.0 |
| there is/are Vertical Distractors extending >5% but less than 30% up from any otherwise linear and continuous contiguity, but which has additional complex contiguities | Assign a value of 0.5 |
| VD extends greater than 30% but less than 50%; | Assign a value of -0.5 |
| VD extends greater than 50% but less than 100% | Assign a value of -0.75 |
| VD is equal to or greater than 100% | Assign a value of -1.0 |
| there are 2-3 Vertical Distractor but which are spatially separated, or which individually extend less than 20% from an otherwise linear contiguities | Assign a value of 0.5 |
| there are multiple Vertical Distractors present in the image (e.g. trees) | Assign a value of -1.0 |
| there are multiple irregular edges on one or more contigs or if a single contiguity without an adjacent color block >30% of the image | Assign a value of -0.25 |
| there is a single contiguity with a poorly defined edge but which is adjacent to at least one continuous color block or a color block >30% | Assign a value of -0.15 |

FIG. 19C

Table 8

| AF$_5$ Rules Table. Color Block Depth$_{100}$ and CBD$_{ST}$ | | | | |
|---|---|---|---|---|
| Value | Quadrant 1 | Quadrant 2 | Quadrant 3 | Quadrant 4 |
| 1.00 | A | A | A | A(B) |
| 0.75 | A | A | B | B |
| 0.625 | A | A/B | C | C |
| 0.5 | A | A | B | C |
| 0.5 | A | B | A | B |
| 0.25 | A | B | C | A |
| 0.1 | A | B | C | D |

FIG. 19D

Table 9

| AF$_6$ Spatial Color-Contiguity Table (compares AF$_1$ to AF$_2$) | |
|---|---|
| Value | Condition Rules |
| 0 | If AF$_1$ = AF$_2$ |
| 1 | If AF$_1$ is greater than AF$_2$ |
| 2 | If AF$_1$ is less than AF$_2$, unless the contiguity number is equal to 0 |
| -1 | If AF$_1$ = 0 |

FIG. 19E

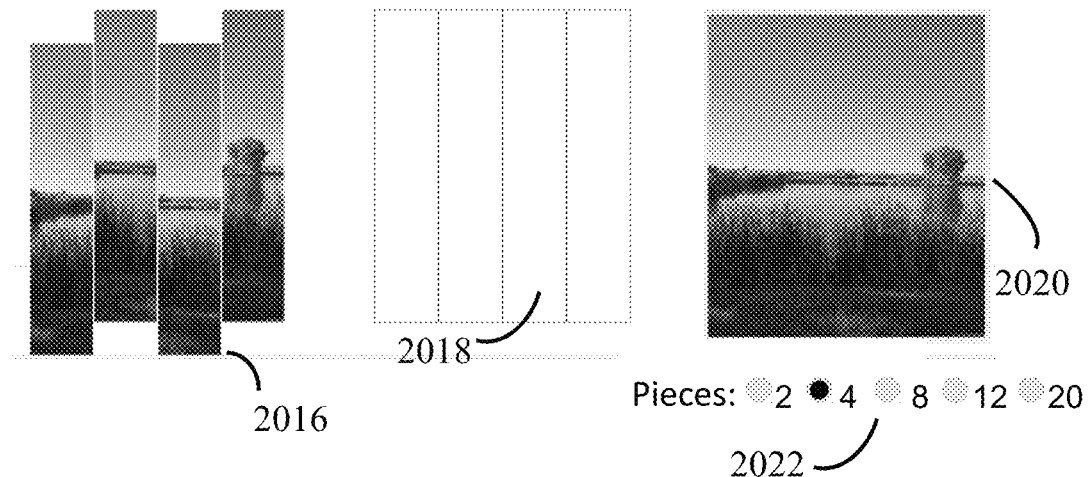
FIG. 20B(1)
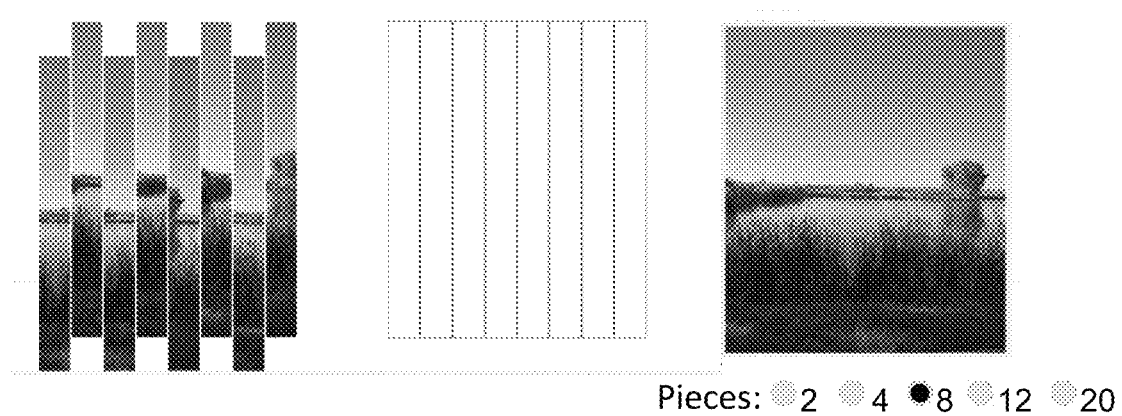
FIG. 20B(2)

MULTI-PURPOSE INTERACTIVE COGNITIVE PLATFORM

PRIORITY CLAIM AND CROSS-REFERENCE TO RELATED APPLICATIONS

This application is a continuation-in-part of U.S. patent application Ser. No. 16/550,022, entitled "Multi-Purpose Interactive Cognitive Platform," filed on Aug. 23, 2019, by Tami Robyn Ellison, which claims priority benefit of U.S. Provisional Patent Application No. 62/721,665, entitled "MULTI-PURPOSE INTERACTIVE COGNITIVE PLATFORM," filed on Aug. 23, 2018, by Tami Ellison;

U.S. patent application Ser. No. 16/550,022, entitled "Multi-Purpose Interactive Cognitive Platform," filed on Aug. 23, 2019, by Tami Robyn Ellison, is also a continuation-in-part of U.S. patent application Ser. No. 16/427,305, entitled "SYSTEM AND METHOD FOR CREATING AN IMAGE AND/OR AUTOMATICALLY INTERPRETING IMAGES," filed on May 30, 2019, which in turn is a continuation-in-part of U.S. patent application Ser. No. 16/262,884, "SYSTEM AND METHOD FOR CREATING AN IMAGE AND/OR AUTOMATICALLY INTERPRETING IMAGES" by TAMI ROBYN ELLISON, filed on Jan. 30, 2019; which claims priority benefit of U.S. Provisional Patent Application No. 62/626,208, entitled "SYSTEM AND METHOD FOR IDENTIFYING CONTIGUITY CHARACTERISTICS IN AN IMAGE," filed on Feb. 5, 2018, by Tami Ellison, which is incorporated herein by reference; and also claims priority benefit of U.S. Provisional Patent Application No. 62/721,665, entitled "MULTI-PURPOSE INTERACTIVE COGNITIVE PLATFORM," filed on Aug. 23, 2018, by Tami Ellison, which is incorporated herein by reference; U.S. patent application Ser. No. 16/262,884, "SYSTEM AND METHOD FOR CREATING AN IMAGE AND/OR AUTOMATICALLY INTERPRETING IMAGES" by TAMI ROBYN ELLISON, filed on Jan. 30, 2019 is also a continuation-in-part of U.S. patent application Ser. No. 15/884,565 entitled "SYSTEM AND METHOD FOR GENERATING COMPOSITE IMAGES," filed on Jan. 31, 2018, by Tami Ellison, which claims priority benefit of U.S. Provisional Patent Application No. 62/499,655, entitled "PHOTAGE 2.5D—METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison; U.S. patent application Ser. No. 16/427,305, entitled "SYSTEM AND METHOD FOR CREATING AN IMAGE AND/OR AUTOMATICALLY INTERPRETING IMAGES," filed on May 30, 2019, is a continuation-in-part of U.S. patent application Ser. No. 15/884,565 entitled "SYSTEM AND METHOD FOR GENERATING COMPOSITE IMAGES," filed on Jan. 31, 2018, by Tami Ellison, which claims priority benefit of U.S. Provisional Patent Application No. 62/499,655, entitled "PHOTAGE 2.5D—METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison; U.S. patent application Ser. No. 16/427,305, entitled "SYSTEM AND METHOD FOR CREATING AN IMAGE AND/OR AUTOMATICALLY INTERPRETING IMAGES," filed on May 30, 2019, claims priority benefit of U.S. Provisional Patent Application No. 62/721,665, entitled "MULTI-PURPOSE INTERACTIVE COGNITIVE PLATFORM," filed on Aug. 23, 2018, by Tami Ellison;

U.S. patent application Ser. No. 16/550,022, entitled "Multi-Purpose Interactive Cognitive Platform," filed on Aug. 23, 2019, by Tami Robyn Ellison is also a continuation-in-part of U.S. patent application Ser. No. 15/884,565, entitled "SYSTEM AND METHOD FOR GENERATING COMPOSITE IMAGES," filed on Jan. 31, 2018, by Tami Ellison, which is incorporated herein by reference; U.S. patent application Ser. No. 15/884,565 claims priority benefit of U.S. Provisional Patent Application No. 62/499,655, entitled "PHOTAGE 2.5D—METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison.

The contents of all of the above listed applications are incorporated herein by reference, in their entirety.

FIELD

This specification generally relates to a multi-purpose interactive cognitive platform.

BACKGROUND

The subject matter discussed in the background section should not be assumed to be prior art merely as a result of its mention in the background section. Similarly, a problem and the understanding of the causes of a problem mentioned in the background section or associated with the subject matter of the background section should not be assumed to have been previously recognized in the prior art. The subject matter in the background section may merely represent different approaches, which in and of themselves may also be inventions.

Cognitive issues affect hundreds of millions of people around the world. Current neurocognitive evaluations are based on decades/century-old siloed skills tests using simple stimuli. Today's "multi-domain" assessments tend to be individual skills assessments compiled into batteries. Not surprisingly, these evaluations are limited by ceiling and floor effects, and lack the sensitivity to detect subtle changes over time, delaying early detection, diagnosis and interventions. Despite tremendous gains in knowledge and technology, there is a lack of non-invasive, objective, quantifiable, authentically related multi-domain assessment tools and training products to support brain health and fitness.

Cognitive platforms can be used for a variety of reasons, including: therapy, diagnosis and treatment of cognitive disorders, performance enhancement, gaming, and even in the field of artificial intelligence. However, new and improved cognitive platforms able to address deficiencies and limitations of prevailing platforms are needed.

BRIEF DESCRIPTION OF THE FIGURES

In the following drawings, like reference numbers are used to refer to like elements. Although the following figures depict various examples of the invention, the invention is not limited to the examples depicted in the figures.

FIGS. 4B-4D show examples of tables of weighted values for an assessment interactivity in terms of its multi-domain processes and skills character.

FIGS. 4E(1)-4E(2) show an example of assessment interactivities combined into a battery and multi-cognitive domain (MCD) values for the battery.

FIG. 4F is an example of a table showing cognitive domains and subdomains which can be assessed with the platform.

FIG. 6B shows an example of a first image that has a central image, but no horizon-type contiguity, used in making a composite image, which is referred to in FIG. 6A.

FIG. 6C shows an example of a second image that is used in making a composite image, which has at least one horizon-type contiguity, which is referred to in FIG. 6A.

FIG. 6D shows an example of a second image that is used in making a composite image, which has a horizon-type contiguity but with vertical distractors (flower stems), which is referred to in FIG. 6A.

FIG. 6E shows a composite image made from FIGS. 6B-6D.

FIGS. 19B-19E show an example of Rules that can be used for measuring ambiguity factors (e.g., $AF_1$-$AF_6$) and other image characteristics (19B), contiguity continuity ranges (19C), color block depth (19D), spatial color contiguity (19E) for a multi-purpose interactive cognitive platform (which are referenced in the discussion of FIGS. 16-18B).

FIGS. 20A-20G shows examples of a Graphical User Interface (GUI) for a multi-purpose interactive cognitive platform.

FIG. 21C shows a partial peel.

FIGS. 24A(1)-24A(3) each show an example of a different component images of the three-image composite of FIG. 24B and FIG. 23A, and the two-image composites of FIGS. 24C-24F.

FIG. 25A shows the component images of the three-image composite of FIG. 23C.

FIGS. 25B-25D show examples of two-image composite images derived from the 3-image composite of FIG. 23C, where each is made from two of the images. The figure shows hierarchical figure-ground relationships based on component image re-groupings in the derived 2-image composites.

DETAILED DESCRIPTION

Although various embodiments are described in this specification may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

The flowchart and block diagrams in the FIGS. illustrate the architecture, functionality, and operations of possible implementations of systems, methods, and computer program products according to various embodiments of the present invention. Each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession, may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In this specification, the term "logic" refers to a specialized circuit, embedded software, middleware, software, a specialized processor, a Very Large Scale Integration (VLSI) chip, a configured Application Specific Integrated Circuit (ASIC), a configured Field Programmable Gate Array (FPGA), or other logic circuit. The logic may be optimized and/or configured for the task in question (see U.S. Pat. No. 6,785,872 for methods for converting algorithms into circuits, which is incorporated herein by reference). Note that embedded software is hardware and middleware includes hardware.

The present invention may be a system, a method, and/or a computer program product. The computer program product may include a computer readable storage medium (or media) having computer readable program instructions thereon for causing a processor to carry out aspects of the present invention.

Figure 1:
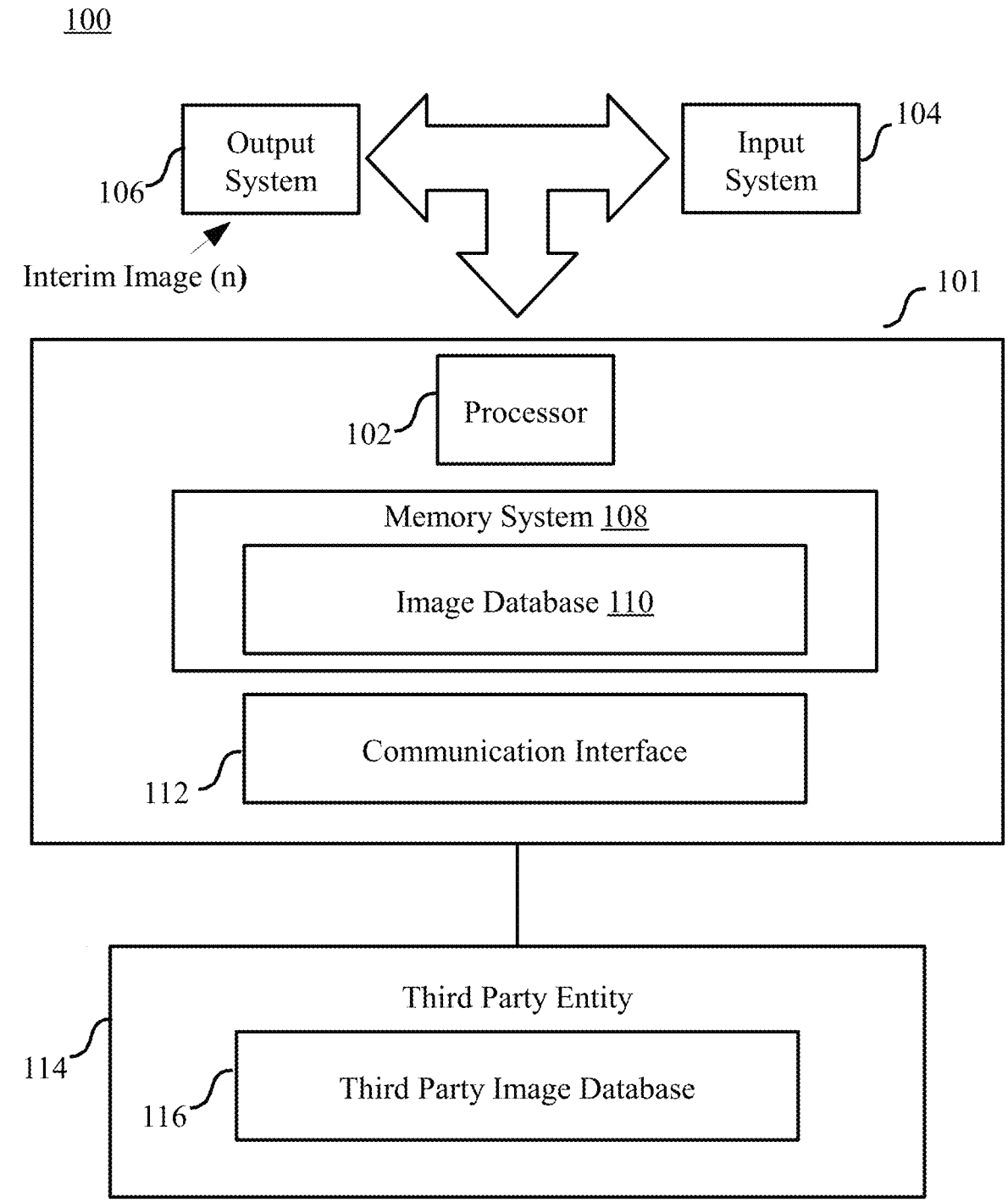
FIG. 1 is a block diagram of an example of a system that analyzes an image for a multi-purpose interactive cognitive platform.

FIG. 1 is a block diagram of an example of system 100 that may be used for assessing cognitive abilities, treating cognitive issues, and/or improving cognitive abilities. System 100 may include machine system 101, which has processor system 102, input system 104, output system 106, memory system 108, image database 110, communication interface 112, third party system 114 and third party database 116. In other embodiments, System 100 may include additional components and/or may not include all of the components listed above.

System 100 relates to a platform that may be used for assessing, treating, and/or enhancing cognitive performance. System 100 may be used a platform for collaboratively treating, enhancing, and/or assessing cognitive performance. System 100 provides interactivities for users to interact with, and system 100 assesses the user's performance. The interactivities may also be used to improve cognitive skills and processing performance. The interactivities may be used to immediately improve cognition just after completing the interactivity (e.g., for children with Attention Deficit Disorder (ADHD) performing the interactivity in the middle of a task may aid the child in staying focused for the rest of the task) and/or to improve cognition on a long-term basis. Also, in system 100, cognition and cognitive processes can be applied to people and/or machine processes, which utilize, and/or which are modeled on, human cognitive and vision processes. In support of brain health, the platform can be applied to people across the cognitive spectrum to support cognitive function, information and language processing, learning, training, screening, stimulation, cognitive skills development and processes improvement, stress reduction, therapy, and remediation purposes. Cognition can be viewed in terms of individual brain and neurological processes as well as holistically considering the totality of conscious and subconscious input and/or stimuli and the interpretation, analysis, storage and translation of such inputs into a wide range of output forms. The platform's image-based interactivities may be used to support human perception, cognition, behavior and interactions with the environment and the world, directly and/or indirectly, such as through a secondary device or other type of interface. The secondary device may be worn, implanted or transmitted signal, in the immediate, short-term and/or for later retrieval.

Cognition can be viewed in terms of allocated cognitive domains and subdomains responsible for critical functions and processes, including: memory, attention, executive functions, language and communication, sensorimotor, and visual-spatial operations. Each of these domains may include a multiplicity of processes and skills Each of the processes within a domain and/or multiple domains may be integrated with one or more other processes and/or domains with crossover relationships as well as with subdomains. Neurocognitive functions provide a framework for how the brain functions and/or a gateway to understanding cognitive differences and dysfunctions.

Brain processes associated with learning, and by default with memory and attention operations, among other cognitive domains, can also be described in terms of thinking skills. Thinking skills are traditionally hyphenated into "higher" order thinking skills (HOT) and "lower" order thinking (LOT) skills. The principles related to thinking can be generalized to learning where processes require the mustering of both higher order thinking skills (including critical, logical, reflective, metacognitive, and creative thinking for analyzing, evaluating, synthesizing and creating) together with lower order thinking (LOT) skills (which include: applying, understanding and remembering). The totality of higher and lower order thinking skills become integrated when considering cognition and cognitive processes and their participation in perception. HOT and LOT skills can be framed by the domains described previously with the application of the processes within the cognitive framework to help people interact with their environment and the world around them. Different learning styles may not only affect learning and training, but also may affect how to appropriately assess cognition and how these (learning, training, and assessments) are conducted to integrate and/or reflect individual learning styles. Individual learning styles may include: auditory, verbal (linguistic) visual-spatial, kinesthetic (movement), among others. Individuals may have a bias toward a particular learning style, but generally display a mix of learning styles, which can be differentially manifested depending on task requirements.

Different learning styles may be accommodated, by system 100, in a variety of ways in the platform. In embodiments of the platform, a visually driven system (e.g., with visual sensory input), may provide triggers (such as by giving visually based hints and/or visually based problems to solve) for visual memory—an important driver and/or indicator of cognition. Further, the associative connections to visual memories and pattern recognition can be used to integrate different learning styles. Learning via associative connections is not defined by books, but rather by inputs and associating neural connections. From a pure learning standpoint, instructions are provided in text, images, and/or audio format. The assessments of system 100 may integrate verbal descriptive responses, sensorimotor, and kinesthetics (moving puzzle piece parts). In system 100, rewards for task completion may be in the form of audio output, and may include background music to provide audio lifts (e.g., music commonly associated with a positive outcome and/or a victory). The platform of system 100 may allow users to express responses and/or demonstrate capabilities, incorporate non-visual content such as tactile stimuli, and expression, which may support a mix of learning styles. When designing interactivities and companion tests/assessments both processes are relevant—the activity and assessments (interactivities may be described as tests in academic settings).

Brain processes, whether in healthy and/or impaired individuals, can be further framed within the context of top-down processes and bottom-up processes. In bottom-up processing multiple sensory inputs can be received, assembled, and integrated through multiple steps. For example, a particular taste, texture, visual appearance, and/or aroma may be assembled together to construct a new concept, such as a new food. Whereas, in top-down processing cognition draws on, uses, and/or applies models, ideas, and expectations (inferences) to interpret sensory data and generally leads to some kind of output and/or response. For example, having information that a particular food will be served, one may infer or learn to infer information, such as from the aroma, visual appearance, and/or the taste (based on a model of a particular food), without actually tasting the food. Sensory input and the upstream and/or downstream processes, including analysis can be complex. For example, recognizing the nuances of fire can mean discriminating between a building that is on fire, an out-of-control conflagration versus a single candle burning on dining room table or knowing that a pot on a stove is potentially hot (an associated connection to fire). Associative neuronal connections to concepts and practices all require some kind of sensory input and the integration of multiple sensory inputs, (seeing the fire, feeling the heat, smelling smoke), prior knowledge and memory inputs (top-down inputs) and woven together in a rich web of connections.

Sensory input to system 100 may include: visual, auditory, tactile, motor/kinesthetic movement, gustatory among other types of inputs which can be sensed directly, and/or indirectly or transduced through a secondary medium and/or device, including an implantable or wearable, as well as through computer-brain/neural interfaces and other human-machine interfaces, whether through permanent or temporary interactions.

The state of cognitive function may be related to brain health, well-being, reasoning, decision-making, learning styles, skills development in both healthy individuals and in those with changes in brain health associated with disease conditions. There are a diversity of processes, changes, differences, impacts, and/or altered states which may be reflected in a range of diseases and conditions that have overlapping symptoms and therefore similar impacts on one or more cognitive processes. Some examples of conditions with a cognitive component, include: ADHD, ADD, Autism, Multiple Sclerosis, Parkinson's disease, Type II Diabetes, Atrial Fibrillation, Stroke, Aging, Mild Cognitive Impairment, Alzheimer's disease and other dementias, stress, chemotherapy, post-anesthesia cognitive dysfunction, Schizophrenia, among other transient, progressive, acute and/or chronic physiological, psychological neuromuscular and other conditions.

The platform (system 100) described herein is designed to support brain health through diagnostic assessment, intervention, and treatment modalities. The platform of system 100 engages cognition in support of learning, skills development, and training enhancements, as a standalone methodology delivered through the platform. The platform of system 100 may use cognition in conjunction with other assessment tools, devices, and/or therapies, such as exercise equipment and/or with a passive and/or active exercise protocols including whole body vibration, transcranial magnetic processes, and/or as an adjunct modality, and/or assessments to support cognitive well-being and cognitive processes.

The platform of system 100 may be used as part of a system to help support brain health as a potential treatment modality, an intervention that can be delivered as a device-based intervention using smart devices, such as a computer, tablet, phone or other type of interfacing device. For example, the interfacing device of system 100 may allow the user to interact with the platform through hands-on, hands-free and/or view-only interactives. Offline, the platform materials and interactive tools may be projected and/or printed on a pre-sectioned substrate (or substrate, which can be sectioned). Offline sectioned platform material and/or interactive tools may allow the parts to be manipulated (e.g., as a picture puzzle that needs to be assembled). Offline platform material may be printed or transferred onto a different medium, and/or are presented in view-only mode printed and/or projected on a substrate. The platform of system 100 may be implemented as a hybrid form of online and offline components. The platform of system 100 may be include a subset of overlapping assessments which can be conducted with both the device-based and offline interactives for crossover multi-modal analysis and tracking. The platform of system 100 may have different interfaces and/or material for verbal and non-verbal users. Nonverbal (or verbal) modes of system 100 may include use cases for minimally conscious individuals who can only access the platform's view-only interactive options. In embodiments for minimally conscious individuals and in the platform's nonverbal use modes, the assessments of interactions may require the use of biometrics, such as eye tracking and/or electroencephalogram (EEG) and/or evoked response potential (ERP) as an index of engagement. EEG and ERP are methods of measuring brain activity. Electroencephalogram (EEG) is a test used to evaluate the electrical activity in the brain. Brain cells communicate with each other through electrical impulses.

The platform of system 100 may provide a method for developing a treatment plan for a patient, or for delivering a multiplicity of interactivities, interventions, and/or user engagements according to healthcare workers (e.g., clinicians, researchers) or other user and/or system protocols to meet and/or address individual and/or group cognitive and/or training requirements for healthy individuals as well as for those who are experiencing cognitive challenges in order to address individual cognitive domains a part of holistically engaging multiple cognitive domain processes and skills as an integrated system. An interactivity is an activity that the user (e.g., a patient) participates in, as part of interacting with the platform. Interactivities include games, puzzles, therapeutic exercises, diagnostic tests, for example. A user can be any one of the following: a patient, an individual, a healthcare worker, a researcher, a professional gamer, game maker, and/or a clinician, for example. In some embodiments, the term "user" can refer to any one or all of the above. In any of the embodiments, each of the terms a patient, an individual, a healthcare worker, a researcher, a professional gamer, game maker, and/or a clinician may be substituted one for another to obtain a different embodiment.

In some embodiments, the term healthcare worker can refer to any worker in the healthcare industry including, but not limited to, a researcher, a doctor, a clinician, therapist, a nurse, and a laboratory technician.

System 100 provides a multi-purpose interactive cognitive platform for cognitive well-being and skills training, and assessment/diagnosis of cognitive dysfunction and/or cognitive differences. System 100 provides a platform for healthcare workers to implement assessments for a variety of cognitive functions, differences, and dysfunctions.

System 100 may be a network of systems including multiple machines communicating via a network, which may be used for treatment and/or diagnosis. For example, system 100 may analyze images, and/or generate composite images by combining multiple images into one image, such as by interleaving multiple images with one another, which a user may interact with as part of an interactivity. In this specification, the words interleave and interweave (and their conjugations) are used interchangeably throughout the specification, either term may be substituted for the other to obtain different embodiments. The interleaving process creates the illusion of depth, a figure and ground relationship described by Gestalt principles. The figure-ground relationship can be characterized as stable or multi-stable. In stable configurations only one image occupies the ground position. Whereas in multi-stable configurations, more than one image can be perceived as occupying the ground position. The image in the ground position is virtually reassembled in the user's mind, a process in keeping with the Gestalt principles of continuation and completion, and based on specific image characteristics and discernible patterns recognized by the viewer/end-user. Multi-stable image sets demonstrate switch characteristics which result in a shift in the viewer/user's attention between the images in an image set and conversely in suppressing a perceptual switch to maintain focus in holding only one of the images in the ground position.

The user may use the platform to analyze images, and/or generate composite images by combining multiple images into one image, while the user's interactivities are monitored for assessment and/or for treatment of a condition, and/or in support of maintaining cognitive health. The composite image sets embed multiple Gestalt principles (figure-ground, closure, continuation), engaging top-down cognition and bottom-up sensory processing, as users identify patterns and image parts to virtually reassemble the spatially separated image parts by virtually reconstructing the intact image. Because the platform uses real-world images with objects and relationships between objects which can be identified, described and analyzed by the user, cognition across multiple cognitive domains (memory, attention, executive functions, visual spatial, language and sensorimotor) can be engaged within each interactivity and between the set of related interactivities in using the same image sets. This approach to cognitive assessment significantly differs from current assessment methods which combine unrelated, single cognitive domain assessments as a reflection of multiple cognitive domains. The invention platform described in the application uses assessment interactivities which have multi-domain characteristics.

Composite images, which are also referred to as composite image sets or image sets, can be generated by serially sectioning and juxtaposing the image sections from two or more images to portray the illusion of depth (e.g., so that the sections of one image of the composite appear as background and section of another image of the composite image appears as foreground). The composite image can also be referred to by the term, "photage" which is a contraction of the terms photo and montage where image sections from different images are placed in a specific pattern and/or sequence to resemble the original whole, but with the parts of the images from different images mixed with one another. Composite images can be formed when component images are sectioned into two or more sections across their entire width and the sections juxtaposed next to sections from a second, and/or third image, such that sections from any one component image is not placed immediately adjacent to one another in an interleaved fashion. The gap between otherwise adjacent sections in a component image may be 1.5%-50% of the image's total width, depending on specifications to effect the re-assembly of the hyphenated image segments to occur, despite the gapped appearance of the construct. The gap may be filled by a second and/or a third image, cut according to specifications or by white or other solid color spaces which can be viewed as a background substrate generated by placement of one of the images with a spatial gap between the image sections. In one embodiment, a solid white background can serve as a virtual or physical substrate for both online and offline composite images and the associated interactivities.

In an embodiment, the foreground may be the portion of the image that represents the object that is closest to the viewer, and the background may be the rest of the image. The illusion of depth may be a visual illusion effect that is rooted in the figure and ground relationships of the individual component images and their relationship to one another when juxtaposed. The illusion can portray a second characteristic if one or more of the component images contain specific image attributes referred to as contiguities. The serially sectioning and juxtaposition of multiple image sections in an alternating fashion generates the illusion of depth based on figure-ground relationship informed by the presence or absence, and/or relative strength of the contiguities present in the image set. Contiguities (which may be referred to as "contigs") may be compared to, horizon-like edges according to certain characteristics, and a contiguity may include horizontal edges that are associated with a horizon. However, contiguities may also contain significantly more information beyond just information about edges. Contiguities may be framed, such as by being characterized by their content, color and context information. The characterizations of the contiguities may be useful in determining what images to combine together in composite image and/or the difficulty of a puzzle interactivity.

The presence of one or more contiguities in a composite image can confer an additional aspect of the visual illusion in terms of the stability of the image which is perceived to occupy the ground. The ground may also referred to as the background position. In one embodiment, the configuration may be referred to as stable when only one of the images in a composite image set contains at least one contiguity. In an embodiment, a contiguity is a continuous region having relatively uniform and identifiable color and content characteristics, which may span the entire width and/or a significant majority and/or a portion of the width of an image. In an embodiment, a contiguity is a region that is recognized by the system as one region.

The gap filling (perceptual completion) of the image perceived to be in the ground position can occur when the intervening spaces are filled with one or two content-rich images and/or when the gap space is filled with a solid color, such as white (empty space). The dynamic re-assembly of the hyphenated image segments of the image occupying the ground position can occur based on the presence of visual, context, and knowledge-based cues as part of the user/viewer's experience base and predictive inferences, continuity, together with gap-filling (perceptual completion) capacity of the information conveyed by and through the contiguities present in the image. For example, a green:blue colored interface extending across the entire width of the image can potentially be identified by the user as a field/sky interface based in part on the color of different regions and spatial characteristics, and the user's knowledge of field and sky. The regularity and continuity of the interface can be anticipated by the user and the intervening disruptive and/or distractor image sections are largely ignored as the viewer tracks to the next image section containing a green-blue interface. Interference can be established with the choice of intervening images and overlapping contiguities between the component images included in the image set. Together the Gestalt principles of figure-ground, closure, continuity, and gap filling (perceptual completion) can be used to understand the scientific basis of the visual illusion and its applications in the platform for assessment, diagnostics, remediation, and training purposes for engaging cognition. Continuity refers to the mind's tendency to complete a continuous region even when disrupted or spatially separated and inferred to be continued based on visual cues, knowledge and experience. The gap-filling capacity of an image set in a viewer's mind despite the hyphenation is consistent with the Gestalt principle of completion, which is that the mind tends to complete an image using inference, logic, pattern analysis and/or by applying previous knowledge and experiences.

Figure 23A:
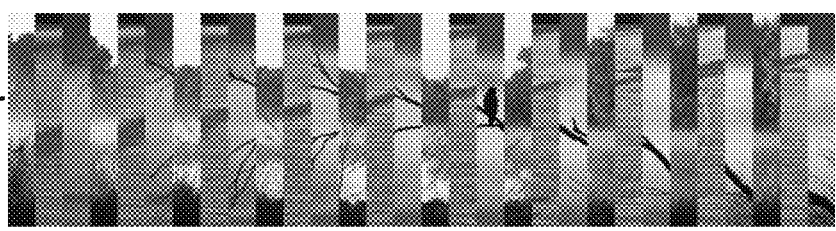
FIGS. 23A-23D show examples of composite images comprised of three images and how the presence of contiguities in one or more of the images affect the stability of the image in the ground position at any point in time.
Figure 23B:
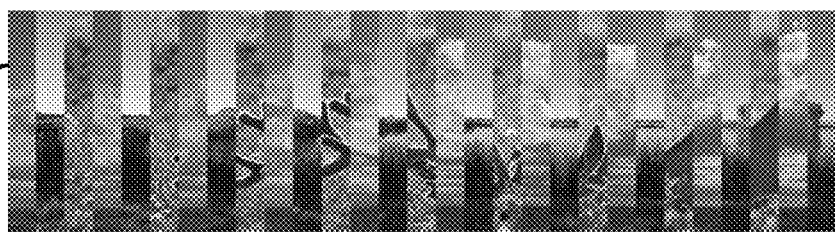
Figure 23C:
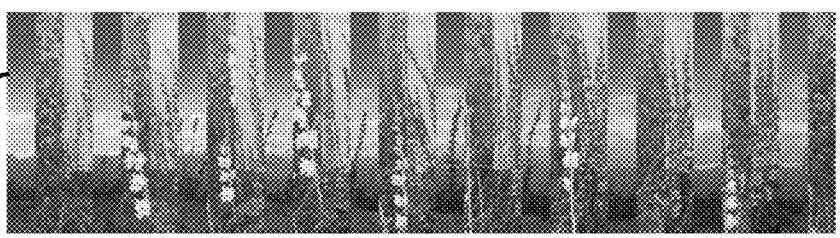
Figure 23D:
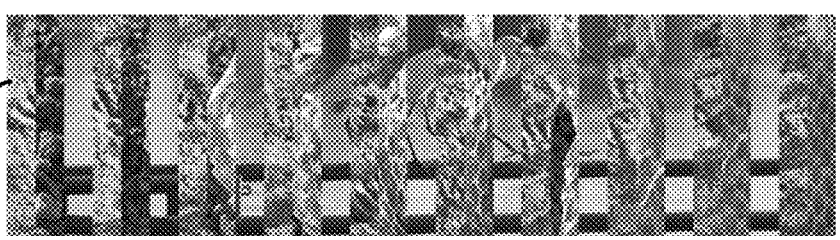

A stable image set is an image set where one of the images is localized in the ground position and the other component image or images is localized and fixed in the figure position (FIGS. 23C and 23D). The term multi-stable refers to the ability of more than one image, or image section or part to assume the ground position (with a concomitant flip or switching/shifting of the previous ground occupant to a figure position).

In a multi-stable image set, the figure and ground relationship of the image set may be perceived in more than one way, e.g., the perception of the image set changes/switches. The flip or switch can occur spontaneously and the different forms are referred to as percepts. In embodiments that use a multi-stable set, the image which occupies the ground position dynamically shifts between the image and/or images in the figure position at a given point in time and is perceived in an alternate fashion by the viewer (FIGS. 23A and 23B), and is described further below. In both stable and multi-stable embodiments, the image, or parts of an image in the ground position can be perceived by the viewer as being intact, confluent, despite the spatial hyphenations between sections of the image (the spatial gaps associated with the hyphenations may be largely ignored).

In describing figure and ground relationships, the terms of recessive and dominant can be used, respectively. Dominant may be used to refer to the image which assumes the ground position in a fixed and/or dynamic fashion in a stable configuration, or images in a multi-stable condition, respectively at any point in time. In the stable condition, the figure position is then occupied by the other image in a 2-image composite or by two images in a 3-image composite, if neither of these images contains a dominant contiguity relative to the image occupying the ground position. For a multi-stable composite, the presence of at least one contiguity in at least 2 of the images in a 2- or 3-image composite, the composite image will generate a multi-stable image set, and/or that each of the three images in a 3-image composite each has at least one contiguity will also generate a multi-stable image set.

Figure 25A:
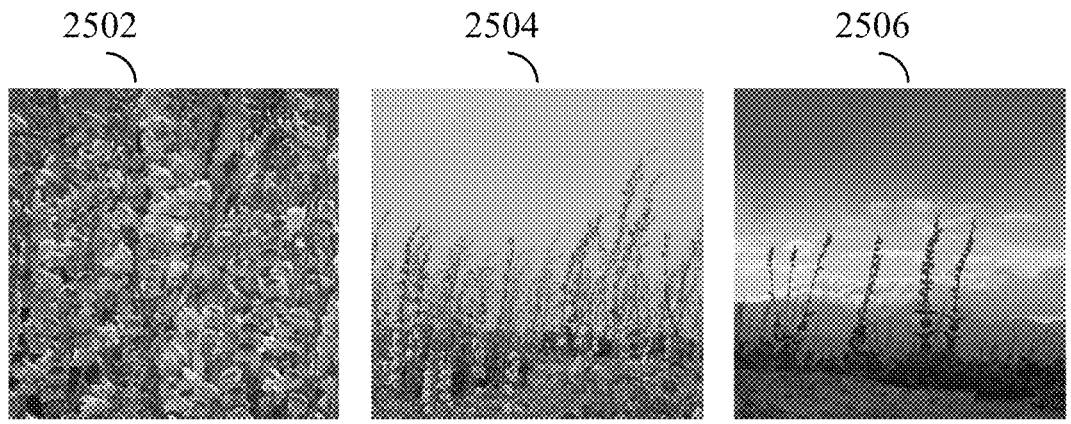
FIGS. 25A-25D show the composite images and component images of the composite images.
Figure 25B:
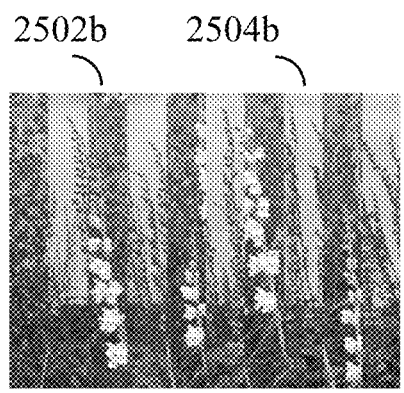

Both stable and multi-stable image sets share the illusion of depth, but differ in their switch/shift capacity as described previously and in the following sections. Not all percepts are equally stable and dominance is relative to the composite's composition, i.e. the combination of images in the image set. For example, if the component images in a stable 3-image composite are extracted and reassigned to a 2-image composite, a previously figure-bound component image in a 3-image composite can assume the ground position in a 2-image composite because of a relative state of contiguity dominance—a hierarchical relationship. See for example, FIG. 23C, which is a 3-image composite, and compare it to FIGS. 25B-25D, in which the component images shown in FIG. 25A have been re-grouped to form 2-image composites. Depending on the grouping 1:2, 1:3 or 2:3 a component image which previously occupied the figure position (FIG. 25C), can occupy the ground position when combined with a second image with a weaker or absent a contiguity (FIG. 25B). The image with the contiguity occupies the ground position, and in the stable configuration, the second image in a 2-image composite; or the second and third images in a 3-image composite will occupy the figure (foreground) position. The image or images in the figure position can appear as columnar pop-outs supporting the portrayal of the illusion of depth. In a stable configuration, the same image always occupies the background position. In a multi-stable configuration the switch capability is high for the image set because of the combination of component images in the composite, for example when both of the images in a 2-image composite or a 3-image composite, and/or when two or three of the component images in a 3-image composite have dominant contiguities. In other words, a weak contiguity can be in the ground position relative to a composite image that has a second component image with even weaker contiguity characteristics, but which can still be relegated to the figure position in a stable composite, if the weak contiguity is dominated by an image with a contiguity with stronger characteristics. In part, one reason that a weak contiguity may occupy the ground position relative to a composite image having a second component image with weaker contiguity characteristics is due to the presence of a minor contiguity (one with a lower relative score) whose contiguity characteristics (while present) were otherwise perceptually masked in the 3-image composite or a 2-image composite. However, the minor contiguity may still be expressed (e.g., as a result of still having the relatively higher score) in certain combinations of the derived 2-image composite and/or in combination with other images. As such, in one embodiment, an image with a weak contiguity can be combined with one or more images which do not contain any contiguities, making the image with the weak contiguity the dominant image and when the sections are combined, the image with the weak contiguity can assume the ground position.

The hierarchy in which the image with the highest contiguity ranking in terms of dominance will assume the ground position can be driven in part by the contiguity's characteristics and user's/viewer's input and/or bias and/or preferences. The multi-stable capacity is nonetheless conferred on an image based on the individual image's essential contiguity characteristics and are metered by the combination of the image with other images in terms of the expression of the contiguity. The multi-stable relationship is evident in comparing FIGS. 24C and 24E, and/or FIGS. 24D and 24F where the contiguities have been removed from the multi-stable 2-image composite in FIGS. 24C and 24D to generate the stable configuration in FIGS. 24E and 24F, respectively. Both stable and multi-stable constructions can be generated using any of the platform's modalities, device-based, offline tangible components, and/or a hybrid version using a Tangible User Interface (TUI) prop and active surface.

Figure 6A:
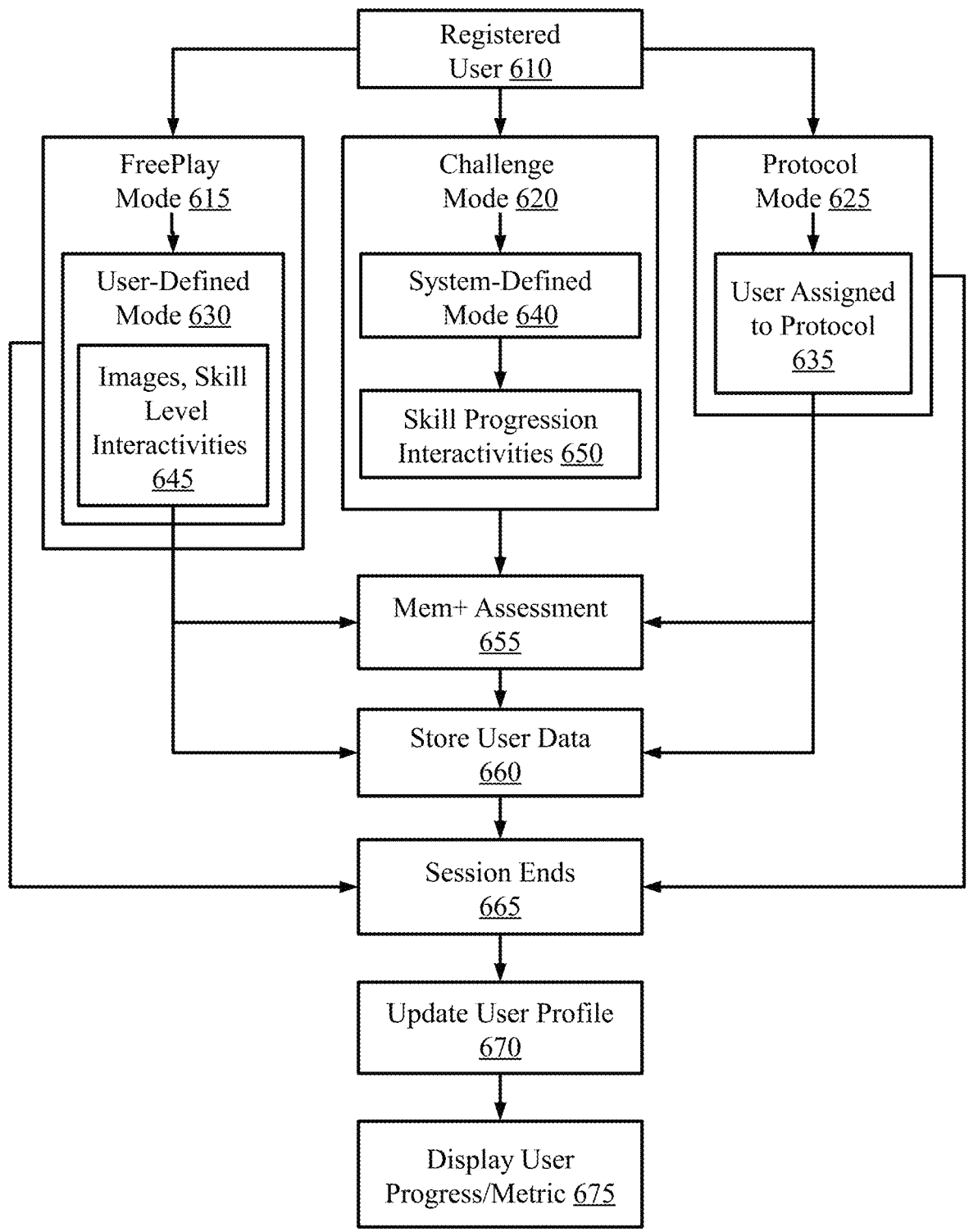
FIG. 6A is an example of a flowchart showing three options for how a registered user may interact with a multi-purpose interactive cognitive platform.

In both stable and multi-stable image sets, despite the disruption with interspersed content-rich image sections and/or blank spaces the image that occupies the ground position can be conveyed as coherent and intact, if the second (or third) image(s) are solid in color. The disruption can be viewed as distractor or attractor elements, depending on the use of the image and the location of the disruption (see FIGS. 6B-6E for an example of an attractor/disruptor element and the discussion of method 600, FIG. 6A). The gap-filling capacity of an image set in a viewer's mind despite the hyphenation is consistent with the Gestalt principle of completion, which is that the mind tends to complete an image using inference, logic, pattern analysis and/or by applying previous knowledge and experiences. While FIG. 6B can be viewed as an attractor/distractor element in the image set, other types of distractor elements, vertical distractors, also referred to as disruptors are evident in FIG. 6D and are discussed in greater detail below. The effect on the figure-ground relationships of these component images is seen in the composite shown in FIG. 6E, where FIG. 6C is easily perceived to be in the ground position as its contiguities as color blocks and edges are dominant across the entire width of the image. By contrast, FIG. 6D can occupy the ground position because the image has one or more contiguities, however, it is perceptually more challenging because of the presence of multiple vertical distractors (flower stems) and because the contiguities do not extend the full width of the image. The hierarchical relationship between contiguities of different images, the attractor/distractor elements, whether a portion of an image assumes the ground or figure position, and/or other image characteristics can be exploited in the platform to make an interactivity more challenging or involve different types and/or modalities of cognition.

The differences in stability allow complex, content-rich image sets to be categorized and ranked for use in the multi-purpose interactive cognitive platform. The differences in stability can be used to convey image sets of varying complexity, with different characteristics, and can be integrated into interactivities-embedded assessments and training protocols. The differences in stability require different cognitive demands in discerning differences, identifying component parts, suppressing distractions, and resolving ambiguities which can be exploited in the platform.

The integration of stable and multi-stable image sets into the multi-purpose interactive cognitive platform allows for dynamic cognitive engagement of the user with the composited image sets, whether in a conscious and/or unconscious mode as perceived by the user/viewer. The engagement is facilitated by selecting and using image sets of differing complexity and switch capacity for select training and treatment modalities, together with the interactivities mix. Contiguity characteristics form the basis of developing a complexity rating for images based on their ground position capacity and/or switch capacity, and/or depending on the image configuration together with image content, color and context variables. The prospective image combinations can be defined according to a set of rules where a composited image scene can be categorized as stable and/or multi-stable, and with a determination in the stable condition which image will assume the ground position, with assignments to varying complexity levels for the various interactivities.

In multi-stable image sets, the switch rate can vary between users and as a function of cognitive status related to: age as a factor and/or neuropsychological conditions, such as schizophrenia and autism.

Switching events and, as such, switch rates for multi-stable images have traditionally relied primarily on user-identified switch events which are signaled by a click of a mouse or other type of device to indicate conscious awareness of a switch event. In general, the images used for measuring altered switch rates are binary ambiguous images, in that the switch occurs between two alternate perceptual states (percepts) within the same image. Examples of these types of images include the Necker Cube and Rubin Wine Glass-Face illusion. The multi-stable image sets used in the platform involve a switch between different images, guided in part by the user tracking (e.g., moving the user's eyes) across a given contiguity or towards salient image parts. As such, interactive measures and/or an analysis of switch rates among different population groups can be improved and used as a diagnostic tool. The interactive measures and/or an analysis of switch rates may use both user-identified switches combined with objective measures such as eye tracking analysis to detect a shift in the user's gaze or eye focus from the spatial location of a contiguity in Image #1 to a contiguity in Image #2 and/or Image #3 or EEG, ERP analyses, and/or functional magnetic resonance images (fMRI) to objectively track switching events. Optionally, throughout this specification, any time an eye is tracked, the eye may be tracked automatically via a camera in system 100, and analyzed by the processor system of system 100 or 200. Switch events such as eye tracking can also be monitored using EEG tools in part, because of the integration of real-world images into these dynamic image sets and the recognition/discovery process which can occur when the ground image becomes confluent coincident with and/or part of a switch event. The potential for identifying evoked/event response potentials together with eye tracking data, as well more sophisticated biometrics, imaging and analytical tools, can be used to improve these measurements and assess their potential value as part of building a diagnostic profile of cognitive function and status.

In one embodiment, the multi-purpose interactive cognitive platform may have a Mem+ assessment, which may be set up to engage cognition with a simple question, such as "what do you see?" together with speed and accuracy, and other data collected from the interactivities. The platform can be used for conducting assessments and delivering therapies and/or training and/or to support cognitive well-being.

The interaction may include user-defined selections from a library of images, and user-defined selection of a subset of interactivities. The complexity of the interactivities may be modulated (e.g., by changes the sectioning strategy and consequently the number playing pieces).

Complexity modulation may be responsive to user interactions as defined by the system. Complexity modulation may include a user-defined scenario and may optionally be available from the beginning of an interactivity and/or user system with system-defined complexity modulation. Optionally, the user can override changes made or that would be made by the complexity modulation. Optionally, there may be user-defined overrides of system-defined gameplay. The sectioning strategy refers to how the image is sliced up, and the number of pieces generated as a result, which may be prescribed and/or recommended to and/or selected by the user, but may be manipulated by the user choosing different difficulty levels. The sectioning strategy does not necessarily change the shapes of the pieces. Sectioning strategy can apply to the shape of the section cut and/or the size of the section cut. Some examples of sectioning strategies that differ by the number of slices and width of the section (same or variable) generated from cutting an entire image are 25% cuts=4 sections; 20%=5 sections. A sectioning strategy may include the types of sections into which an image is divided into for solving a puzzle interactive. For example, the image may be divided into horizontal or vertical strips and pieced together according to the sectioning strategy. The pieces may be sorted, placed in a desired location, matched with one another or other pieces, and/or assembled into an image. The platform may include a timer that tracks total time in which the user completed the interactivity, time per move and/or the time per step. The platform may also track the number of steps that the user required in completing the interactivity. Logic may be built into the platform for assessing users, guiding users, and/or facilitating activities of practitioner activities. The platform may or may not necessarily automate the analysis of images in terms of color, content, contiguities, or assign complexity to images, for example.

The term "Mem+" refers to assessing for memory plus other aspects of cognition that may or may not be related to memory, including: attention, visual-spatial, executive function, sensorimotor, and language domains which include associated skills and processes. For example, the Mem+ assessment includes interactivities that may cooperatively involve the use of memory and/or other cognitive domains. In an embodiment, the Mem+ assessment may be part of the Protocol Mode, and whenever a Protocol mode is used, the Mem+ assessment may be incorporated into a protocol. In Protocol mode, a user is expected to follow (and may be tasked with following) a specific predefined protocol or regimen of interactivities. The platform may use real-world images, illustrations, and/or drawings—e.g., having enriched visual stimuli—to cooperatively engage global cognition (thereby simultaneously and/or cooperatively engage skills and processes across multiple cognitive domains).

Throughout this specification, the phrases "tasked," "tasked with," and "tasked to" refer to the user being presented with one or more interactivity screens having the tools for performing the task in question and being presented with indications of what task to perform.

The interactivities using enriched real-world images include assessments embedded in interactivities, and which may include assessments of speed and accuracy measurements. The interactivities using enriched real-world images may be combined with simple questions (e.g., about the image). The use of enriched real-world images may improve the quantity and quality of captured data (as compared to other images and/or questions used), allowing for direct measurements of overall cognitive status as well as domain-specific task/skill metrics, towards developing sensitive, reliable cognitive tools. There is no requirement to use real world images—any image may be used, but the integrated use of enriched, real-world color image content increases the effectiveness of the platform's cognitive assessment capabilities as compared to simplified black and white illustrations and/or drawings of individual images for descriptions and user interactions with the content and interactivities, and as general input stimuli for engaging cognition. The use of enriched, real-world color image content helps keep the user interested and also engages (or at least tends to engage) more cognitive abilities in a given task based on the complexity of the information that the user is processing. Assessments data may be derived from speed and/or accuracy measurements made using the App, and/or from questions, including SQ2 (Spatial, Quantitative and Qualitative) type questions, such as "what color was the flower?," "what do you see?," "where was the bird?," "which bird's looks most like the one you saw?," and/or what do recall seeing, for example. In an embodiment, the question asked regarding an image may be open ended or closed. In an embodiment, the question is one that only requires a one word or one phrase response. In an embodiment, the question is seven or less words. In an embodiment, the question is 10 or less words. In an embodiment, the question is 15 or less words. In an embodiment, the question is 20 or less words. In an embodiment, the question requires that the user analyze interleaved image sets, focusing a range of cognitive abilities in the process, including language and memory domains and subdomains, but may also make use of attention, visual spatial, and/or executive function processes and skills. In situations where some users may not have firsthand experience with the content of an image, for example, a field of sunflowers, but the user has experienced flowers, the image set can still be of value in training, treatment, and assessment. Similarly, while lakes are familiar to a significant number of people, even those who have never experienced a lake can recognize a lake and the lake's relationship to water and/or a body of water.

In one embodiment, the platform can be deployed in and/or through a device with components on a tablet, computer, phone, television, smart device and/or other virtual, augmented, and/or mixed reality devices and/or other media. For example, the platform may be implemented as part of an ecosystem of interconnected devices of the Internet of Things (IoT). The interactive components can be used in hands-on and/or hands-free and/or virtual view-only mode. The hands-on mode may include manipulatives with multiple types of input devices including touch-screens, mouse, stylus, pads, and/or Tangible User Interface props, virtual projections, voice commands, and/or other types of input devices. The hands-free modality may include multiple types of interfaces, including neural feedback, eye-tracking, biofeedback, sensors implanted into the human body, assistive devices, sensors attached to the human body wearable, and/or other types of add-on system and/or device, or other biometrics tools to facilitate and/or allow for the manipulation of the image set, in part or as-a-whole. The input may include Wi-Fi (e.g., via a radio frequency local area network), infrared, ultraviolet, low frequency sound, ultrasound, and/or Bluetooth, for example. The interactivities can include hands-on, hand-free, and view-only interactions. Hands-on interaction can occur with physical and/or digital manipulatives. However, hands-on interaction is not necessary as part of the process of working with the multipurpose interactive cognitive platform, because physical reassembly is complemented by virtual assembly of the hyphenated image parts, interactivity can occur in the user/viewer's mind. The virtual view-only interaction is also as an interactivity because the view-only interaction requires the user's engagement, whether it is conveyed to the user, actively or passively. View-only is a default aspect of both hands-on and hands-free interactions, but also represents its own type of interaction when the user views the image set. Hands-free and view-only interactions are distinguished in that hands-free interactions involve physically or digitally moving parts of the images or image set, while view-only interactions and manipulations occur virtually, i.e. in the viewer's mind. In other words, in view-only interactions the image set is not physically or digitally changed.

The platform's multi-modal interactions and integration of real-world content rich images, together with the option for timed and/or untimed assessments, and the dynamic aspects of the image sets, the stable aspects of the image sets, and/or other features make the platform a versatile multi-purpose platform suitable for use across a range of user capabilities and environments. The platform includes assessment of multi-domain cognitive skills and process capabilities that are performed by default as users' work on and/or complete an interactive task.

System 100 may include a view-only mode, in which the user views the image and performs the interactivity in their mind. The view-only mode may be used by people with limited mobility (e.g., older adults, paraplegics, and others) and/or fine motor control such as can occur following a stroke. The view-only interactivity mode may be used by the user without anyone monitoring the user's response and/or in the presence of a healthcare practitioner to monitor the user's response. Alternatively, the view-only mode may be performed while the user's response is monitored by a facilitator, and/or by monitoring the user's brain waves, body temperature, eye movements, facial expressions, movements of other parts of the body, heart rate, and/or pulse rate, The interactions may be through the mind's interactions as virtual interactions. The view-only mode may be presented to the user in digital and/or traditional print formats.

In an embodiment, a tangible user interface (TUI) may be used. A TUI is a user interface in which the user interacts with digital information through the physical environment. The TUI gives physical form to digital information, and may include one or more sensors to sense the manipulation of physical objects and materials other than a keyboard. In an embodiment, the TUIs of this specification does not include a mouse (although, in this embodiment, mouse input may be used, without a TUI, instead of a TUI, and/or in addition to a TUI, a mouse is not included in the scope of the term TUI of this specification). The TUI may include a prop. The TUI prop provides a tactile interface, giving digital information, such as digital puzzle pieces, a physical form. The TUI prop transforms digital information into manipulatable and tangible parts of the platform, akin to traditional, offline puzzle-type interactivities. TUI props, within the Internet of Things space, can be embedded with additional sensors to capture otherwise inaccessible user data as can be obtained through traditional active surface devices or other types of inputs such as grip strength. In an embodiment, a TUI may include a physical representation that is computationally coupled to underlying digital information, such as images and text. In an embodiment, a TUI includes space-multiplexed both input and output, concurrent access and/or manipulation of interface components, specific devices (via which input is sensed); spatially aware computational devices; and/or spatially reconfigurable devices.

In one embodiment, the platform includes offline interactive components which can be delivered visually through printed matter, including, but not limited to: paper, plastic, glass, and/or wood substrates (or pieces). The offline components may include manipulatives where images are printed in sections on wood substrates. In one embodiment, each component image of a composite image containing two or more images is divided into four sections, which are printed on four (4) 14 cm×3 cm substrates, for a total single composed picture measuring 14 cm×12 cm in size. Different sized manipulatives may be printed based on the substrate used, including varying the width of the sections, and number of sections, including half and quarter-sized sections and smaller. In one embodiment, individual image manipulatives may be printed on a chipboard substrate and cut accordingly, or a printed image may be sectioned and mounted onto a substrate rather than being printed, transferred, and/or sublimated onto a substrate, or can use snap-together sections which can be split and/or combined together in different ways. In one embodiment, the hybrid system may include the use of a TUI prop. In an embodiment, the prop's digital display surface may show an image section, an image section part, or an image element, which may be "released" to an active surface when the user correctly places the image part, displayed on the prop surface, proximal to the mapped game board interactive surface.

In one embodiment, the platform may include all of its integrated components, including: an image library, image sets, and an image database. The platform may include integrated software, delivery and server-side storage, inter-activities, recognized skill levels, interactivity progressions algorithms, complexity values, composite values, user interfaces, user data tracking, real-time feedback, data logging, assessments, and/or reporting and alert tools to provide users and/or professionals with one or more metrics of cognitive status. In one embodiment, the platform may also be represented as multiple modules which can be interchanged and/or configured to meet individual and group requirements according to clinical health specifications.

Machine system 101 may include one or more machines that run an image analysis system. Each machine of machine system 101 may run the multi-purpose interactive cognitive platform/image analysis system independently and/or as a distributed system. Machine system 101 may include one or more Internet servers, network servers, and/or a system for analyzing images. Machine system 101 may include one or more mobile machines and/or may include other machines that include machine vision, for example.

In at least one embodiment, in machine system 101, each image and/or each image of a plurality of images may be analyzed to identify contiguity characteristics in the image that facilitate identification of visual qualities and characteristics indicative of how the viewer is likely to observe the image for use in treatment and/or diagnosis of cognitive issues. Comparisons of how the user uses the image and the characteristics of the image (which may be performed automatically) may be indicative of cognitive and/or mental health status, and or changes in the user's cognitive status over multiple time points.

The value of a color may be represented as Hue-Saturation-Value instead of by wavelength of light. The pixel values may be used to represent the Hue-Saturation-Value or the color. Alternatively or additionally, each color may be represented by a separate pixel value. Returning to the discussion of uniformity, in another embodiment, a color is considered uniform if the variation of the pixel value representing the color varies by less than 10%, less than 5%, or less than 1% (depending on the embodiment). In another embodiment, a color is considered uniform if the variation of the pixel value representing the color varies by 10% or less, 5% or less, or 1% or less (depending on the embodiment). In another embodiment, a color is considered uniform if the variation of the pixel value representing the color varies by no more than 25 bits, no more than 15 bits, no more than 5 bits, no more than 3 bits, or no more than 2 bits (depending on the embodiment).

In an embodiment, contiguities (which may be referred to as "contigs") may be compared to horizon-like edges according to certain characteristics, and a contiguity may include horizontal edges that are associated with a horizon. However, contiguities may also contain significantly more information beyond just information about image and/or object edges. A contiguity may be any generally horizontal feature, such as a line or a block of pixels that are within a predetermined threshold of uniformity of color between pixels that are within a predetermined number of pixels or distance from one another (thereby having a "local uniformity"). Local uniformity refers to the uniformity in color between nearby and/or neighboring pixels. In an embodiment, contiguities extend for at least half the width of the image. In other embodiments, contiguities extend for other distances. Contiguities may be associated with a multiplicity of characteristics within a given image and any given contiguity may have associated relationships between that contiguity and other contiguities that are in the same component images as conveyed in a composite image of two or more component images. Contiguity characteristics include: contiguity number, contiguity stacking, linearity, continuity, angularity, depth/saliency, regularity, and color composition. In an image that has multiple contiguities, the vertical spatial separation between contiguities can be referred to as the stacking. In other words, the stacking describes how the contiguities are spatially arranged with respect to one another both in a single component image and relative to contiguities to other images in constructing a composited image. For example, the stacking describes how closely packed the contiguities are and/or how much space is between the contiguities. The contiguity number representing the number of contiguities in an image, which may be arrived at by averaging different ways of counting continuities, for example. Contiguities may be framed i.e., characterized by their content, color and context information. The characterizations of the contiguities may be useful in determining what images to combine together in composite image and/or the difficulty of a puzzle-type interactivity.

In an embodiment, the contiguities that can be of interest are those that extend horizontally across the image, which for example extend at least 75% of the width of the image (in other embodiments smaller or larger percentages of the width may be used). In an embodiment, the contiguities of interest can make an angle of 45 degrees or less with a horizontal line (in other embodiments the angle may be 75 degrees or less, 60 degrees or less, 30 degrees or less, or 15 degrees or less, for example). A contiguity can separate regions of the image and/or may define a region of the image. In at least one embodiment, the contiguity characteristics may include contiguity lines that separate different color segments in the image, e.g. the contiguities may form edges between the color segments. A contiguity line may separate a contiguity from other regions. In at least one embodiment, the images display landscape scenes in which the contiguity lines are naturally occurring horizon edges, horizon type edges, and/or border lines (e.g., edges that extend more than 50% of the width of the image and that are at an angle of less than 45 degrees). In an embodiment, a contiguity line may also be horizontal, diagonally oriented, uniform across the edge and/or irregular. For example, in urban settings contiguity lines can be horizontal, but may depend on the subject matter. The edges of the contiguity may separate color sections of the image. For example, the edges of a contiguity may separate between the background and the foreground, between objects, between different parts of a background, between different parts of a foreground, between different parts of an object, and/or the like. Optionally, an automated process may be used to define object and image elements in the foreground and background, and define objects in the relative foreground and background.

The contiguity characteristics may enable a person viewing the image to mentally organize parts of the scene displayed, thereby lowering the interactivities complexity or difficulty. A contiguity in the image into different areas that allow the viewer to understand what is shown, and can also be used to train a computer vision system to recognize continuities even between disrupted contiguities, which may be separated, absent, occluded, and/or obstructed. The terms disrupt and disruptor are used interchangeably with the terms distract and distractor. Either may be substituted one for the other to obtain different embodiments. The contiguity lines can provide a contrast, enabling the person's brain or the computer vision system to organize, to evaluate, and/or to resolve ambiguities in the image, image set, and/or image scene. In at least one embodiment, contiguities may be used to inform image classification (that may be at least one factor used in determining the classification of an image) and can be used to identify content and aid in finding objects and/or regions in the image, when used in an interactivity. The classification of an image is at least a part of identifying the content of the image, and thereby may help a user decide which image to choose for an interactivity. A classification system may have categories and subcategories and the smallest subcategories may be objects or parts of objects that have been identified in the image, including figure and ground relationships.

In at least one embodiment, a contiguity may be defined and used to train systems to recognize parts of a whole. For example, a contiguity may correspond to (and thereby the contiguity may identify) a single object or a contiguity may correspond to (and thereby the contiguity may identify) a distinctive part of an object. When training a machine (and/or while performing an interactivity), it may be helpful to identify contiguities in both single images as well as composites, and in composite images the contiguities may be split (or divided) by the other images of the composite image. A composite image is an image formed by combining at least two images together. For example, at least two images may be interleaved with one another. The figure and ground relationships in a composite image is another value vis-a-vis training sets that may be used to further define relationships of objects in an image, and/or between the component images in a composite, and/or in understanding how image characteristics may interact with other image characteristics in the same image or between multiple images in a composite. An element, object, or region of an image is in the figure position when the element object or region is located, where a foreground object of an image (e.g., a photograph) would be located. In an embodiment, an element, object, or region is in the ground position if the element, object, or region forms a contiguity that stretches across all or part of the image. Whether an object is in a ground or figure position may affect the word lists associated with an image and/or questions asked about the image.

In at least one embodiment of the multi-purpose interactive cognitive platform, the user's ability to recognize the parts of the whole, to apply a label, to virtually reconstruct the hyphenated image segments, and/or to differentially focus attention on the figure or ground positioned image in a composite makes use of a coordinated, multi-cognitive domain engagement. The multi-cognitive domain engagement may be used in resolving the ambiguities inherent in the image sets, based on the user's knowledge, experience, and/or memories with the interplay of multiple cognitive domains, including executive function reasoning and problem-solving skills and processes. In at least one embodiment, the user's interactions with the image sets (e.g., image sets of the composite of interleaved image sections) may be gamified. The interaction with the image parts and the interactivities mix may be defined, via the platform, by the user, a clinician, a therapist and/or researcher.

As another example, two contiguities may, or contiguity lines may, section off a region of an image that is one object or a group of related objects. Contiguities may be familiar horizon lines, interfaces with a known and/or predictable color, color "context," and/or content characteristics, and may include information about the location of shapes and information about the density of a feature. The "context" of the color context can refer to an assigned context, a context that is known for other reasons, a context that is predictable, and/or a context that is probabilistically inferred. For example, a context of an image may be knowledge that the image is of a beach, which may be known to the system as a result of external input and/or a category or class in which the image was categorized. The determination of the context may be based on the source of the data and/or user input specifying the context. For example, the user may be provided with the option of selecting tags or other inputs, which may provide image attributes. The inputs may allow the user to input one or more words for a word list and/or associate one or more words of word lists with, or as, attributes of the image. As an example for how the context may be useful, if the data has a known context, the accuracy of identifying objects may be improved and/or facilitated. The word "density" may refer to a concentration of colors or to the saliency of elements within a defined space, which may have additional context, optionally, as a result of the co-localization of the elements within the given context of the image. The additional context may help in identification and/or correct placement of the image part, as the user works through the platform's interactivities. Regarding the density, for example, the interface with a vertically positioned blue region in an upper region of the image of relatively uniform density is likely to be the interface between the sky and another element (e.g., the ground or a lake, depending on the location). A dark element on the surface of the interface of a darker blue region and lighter blue region is likely to be a ship based on known contexts, associations, and references that were previously learned over time and can be inferred and/or deduced by its context by the user (e.g., of an interactivity) and/or machine vision.

As a further example, bodies of water often form contiguities and are regions with a high density of water droplets. As another example, color blocks may aid in the identification of objects or regions contained in an image or a plurality of images or image scene. The context may aid the user of an interactivity (or a machine) in interpreting whether a contiguity is water. Water is transparent, but reflects the colors around it—a stormy sea with dark clouds will have very different characteristics than a calm sea or lake reflecting a blue sky with still water. Nonetheless, based on the context each can still be recognized and/or inferred as a body of water.

In at least one embodiment, the system 101 may be configured to identify the contiguity lines by applying various image processing filters to the image, e.g. Sobel, thresholding, and/or the like, to identify the contiguities in the image as edges. In at least one embodiment, the system can be configured to perform a stitch analysis of the image to designate the contiguity characteristics that are preferred for use for analyzing components in the image and to facilitate identifying images with similar or overlapping characteristics.

A stitch analysis facilitates the analyses of contiguities in an image by juxtaposing non-adjacent image segments and masking a portion of the image in the process. This regrouping of image segments provides a rapid snapshot of the symmetrical and/or asymmetrical, color differences and contiguity regularity and continuity in deriving Aesthetic and Ambiguity Ratings, and towards developing a Compositing Factor for an image. Stitching may involve removing (or masking) portions of an image. For example, vertical sections of the image may be removed or masked. Throughout this specification, the terms "remove" and "mask" and their conjugations, when used in reference to removing or masking part of an image are used interchangeably. Throughout the specification, the terms "remove" and "mask" and their conjugations may be substituted one for another to obtain different embodiments. The vertical sections removed may be of the same size as one another and equally spaced from one another. The juxtaposition and masking may be part of a stitching method where an image may be divided into 3 sections (panels 2118*a*, 2120*a* and 2122*a*, FIG. 21A), which may include two side regions and a center region. Section 1 (2118*a* in FIG. 21A or 2138*b* in FIG. 21B of the image) may be placed juxtaposed next to section 3, panel 2122*a* in FIG. 21A or 2142*b* in FIG. 21B. Section 2 (panels 2120*a* in FIG. 21A, which is in between sections 1 and 3) may be masked in the process and gradually revealed as the stitched image is peeled (FIG. 21C). Measurements may be taken of the combination of one or more contiguities based on the complexity of the images comprising the image sets for image analysis purposes. For example, the system can be configured to identify and designate contiguity lines that are horizontal, vertical, and/or diagonal within a predetermined degree of angle deviation and/or the like, according to predetermined parameters provided to the system. Peeling or backstitching refers to putting back parts of the image that were masked or removed. In at least one embodiment, the system can be configured to identify the contiguity lines by applying various image processing filters to the image for edge analyses, e.g., via a Sobel filter, thresholding, and/or the like, to identify the contiguities in the image. In at least one embodiment, the system can be configured to perform a stitch analysis of the image to designate the contiguity characteristics that are preferred for use for analyzing components in the image and to facilitate identifying images with similar or overlapping characteristics. In at least one embodiment, the stitch analysis can enable the system to identify contiguity characteristics that are obstructed by objects in the image that segment or split the contiguity.

In at least one embodiment, the stitch analysis may be implemented by dividing the image into a predetermined number of sections, e.g., three sections as in using a 1:3 stitch. At least one of the sections can be manipulated, e.g., shifted, to mask or overlap another section in the image. The overlapping section can then be peeled off the masked section to reveal portions of the masked section such that the contiguity line can be identified from the portions of the image being revealed via the peeling. An abrupt change in pixel value or Hue-Saturation-Value (HSV) in regions of the stitched image may indicate a potential disruption in the contiguity making the region a target region for further evaluation. A change in pixel uniformity or a progression between regions along a hue spectrum in other regions of the contiguity would represent the degree of continuity of the contiguity across the width of the image. The identification and analyses of contiguities in images may be used to assign contiguity characteristics, complexity values, and figure-ground specifications as related to the image itself and in relationship to other images of a set of one or more other images that are combined into a composite image.

Processor system 102 may include any one of, some of, any combination of, or all of multiple parallel processors, a single processor, a system of processors having one or more central processors and/or one or more specialized processors dedicated to specific tasks.

Input system 104 may include any one of, some of, any combination of, or all of a keyboard system, a mouse system, a trackball system, a track pad system, buttons on a handheld system, a scanner system, a microphone system, a connection to a sound system, and/or a connection and/or interface system to a computer system, intranet, and/or internet (e.g., IrDA, USB), for example. Input system 104 may include a graphical user interface with which third parties can interact.

Output system 106 may include any one of, some of, any combination of, or all of a display, a monitor system, a handheld display system, a printer system, a speaker system, a connection or interface system to a sound system, an interface system to peripheral devices, and/or a connection and/or interface system to a computer system, intranet, and/or internet, for example. Output system 106 may include a network interface via which third parties interact with machine system 101. Input system 104 and output system 106 may be the same system or different systems.

Memory system 108 may include, for example, any one of, some of, any combination of, or all of a long-term storage system, such as a hard drive; a short-term storage system, such as random access memory; a removable storage system, such as a floppy drive or a removable drive; and/or flash memory. Memory system 108 may include one or more machine-readable mediums that may store a variety of different types of information. The term machine-readable medium is used to refer to any non-transient medium capable carrying information that is readable by a machine. One example of a machine-readable medium is a non-transient computer-readable medium. Another example of a machine-readable medium is paper having holes that are detected that trigger different mechanical, electrical, and/or logic responses. Memory system 108 may store one or more images for users to select from and/or that users may use.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., non-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, and/or either source code and/or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server.

In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, and/or other programmable data processing apparatus to produce a machine, such that the instructions, which execute via the processor of the computer or other programmable data processing apparatus, create a means for implementing the functions/acts specified in the flowchart and/or block diagram block or blocks. The computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Image database 110 may be a database of images that may be analyzed, that were analyzed, and/or from which composite images may be formed. Optionally, image database 110 may include a relational database. Optionally, image database 110 may associate images and/or portions of images with attributes, such as contiguity, ambiguity, juxtaposition (which are ratings of a contiguity and/or group of contiguities in an image, and which will be discussed further below), a color map and/or other color properties, saliency, complexity, aesthetic value, edge information, context information, content and/or category description, spatial information about contiguities, and/or threshold information. Optionally, image database 110 may be associated with a database server for retrieving information from image database 110. Optionally, the image server (if present) may be a relational database and the database server may be executed by processor system 102 or by its own processor system. Image database 110 may include a library of image that may be used for constructing interactivities.

Communication interface 112 is an interface, via which communications are sent to and from machine system 101. Communications interface 112 may be part of input system 104 and/or output system 106.

Third party system 114 is a third party system and interacts with machine systems 101 to analyze images. This party system 114 may communicate, via communications interface 112, with machine 101. Third party system 114 may include third party database 116, which stored images of the third party system 114. Third party system 114 is optional.

Processor system 102 may be communicatively linked to input system 104, output system 106, memory system 108, and communication interface 112. Processor system 102 may be communicatively linked via any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves, such as infrared and/or radio waves, and/or systems for sending sound waves.

In at least one embodiment, machine system 101 may be configured to implement the platform and/or receive an image from third party system 114, for example. The image may be stored in the image database 110, which may store other images. Processor system 102 may retrieve, and/or the image may be provided to processor system 102 for the contiguity analysis. Processor system 102 may implement an interface for testing users, providing therapy to users, analyzing tests taken by users, for planning and/or constructing a therapy, and/or test and/or training regimen for a user. In at least one embodiment, machine system 101 may be configured to size and crop the image to a predetermined size and/or to divide the image into sections and each section may be sized and cropped. The cropping may remove portions of the image or the portions of the image that are not wanted, or edges of the image that cause the image to be too large for generating the composite image, and/or to centralize dominant contiguities and color blocks in the image or in a portion of an image. In at least one embodiment, machine system 101 can be configured to generate an image grid map. The image grid map may be generated, for example, by designating the Cartesian coordinate system to the image designating numerical coordinates of the image. In at least one embodiment, the numerical coordinates may be pixel locations of the image. The numerical coordinates may be used to construct (and/or define) quadrants, sub-quadrants and/or some other predetermined areas of the image.

Third party database 116 may include a collection of images that may also be used for constructing interactives/ interactivities. Images may be contained in an image library, which may be part of image database 110 and/or third-party database 116, and can be tagged with attributes. Attributes can include text and/or audio labels of image content and elements, a category label, and assessment attributes, for use with Word List Recall using the image's embedded visual cues, and associated SQ2 (Spatial, Quantitative and Qualitative) questions, Object ID and Dimensional Descriptors assessment interactivities. Each image may be analyzed based on its contiguity characteristics to derive aesthetic and ambiguity values which are used to define the complexity of the image and its potential complexity contributions in a composited image set.

The image library of image database 110 and/or third party database 116 may be restricted to include a subset of images which may be presented to select user groups, depending on skills and/or learning requirements. For example, in an embodiment, the use of nature-themed images in the platform leverages prevailing knowledge about interactions with nature and the effect of the interactions with nature to improve well-being based on Attention Restoration Theory and Stress Reduction Theory. System 100 may be configured to deliver defined images based on the content of the images, and/or a subset of image content, to meet therapeutic and/or training requirements. For example, system 100 may be configured to deliver defined images to train or test the end user's memory and/or attention, as well as other cognitive domains skills and processes such as visual-spatial, executive function, language and/or sensorimotor. In one embodiment, the platform may be configured to use images with people's faces or with portions of people's faces, such as a profile. The images with people's faces or with portions of people's faces may be included to support facial recognition and/or other biometrics-styled interactivities for training users with facial recognition deficiencies associated with a variety of conditions including, Alzheimer's disease, post-stroke, traumatic brain injury and in people with Autism Spectrum Disorder who may also have difficulties with facial-emotion recognition.

The library of image database 110 and/or third party database 116 may include a searchable index and categorical groupings to facilitate use of images and/or searching for/ selecting images. Contiguity characteristics and/or relationships of contiguities to establishing figure-ground relationships in and between images not only provides visual landmarks, which can be used as search parameters, contiguity characteristics and/or relationships of contiguities to establishing figure-ground relationships, but can also be used for general image analysis purposes in computer vision applications, and which apply principles of visual perception and attention.

In some embodiments, the platform may be utilized to deliver a subset of interactivities for entertainment purposes and/or as part of a marketing and promotions strategy using visual content to support customer engagement, acquisition, and retention. Content may be user-supplied and/or content supplied by a third party, which may be used to provide users with incentives, rewards, discounts and other promotions related to the content and or the promotional objective. The incentives may include travel and tourism, entertainment venues and film, and/or other entities with promotion objectives which can utilize an interactive and/or engagement tool to engage current and prospective customers and/or users.

Figure 2:
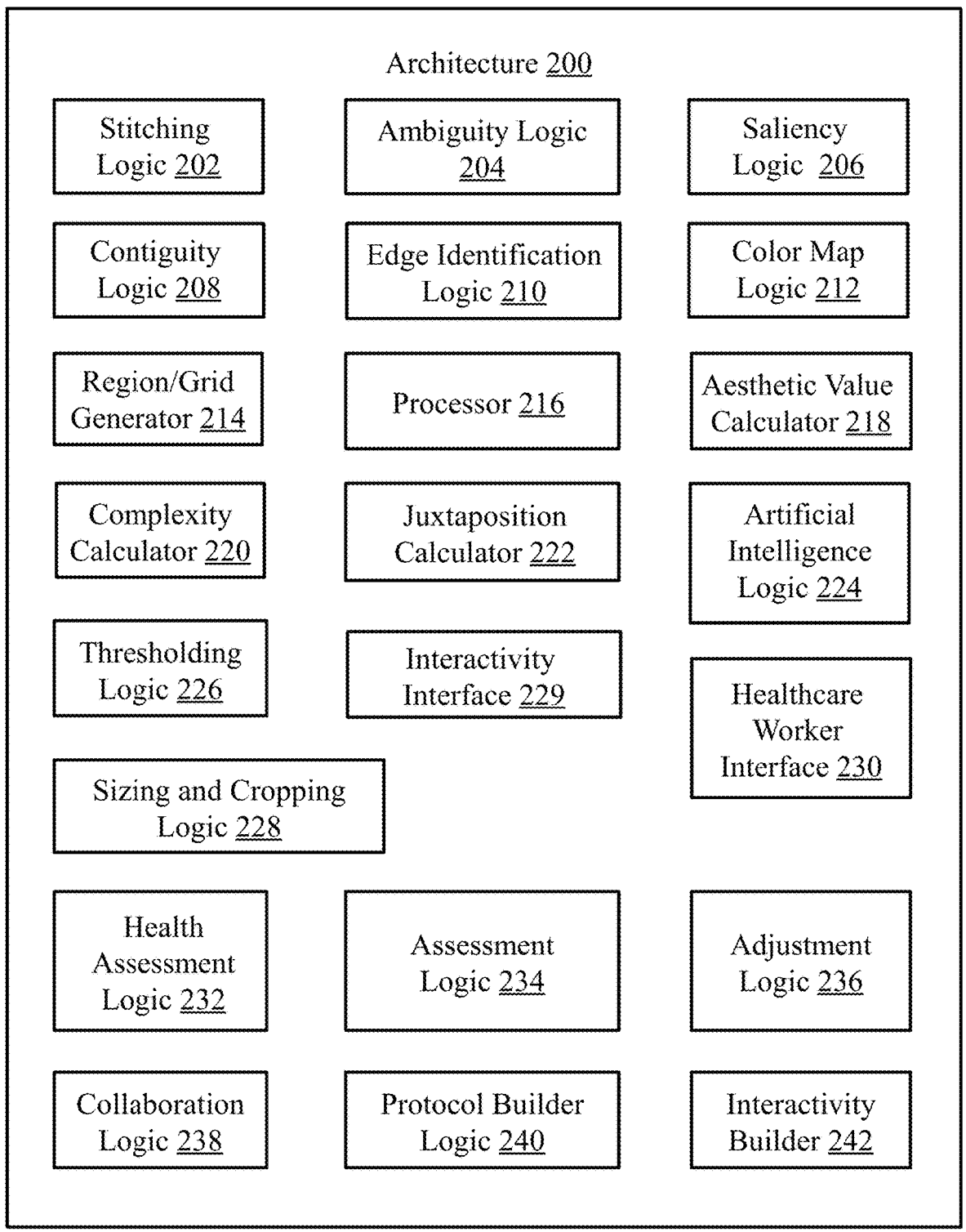
FIG. 2 is a block diagram of an embodiment of the architecture of the machine system of FIG. 1.

FIG. 2 is a block diagram of the architecture 200 of machine system 101, which may be designed to analyze an image and/or create composite images for a multi-purpose interactive cognitive platform. Architecture 200 may include stitching logic 202, ambiguity logic 204, saliency logic 206, contiguity logic 208, edge identification logic 210, color map logic 212, region/grid generator 214, processor system 216, aesthetic value calculator 218, complexity calculator 220, juxtaposition calculator 222, artificial intelligence logic 224, thresholding logic 226, sizing and cropping logic 228, interactivity interface 229, healthcare worker interface 230, health assessment logic 232, assessment logic 234, adjustment logic 236, collaboration logic 238, protocol builder logic 240, and interactivity builder 242. In other embodiments, architecture 200 may include additional components and/or may not include all of the components listed above.

Stitching logic 202 performs the stitching of an image During the stitching, a portion of an image (e.g., one or more horizontal strips) may be removed from the image After removing the portions of the image, the image may be analyzed, such as by computing the contiguity, and optionally other characteristics of the image, such as the saliency, color block depth, ambiguity, color map, edge detection, color threshold map, brightness map, and/or threshold map. After removing the portions of the image, and analyzing the image, the portions may be returned. After each portion of the image is restored, the image is again analyzed to determine contiguity characteristics, perform a multi-contiguity analysis, and optionally determine other characteristics.

Ambiguity logic 204 determines the ambiguity of an image and/or of a portion of an image. The ambiguity is a measure of the degree to which there are elements that may have multiple interpretations, and relates to an image's contiguity characteristics.

Saliency logic 206 computes the saliency of an object, image, or portion of an image. The saliency is a measure of the contrast within and between objects or elements. Specifically, the saliency is a measure of internal contrast. Regions of high saliency may be regions that include a foreground type object. In other words, if the saliency is above a predetermined threshold value the saliency may be one or one of multiple factors used to determine whether a region is a foreground object or part of a foreground object. Alternatively, the saliency value may be part of a formula for determining whether a region is part of a foreground object. Regions of high saliency may be identified and are used by the platform to focus attention, and/or which provide distractor and/or attractor-type image elements in determining image combinations in composites.

Contiguity logic 208 identifies contiguities in an image and/or contiguity lines in an object. Contiguity lines may aid in identifying separate regions that have different meaning from one another, such as separating land from sky, foreground from background, street from buildings, plains from mountains or hills (a prior discussion of contiguities and contiguity lines appears above in conjunction with system 100, machine system 101, and FIG. 1).

Edge identification logic 210 may identify edges in an image Note that all contiguities have edge characteristics but not all edges are contiguities. In an embodiment, edge identification logic may divide images into regions that have pixels with brightness values above and below a particular threshold and/or have a wavelength of color within a particular window, to help identify regions in the image. Edge identification logic 210 may also divide regions that are below a particular color threshold.

Color map logic 212 maps the color of different regions. The image may be separated out into sub-images of different colors and color maps of the image may be constructed (e.g., a blue image made from the blue pixels of the image, a red image made from the red pixels of the image and a green image made from the green pixels of an image).

Region/grid generator 214 may generate a grid and/or divide the image into multiple regions (e.g., quadrants, halves, thirds, eighths), which may be further divided into sub-regions. The regions, sub-regions, and grid may be used to identify the locations of elements in an image. Processor system 216 may be an embodiment of processor system 102, and may be capable of implementing a stitching analysis, determining contiguities, computing aesthetic value, complexity, and/or juxtaposition of an image and/or portions of an image (and may be capable of performing any other functions of architecture 200).

Artificial intelligence logic 224 may be a neural network or other artificial intelligence logic. Artificial intelligence logic 224 may receive a training set of images, and/or stitched images that are associated with the contiguity values, an identification of contiguities, an identification of contiguity lines, an aesthetic value, a complexity value, and/or juxtaposition values, and an identification of objects and/or of object parts in the image. After receiving the training set, artificial intelligence logic 224 may be trained to identify objects based on the stitched images that are associated with the contiguity values, an identification of contiguities, an identification of contiguity lines, an aesthetic value, a complexity value, content-context relationships, and/or juxtaposition values, for example.

Thresholding logic 226 creates a derived image by setting all pixels above a threshold to one value and below the threshold to another value, which may be helpful in identifying edges and/or other features. Thresholding logic 226 is optional and may be part of edge identification logic 210.

Sizing and cropping logic 228 may automatically size and crop the image or portions of the image (e.g., based on prior input from a user). Sizing and cropping logic 228 may also provide tools for a user to size and crop and image.

Interactivity interface 229 is the interface via which the patient (whom may be referred to as a patient user) or anyone else that interacts with the system 100 by performing interactivities. Interactivity interface 229 may be used by the patient for taking assessments, which may be in the form of interactivities (multi-cognitive domain games), for measuring cognitive ability. Alternatively or additionally, interactivity interface 229 may be used for providing therapy to the patient (or other user). Optionally system 100 may include a generic interface that may be used for non-therapeutic uses may be used for other therapeutic and non-therapeutic uses, and/or for mixed uses.

Healthcare worker interface 230 is the interface via which the healthcare worker (or other practitioner) interacts with the system 200 for collaborating with other healthcare workers, reviewing test results, and/or progress of patients, and/or for assigning assessment and/or therapy to patients. The terms healthcare worker and practitioner are used interchangeably throughout the specification and may be substituted one for another to obtain different embodiments.

Health assessment logic 232 is the logic that correlates the performance and progress of a user with the user's health. Health assessment logic 232 may assess cognitive abilities of a patient and/or progress of a patient in response to a therapeutic treatment (the treatment may be in the form of interactivities played on system 200 by the patient and/or other treatments). Health assessment logic 232 may be based on previous performances by the user over time, how the user's performance compares with other patients at the same difficulty level and/or with similar health conditions, and/or how the user's performance compares with the general public.

Assessment logic 234 is the logic that assesses the performance and progress of a patient user in taking a particular test or group of tests, which in turn may be used to evaluate the skill level, progress, and/or health of a user, and/or the effectiveness of an interactivity or treatment regimen. Health assessment logic 232 may use assessment logic 234 to evaluate a patient's health.

Adjustment logic 236 is the logic that adjusts the difficulty of the test based on the user's skill level. In some embodiments, the difficulty may need to be increased due to the user becoming more comfortable with the test (becoming an "expert" on the test or through practice effects). Practice effects refers to a user's abilities increasing due to a repetition of the same or similar types of activities. Adjustment logic 236 may use the results of assessment logic 234 and/or health assessment logic 232 to adjust a treatment regimen, such as by changing the difficulty of an interactive and/or changing which interactivities are presented to the user. In some embodiments, the test difficulty may be reduced because the user is not getting enough of the answers right. In some embodiments, if the user is not getting 50%, 40%, 30% 25%, 20%, 15%, 10%, 5% or less right, and/or if the patient is taking a longer time, by a predetermined threshold (e.g., by 1, 1.5, 2, 2.5, 3, or 3.5 standard deviations) than most patients or relative to referenced norms, for example, the difficulty level is adjusted down. In at least one embodiment, speed and/or accuracy thresholds may be set based on one or more of the following: gender, age, and known cognitive health status. In some embodiments, if the user is getting more than 50%, 40%, 30% 25%, 20%, 15%, 10%, 5% right, and/or if the patient is taking less time than an average person by a predetermined threshold (e.g., by 1, 1.5, 2, 2.5, 3, or 3.5 standard deviations) the difficulty level is adjusted up.

Collaboration logic 238 provides logic that may be used by healthcare professionals to collaborate regarding care of patients and protocols to use for various purposes. Protocol builder logic 240 may be used by healthcare providers to build a protocol. Interactivity builder 242 may be used by a patient, healthcare provider to build an interactivity, and/or may be used to automatically build an interactivity, based on a user performance on an interactivity.

Figure 3A:
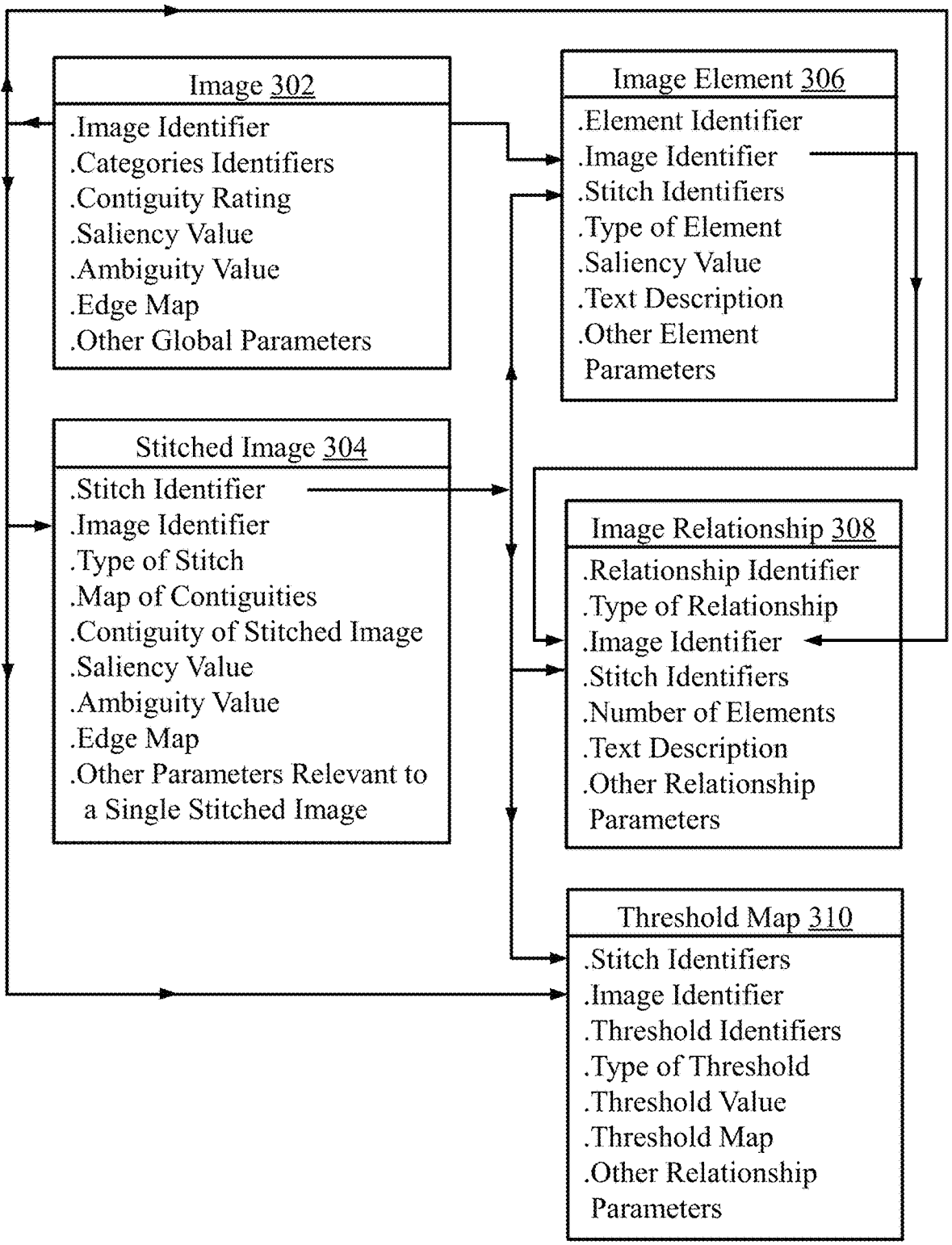
FIG. 3A shows an example of entity relationship diagrams of an embodiment of a database schema of the system of FIGS. 1 and 2, related to the organization and/or classification of images.

FIG. 3A shows an example of entity relationship diagrams of an embodiment of a database schema 300 of the system of FIGS. 1 and 2. Database schema 300 may include an image table 302, a stitched image table 304, an image element table 306, a relationship image table 308, and threshold map 310. In other embodiments, database schema 300 may include additional components (such as tables) and/or may not include all of the components (e.g., tables) listed above.

Database schema 300 relates to a database for analysis of images (in addition to organizing how the images are stored and categorized). Database schema 300 may be used for determining which images to combine into a composite image to create a particular type of effect.

Image table 302 may include various attributes associated with the image. A particular object in a table may be found by searching the attributes of the object. For example, a user may find a particular image by searching for an image having a particular set of attributes. For example, image table 302 may include among its attributes an image identifier, category identifier, a saliency value, and a contiguity rating value (or juxtaposition value), edge map, and/or other attributes such as content and/or color preferences. Image table 302 may also include an edge value, which may be generated by an edge identification table. The image identifier is a primary key and a unique identifier of an image.

Each of the stitched image table 304, an image element table 306, a relationship image table 308, and threshold map 310, have the image identifier as a key, so that each threshold map, image relation, image element may be associated with one image. The stitched image table 304 lists each stitched image of each image. Each image may have multiple stitched images. The attributes of the stitched image table 304 may include the image identifier, stitched image identifier, map of contiguities, stitched image contiguities, saliency value, ambiguity value, edge map, and other attributes. The image identifier identifies the image that the stitched image was generated from, and the stitched image identifier uniquely identifies the stitched image. Stitched image table 304 may also include a type, which describes the type of stitch, which may indicate how much of the image was removed and/or the portion removed. The saliency, ambiguity, and edge map may be the saliency value, ambiguity, and edge map of the stitched image.

Image element table 306 may be a table of elements identified in images. Image element table 306 includes an image identifier identifying which image the element was found in, and an element identifier identifying the element. Image element table 306 includes an image identifier, relationship identifier, stitched identifier, type of element, text description, and/or other attributes. Image element table 306 may include a descriptor that identifies any relationship that involves the element. Image element table 306 may include a type of element that describes the type of element.

Image relationship table 308 may be a table of relationships identified in images. Image relationship table 308 includes an image identifier, relationship identifier, stitched identifier, type of relations, text description, number of elements and other elements. The image identifier identifies which image the relationship was found in, and the relationship identifier uniquely identifies the relationship. Image relationship table 308 may include a descriptor that identifies any objects in the image that are related by the relationship. Some examples of relationships may include figure position, ground position, background, foreground, relative background, relative foreground, an identifier of a location of the object (e.g., top of table), and/or other more detailed relationships, such as wheel of car or cat on table. A first object is in a relative background with respect to second object if the first object is an object that is supposed to be further to the viewer than the second object. A first object is in a relative foreground with respect to second object if the first object is an object that is supposed to be closer to the viewer than the second object.

Threshold map table 310 may be a table that lists all the threshold maps. The attributes of threshold map table 310 may include a relationship identifier, stitch identifier, type of threshold, threshold value, and threshold map. The image identifier identifies the image from which the threshold map was created, and a threshold map identifier identifies the threshold map. The type of threshold indicates the type threshold, such as whether the threshold map is a black and white threshold map or color threshold map. Threshold attribute is the value used as the threshold for making the threshold map.

Figure 3B:
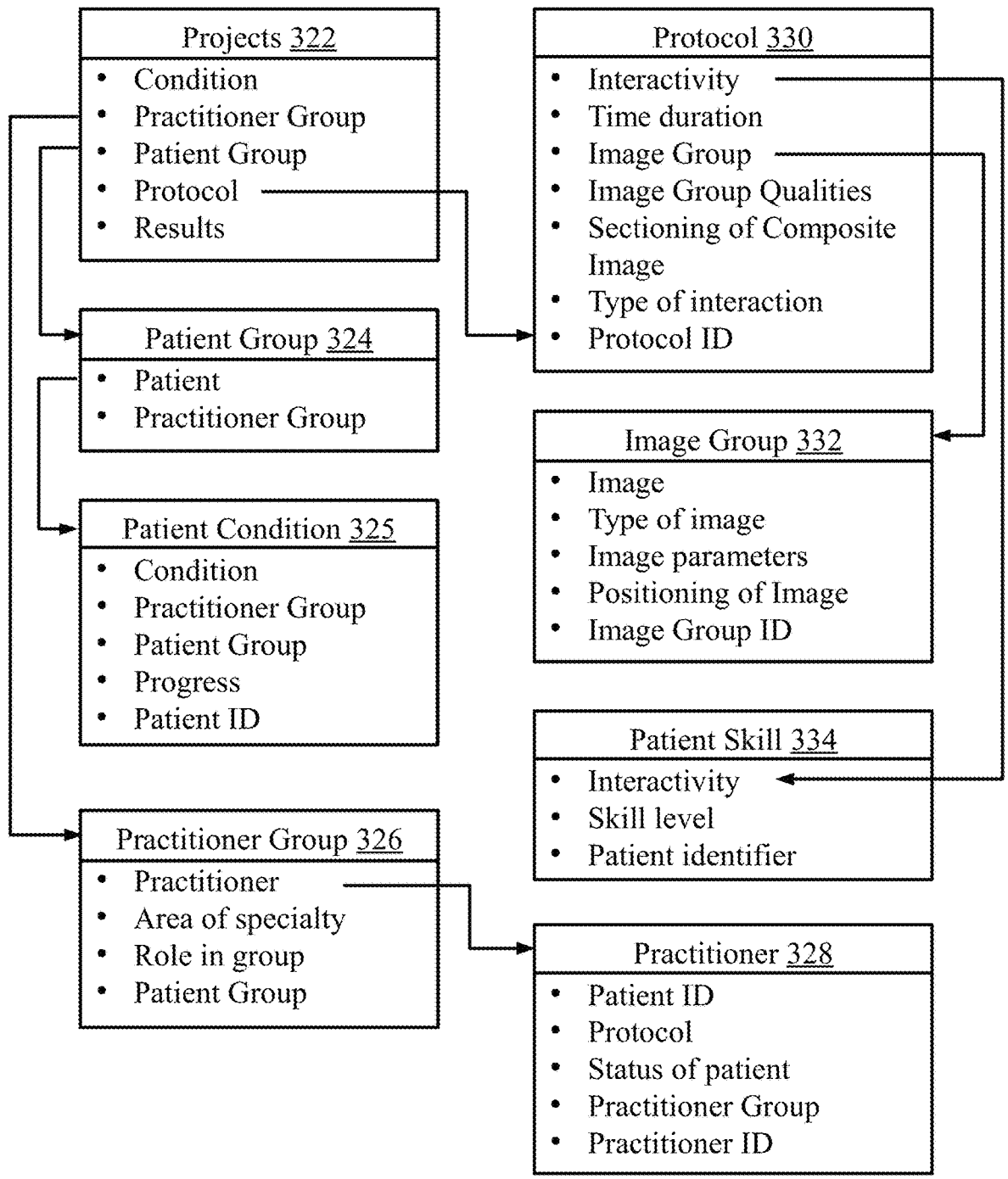
FIG. 3B shows an example of entity relationship diagrams of an embodiment of a database schema of the system of FIGS. 1 and 2, related to the association of practitioners, patients, and interactivities.

FIG. 3B shows an example of entity relationship diagrams of an embodiment of a database schema 320 of the system of FIGS. 1 and 2, related to the association of practitioners, patients, protocols, and interactivities.

Database schema 320 may include a projects table 322, a patient group table 324, patient condition table 325, a practitioner group table 326, a practitioner table 328, and protocol table 330, image group table 332, and patient skill table 334. In other embodiments, database schema 320 may include additional components (such as tables, inheritances, attributes, and/or keys) and/or may not include all of the components (e.g., tables) listed above.

Database schema 320 may be used to determine the effectiveness of a protocol, the progress of individual patients, the appropriate protocol for a given patient, and the effectiveness of a treatment modality, and/or effectiveness of an interactivity in effecting a change in cognitive status. Database 320 may be used to determine adjustments to make to interactivities and protocol regimens. Database 320 may assist in coordinating activities of different practitioners in treating individual patients and/or groups of patients.

Projects table 322 may include a collection of projects and various attributes associated with each project. Each project may be related to a set of conditions that are being treated and/or tested by one or more protocols. Each project in the projects table 322 may have various attributes, such as patient group, a practitioner group, a role, and results. The patient group may include information about a group of patients that share the condition and/or that are being tested for the condition. The practitioners group may be a group of practitioners that are collaborating and/or that are treating and/or testing for the condition of the project. The role may be the role of the practitioner within the group. For example, one role may be leader of the group and another role may be participant. The results may include information about the results of the protocol and/or test related to how successful the protocol and/or tests were.

Patient group table 324 includes information about each patient group. The attributes of the patient group may include patient identifiers, contact information for the patient, the name of the patient, health history of the patient. A list of patient groups that the patient is associated with and a list of practitioners and/or practitioner groups that are treating the patient. By filtering the rows to show only those rows that have a particular patient group ID, a list of the patients in the patient group can be found.

The patient condition table 325 may include attributes such as a condition of the patient, the patient group associated with that condition that the patient is a member of, a practitioner and/or practitioner group that is treating that condition, and progress related to treating that condition. If a patient is being treated for more than one condition or is in multiple patient groups, there may be multiple records for that patient which can be cross-referenced for easy access to user records.

The practitioner group table 326 may include identifiers of practitioners that are members of the practitioners group, and other information about the practitioner, such as the role of the practitioner in the group, the area of specialty of the practitioner. By filtering out all but one practitioner group, a list of all of the practitioners in the practitioner group may be constructed.

Practitioner table 328, which may store further information about the practitioner, such as the patients that the practitioner is treating and/or the patient groups that the practitioner is treating, the practitioner groups that is treating the patient. The condition and/or status of the patient and the progress of the patient. The collection of records having the same practitioner ID, will show all the patients and patient groups that the practitioner is associated with (e.g., and is treating).

Protocol table 330 may include further information about each protocol. For example, each protocol may include a series of interactivities. One attribute of the treatment table may include an interactivity identifier. Other attributes may include an identifier of a group of images that make up the interactivity, the sectioning strategy used in the interactivity (e.g., such as the size and shape of the pieces of the component and/or composite image that is used for the interactivity), the duration of time allocated for the interactivity, a type of the group of images, the sectioning of the composite image, the type of interaction, and/or the multi-domain characteristics of each of the interactivities associated with a protocol, and the interactivities set. The type of interaction may be whether the user is asked to assemble a composite image and/or fill in missing pieces from an image or composite image and/or match pieces to an image or composite image. By collecting all the records with the same protocol ID, the collection of interactivities that are used in the protocol can be found, and modified to identify and address specific cognitive domain issues as well as engaging multiple cognitive domains simultaneously.

The image group table 332 may include information about the images used for making a composite image for the interactivity. Each image may be associated with one or more attributes representing a positioning in the group of images, such as what percentage of the composite image is made up by the component image in question, and/or how wide are the sections containing the component images. Additionally or alternatively, each image may be associated with an attribute representing how far apart, within the composite image, each section of the image is from the next section of the same image. Each image may be associated with parameters (e.g., a contiguity rating, an aesthetic value, a saliency value, and/or an ambiguity value, which are discussed further below). The information about each image may include the information associated with image table 302. Image table 302 may include pointers to the images of image table 302. The information about each image may include information about whether the image is intended to be in the figure or ground position of the composite image. The collection of records with the same image group ID may indicate the images used to make the composite image of the image group.

Patient skill table 334 may include as attributes interactivities and the skill level of the patient using the interactivities. Patient skill table 334 may include the interactivities that each patient has interacted with and the skill level of the patient associated with that interactivity. The collection of records with the same patient id indicates the collection of interactivities with which the patient interacted.

Figure 4A:
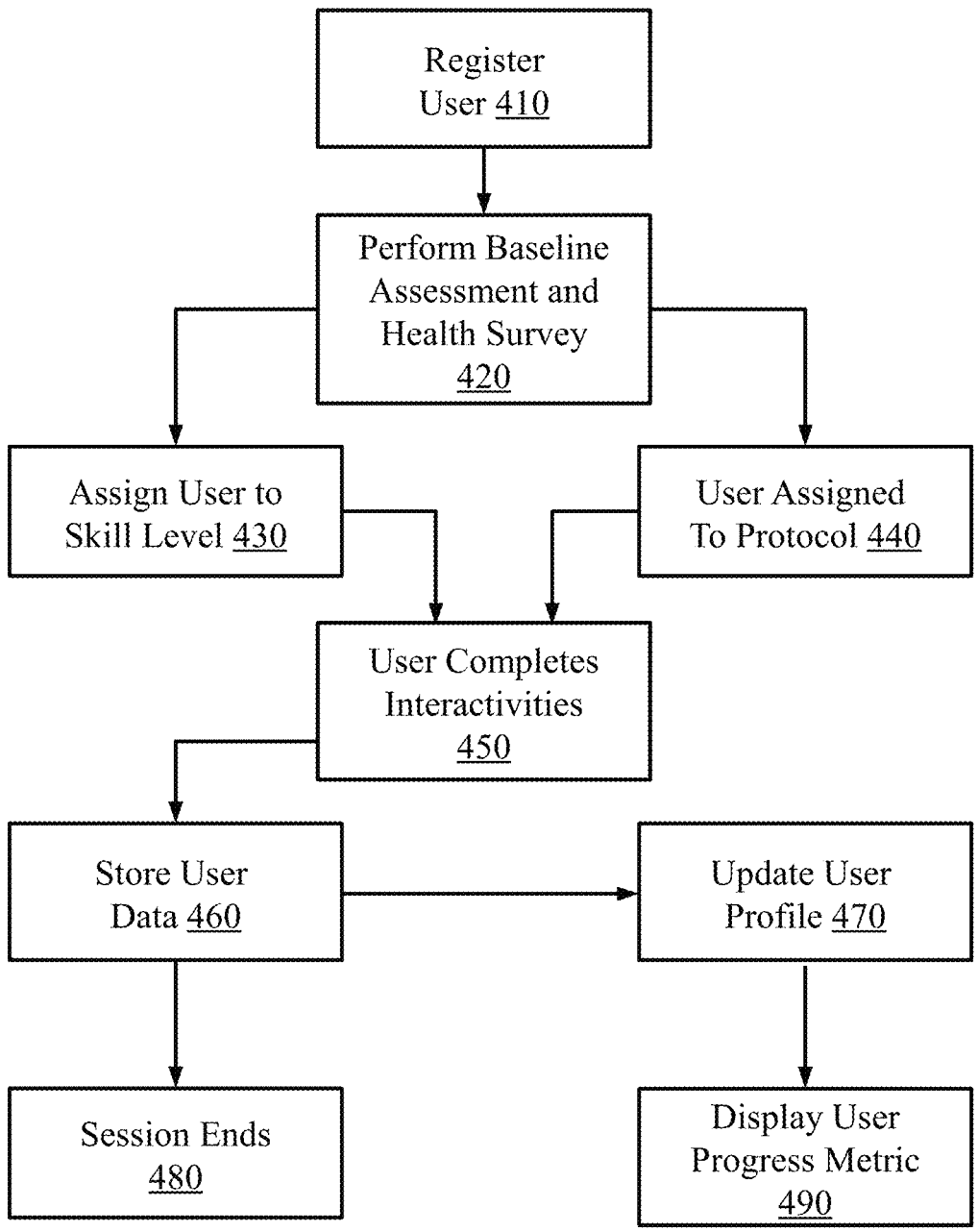
FIG. 4A shows an example of a flowchart of a method to build a user profile for a multi-purpose interactive cognitive platform (a method of on-boarding).

FIG. 4A provides an embodiment of a method 400 for building an initial user profile (which may be referred to as "on-boarding" the user).

In step 410, a user is registered, via communications interface 112 and/or interactivity interface 229. The process of registering may include setting up a login, including a username and password. The platform may include the integration of image-based passwords which can be integrated into a pre-, intra and/or post-interactivity assessment. Other information may be included such as information about a user's health, age, medication, and cognitive and physical status. Other information may also include a doctor, clinician, and/or researcher that the user is associated with as well as contact information. In some embodiments, if the user is a healthcare worker, information about the hospital, specialty, research subject, education, and registrations associated with the healthcare worker may be included.

In step 420 a baseline assessment and health survey of the user/patient is performed, via assessment logic 234. The assessment may include information about the cognitive and physical health of a user, language preferences, and information about diet, sleep and exercise habits, and vision issues. In other embodiments, the information may include a simple test, a use of a third party, standardized neurocognitive test, or use of the platform in which an assessment of a first test are used to establish a baseline reference assessment for comparison to future assessments of the user.

In step 430, the user is assigned a skill level based on the information received in steps 410 and 420. The user (and/or the user's healthcare worker) may review the skill level to identify whether the chosen skill level is appropriate. If not, the user or healthcare workers can re-evaluate the information in steps 410 and 420. The user, as part of step 430, may be assigned a skill level automatically (based on tests) or may be assigned a skill level by a healthcare provider.

However, in some embodiments, as part of step 430, the user may assign him or herself a skill level, and/or the skill level may be automatically assigned based on a formula provided by the multi-purpose interactive cognitive platform.

In one embodiment, as part of step 430, each of the skill levels: Easy, Medium and Hard can include an expandable list of sub-levels and interactivities at each sub-level within a given skill level according to a professional or user-defined protocol. Each skill level does not need to have the same number of sub-level interactivities. When a subset of interactive criteria are met at a pre-defined threshold level range—a metric based in part on: time to task completion, correct responses (error rate), time/move, reaction time, combined with post-activity assessments (testing for language, memory and attention) with Word List (WL) Recall (the recall may be immediate recall, delayed recall, and/or extended recall) and SQ2 questions (Spatial Quantitative, Qualitative), Object ID and Dimensional Descriptors may be assigned to images that facilitate evaluating memory, vocabulary, figure-ground relationships, and concepts. Descriptors may be assigned to images that indicate attention-focusing requirements for object-cued Object ID (OID) and Dimensional Descriptors may be assigned to images that facilitate uses in composite images for language, memory, visual spatial and executive function analyses. The user may be given the dimensional descriptors as part of a word list type assessment and the user may be asked to recall the word list, while assisted by the image of the interactivity (e.g., as result of just having performed the interactivity and/or as a result of having the image still in front of the user which recalling the word list). The user can be progressed and/or regressed to a sub-level within a skill level and/or the previous/next skill level. A possible new level and/or an achieved new level may be assessed for user consistency and user progression/regression to meet the new requirements and for tracking changes over time. If consistent, the user can engage with the interactivities at or within that skill level until the user reaches a different threshold, and the interactivities and associated metrics of interactivities, number of images, image complexity, sectioning strategy and/or number and size of interactive elements (game pieces) is delivered to the user. The matching-type interactivities can use whole sections, parts of a section, or can span multiple sections with shape variability of the presented parts.

The platform may utilize puzzle-styled interactivities to engage cognition using images and composited image scenes which portray real-world content. Users engage with images and/or their composites which can be presented as two or three image combinations through a selection of interactivities and which can be rated according to the interactivity, skill level and image complexity, and metered by the cognitive status and/or capacity of the user in developing metrics. Each interactivity-based assessment is assigned Multi-Cognitive Domain (MCD) values which reflects the participation of each domain in the interactivity as well as an overall MCD value for the interactivity (see FIGS. 4B-4F for example MCD assignments and legend). Assessments are designed to cooperatively engage processes and skills across multiple cognitive domains. Assessments are embedded in the interactivities themselves, applying a modified "activity is the assessment" model to capture both intra-activity speed and accuracy data, together with process data, and/or post-activity data. Through combinations of the interactivities, the platform is used to capture a range of MCD data using speed, accuracy measures, reaction time, error type as well as process metrics inferred by user screen movements, part placements and image part selection patterns. Assessments of cognition may also be based on and taken during user activities, prior to performing an interactivity (such as the process of selecting which interactivity the user wants to select or the process of the user reading the instructions and initiating the interactivity). Alternatively or additionally, the assessment may be taken during (or based on) activities performed after an interactivity (such as the process of closing the interactivity, answering questions after the interactivity, and/or logging off the platform). Assessments may be based on multiple activities, designed to target global cognitive functioning while at the same time addressing individual cognitive domain skills and process requirements for training and/or remediation purposes.

System 100 may include a reporting function that produces reports showing the skill level of the user, the user progress, the user's speed and accuracy as reflected in skills and processes, the relative engagement of different cognitive domains, areas of improvement and cognitive areas in need of improvement, together with point in time cognitive profiles and changes in cognitive status over time with cognitive signatures. The reports may be sent to practitioners caring for the user, to the user, care givers, and/or may be presented to the user while the user in engaged in an interactivity and/or immediately following an interactivity or set of interactivities. The reports also may be retrievable by the user or a caregiver prior to or after the user engages in an interactivity.

The tasks of the interactivities may include practice opportunities. (The indications may be which may be audio and/or text based for example.) The grid may vary in size. The number of pieces to be placed on the grid may be varied. The number of images may be varied, and whether the composite is of a stable or multi-stable type may be varied.

In a FreePlay type of scenario (or other scenario), where the user selects the features of the "game/interactivity," size, number, the percentage of the image that individual pieces make up, and/or the shape of the pieces, as well as the images comprising an image set, may all be variables that the user may control. Similarly, in a protocol or fixed progression type of engagement with the multi-purpose interactive cognitive platform the variables may be pre-configured and related to skill level and image complexity. Similarly for baseline assessments users can be assigned to a skill level based on age, gender, cognitive status using referenced norms, and adjustments made to the skill level for follow-up assessments as dictated by the user's health/cognitive status, including changes in vision, and fine and gross motor control for example.

Figure 19A:
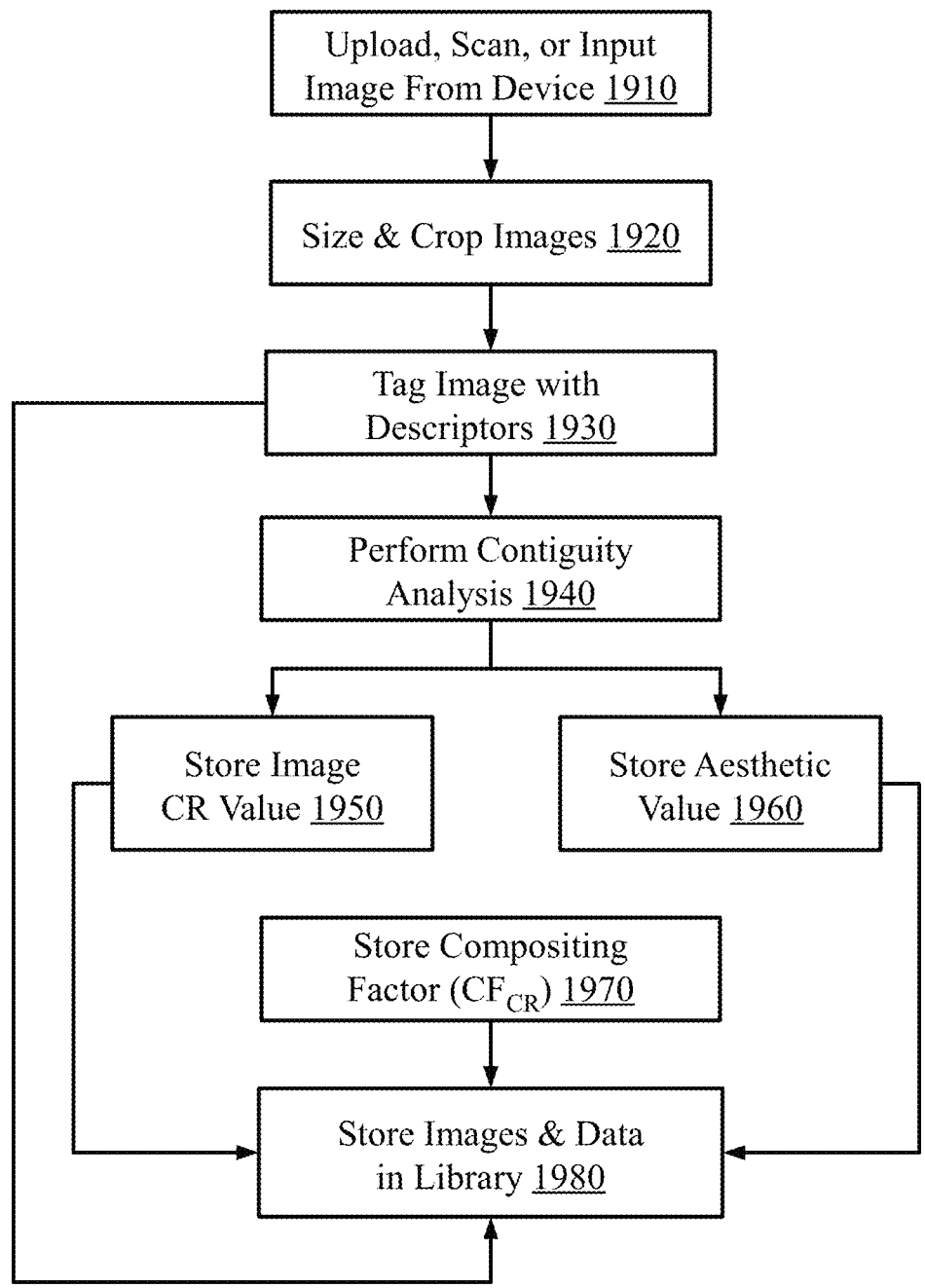
FIG. 19A shows an example of a flowchart of a method of storing images and image data to a library for use with a multi-purpose interactive cognitive platform.

For the FreePlay mode, the user may be allowed to override suggested skill levels at defined points in time. For a training mode, any assessments which are embedded directly in the user data (for example, speed, accuracy, reaction time, movement mapping), and specifically where the user is not required to answer questions after the interactive as part of an assessment, can facilitate compliance and data gathering. In some embodiments, FindIT-type games which require visual scanning, a visual-spatial process, are integrated into the platform. Optionally voice and/or text-based inputs may be eliminated during FreePlay, Clinical Assessment, and/or training modes. A FindIT-type interactivity is an interaction in which a user is tasked to find something, such as find a face of an individual in an image or the bird in a composite image, other image element or object. In the FindIT-type interactivity, the user may be given a list of items to find in an image or image set. The list of items may include relatively easy to find image parts (that is, salient image parts that may have a relatively high saliency score, such as a high ambiguity saliency value) and parts of the image that are relatively hard to find (and that may have a relatively low saliency score.) The saliency score is a sum of a subset of the ambiguity factors, see FIG. 17, step 1732 and FIG. 19B. The size, contrast, camouflage, and/or competing (flanking) content may also be factors in determining the difficulty of finding an item. An example of different competing content having different degrees of difficulty may be a yellow flower with brown center, which is relatively easy to find versus a yellow flower with yellow center, which is relatively hard to find, and can depend on the surrounding and/or competing content. The "reaction time" may be evaluated by evaluating the time used by the user to match as many image parts within a specified time, or to sort a mixed grouping of image parts from more than one image, and/or to sort a single image but which has been subjected to multiple sectioning strategies with respect to width of the sections or the orientation of the sectioning, such as horizontal (width) or vertical (height) cuts. In a reaction time evaluation, the user is given a task to accomplish and the user is timed and scored based on the time taken to complete the task together with error analyses. As some examples, reaction time evaluations can include: find the red-roofed house in a landscape image or find the red-roofed house from within a group of non-red roofed houses. During the red-roofed house reaction time evaluation, the user may be timed on how long it takes the user to find, and optionally click on, one or more red-roofed houses. As another example, the user may be timed on how long it takes the user to find, and optionally click on all brown-centered flowers in a scene which also contains yellow-centered flowers. As an aside, a reaction time evaluation may also be used as a positive or negative Turing test, depending on conditions.

In step 440, the user is assigned to a protocol, which may be a protocol for providing therapy, treating a condition, improving a cognitive ability, assessing the cognitive safety of a drug or therapy, and/or evaluating a patient. Step 440 may occur in combination with step 430 or separately. In some embodiments, the user is part of a research protocol, in which case the skill level may not be needed. The user may be assigned a protocol by a healthcare worker.

In step 450, the user completes the interactivities that are provided based on the user's skill level or a protocol in which the user is participating (e.g., a healthcare worker or research protocol or study). In each of the interactivities, one or more images, image sections or image segments (parts) can be used. The sizes can be varied to change the complexity level of the task and corresponding skill levels.

The interactivities may include one or more of any of the interactivities contained in the platform. Some examples of interactivities that may be included in the platform include: Missing Pieces (MP), Extrapolate (EX), MatchMe! (MM), MatchIT! (MIT), Mutation (MUT), Compose (COM), Construct (CON), Object ID with memory (OIDm), Dimensional Descriptors (DD), and/or Parts of the Whole (POW). All interactivities are weighted according to each cognitive domain, ensuring that a battery of selected interactivities reflects and simultaneously engages multiple cognitive domains.

Prior to continuing the discussion of method 400, a description of the different interactivities and of FIGS. 4B-4F follows.

FIGS. 4B-4D, Tables 1-3 show examples of weights for scoring a user's performance, based on different sectioning strategies for assessing cognition (however, other scales and ways of scoring the user may be used). FIGS. 4B and 4C relate to different sectioning strategies of the MatchIt interactivity, FIG. 4D relates to an alternate scale with weights used for different degrees of Alzheimer's, progressive MCI, Mild Cognitive Impairment (MCI) and healthy older adults, whereas FIG. 4E shows multi-cognitive domain characteristics for a subset of interactivities configured as an interactivities set, i.e. an assessment battery. FIGS. 4B-4E show Tables 1-4. Table 1 shows examples of weighted values of an interactivity and Table 2 shows an example of weighted values for an interactivity based on different sectioning strategies and scales, related to method 400. In Tables 1 and 2, the first column indicates the type of interactivity. The letters "MIT" (in FIGS. 4B-4E, Tables 1-4A) indicates the MatchIT! interactivity. The notations A1-A11 of Tables 1-4B are described as follows. A1 is a MCD value, between 1 and 6 (or other values), which is assigned to each of the listed cognitive domains, M—Memory, A—Attention, VS—Visual Spatial, EF—Executive Function, SM—Sensorimotor and L—Language across the associated row for a given interactivity at a given skill level. In other embodiments, other value ranges and cognitive domains and sub-domains may be used. The A2 designation in Tables 1-4A is the sum of the individual domain MCD values for a given interactivity, for a given sectioning strategy for the same interactivity, for an alternate scale based on cognitive status, and/or for an assembled battery of the interactivities where each interactivity is considered on its own and also for its contribution to the battery's MCD character. A general formula for A2 is given by: (IX(D1)+IX(D2) . . . +IX(Dn)).

In other embodiments, A1 may have other values, which may have different upper and lower bounds. In other embodiments, any one of or any combination of the cognitive domains, M—Memory, A—Attention, VS—Visual Spatial, EF—Executive Function, SM—Sensorimotor and L—Language, may be further divided into subdomains. In other embodiments, not all of the cognitive domains listed may be included and/or other categories of cognitive functions may be used instead of or in addition to one or more of, M—Memory, A—Attention, VS—Visual Spatial, EF—Executive Function, SM—Sensorimotor and L—Language, may be further divided into subdomains. Additionally or alternatively, other ways of dividing and/or categorizing different types of cognitive functions may be used instead of, or in addition to, M—Memory, A—Attention, VS—Visual Spatial, EF—Executive Function, SM—Sensorimotor and L—Language. In other embodiments, the weights may be computed in a different manner and/or using different quantities instead of, or in addition to, IX(D1), IX(D2), . . . IX(Dn). In an embodiment, fields may be provided to the practitioner (a user) for specifying the weights, specifying how to compute the scores IX(D1), IX(D2), . . . IX(Dn), and/or how to compute the weights.

A5 is given by A1 (the MCD value for each cognitive domain and/or subdomain), divided by A2; A5 represents the percent contribution of each cognitive domain to the interactivity's overall MCD character.

A3 is the average domain MCD value which is given by the individual MCD values assigned to each of the cognitive domains divided by the number of domains (A1(D1)+A1(D2)+ . . . A1(Dn)/n. The values for A4 and A6 represent the averaged and individually weighted values of the cognitive domains for the interactivity, and which can be compared across all interactivities, individually and within a battery for significant deviations from a multi-domain interactive cognitive platform's integration of interactivities-embedded assessments which are designed to reflect skills and processes across multiple cognitive domains.

The letters "CON" (in FIG. 4E(1), Table 4A) stand for Construct, MP (in FIG. 4E(1), Table 4A) stands for Missing Pieces, the letters "DD" (in FIG. 4E(1), Table 4A) stands for Dimensional Descriptor, "OID" stands for Object Identification and the letter "m" stands for a memory test of the objects identified by the user at the completion of the interactivity set. The letters IX, stand for interactivity and the letters "MCD" stand for Multi-Cognitive Domain.

A baseline weight for each interactivity is assigned with a plus-minus scale used to adjust the weight assigned to the interactivity based on its increased or decreased complexity and its contribution to the MCD rating for the interactivity.

Thus, MIT 4/8 (in FIGS. 4B and 4C, Tables 1 and 2) stands for MatchIT! where the user is tasked with matching 4 whole pieces or parts in an eight section 2-image composite in which each image was sectioned into 4 pieces. The alternate symbols "8UP" or "8-UP" can be used to refer to a 2-image composite where each image has been sectioned into 4 pieces and combined to generate a composite with a total of 8 pieces.

In Tables 1 and 2 (FIGS. 4B and 4C), MIT 2/4 is followed by "(−0.25)" and MIT 4/8 is followed by "(0.0)," for example. The designation "(0.0)" represents the standard for a particular scale and which includes particular time and accuracy thresholds; and "(−0.25)" and other parenthetical +/− designations in Tables 2-4, indicate that the interactivity is more difficult (+) or easier (−) than the standard. The (−0.25) is used to adjust the MCD values for each cognitive domain by that amount, where for example the MIT4/8 (0.0) for the memory domain is 2.00, for the MIT2/4 interactivity (which tasks the user to place 2 pieces in a 4-UP two-image composite) has an MCD value of 1.75, indicating a reduction from the 0.0 value by 0.25. The baseline is metered by sectioning strategy and other variables such as cognitive health condition. Table 3, FIG. 4D uses a scale that is different from Tables 1 and 2, with a different (+0.0) baseline. In the example of Table 3, the (0.0) is MIT 2/4 and which is metered by cognitive health status and/or condition.

Applying the weighted scales noted above, MIT 2/4 (in FIG. 4C, Table 2) would have a lower weighted MCD (i.e. less cognitive demand) relative to MIT 4/8, whereas MIT 5/10 or MIT 6/12 would have a higher MCD weight score relative to MIT 4/8.

CON10UP (in FIG. 4E(1), Table 4A)—stands for a Construct interactivity. The symbols "10UP" and "10-UP" indicates that the interactivity uses a composite image composed of 2 images. Each image is cut into pieces that are 20% of the width of each component image, and thus each image is cut into 5 whole pieces from each image for a total of 10 pieces.

MP5×5 (in FIG. 4E(1), Table 4A)—stands for the Missing Pieces interactivity in which the image is located on a 5×5 grid, dividing the image into 25 equal-sized and equal-shaped pieces. In one embodiment, of the 25 pieces, 5 pieces are presented to the user. They are tasked with spatially determining the location of the presented pieces on a blank 5×5 grid using a reference image to identify the pieces location. In one embodiment, the user is presented with 5 pieces/parts which correspond to missing sections in an image. The user needs to place the 5 pieces in their proper locations. MP5×5 is an example of the Missing Pieces interactivity, other grid sizes 3×3, 4×4, 6×6, 8×8 and 10×10 for example and a variable number of missing pieces parts to be placed. MP10×10 would refer to a 10×10 grid and where the image is divided into 100 pieces. The user would be given 10 pieces to place either which are missing or to be placed on a grid. The size and/or shape of the pieces can vary and contributes to the complexity rating of the task as does the content of the image and/or image piece to be placed. For example, the complexity of a MP5×5 interactivity using image pieces which are distinct from one another may be at an easier skill level than a MP3×3 or a MP5×5 where all of the pieces to be placed are similar, such as tasking the user to place all blue sky pieces.

OIDm (in FIG. 4E(1), Table 4A)—stands for Object ID memory, where the user is presented with an image and is asked to identify 7-10 items in a single image. In one embodiment, the user is allotted 15 seconds to complete the task and challenged to recall the user-generated list at a later time during the session, after the session and/or at another session. In other embodiments, the user may be tasked with identifying and/or remembering 5-7 items, or 3-5 items, or to identify as many items as they can within a specified time period. The user may be tasked with recalling their identified objects list at a later time during the session, at the end of the session and/or at another session.

DD (in FIG. 4E(1), Table 4A)—stands for Dimensional Descriptors, in which the user is tasked to identify dimensional aspects of a composite of two images, such as which image or images is in the foreground and which image is in the background in a stable composited image. The user may be asked to identify 5-7 descriptive items per image, and may be allotted 15 seconds, or 20 seconds, or another timeframe per composite image and/or to identify some other number of descriptive items in only one of the images in a stable or multi-stable composite image, within a specified time period. The user may be presented with a series of interactivities that include composite images, in which a component image is in the ground position in one composite image and in the figure position in another composite image. The nuanced differences between the composite can be used as a measure of attention and pattern analyses for a parts matching type of interactivity and/or dimensional description interactivity can be used to identify subtle cognitive differences.

In the example of FIG. 4E(1), Table 4A, individual interactivities are combined to create a battery of interactivities, also referred to as an interactivity set. The MCD character of an interactivity set is defined by the contribution of each interactivity, according to its multi-domain character, and is reflected by the averaged values to develop an MCD value for a collection of interactivities with the computation of additional values represented by A7-A11 in FIGS. 4E(1)-4E(2), Tables 4A and 4B. The designation A7 is the sum of MCD value for each cognitive domain from each of the interactivities. For example for the Memory domain (D1) for interactivity 1 (IX1), given by the designation IX1D1, the sum of A1 is equal to A7, and so on for each domain (D(n)) across all of the interactivities in the battery (IX1 . . . IXn). A8 in FIG. 4E(2), Table 4B is the average MCD value for a given domain across all of the interactivities.

The values of A9-A11 in Table 4B reflect the MCD characteristics of the interactivity set as follows: A9 is equal to the sum of A7, the tally of MCD values for the interactivities set and where A10 represents the average of A8, i.e. the MCD value assigned to each cognitive domain for the IX1 . . . IX(n), across all cognitive domains (D1 . . . D(n)). While not shown, the percentage of each MCD represented by each cognitive domain for a given interactivity set can be computed by D(x)A8/A9. Similar to the computed A4 value, A11 is computed by A10/A9. In other embodiments, additional computed values and weighted averages can be applied to individual domains, interactivities, scales and interactivities.

Each of the domains contributes differentially to the MCD value. When an interactivity is reported not only would the speed and accuracy be representative of a single domain, but the score represents the whole of cognition because each interactivity has a multiple cognitive character. The weights divide the total score similar to a pie chart.

If one completes an interactivity XYZ with 100% accuracy and within 100% of the time threshold allotted to Interactivity XYZ, if we take a look at the MCD character of a given interactivity then you get memory represented by A; Attention by B; V-S by C . . . etc. it is 100% represented. If the accuracy is less than 100% then the accuracy missteps are reflected not only by a single domain but across all domains to different degrees.

The reporting can be by domain, by MCD, by comparison to a "normal" (+0.0) MCD. However, for someone known to have a cognitive issue, a different scale may be used.

When a person enters a set of interactivities the MCD character is displayed. When a set of interactivities are being defined for a protocol the MCD character of the IX (interactivity) is displayed to the developer. The division of the score into contributions from different domains allows the developer to focus on global cognition and specific cognitive domains.

If a practitioner wants to compare an unknown group and see how the unknown group score compared to other groups, or is a previously unknown person is assessed for the first time, then a (0.0) starting point might be assigned based on age and health status, and scaled up and/or down responsively to see the new group or persons baseline should be.

In an alternative embodiment, the practitioner can set an MCD value and a group of interactivities are assembled for the practitioner which matches the target MCD for whoever is being tested. Optionally, the practitioner can also specify the desired weight or combination of weights for different domains, and the system will find interactivities with the desired combination of weights (if present) and/or select images for an interactivity so that the interactivity will have the desired set of weights and/or MCD value for targeted assessment, treatment and/or training requirements. Each interactivity (IX) of Tables 1-4 has Multi-Cognitive Domain (MCD) characteristics. In an embodiment, each IX has a MCD value between 1-6 assigned to each of six cognitive domains (in an alternative embodiment, the MCD values may have a different range of values (e.g. 1-10 or 1-100) and the number of cognitive domains and/or subdomains may vary. Each IX has a standard set of values for a given sectioning strategy, number of pieces and size of the pieces. The MCD value may be adjusted based on the changes to the sectioning strategy. The MCD value is further modulated by the image(s) used in the interactivity or interactivity set in terms of the image(s), which may include, Ambiguity Values, Compositing Factor, Switch Capacity, Image Count, and Reference Image presentation (on, hidden, preview).

Each interactivity may be associated with multiple scores that relate to different cognitive domains. For each score for each cognitive domain, a different column is allocated. The column headings M, A, VS, EF, SM, and L stand for M—Memory∥A—Attention∥VS—Visual Spatial (visual spatial)∥EF—Executive Function∥SM—Sensorimotor∥L—Language. Each of these domains may have one or more subdomains. In other embodiments, there may be fewer, more, and/or different cognitive domains that are assessed by an interactivity for which score maybe given. For example, memory may be subdivided into working, short-term and long-term memory metrics. The different scores for speed and accuracy can be attributed to individual cognitive domains (attention, visual spatial, executive function, sensorimotor functions, and language) based on the percent contribution of each domain to the MCD (that is based on the weights). The individual percent contribution of all of the domains may be aggregated into a single score, which is the multi-cognitive domain score/value (MCD=Multi-Cognitive Domain) as a point in time measure, and also compared over time for changes in cognitive status. In an embodiment, the reference chart values (the weights) of FIGS. 4B-4E may be further adjusted by complexity factors by modifying the relative size of the pieces with respect to the image, the number of images in a composite, the ease with which the images switches/does not switch between which elements assume the ground or figure position. In an embodiment, the weights are standardized against large numbers of people, across multiple age ranges and conditions. Some factors that are measured during an assessment may include, the Total Time $T_{(tot)}$ (which can be recorded in sec or in millisec), the Average Time/move $T_{(x)}$ (and/or the average to complete the task), the time to the first move or response RxnT, Rxn Time. The Percent Error, PE, may be computed and reported, which may be the number of error divided by the total number of moves made. The Inverse Error Score (IES) may be computed and reported, which may be a method for relating RT to # of Error, such as by the formula, $$IES=RT/1-PE,$$

Optionally, the reference chart values (Tables 1-4, FIGS. 4B-4E) can be metered/adjusted by age, gender, cognitive status (for example, Alzheimer's disease, Mild Cognitive Impairment (MCI), Multiple Sclerosis (MS), anesthesia, and peri-operative). The reference chart values (FIGS. 4B-4E) can be further metered/adjusted by image set and interactivity complexity factors, such as percentage sectioning, number of images, and/or switch/non-switching images sets (% sectioning is the percentage of the image that each piece contains from the image). The reference chart values (FIGS. 4B-4E) may be standardized against large numbers of people, across multiple age ranges and conditions.

Patterns such as Repeat Errors, which refers to the user's tendency to repeat the same error, may be computed and reported. The interactivities may be scored for Patterns. Placement patterns refer to the pattern in which the user places the pieces on the grid or other canvas for problem-solving interactivities. Placement pattern may be user-specific such as the user's pattern is to place easy pieces first; single image parts identifying outer edge pieces first; and/or by color preferences; Error Averse (slower placements with (or without) fewer errors) versus Risk-takers (faster placements with or without more errors), and which may be metered by age and other cognitive issues.

The image may be located on a canvas, which may be divided into grid units, which may be squares, rectangles, hexagons, and/or any combination of shapes, for example. The image is divided into image parts, and each image part may be vertically oriented and/or horizontally oriented spanning across multiple grid units and/or filling a single grid unit. The size of the image parts can represent between 1.5% to 50% of an image, for example.

In general, in the Missing Pieces Interactivity as well as in other interactivities, the user can move an image part to the reference image and then over to the grid, or only to the reference image, or only to a grid after previewing the reference image which can then be hidden specifically targeting both memory and visual spatial skills and processes for assessment. The user may be allowed to perform additional back and forth movements in which the user moves the image part between locations that are over the grid and the image part's original position (or another position) in deciding where to place the image part as part of the Missing Pieces interactivity and/or other interactivities. Allowing for the back and forth movements may aid the user in deciding on the correct placement of the image part, through estimation and/or approximation of the location of the image part on the grid.

The Missing Pieces Interactivity, as well as for the other interactivities, can be used to evaluate user decision-making and/or problem-solving skills with a given game piece against a reference image or other interactive resource, and which can include movement mapping analysis to track a user's directed placement, whether correct or incorrect, in performing a task.

Extrapolate is a variation on Missing Pieces, but instead of using individual images, the interactivity uses a composite image set comprised of two or three component images. The user is tasked with extrapolating the position of the image part from the composite and placing it in its proper location on a grid. In one embodiment, the user is tasked with extrapolating the position of one or more image parts from the composite to two or three separate grids, each representing the component images comprising the composite. In one embodiment, the grid represents the composite, and the user is tasked with extrapolating the location of one or more image parts from a reference image to the grid; in both Missing Pieces and Extrapolate the user leverages visual-spatial skills and processes in deriving solutions.

MatchMe! is an interactivity in which the user matches isolated sections of a single image to portions of a reference image MatchIT! uses composite image sets and applies the same strategy of matching whole sections and partial sections, including spans. Spans refer to playing pieces which span across multiple images sections in a composite. In one embodiment of a MatchMe! interactivity, the user is tasked to identify one or more matching sections and/or segments from a collection of image parts to a reference image which provides the user with an active template. Segments in single images can range in size, in both the horizontal and vertical orientation of 1.5%-50% of the total image and/or can consist of a mixed variety of section percentages. In one embodiment, the reference image template is intact and the user looks for a matched section. In one embodiment, the reference image template is missing sections leaving holes in the reference image template, similar to an incomplete puzzle where the pieces are to be placed. The pieces can be the same size or of different sizes as one another. In one embodiment, using 2- and/or 3-image composites, the MatchIT! interactivity involves a missing segment and the piece that is to be inserted to that position. The missing segment (or the segment that needs to be matched) can be a span of multiple sections from more than one of the component images. In other words, the missing section or the section that needs to be matched and filled may include two or more adjacent image sections in a composite image.

Mutation is an interactivity in which parts of an image are altered, and the user is tasked with identifying the altered portions, such as by correcting or removing the alteration. In one embodiment of the Mutation interactivity, the user is tasked to identify introduced changes to the image set and/or individual images that result in an error of some type in the image or image set's composition. Examples of mutations include, but are not limited to, (1) the duplication of elements that are not duplicated in the original image, (2) the insertion of an unrelated image part, (3) the deletion of an element of the image, (4) the inversion of an element of an image, (4) rearrangements of elements in an image, and/or (5) transpositions of two or more elements of an image with each other, among others. In one embodiment, the transposition-type mutation involves a composite where a section or a segment and/or segments/sections belonging to Image #1 is reciprocally transposed or non-reciprocally inserted into Image #2 or Image #3. In one embodiment, the inversion type mutation is where an image section or segment can be vertically or horizontally flipped. Smaller segments may be involved. Smaller segments can increase the challenge level in looking for what is different from the template, reference image, or what is not correct in a presented construct. An image and/or image set may contain more than one mutation and can include more than one type of mutation, and can be provided with a count on the number of mutations present, and a countdown as these are found by the user. The user may be presented with a series of progressively more challenging Mutation interactivities, for example such as using smaller image parts or more subtle changes, and/or the Mutation interactivity can be combined with another interactivity as part of a therapeutic and/or training protocol.

In an embodiment, the user is first shown the unaltered image, and then based on memory identifies the alterations. In an embodiment, the user is allowed to directly compare the altered and unaltered images to find the alterations. In another embodiment, the user is not shown the unaltered image. Instead, the user identifies the alterations based on anomalies in the image. For example, the image may be divided into squares (or other shapes) and random squares are rotated randomly into other orientations that the same piece fits into the same location. Alternatively or additionally, the locations of some of the parts of the image may be moved to other locations of the image. For example, the locations of two parts of the image maybe switched. As another example, part A of the image may be placed where part B of the image should be located. In the location where part A was originally located may be another part (e.g., part B or part C). Alternatively, the location where part A was originally located may still have part A even though a duplicate copy of part A is not located where part B belongs.

Compose is an interactivity in which the user assembles isolated parts of an image into a complete image; whereas Construct tasks the user with constructing a composite image from the isolated sections. In one embodiment of the compose interactivity, the user is presented with a sectioned image and/or images, and the user is tasked to construct a matching pattern using a reference image. The reference image can be presented to the user for a specified period of time. Alternatively, the reference image may be available throughout the interactivity session and/or previewed by the user prior to the start of the interactivity, and/or is available to the user on demand.

If the interactivity involves constructing a composite of two or more images, which is referred to as the Construct interactivity, then the user may also be required to sort through the image sections to find the appropriate sections matching each of the sections of the component images. The user's placement pattern and order of placement (end pieces, completing one entire image first, then constructing the second image) can provide insight into the user's cognitive and thinking processes.

Behavioral patterns associated with age can also play a role in user interactions, patterns, and process analysis with regard to risk tasking users, for example, choosing rapid placements at the expense of errors versus risk averse users, who might choose slower placements to make fewer mistakes—and other variations. The user can also be directed to place parts belonging to only one of the images, as part of an attention task to see the extent to which the user can successfully ignore flanking and/or distracting image pieces.

User behavior and performance on tasks can be impacted by frustration, anxiety, and stress. The source of the stress may be external to the interactivity and/or created by the interactivity. For example, user cognition can be evaluated under stress conditions, internal to the interactivity, by changing the assessment conditions, the mix of interactivities, and the number of speed rounds. In one embodiment of the Construct interactivity (i.e., using composite images), the platform can use a single sectioning strategy for each of the images or a mixed multiple sectioning strategy (see pieces 2024 and 2026 of FIG. 20F) for each individual image in a composite and within an individual image (see FIG. 23E). Optionally, some of the slices of a composite image can be thinner than other slices of the composite image. For example, the thin sliced image of a three-image composite may have sections that are mixed with one image having multiple sections which are 1.5% and other sections which are 40% each; and, where the other two images may be cut into 20% sections.

In the Jumble-Sort interactivity, the system presents the user with a mixed grouping of one or more images that can include both vertically and horizontally sectioned pieces which can be the same width (all 25%, 20%, 10% for example) or of mixed width. The user is tasked to separate not only the part of each image from the parts of the other images, but to separate parts of the images according to their sectioning strategy. For example, in the mix of images parts may have two versions of the same image, but each uses a different sectioning strategy. In Speed Sort, the sorting process, accuracy, and number of pieces sorted are measured against a fixed time; for example, 15, 20, 30 or 60 seconds, depending on testing conditions and the user's status.

In one embodiment, the user may work with a reference image which represents the original image in its entirety and/or the reference image may be a part of a larger reference image, from which the smaller reference image was extracted, and the user may be tasked with figuring out what the larger image is. Once the larger image is determined, the larger image may become the new reference image. Alternatively or additionally, a smaller image is extracted from a larger image and the smaller image is used as the new reference images. Corresponding image parts to be placed by the user are presented to the user for placement on a grid. In one embodiment, a portion of the reference image is masked and/or removed as a visual reference, and the user is tasked with placing image parts from the masked section on a grid. Masking part of the reference image can also be applied to other interactivities such as Missing Pieces, MatchIt!, Compose and/or Construct requiring that the user rely on their memory and attention to detail to complete the interactivity with speed and/or accuracy.

The interactivities may include one or more of any of the interactivities provided herein and configured as a battery of multi-domain type interactivities, which may be analyzed in a variety of ways through using Mem+ assessments obtained directly by using the interactivities for processing speed type, reaction time assessments (time-limited placements), accuracy, and figure-ground (f-g) recognition within the interactivities and after the interactivities. (Examples of composite images with different figure-ground relationships is discussed in conjunction with regards FIGS. 23A-23D, 24B-24F, and FIGS. 25B-25D, and examples of interactivities are shown in FIGS. 20A-20G).

The Word List (WL) Recall (which may be referred to as Memory Recall) may be a memory recall of three, five, or seven words, for example. For example, at an initial predetermined time (e.g., T=0'), the user may be given a set of words and optionally immediately asked to recall the words. Later, after an intervening distraction activity, at a second predetermined time (e.g., at T=5'), the user may be asked to recall the words of the same word list (the second recall may be referred to as a Delayed Recall). Optionally, the WL Recall may also include additional recalls of the word list at a later predetermined time. In an embodiment all of the predetermined times are spaced apart by approximately the same time interval, during which the user is distracted with other interactivities. For example, there may be another Word List Recall at T–15', which may be referred to as an Extended Recall. Alternatively or additionally, there may be another word list recall at T=20'. In an embodiment, the time from initially receiving the Word List and the last Word List Recall may be between 10' and 20', or other time differences. In other embodiments, the time between requesting the user to recall the word list may be several minutes, or hours, or days. In other embodiments other durations of time may be used and/or chosen (e.g., automatically) based on the user's cognitive abilities and/or cognitive issues, as can the number and nature of the word lists, including image-cued word lists with a varying number of image-cued words.

Images can be sectioned in a pre-determined manner with the corresponding number and size of image parts/sections provided. In one embodiment, the user may be tasked to place a special image section which is presented separately from another image section and/or sections and highlighted for the user. The user is tasked to place the "special" image parts into the correct locations within a defined time-period. Depending on the configuration, and/or depending on whether the configuration is for assessment, training, and/or treatment purposes, the user may be penalized or not penalized on the task, and a type of reward assigned or not assigned for the correct placement of the image part. The task can be used for assessing and/or improving accuracy, improving reaction time, and/or evaluating speed. The task may be used to assess user responses to changes in piece size, changes in the color of the pieces, changes in the shape of the pieces, and image content. The task can be used for assessing user responses to changes in the sectioning strategy, for assessing whether to advance the user to a higher level, and/or for assessing a threshold for whether to fine-tune the interactivity to the user's skill set and/or cognitive abilities.

In one embodiment, the user is presented with whole sections or with parts of each section (smaller interactive elements) for the interactivities. The use of smaller interactive elements and/or different sectioning strategies can be used to vary the complexity of the interactivity and the attention to detail required, as well as the image content and color characteristics.

Interactivities involving composite image sets may use 2- or 3-images with any number of sections between 4-100 and/or image parts representing 0.1% or less of an image, depending on the intended interactive tasks, level of complexity and purpose of the interactivity.

The platform can be used for multiple learning styles based on the interactivities' mix that are used. Accommodating multiple learning styles allows users to demonstrate their skills in one or more areas and their differences in skills in different areas, without penalty for having to match skills to a specific learning style. Instead, the interactivity may be adjusted based on user's capacity and capabilities using multiple related scales to mitigate floor and ceiling effects.

A unique feature of the platform is the integration of composite image sets with the inherent ability to interact with the user on a subliminal and/or subconscious level.

The inherent ability to interact with the user on a subliminal and/or subconscious level is an effect due in part to the illusion of depth, which is generated by juxtaposing image sections in both stable and multi-stable image sets. The inherent ability to interact with the user on a subliminal and/or subconscious level may be further amplified by the dynamic shifting of images in the figure-ground positions, which users may perceive with multi-stable types of image sets, but not in stable image sets. As the user is interacting with the image sets, a switch may occur in which an image appears as background, e.g., in the ground position but can switch to the figure position with a reciprocal exchange of the second image in a two-image or three-image composite based on the presence of contiguities in the component images. The switch in which image appears as background engages a second process as the confluency gaps of the ground image are largely ignored based on Gestalt principles (e.g. that is based on the appearance of the image as-a-whole) and is perceived as re-assembled. The switch between images can occur independently of the user's conscious awareness and/or by tracking across alternative contiguity lines, and which may be used to trigger a perceptual switch. The perceptual switch, while occurring subconsciously, can also be linked to active engagement of cognitive processes where the user is guided and/or made aware of the switch and/or alternate percepts and/or other contiguities, and is directed to focus on particular areas of the image set. The value-added subconscious engagement of cognitive processes can be factored into the cognitive benefits offered by the platform, and which can be evaluated with functional Magnetic Resonance Imaging (fMRI) and/or directed Electroencephalogram (EEG)/Event Related Potentials (ERP) signals and/or eye-tracking to provide users with an adjusted baseline. Functional MRI is a type of specialized MRI scan, which measures the hemodynamic response related to neural activity in the brain or spinal cord of humans or other animals. Higher amounts of blood flow are seen as indicating activity areas of the brain that have higher amounts of brain activity. Thus, fMRI measures areas of activity—the theory being that the user is lighting up areas of the brain involved in performing the interactivities. Monitoring the brain with fMRI or EEG/ERP spikes associated with the user's interaction would occur in a clinical setting. The fMRI or EEG/ERP can also be used to differentially evaluate multi-domain cognitive engagement especially in patients/users who have suffered traumatic brain injury, concussion, or following stroke where other areas of the brain may compensate for loss of function in one area. A regular user might use a commercially available EEG headset (like Muse) which is configured for the platform, or use an eye-tracking system which can be used today with an App or Google glasses to track user eye movements across and around image/image sets. However, a home user could also be given access to these types of clinical measurements for remote monitoring.

By supporting and/or improving awareness and thinking skills among users with cognitive impairments and/or other changes in cognitive status, and/or in building cognitive reserve through attention focusing, memory triggering, and/or language-building interactivities, the platform has the capacity to affect ADL (Activities of Daily Living). ADL refers to the skill set a person has to manage and accomplish everyday tasks such as grocery shopping, personal hygiene and grooming, and eating among other activities. The platform's efficacy in supporting cognitive health can be measured for its impact on ADL with practical improvements to the lives of platform users as a result of using the platform to engage and improve cognition.

Returning to the discussion of method 400, in step 460, the data collected from users of the interactivities (e.g., performance data) is stored in association with the information about the performance of steps 410, 420, 430, and 440.

In step 470, the user's profile may be updated based on the results of the interactivity. Step 470 may include a change in information about the user's diagnosis, cognitive health, physical health, skill level, and/or which protocol the user should be assigned.

In step 480, a progress metric is displayed for the user, giving the user the results of the interactivity in combination with information about the user's skill level, progress, diagnosis, and other profile and/or signature features. The progress metric may be displayed only to the user, the user's clinician, and/or a researcher. Alternatively, the information may only be provided to a healthcare worker who may then decide how to communicate the information to the user. After the progress metric is displayed, the session ends in step 490.

In an embodiment, each of the steps of method 400 is a distinct step. In another embodiment, although depicted as distinct steps in FIG. 4A, step 410-490 may not be distinct steps. In other embodiments, method 400 may not have all of the above steps and/or may have other steps in addition to or instead of those listed above. The steps of method 400 may be performed in another order. Subsets of the steps listed above as part of method 400 may be used to form their own method.

In some embodiments, the platform (system 100) uses images and image sets as the basis for hands-on, hands-free, and/or virtual view-only challenges and interactivities. However, other parts of system 100 may be configured with non-visual content for a subset of puzzle-styled interactives (interactivities that are in the form of a puzzle) and/or may be combined with non-puzzle-type interactivities. For example, tactile inputs derived from 3D-printed images or image parts can provide visually-impaired individuals with non-visual content. The tactile stimuli can be complemented with other sensory inputs cues for a subset of interactivities including sorting, matching, compose and construction to support cognitive assessment, remediation, therapy and training requirements and/or needs for people with visual impairments. The perceived illusion of depth associated with composites can be conveyed through different thicknesses of printed tactile interfaces and dynamic digital interfaces.

Visual inputs may be conveyed through a variety of means including, but not limited to, sighting, implants, signal-transducing wearables, other devices, and/or brain-computer interfaces (which may be part of interactivity interface 229). For visual inputs, the interactivities may be applied to individual images, or to composite images, and/or to the individual images (component images) comprising the composited constructs.

In one embodiment, the platform may utilize content-rich, real-world images. Images can be color, halftone, black/white (b/w), degraded images/photographs, and/or other types of source images. Some examples of types of source images may be video-type content, individual frames of a video, artwork, illustration, drawings, and/or paintings in various combinations, including source images designed for younger children ages 3 and up, such as cartoonified drawings and/or simplified illustrations. In one embodiment, individual images can depict single objects as line drawings, illustrations, photographic images, and/or other type of representations with and without applied graphical filters and masks Some examples of representations that may be used by the platform may include a degraded image or an image with partially obscured image content. A degraded image or partially obscured image may be used for a subset of interactivities primarily related to one or more of the following: building objects, pattern recognition, language skills, attention skills, executive function among other learning and/or skill-based objectives.

Images with content-rich elements can depict a scene with people, animals, inanimate objects in various combinations, and/or be set in an urban or rural environment, in a multiplicity of combinations. The term "images" can include static images, a combination of images, a sequence of images, or moving images. Some examples of moving images that may be included in the term "images" are video or film scenes and clips, as well as static screenshot-type images captured from video or film sources. Images can be sourced from pre-screened libraries of selected images and/or be supplied by the user, according to image specifications and security requirements. The images may be tagged according to the platform's requirements with image characteristics (color, content, context, and contiguities) analyzed as described previously.

Composite images can be generated by serially sectioning and juxtaposing the image sections from two or more images to portray the illusion of depth (e.g., so that the sections of one image of the composite appear as background and section of another image or of a plurality of images in a composite image appear as foreground. The perception of depth may be a visual illusion effect that is rooted in the figure and ground relationships of the images and owed in part to differences in values similar to Mach bands. The serial sectioning and juxtaposition of multiple image sections in an alternating fashion generates the illusion of depth based on figure-ground relationship. The visual illusion can portray a second characteristic if one or more of the component images contain specific image attributes referred to as contiguities. The presence of one or more contiguities in a composite image can affect the stability of the image which is perceived to occupy the ground and/or background position. In one embodiment, the configuration may be referred to as stable when only one of the images in a composite contains at least one contiguity. The image with the contiguity occupies the ground position, and in the stable configuration, the second image in a 2-image composite; or the second and third images in a 3-image composite will occupy the figure (foreground) position. The image or images in the figure position can appear as columnar pop-outs supporting the portrayal of the illusion of depth. In a stable configuration, the same image always occupies the background position. A multi-stable configuration is one where at least two of the images in a 3-image composite or both images in a 2-image composite can occupy the background (ground) position; the switch capability as such is high for this type of image set because of the combination of component images in the composite. Both stable and multi-stable constructions can be generated using the platform's device, offline components, and/or a hybrid version.

Content, color, and/or context may aid in defining a contiguity or the interpretation of a contiguity. As such, in an embodiment, contiguities in an image can provide visual cues that the user can use to track across an image or composite image. For example, when two or more images are combined in a specified fashion, and where at least one image contains a contiguity or when two or more images contain contiguities in a composite of two images or in a composite of three images, a contiguity may also provide visual cues to track across the image or composite image. A contiguity does not need to span across the entire width of an image and a specific contiguity's characteristics can change across the width of an image from being pronounced to less defined, and vice a versa. The visual effect of the composite and the impact of the composite on the user differs, depending on each image's contiguity characteristics with a set of variables, including: color, content, context and the image's overall complexity, and which can be used to personalize image sets, and by default, the user's interactive game boards/interactive surface and experience. Users with higher degrees of and/or healthier cognitive abilities may be able to piece together an image in their mind with fewer visual cues, such as contiguities and/or contiguities that are less noticeable, as indicated by the numerical values associated with the contiguity's characteristics. Similarly, users with higher and/or healthier cognitive abilities can have a higher tolerance for distractions as compared to users with attention-related issues. As a result, interactivities may be chosen based on the characteristics of the image and the contiguities in the images to test for higher and lower degrees of cognitive ability and/or cognitive status.

The use of the platform in enhancing team-building, health, business, changes in rules and/or protocol can be viewed as a combination of entertainment and learning facilitation, according to the platform's cognitive engagement capacity. Regarding team-building, users may engage in competitive play in which the users are organized into teams, and the teams may be scored based on the number of games played, and time to completion of the interactivities.

FIGS. 4B-4E shows Tables 1-4 were discussed above. FIG. 4F, Table 5 provides a summary of cognitive domains and subdomain processes and skills which can be assessed with a multi-purpose interactive cognitive platform.

FIGS. 5-8 provide embodiments of methods of using the multi-purpose interactive cognitive platform by a user. In an embodiment, the first time the user logs in or registers the method 400 is performed, subsequently, one or more of the methods of FIGS. 5-8 are performed.

Figure 5:
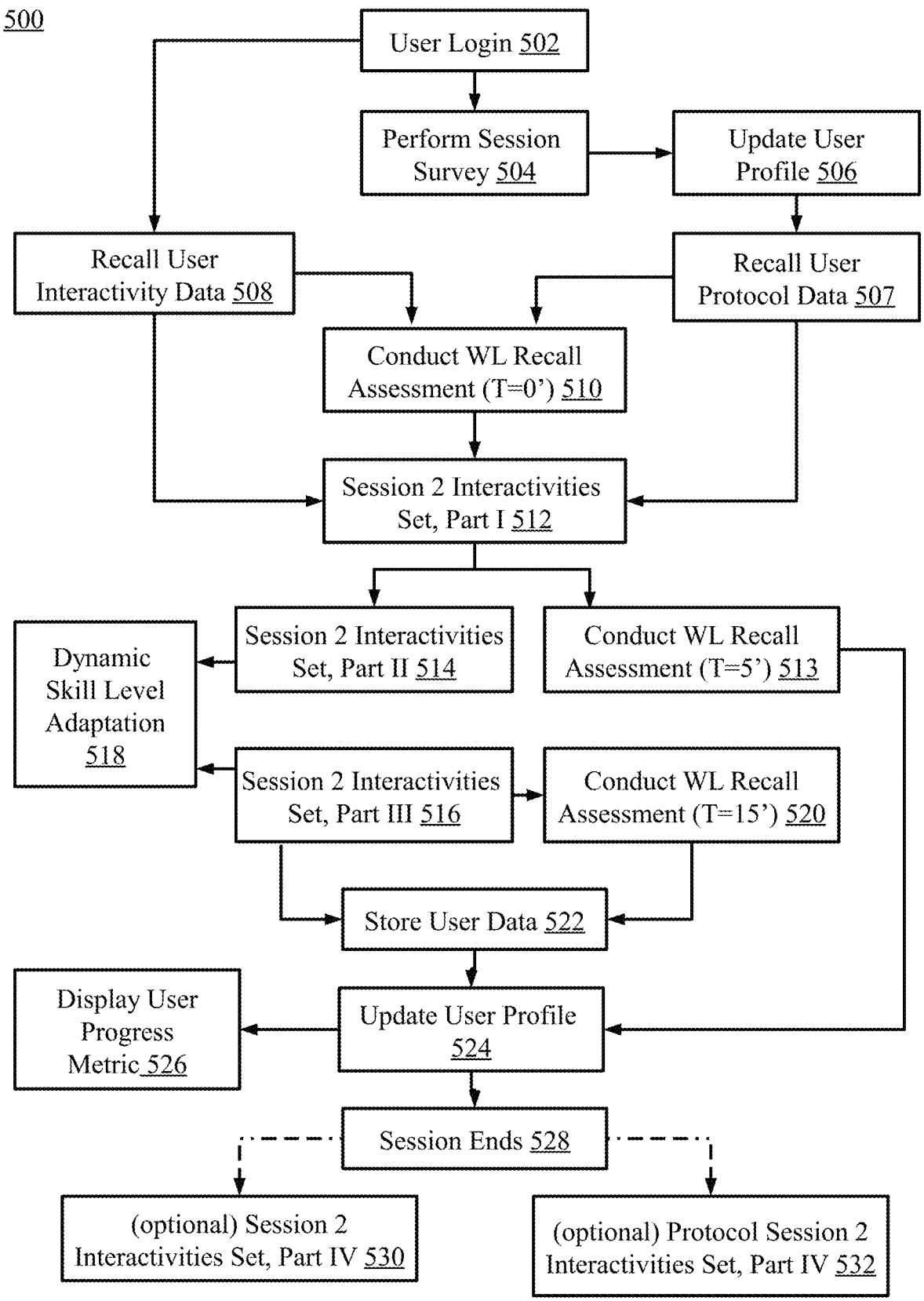
FIG. 5 shows an example of a flowchart of a method of using a multi-purpose interactive cognitive platform for a returning user (a multi-session protocol).

FIG. 5 provides a multi-session protocol for a returning user. In an embodiment, the first time the user logs in or registers the method 400 (FIG. 4A) is performed, subsequently, method 500 is performed. Alternatively, although method 400 is performed at least prior to the first performance of method 500, method 500 may be performed if a Mem+ assessment is desired. Both professional users (e.g., healthcare workers) and end-users (e.g., patients) may access the platform's multiple interactive modes, including: FreePlay, Challenge, and Protocol modes. Optionally, there may also be a Cognitive Health Sequence mode and/or other types of modes.

The Freeplay mode allows the user to choose what interactivity the user would like to use and to engage with any given interactive for as long or as short of a time period as desired with user defined selections for skill level and images. The Challenge mode includes interactivities that challenge the skill level of the user with preset progressions. Based on instructions given to the user by the professional, and/or as the user directs themselves, a subset of interactivities may be performed for a specified period of time and/or according to a prescribed frequency and/or as directed by the system. The frequency and skill level may be as part of an intervention or maintenance regimen to support cognition. Optionally, the user (a patient or practitioner) may manually engage the assessment mode for a specific interactivity or set of interactivities, and update the measurements of cognition and/or ability from the assessment mode to their user profile. In the Cognitive Health Sequence, the user may choose their own self-guided assessment of their cognitive health. The user may choose which assessments the user would like performed based on their interactivities and/or choose which interactivities to perform.

FIG. 5 shows a multi-session protocol for a returning user 500. In step 502, a returning user is provided with a login interface (which may be part of communications interface 112, interactivity interface 229, and/or healthcare interface 230), via which the user may login (see also 410 in FIG. 4 for login information that may be required).

In step 504, the user performs a session survey. The session survey is presented to the user. The session survey may include questions asking the user whether the user found the previous interactivities and/or the cognitive protocol useful. Questions may be presented to the user, via the platform, to identify specific information that allows the multi-purpose interactive cognitive platform to be better personalized to the user. There may be other questions requesting other information to determine whether the protocol is helping the user (e.g., via diagnosis or treatment of a disorder). Alternatively or additionally, the survey may ask whether the protocol has been entertaining and/or engaging to the user to further support continued compliance. For example, questions may include, but are not limited to, how long the user sleeps, sleep patterns, diet, dietary habits, current medications, medication changes, stress levels, for example. The variables associated with the questions can affect user data, by explaining why scores may be significantly different from a baseline score, such that the observed changes are not progressive or permanent, but rather are conditional and/or temporary that may affect the user's performance for a given session. Without the input from the questions, the changes in the user's score may erroneously be interpreted as changes in cognitive status, but which are situational. However, in an embodiment, situational changes are tracked to facilitate identification of actual changes in cognitive status which can be associated with long-term changes in sleep, diet, exercise for the user and which may be applied to other users in developing predictive analytics. In some embodiments, the survey can include questions about whether the clinician or practitioner found the interactivity useful.

In some embodiments, the session survey identifies what type of learner a user is in combination with previous progress metrics. For example, an interactivity where a user is unable to perform a certain task with accuracy or within a predetermined time threshold, may be used as an indication of the user's cognitive status. The user's cognitive status may be further assessed using alternative protocols within the platform, optionally together with third party assessments of the user. For example, visual-spatial tasking can be highly developed in some users but who have deficits in other areas, as a matter of history (despite, for example, a statistical correlation between those other areas in which the user is deficient and visual tasking, indicating that it is unusual for someone with this user's deficiencies to be highly developed in visual-spatial skills), and the high visual spatial skills is normal for this user, and is therefore not an indication of changes in cognitive status over time or due to a condition (even though a temporary further exacerbation of their inabilities may occur). As another example, a user who has historically been an auditory learner (and not a visual learner to a lesser degree) would find certain tasks challenging as a matter of course, and the difficulty would not necessarily be a function of the user's condition or cognitive status. Consequently, the poor performance of this user on those visual tests and good performance of this user on those auditory tests is not necessarily a result of a change in this user's current condition or cognitive status. The converse may also be true in that a strong visual-spatial learner may have auditory learning deficiencies. Similarly, there may be users having an array of mixed types learning styles along a continuous spectrum. The platform can accommodate different learning styles and different users who may be scored differently based on their learning style.

An assessment of changes in cognitive status is informed by the user's general abilities and the user's learning style as a factor in choosing and evaluating the value and validity of certain types of assessment indices. The variability in learning styles is used as a factor in personalizing game boards and interactivities to better meet user needs, rather than seen as a deficiency to be remedied and/or negatively contributing to a user's evaluation. The dynamic aspect of the platform allows for the integration of multiple learning styles in order to foster cognitive gains whether for remediation, training, and/or skills development.

In step 506, the user's profile is updated based on the information received via an assessment survey.

In step 507, the user's previous protocol data is retrieved. The retrieval may occur to enable the protocol to choose a skill level, to identify which protocol, and/or interactivities the user should perform next, perhaps based on a clinical protocol the user is involved in, or based on the user's preferences.

In step 508, the user's interactivity data is retrieved. Optionally, the assessment survey may be skipped and the user may be immediately presented with the interactivities. Along with retrieving the user's interactivities data and presenting the interactivities pages to the user, the interactivities may be personalized and a new interactivities page (with new interactivities) may be presented to the user based on the user's previous personalized interactivity and/or stored preferences.

A significant part of the assessment protocol is that the assessment protocol may be built into the platform—the assessment may be an embedded assessment that is embedded in the interactivity process, which may be implemented as the user engages in the interactivities, as described below. In step 510, the system conducts a Word Language (WL) Recall assessment at T=0'. Step 510 may be performed based on the user protocol data recalled in step 507 and/or the user interactivity recalled in step 508. In the pre-session survey, the user is also tasked with a word list recall assessment administered at T=0'. The Word Lists are derived in part from objects and elements contained in the images and/or image sets which are used as the basis of the interactivities. As such, the words in the Word List which the user is tasked to remember over time are image-cued and embedded in the interactivities. During the interactivities, the user may physically manipulate, or in the case of a View-only option, the user may mentally manipulate, the image parts, and interact with a subset of the objects and elements in the user's Word List (WL) both on a conscious and subconscious level. The Object ID Memory (OIDm) assessment has similarities to Word List Recall assessment in that the words are image-based and image cued, only with OIDm, the user derives the word list from an image. With OIDm, they are given 15 seconds to come up with 5-7 descriptive words about the image. After 3-5 minutes of engagement with other interactivities and which serve as a distraction, the user is tasked with recalling as many words as the user previously listed.

Returning to the description of Word List Recall, each image may be tagged with descriptors which identify objects and elements contained in each image and from which images or parts of images are associated with a list of words, creating an image-associated Word List that may be derived for the user and/or with one or more user sessions. A Word List Recall assessment may contain three (3) or more words. The number of words to be recalled is also metered to the user skill level and cognitive status. For example, Image #1 may have representations of a bird, a branch, sunrise, day, a silhouette, a hawk, no leaves, a tree, and golden. The words associated with an image can be represented in the image as visual elements or derived from the image inferred, such as the "day" tag. The number of words used in the assessment is based on, and/or derived from, an image and/or image set is approximately between thirty (30) to forty (40) percent of the total number of words in a Word List assessment. For example, for a 3-Word WL, at least one word is based on, and/or derived from the image and/or image sets. Similarly, in a 5-Word WL, at least three image-cued words would be integrated into the assessment.

In one embodiment, the words in a WL would not include any image-cued words, in other words, none of the words in the WL are contained or represented by elements or objects in the image. This type of assessment can be used as a measure of improvements in recall, if the user is able to recall more and more easily non-cued words as compared to a baseline memory recall assessment.

In an embodiment of the Word List Recall assessment, the user is tasked to recall the word list (WL) at multiple time points. The first time point is T=0'. Similar to traditional Recall assessments, the user, after hearing, and/or reading the list of words aloud, is optionally tasked to repeat the words back into a microphone of system 100, twice, for example. A Delayed Recall assessment is deployed at or about T=5'. During the intervening time, between T=0' and T=5' (or between other time periods of other lengths of time), the user is tasked with performing a set of interactivities. The interactivities during the intervening times may use the images that were tagged with words related to and/or conveyed by the image or image sets, depending on the interactives that the user has been tasked with in a session.

Traditional cognitive assessments which integrate a Word List Recall and Delayed Recall protocol generally use only T=0' and T=5' time points results to calculate a cognitive metric. The cueing used during the intervening time, if used relies on tangible, real-world objects readily available in the user's immediate environment with words such as chair, desk, table, window—familiar and within the user's visual field, which can test the associations the user makes between words and images. The multi-purpose interactive cognitive platform uses visual cues, as well but the visual cues are embedded in the image sets with which the user is tasked to interact with, to generate a "do" operation. In an embodiment, a "do" operation is when the user is working with the image sets that have word list cues embedded in the images, which may help the user remember the word list. The do operation may reinforce learning, and may be used with Hands-on and Virtual View-only interactivities. The "do" operation enables an enhanced potential for user learning, memory retrieval, attention focusing, and skills development through the interactivities and the use and/or manipulations of the image (and/or image sets) as well as the reference image to support a user's solving stratagem.

The platform provides the user with directed interactions with associated cues with the goal of fostering a stronger connection and memory recovery, recall, collaterally associated memories, and memory building opportunities through an active learning approach and potential associative scaffolding through interconnected neuronal networks. In other words, by asking the user to recall the word list, while performing the interactivities, can help establish an association between the words of the word list and the elements of the interactivity as portrayed in the image set, and the user's multiplicity of linked memories and experiences associated with a picture element. An example is water and the diversity of experiences and memories which can be associated with the word, water (i.e. ocean, beach, cooking, drinking, desert, lake, swimming, vacation, salt/fresh, ice, winter). The range of experiences with water are both unique to the users experiential base and the memories and associations they have formed, as well as having universal aspects relatable on some level, to greater and lesser degrees across a broad spectrum of age, culture, gender and geography.

In one embodiment, the platform uses an extended time point for conducting a recall assessment, which is timed to occur at T=+10' from the start of the user's interactions with the image-based interactivities and/or within that time frame up to approximately T=15' in one embodiment and/or to the completion of an active interactivity. In one embodiment, parts of the recall assessment can extend to longer time-periods within a given session, or may extend beyond a given session to another designated time point within a treatment protocol or beyond the treatment protocol depending on the requirements of the treatment and/or training requirements. The number of correct and incorrect absolute responses, such as the recall of the precise word and/or words is assigned a score. As the recall assessment assigns points, users may receive partial points for errors in assessments of remembering word lists, if the words the users recall are in the same category as the correct word. For example, the word, "table" might be recalled as furniture by the user or might be called, desk or dining room table with an elaboration on the to-be-recalled word or words, which may be assigned a partial score.

In one embodiment, users can be tasked to place object labels on associated objects. Placing object labels on the associated objects can be used to reinforce learning for those with cognitive and/or language impairments. Text labels may be configured as part of a multi-language pack to make the platform user-friendly to non-native English speakers and/or to people who have linguistic and/or verbal language skill challenges associated with cognitive changes and/or a condition or state with cognitive aspects or other communications' challenges. In one embodiment, an auto-sequence may run where the system places object labels on image objects to support recovery and learning for users with limited fine and/or gross motor control. The interaction in the auto-sequence may be Virtual View-Only, but offers mock-ups (animated sequences of the interactivities for viewing in addition to viewing engagement of the image sets themselves.

A Tangible User Interface (TUI) device and/or prop (which may be part of interactivity interface 229) can also be programmed to present a word label and which can be complemented with an audio feature. The user would then place the device with a label proximal to the object as part of the interactivity and/or assessment. In one embodiment, the labels can be on-demand activated or automatically displayed by the system in order to assist a subset of users with specific cognitive issues. For example, cognitive issues that may be assisted may include linguistic challenges and where tagging of image elements can help support cognitive health and/or language development and/or recovery.

In step 512, Session 2 begins with interactivity set part I. Step 512 may be performed based on the WL recall assessment of step 510, the user protocol data recalled in step 507 and/or the user interactivity recalled in step 508. From step 512, method 500 proceeds to steps 513 and/or 514. In step 513, a WL recall assessment may be conducted at time T=5'. In step 514, Session 2 proceeds to interactivity set part II. Step 514 may receive input from steps 512 and 513, so that the interactivities chosen in interactivity set part II may be based on the interactivities already performed in step 512 and on the results of the assessment 513. In step 516, Session 2 proceeds with interactivity set part III. Method 500 may proceed directly from step 514 to step 516.

In step 518, a dynamic skill level adaptation assessment is performed based on Session 2, in particular based on the interactivities' sets of parts II (step 514) and III (step 516).

Parts I, II and III is a shorthand used to describe interactivity sets, where parts I, II and III may be an interactivities set 1, interactivities set 2, and interactivities set 3. Each set may be comprised of a collection of interactivities using the same images, and/or component images, and/or image sets throughout. In one embodiment, each set may be comprised of a different image set, or another type of variation of the image set such as using halftone images versus full color versions, or other types of image manipulations. In one embodiment, since there is a minimum 5-minute time gap between WL Recall T=0' and T=5' and similarly between T=5' to T=10', the time can be filled with the interactivities' sets. For example, a healthy young person might complete a standard interactivities set 1 in a minute, making the time interval required for performing a WL Recall (immediately then delayed) in need of additional filler interactivities to have a total change of time of approximately 5' to get to T=5' and then to the T=10' recall time points. Optionally, the user may automatically be given other interactivities to fill the remaining time. In other embodiments, a time interval that is different from 5 minutes may be used, and/or different time intervals may have different durations of time. After step 516, method 500 proceeds to step 520 and/or 522.

In step 520, a WL Recall assessment is performed at time=15 minutes after Session 2 interactivities of Part III (step 516). In addition to a T=+5', T=+10' and/or a T=+15' recall as part of the extended Word List Recall, a modified Word List Recall assessment can use compiled word lists from multiple sessions and associated images, and where the user is assessed at another session and/or at the midpoint and/or conclusion of a therapeutic protocol.

The Word List Recall assessment, together with other assessments, can be conducted in sessions in the presence of a healthcare worker. Assessments can also be conducted in a self-directed manner by the user themselves using audio recordings and analysis of the user's responses for Word List Recall assessments. Alternatively or additionally, the assessments may be made for SQ2-type questions (Spatial, Quantitative and Qualitative), which can also be verbally transmitted. Alternatively or additionally, the assessment may be transmitted using a device including direct input into a device, and/or through a secondary device, such as a scanner where the user's inputs are recorded on paper and then scanned for analysis by the platform and/or healthcare worker.

Similarly, for a facilitated assessment the user is tasked to recall the Word List at specified times and to verbally state and/or manually record their responses. The recall and the recording of the recall can be performed with a compiled list of words from the word list as well as non-image cued word list words. The user is then tasked to identify from the mixture of words, only those words contained in the word list. The audio recording of the user's verbal responses can be used as a biometrics tool to indicate changes over time in various vocal and/or voice related metrics. A mixture of image-cued and un-cued words in a word list (where the words may be used both positively and negatively associated with an image or image set). After performing multiple interactivities with word lists, more of the un-cued words may be remembered more easily than prior to performing the interactivities, because the user's overall memory operations may be improved by the use of cued words.

In step 522, the user data is stored. Storing the data occurs in either alternative, after steps 515, 516, and/or 520. The data stored in step 522 may result from session II interactivities of step 516 and the WL recall assessment of step 520. The data stored in step 522 maybe used in future sessions to identify an appropriate skill level and/or personalized interactivity for the user, and/or in generating a progress metric.

In step 524, the user's profile is updated with the information stored in step 522.

In step 526, the user's progress metric is produced and displayed.

In step 528, the session ends, although if the user and/or clinician desires, a fourth part of the session can be started in step 530 or 532 with Session 2 interactivities within the same sitting, which may be used to further test the user's memory abilities (and/or as further reinforcement of a message, policy, and/or instruction, for example). Step 530 is performed by users that are using the platform in a FreePlay mode (where the user decides and chooses the images, interactives and/or skill level) or in a Challenge mode (where the user decides that the system should automatically find interactivities that are challenging based on the user's skill level). Whereas, step 532 is performed if the user is using the system in a Protocol mode (where the user is following a specific predefined protocol or regimen of interactivities).

In an embodiment, each of the steps of method 500 is a distinct step. In another embodiment, although depicted as distinct steps in FIG. 5, step 502-532 may not be distinct steps. In other embodiments, method 500 may not have all of the above steps and/or may have other steps in addition to or instead of those listed above. The steps of method 500 may be performed in another order. Subsets of the steps listed above as part of method 500 may be used to form their own method.

FIG. 6A is an example of a flowchart showing different options for how a registered user may interact with a multi-purpose interactive cognitive platform resulting in the display of a user progress metric. Method 600 may be an embodiment of step 512, 514, and/or 516 (FIG. 5). The user may choose FreePlay Mode, Challenge Mode, and Protocol Mode. In addition to choosing the mode, the method provides many steps that allow the user to personalize the GUI, the interactivity, and/or to include a Mem+ assessment which includes the collection of intra-activity speed, accuracy and process data (which is referred to as alpha-type data) and post-activity data (which is referred to as beta-type data), and optionally third party and/or biometric-type data (which is referred to as gamma data) as described further below. Intra-activity speed is the time that the user takes to complete an interactivity. Accuracy is a measure of how many errors are made. Process data (alpha-type data) and post-activity data (beta-type data), and optionally gamma data (biometrics-type data) are discussed below. The personalization process may include interactivity sequence and skill level progressions as well as customization of the User Interface (e.g., interactivity interface 229 and/or healthcare worker interface 230) to allow the user to adjust and manipulate the left-right, top-bottom configuration of interface elements. The personalization process may include spatial manipulations of the reference image, changing templates and/or grids, changing the work area containing interactive elements, the resizing of elements, performing zoom capabilities, changing when the image library is hidden, changing the timer toggle, among other platform features.

The platform presents the user and/or healthcare worker with a Protocol mode, which can deliver multiple therapeutic and training interventions based on the user's requirements and dynamic cognitive status using a Standard Protocol template or a customized protocol. Mem+ assessments may also be implemented by a healthcare worker to address user-specific issues, as part of a chronic and/or transient condition to help support brain health and/or as an assessment for obtaining a baseline of a user's cognitive status for tracking changes over time. Mem+ assessments may be implemented to address the introduction of new medications, drug safety during drug development, cognitive norms following anesthesia administration, and/or to evaluate the effectiveness of an intervention. The Standard Protocol template delivers a series of interactivities in a directed fashion, and/or as part of a progression. The template may be divided between Easy, Medium, and Hard levels which may be entered at any of the sessions automatically and/or according to a healthcare worker's directions (in other embodiments there may be fewer or more gradations of the level of difficulty of a test or battery of tests) and Mem+ alpha, beta and optionally gamma-type assessment data collected through the interactivities.

In one embodiment, each Easy, Medium and Hard level has a minimum of number of sessions (e.g., 12 sessions per level) and may use the same image set for a predetermined number of sessions (e.g., for groupings of 2 sessions) over a predetermined time-period (e.g., on a weekly basis), for example. Within each skill level, the interactivities may also range from easy to difficult along a continuum or vary only with the image sets presented to the user which are used in grouped sessions (for example the grouped sessions may be weekly sessions—sessions grouped by the week). In general, all platform modes can use switch-capable image sets (multi-stable), non-switchable image sets (stable) and/or a mix of switchable and non-switchable image sets, as well as, the component images, according to the therapeutic and/or training protocols, and/or according to user-defined choices.

The Standard Protocol may have multiple sub-modes which may allow the user to develop and/or advance their skills using a subset of the interactivities which target specific skills and processes. Interactivities are assigned weighted values based on their engagement of individual cognitive domains. In one embodiment of the Standard Protocol, where the user seeks to further develop attention-focusing skills and processes, the user is presented with a series of interactivities using image sets that might utilize a variable sectioning strategy, which can be portrayed as an attention-focusing progression, but where the sum total of the collection of interactivities or the individual interactivity is still multi-domain in character to greater and lesser degrees across the different cognitive domains. Continuing with the attention focusing example, the platform may also deliver a subset of images, which may also contain distractor and/or attractor elements (e.g., the flower of FIG. 6A, while in the image of FIG. 6E). The image and/or image set's content objects may be represented as part of an image or may be represented as the image itself in its entirety. For example, in the case of a flower, the flower may be viewed as either an attractor or distractor depending on the context, and the second, and/or third images in a composite (See FIG. 6B-E, the flower of FIG. 6B is the attractor-distractor of the composite image of FIG. 6E. The user interacting with an image or image set which contains the flower element may then be tasked with an appropriate measure of attention using Mem+ post-activity (Mem+ beta) assessments such as SQ2-type questions related to the flower image and/or one of the other images in the composite. For example, with the image set stimulus removed, the user can be tasked to answer the question, "what color was the flower?" and/or, given a selection of multiple choice options to identify, the choice flower most similar to the one in the image or image set. In an embodiment, the user can be tasked with identifying a subset of flower images in a complex field of flowers which may include flowers with subtle differences and/or significant differences from the target flowers to be identified. Other distractor elements may be presented to the user separate from the image and/or image set content, such as environmental changes, audio distractions and other sensory-stimulating and/or deprivations to create a stressful and/or distraction-rich environment. Image-based distractor and attractor elements can vary from user to user in terms of areas of interest within an image which attract a user, and may distract the user from the task. Attracter/distractor elements can be large or relatively small and represent another nuanced aspect of the platform which can be personalized to meet individual user needs and interest.

In step 610, a registered user starts methods 600. If the user is not registered, the system may not allow the user to start method 600 and/or may request the user to register (see also step 410 in FIG. 4), and performs method 400 of FIG. 4. In method 400, each new user is tasked with completing a baseline set of interactivities, given at one of three different skill levels, depending on their assessed, estimated and/or projected abilities to obtain a baseline measure using standardized references for a variety of variables, including: age, gender, education, pre-existing medical and/or psychological and cognitive health status. In method 400, the user may self-register to use the resources and perform method 600 or the user may be registered by a facilitator (practitioner, professional, therapist, and/or caregiver). In step 610, the user decides whether to activate the FreePlay (User-defined) mode, the Challenge mode, and/or is directed to access the Protocol mode using a standard protocol or a customized protocol. In an embodiment, if the user is engaged with the platform in a self-directed manner, the user can access one or more of the following modes in a session: FreePlay, Challenge, or Open Protocols (in other embodiments there may be other options which are specific to a subset of cognitive deficits and/or to skills performance improvements). The Protocol mode may offer the user the option of participating in a research study or to assist in testing a custom protocol in development. Multiple types of registration would be available to the user for a user-initiated registration in the Open Protocols mode option. A re-evaluation of the user's skill level and/or cognitive abilities may be conducted periodically and the initial data may also be compared to other data from another player, and/or to another point-in-time. Users of different ages, genders, demographics, conditions, and/or other parameters may be compared to one another for comparative purposes in building predictive analytics for early diagnosis and identification of cognitive changes over time. Users engaged in the Protocols options are assessed within the protocol, relative to the user's baseline measures and the assessment may be compared to other normalized data sets.

If, in step 610, the user chooses the FreePlay mode the method proceeds to step 615. If in step 610, the user chooses the Challenge mode the method proceeds to step 620. If in step 610, the user chooses the Protocol mode (or if the protocol mode is chosen for the user may a practitioner) the method proceeds to step 625.

In step 615, the user activates the FreePlay Mode. In FreePlay mode, the user may resume a saved interactivity or begin a new one. The user is provided with tools for choosing the images, interactivities, and skill level. In FreePlay Mode, the interactivities and skill level may be chosen at the discretion of the user. The user's progress, during FreePlay may be measured according to, and/or based on speed and accuracy measures, including error-type assessments in which the user completes the interactivity or interactivity set as Mem+ alpha-type assessment data is always collected from the interactivities. The best time in which the user finished the interactivity and/or the user's score may be posted and compared to other users scores using the same scenario (images, skill-level, and interactivities) in a modified type of competitive play against other users and themselves to improve their personal scores. Step 615 may optionally include substeps 630 and 645. Optionally, after step 615, the method proceeds to steps 655, 660, and/or 665.

Alternatively, in step 620, based on the user's prior selection the Challenge Mode is activated. In the Challenge mode, users are also provided with a fixed battery of interactivities that may be chosen based on their difficulty and the user's skill level. The interactivities may be selected by the system so that the user feels he/she is being challenged. In the Challenge mode, the user may be prompted to try a higher skill level, or the system may, in a responsive adaptive manner automatically adjust the interactivity's skill level, via adjustment logic 236. In the Challenge mode, completion of the tasks progresses the user through levels of increasing difficulty and/or complexity with respect to image content, sectioning strategy and/or the number of tasks required to complete the level. Completion statistics are available for each user at each level and sub-level, and which can be made available to peers using the site based on user privacy settings. In addition to a professional collaborative space, a challenge collaborative space can be included in the platform which encourages users, through game design and competitive play between users, to develop and share their own user-defined interactivities and/or interactivities set configurations. The social space allows for peer-to-peer interactions, such as to see one another's scores (depending on privacy settings), and may also include statistics, chats, and potentially live tournaments similar to multi-player game sites where time to completion, number of steps, number of errors, and types of errors are a metric of success. In addition, the cross-over opportunities may include testing of professional game boards (interactivities sets) with volunteer end-users; and/or, the development and sharing of a wider range of interactive tools suited to different user groups with different health conditions through the different types of collaborations, including the migration of user-developed interactivities sets to Protocol mode. Optionally step 620 includes steps 640 and 650. After step 620, the method proceeds to step 655.

Alternatively, in step 625, the user may choose to proceed or be directed to Protocol Mode. In Protocol Mode, the user engages with interactivities that are part of a protocol for assessing and/or treating a condition and/or a protocol developed for improving a skill, ability and/or process and/or processes. Protocols may be developed by clinicians for users and/or suitable to groups of users across ages, gender, language and motor capabilities, and/or conditions. Users may be individuals who have been selected by professionals to participate in one or more healthcare programs. Optionally step 625 includes step 635. After step 625, method 600 proceeds to steps 655, 660, and/or step 665. In some embodiments, as part of the Protocol mode 625, the session ends in step 665 because the user is not assigned to a protocol yet or because the timing of the protocol does not allow a user to participate at this time. The Protocol mode can include multiple clinician-defined protocols and includes a professional collaborative space for peer-to-peer sharing of user experiences, research collaborations and developed or in-development protocols for specific conditions.

In step 630, the user performs the interactivities of a User-defined Mode which is a mode that is defined by the user. The User-defined mode may be defined as part of steps 615 and/or 630 or at an earlier time. The User-defined mode may be a set or interactivities that were chosen by the current user or another user. Interactive protocols developed by non-professionals or professional may be placed into a test bed area and which can be shared with other general users (optionally the protocols developed may be protocols that were tested and proven treatments, but which may need to be tested for software bugs or optionally may be part of a research program).

User-defined mode may include any choices the user made previously to personalize one or more interactivities, the GUI, the images, interactivities and skill level, unless the user is participating in a protocol where user settings are defined within the protocol. After substep 630, method 600 proceeds to substep 645. Substep 645 may be a substep of substep 630.

In step 635, optionally as part of step 625, a user is assigned to a protocol by a healthcare worker. In some embodiments, after the user is assigned to a protocol, a Mem+ assessment occurs (step 655). After step 635, method 600 proceeds to step 655, 660, and/or 665.

In step 640, optionally as part of step 620, as part of the Challenge Mode (step 620) a System-defined mode is activated. The System-defined mode may be defined by the system, based on the user's skill level, so that the user finds the interactive challenging. The interactives of the user defined mode may be chosen solely on the user's skill level (e.g., without regard to any protocols for treating any particular condition or improving any particular cognitive ability). The System-defined mode may optionally be based on protocols provided by healthcare workers or researchers for a current user. Alternatively System-defined mode may take into account all of the previous information about the user and, via an algorithm, decide which mode would be best for the user. After step 640, method 600 proceeds to step 650.

In step 645 (optionally as part of steps 615 and 630), images, skill level, and interactivities are chosen by a user via the User-defined Mode, which defines the activity. After step 645, method 600 proceeds to Step 655 if Mem+ assessment is desired, or method 600 proceeds to Step 660 where user data is updated. As described in detail below for collecting Mem+ alpha, beta and/or gamma-type data through the interactivities.

In step 650, the user's skill is assessed and the user is provided with interactivities that match the user's new skill level. Optionally, the skill progression interactivity may be an interactivity that is performed, to assess the user's skill, as part of a process of the system automatically defining an interactivity. The skill progression interactivities may also include interactivities that are more difficult than interactivities previously provided to the user. The increased level of difficulty may be based on the user's increased skill that resulted from interacting with the initial set of interactivities and/or are provided by the system based on either the images, achievement thresholds, skill level, for example, based on one or step 640 as part of the User-defined mode, or chosen by the user based on the System-defined mode implemented in step 635.

Steps 610-650 may be an embodiment of steps 450 (FIG. 4), 512, 514 and/or 516 (FIG. 5).

In step 655, a Mem+ assessment is launched by the system. The assessments may be based on a set of interactivities which the user is tasked to complete. The time to the completion of the task contributes to building the metric. Other factors that may contribute to the metric are: how the task is completed, the number of correct or incorrect placements and/or responses, repeat errors in placements, and/or reaction time. The user may be rated according to the overall skill level, and skill level adjustments, via adjustment logic 236, may be performed during the interactive (e.g., based on the rating assessed during the interactivity and/or the same session).

Stable or multi-stable image sets may be used to assess the user's cognitive capabilities and/or skill level. The user may be rated based on the overall complexity of the multi-domain interactive or a selected battery of multi-domain interactivities. The user's interactivity pattern may be factored with multiple variables, including: time of day, sleep patterns, medication changes, stress/daily impacts, and other changes in health status which can be assessed through onboarding and pre-session surveys. The Mem+ assessment may be based (e.g., inferred from) on performance in the interactivities of steps 615, 630 and/or 645, on steps 620, 640, and/or 650, or on steps 625 and/or 635 (optionally, without expressly performing method 500). Optionally, the interactivities of steps 615, 620 and/or 625 may be performed as the interactivities of steps 512, 514, and/or 516 of method 500. Similarly, steps 502-510 may be part of step 610, step 518 may be performed between different instances of steps 615, 620, and/or 625. Alternatively and/or additionally, further interactivities may be performed in order to implement method 500 of FIG. 5.

In step 660, the user data created by steps 610-655 is stored. Step 660 may be an embodiment of step 522. The data stored may have been generated during any of steps 615-655. In step 665, the session ends. Step 665 may be an embodiment of step 528. Returning to step 625, in an embodiment, if the user is not assigned to a protocol yet or if the timing required by the protocol does not allow a user to participate at this juncture, method 600 may proceed from step 625 directly to step 665 without the user performing any interactivities. Protocol users may also be users in research and/or clinical studies. Protocol users may also be represented by general users who have an interest in the healthcare program, e.g., self-recruited into the program studies to test software and/or as participants in the studies directly. Protocol users may also access a separate development area for non-professionals (or professionals) as developers for developing new interactivities sets, new protocols for new therapies and/or to evaluate a condition-related assessments. The interactivities can also be made available to Professional Protocol Developers for use (and/or for further subsequent study).

In step 670, the user profile is updated after the session ends, and, if desired by the user or the healthcare worker. Step 670 may be an embodiment of step 524. In step 675, the user progress/metric is displayed. Step 675 maybe an embodiment of step 526. After step 675, steps 530 and 532 may be performed. Optionally, steps 524/670 and 526/675 may be performed between and/or as part of either of both of steps 660 and 665.

In an embodiment, each of the steps of method 600 is a distinct step. In another embodiment, although depicted as distinct steps in FIG. 6A, step 610-675 may not be distinct steps. In other embodiments, method 600 may not have all of the above steps and/or may have other steps in addition to or instead of those listed above. The steps of method 600 may be performed in another order. Subsets of the steps listed above as part of method 600 may be used to form their own method.

FIG. 6B shows an example of a first image that has a single centrally placed image with some edge characteristics and a relatively uniform background; FIG. 6B has an atypical contiguity and a low ambiguity value. FIG. 6B is used in making a composite image, which is referred to in FIG. 6E.

FIG. 6C shows an example of a second image that is used in making a composite image, which has a contiguity. FIG. 6D shows an example of a third image that is used in making a composite image, which has a contiguity. FIG. 6E shows a 3-image composite made from FIGS. 6B-6D.

The flower of FIG. 6B is an example of an Attractor-Distractor which operates as a disruptor element, because of the relatively solid color of the flower, and consequently the flower appears in the figure position. The shoreline of FIG. 6D has defined contiguities with both a horizon-type shoreline and color block. FIG. 6D contains disruptor elements, vertical distractors with the long-stemmed flowers in the foreground. The contiguity and/or contiguities of the image of FIG. 6C has dominance as the image is perceived to assume the background position relative to the other images of the composite FIG. 6E. The image of FIG. 6C is dominant to the image of FIG. 6B, because the contiguities of FIG. 6B are better defined than those of FIG. 6C. The contiguity edges in the image of FIG. 6C are more irregular as compared to the edges of the contiguities in the image of FIG. 6B. Similarly, the contiguity characteristics of FIG. 6D are dominant over FIG. 6B on the left side of the composite shown in FIG. 6E, but less so in the portion of the composite on the right, but FIG. 6D is not dominant over FIG. 6C. For example, contiguity hierarchies can be seen in the composite of FIG. 6E, the 3-image composite of FIGS. 6B-6D, and in the 2-image composites of FIGS. 23B-D of the alternative groupings of the component images in FIG. 23A.

Figure 7:
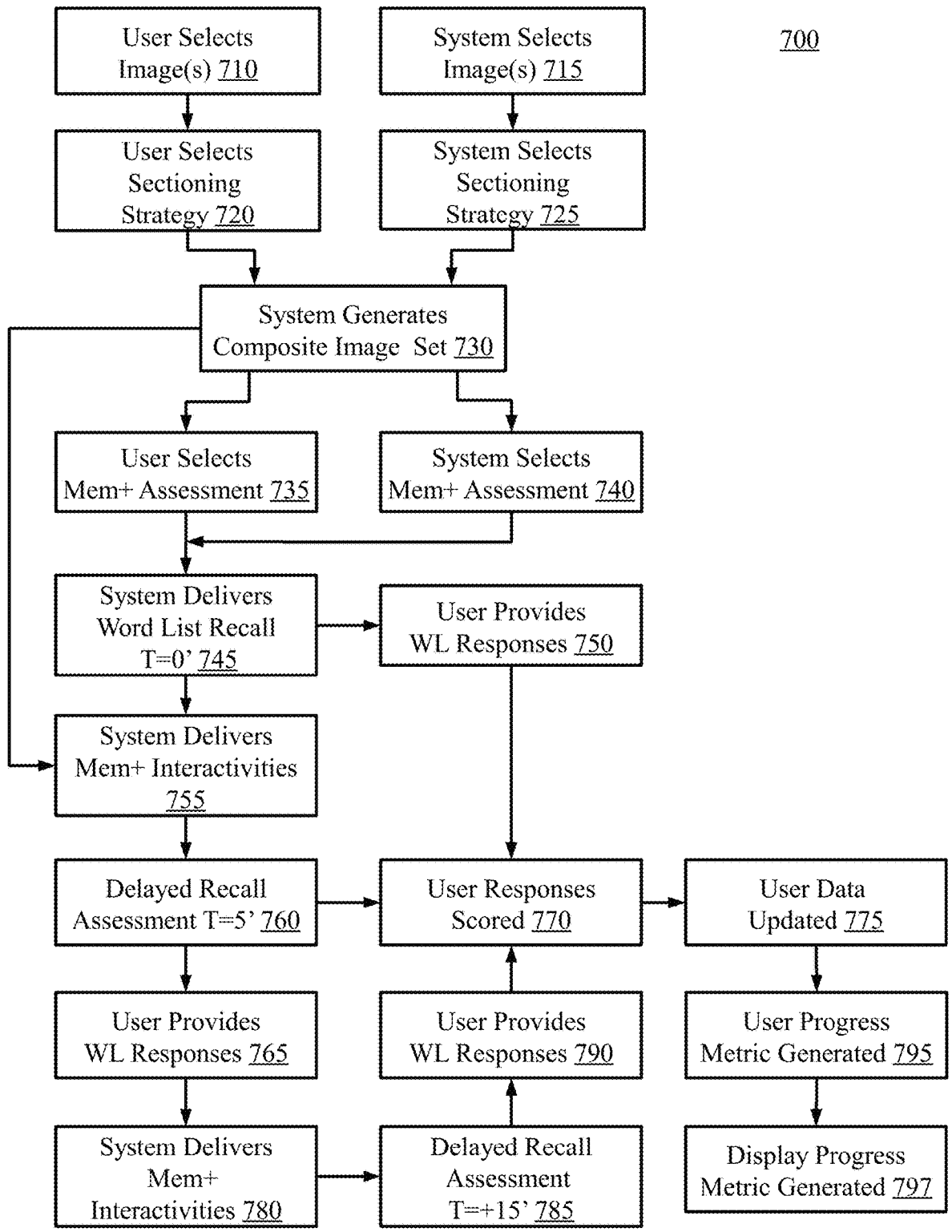
FIG. 7 is an example of protocol options for a user starting with the selection of one or more images from a graphical user interface.

FIG. 7 is an example of protocol options 700 for a user starting with the selection of one or more image from a graphical user interface (which may be part of patient interface 229 and/or healthcare worker interface 230). In an embodiment, the option 700 can be used whether the user or the system selects the images that are then used for interactivities for the multi-purpose interactive cognitive platform. Method 700 may be an embodiment of step 630 or 645/650 (FIG. 6A). Method 700 may also be performed prior to the performance of step 625 so as to establish a protocol for the user to use as part of step 625 (FIG. 6A). Method 700 may be an embodiment of step 440. See FIGS. 22A-22D and FIGS. 23A-23F for examples of 2- and 3-image composite image sets that have been sectioned in various ways.

In one alternative, the user selects one or more images in step 710 from a library of images. Alternatively, the user may upload one or more images.

Alternatively or additionally, the system selects one or more images in step 715 from a library or may select from the upload of one or more images. In step 715 the system may select an image based on a protocol, a previously entered user criteria, and/or previously entered clinical criteria.

In step 720, the user selects the sectioning strategy for the image or images that the user selected in step 710 and/or that the system selected in step 715. The user may select the sectioning strategy based on personal preferences.

Alternatively or additionally to step 720, in step 725, the system selects the sectioning strategy for the image or images that the user selected in step 710 and/or that the system selected in step 715.

In step 730, whether the images are selected by the user or the system, the system generates composite images sets based on the images and the sectioning strategies chosen (assuming an interactivity is chosen or determined and involves a composite image). Depending on the embodiment, after step 730 is performed, method 700 proceeds to either step 735 or step 755.

In step 730, whether the images are selected by the user or the system, the system generates composite images sets based on the images and the sectioning strategies chosen. After step 730, the system may immediately deliver the interactivities to the user (step 755), including activating the Mem+ assessment tools for collecting user alpha and/or beta data or the User may select to include a Mem+ assessment which would include questionnaires, data analysis and reporting tools with an option for post-interactivity assessments (beta assessments) and/or integration of biometrics/physiologic assessment tools (step 735). In an embodiment, there may be a chart indicating changes to the user's performance. In an embodiment, the user is not shown significantly decreases in their scores, but instead results are shared via private email communication or with a designated individual including family, caregiver, and/or medical personnel, such as a primary physician. In an embodiment, users' cognitive scores are monitored automatically and the score may be reported to remote locations automatically. In an embodiment, the magnitude of the change in a score is greater than a threshold value and/or is a score changes and crosses a threshold, an alert may be sent to a caregiver, professional caregiver, and/or medical professional.

In step 740, alternatively, the system may activate the Mem+ assessment tool based on the composite image set to alert a user to participate in a cognitive health checkup.

In step 745, the system may deliver a Word List Recall activity to the user at T=0'. The Word List recall and WL recall methods are discussed in detail in FIG. 5 (see step 510). Step 745 may be an embodiment of, or embodiment of part of, step 510 (FIG. 5). However, the embodiment of step 745 includes a timed aspect. Optional visible timers may be used. While embodiments have primarily focused on individual users, the system can be used in a group setting, allowing multiple users to work on the same game board of interactivities but in turns and/or in teams. Optional timers may be used to set a time limit within which each turn must be completed. In an embodiment, in some interactivities users are provided with a special piece that may need to be placed within a specified time in order to score the number of full points and/or to meet a specified threshold for error, time, and/or reaction time metrics. The reward and/or rewards attendant awards the rewards, when the piece is correctly placed by a user in compliance with an incentive program. In one embodiment, such a program is designed to encourage user compliance with a "you win" strategy to promote adherence to a protocol, to introduce new platform features and/or to include a special points reward earned to support and/or encourage user progress or completion of a task associated with an interactive mode of any type.

The use of rewards in interactivities may include audio rewards, points in a game-type setting, to indicate progress and/or regression. The rewards may be incentivized tangible rewards offered through third parties, such as coupons, discounts, tickets or other premiums, and/or intangible rewards such as a placement of completed image set posted in a user gallery, and/or high scores/best times posted on a leaderboard, depending on the configuration. The configuration can be designed for competitive game play for team building and/or for remediation and treatment with incentives offered for compliance with a therapeutic regimen, and/or protocol, and/or related to a performance enhancement training regimen. The rewards approach can be applied to the entire user interactive experience or to parts such as with the "special" interactive element (game piece) which has a reward beyond what may be included in generalized interactivity such as with FreePlay and/or Challenge mode.

The use of a score or other value, and/or built cognitive profile may be provided to the professional and/or user to assist them in measuring the effectiveness of the user's efforts and to identify areas of improvement and/or areas in need of improvement. The metric is factored with other "point in time" measures as well as the Mem+ assessments delivered to the user as part of the baseline measurements, and through subsequent formative and summative assessments during a given protocol. The assessment may be based on data collected intra-activity (Mem+ alpha assessments), post-activity (Mem+ beta assessments), and/or with third party assessments to obtain a comprehensive Cognitive Profile which includes "glocal" markers and indices of change. Glocal markers demonstrate global cognitive engagement skills and processes across multiple cognitive domains using related interactivities, but which also demonstrate domain-referenced skills, which are local.

Returning to step 730, in an embodiment in which method 700 proceeds from step 730 to step 755, after step 730, the system may immediately deliver Mem+ assessment interactivities to the user (step 755) or the User may manually select the Mem+ assessment (step 735).

Steps 710, 720, and 735 may be part of step 615 (FIG. 6A). When steps 710, 720, and 735 are performed as part of step 615, step 730 may also be performed as part of step 615. Steps 715, 725, and 740 may be part of steps 620 and/or 625 (FIG. 6A). When steps 710, 720, and 735 are performed as part of steps 620 and/or 625, step 730 may also be performed as part of steps 620 and/or 625.

Step 745 may be an embodiment of, or embodiment of part of, step 510 (FIG. 5).

In step 750, the user provides a response to the word list, which may be the user recalling and verbally and/or inputting the words of the word list that the user was able to immediately recall. Step 750 may be an embodiment of a second part of step 510 (FIG. 5). After step 750, method 700 proceeds to step 770, which is discussed below.

In step 755, based on the Word List (WL) recall, the system delivers Mem+ based assessment interactivities, which may be used in step 512 (or any of steps 512-516) (FIG. 5) as part of steps 615, 620, 625 and/or 655 (FIG. 6A). The interactivities provided by step 755 provide alpha and beta assessment data while at the same time also serving as distractor-type interactivities or filler interactivities, which the user interacts with until 5 minutes have passed since step 745 or 750 for conducting a delayed recall memory assessment. In one embodiment, the Word List Recall is not included in an assessment battery and an alternative, such as Object ID-Memory and/or Dimensional Descriptors can be used (e.g., in step 655). In one embodiment, a language-based memory assessment may not be included though other memory assessments are included in interactivity battery to capture working, short- and long-term memory functions. The Mem+ assessment interactivities can be any of those discussed herein. In some embodiments, the Mem+ assessment interactivities may be chosen by the user, based on user preferences, and/or chosen by a healthcare professional.

In step 760, a delayed recall assessment is delivered to the user at time equal to approximately 5 minutes. In other words, the user is allocated approximately 5 minutes in which to complete a set of interactivities. At the completion of the interactivities, the user is given the word list delayed recall assessment. The set of interactivities performed from time equal to 0 to the five minute time point serves to provide assessment data but also as a distractor. Step 760 may be an embodiment of, or part of an embodiment of, step 519 (FIG. 5). After step 760, step 770 (which is discussed below) may be performed prior to or after performing step 765.

In step 765, the user provides the word list (WL) responses. Step 765 may be an embodiment of a second part of step 519 (FIG. 5). After step 765, method 700 proceeds to step 780.

In step 770, based on (and after) step 750, user responses are scored. Step 770 may be an embodiment of a third part of step 519 (FIG. 5). In step 775, based on step 770, the user data is updated. Step 770 may be performed multiple times, once after step 750, once after step 760 and once after step 790. Alternatively or additionally, step 770 may be performed (e.g., once) based on steps 750, 760, and/or 790. Step 775 may be an embodiment of step 524 (FIG. 5) and/or an embodiment of a part of step 670 (FIG. 6A). After step 770, method 700 proceeds to step 795, which is discussed below.

In step 780, the system delivers a set of Mem+ assessment interactivities in step 765. The interactivities delivered in step 780 may be used in steps 514 and 516 (FIG. 5). In step 785, a delayed recall assessment is made at approximately T=10' to 15 minutes, but can be at other times in other embodiments (e.g., at 20 minutes, at 60 minutes). Step 785 may be an embodiment of a first part of step 520. In step 790, the user provides the WL responses in response to step 785. Step 790 may be an embodiment of a second part of step 520. After step 790, step 770 is performed (e.g., another time).

In step 795, the user baseline and/or progress metric is generated (which may be performed prior to performing steps 526 and/or 675). The user's responses from each of the recall assessment interactivities, are stored. Storing the responses may include actual voiceprint recording data, the user's responses may updated, and/or a progress metric may be generated (see steps 770-797).

In step 797, user metrics are displayed and/or sent to a remote location.

In an embodiment, each of the steps of method 700 is a distinct step. In another embodiment, although depicted as distinct steps in FIG. 7, step 710-797 may not be distinct steps. In other embodiments, method 700 may not have all of the above steps and/or may have other steps in addition to or instead of those listed above. The steps of method 700 may be performed in another order. Subsets of the steps listed above as part of method 700 may be used to form their own method.

Figure 8A:
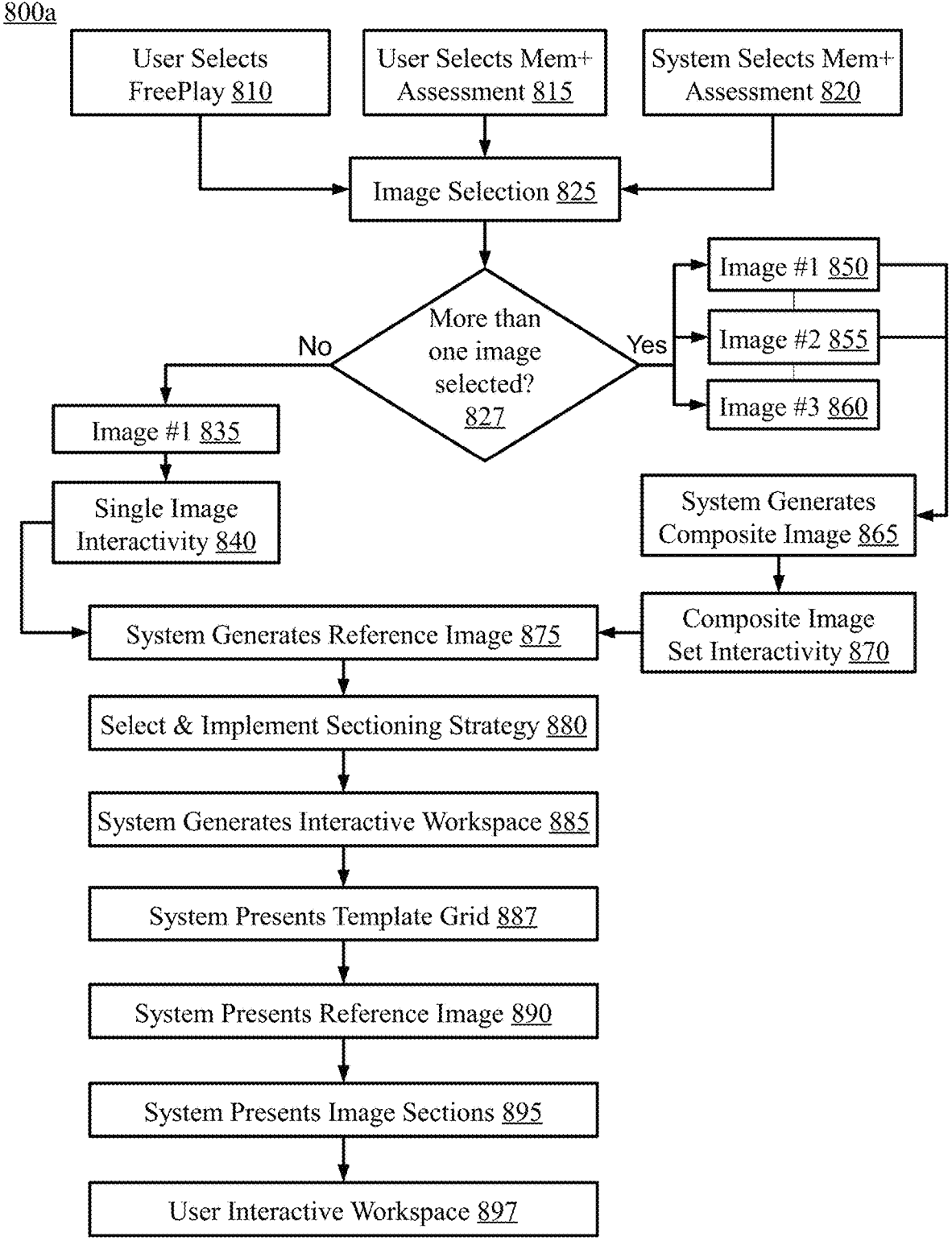
FIGS. 8A and 8B are an example of a method of making a user interactive workspace.

FIG. 8A is an example of a method 800a of making a user interactive workspace. Method 800a may be implemented by interactivity builder 242. The workspace may be produced in one of several ways. Method 800 may be an embodiment of steps 710-730 (FIG. 7). See FIGS. 20A-20G for an example of a graphical user interface or workspace. The user may be tasked to work through a series of interactivities using the individual images, and/or through a series of interactivities related to composite images comprised of 2-3 component images where the individual component images are serially sectioned and juxtaposed to generate an interspersed pattern of non-adjacent component image sections.

Interactivities may include hands-on as well, hand-free activities, and/or as virtual view-only interactivities, and where a hands-on interaction can be with physical and/or digital manipulatives. Virtual view-only interactivities occur in the user/viewer's mind (user input may be received via a microphone and/or still and/or video camera, EEG, and/or eye tracking, or there may not be user data captured). The virtual view-only interaction of method 800 is also an interactivity, because the view-only interaction requires the user's engagement. Whether actively or passively conveyed to the user and whether the user is consciously, or subconsciously, engaged in the interaction, the user is still engaged and therefore the user is performing an interactivity, such as resolving the figure-ground ambiguities in an image set, identifying objects as parts of the whole, tracking across contiguities in virtually re-assembling the image in the ground position, and if using multi-stable image sets observing the switching of images in the ground position. To conduct assessments in Virtual View-only mode, however, requires the use of additional biometrics-type tools such as eye tracking and EEG. Modified speed and accuracy measures can be taken, but these lack the precision of device-based, hands-on interactivity-based assessments. As such, speed and accuracy measurements would not necessarily be available for detailed analysis. The lack of refined speed and accuracy data, however, does not diminish the value of the platform, but does limit the availability of a subset of data for analyses and reporting.

Similarly, offline assessment interactivities are more challenging to monitor in terms of speed and accuracy measures, and in monitoring and tracking user movements for process analyses. The hybrid TUI prop system described previously can provide users with a tangible tactile prop similar to an offline interactive but provides a means of capturing speed, accuracy and movement mapping data.

In step 810, the User selects FreePlay mode. Step 810 is performed if the user decides to interact with system 100 in FreePlay mode. FreePlay is discussed in FIG. 6A (step 810 may be part of step 615). Alternatively or additionally, in step 815, the user selects to include Mem+ assessment data tracking.

Alternatively, in step 815, the system selects a Mem+ assessment to be launched based on stored user information and/or provided when the user logs in. Step 815 may be performed if the user chooses to include a Mem+ assessment. Step 815 may be performed as part of a Challenge mode.

In step 820, the system selects the Mem+ assessment based on the user information stored and provided when the user logs in. Step 820 is performed if the user decides to have the system choose a Mem+ assessment level with associated interactivities based on stored user data. Step 820 may be performed as part of Protocol mode. Next, after steps any of steps 810, 815, or 820, in step 825, one or more images are selected.

In step 827, in all cases, a determination is made as to how many images are to be used to create an image (e.g., a composite image) for the interactivity set. The image or images may be combined into 2-3 image composites, depending on the number of component images and where the individual component images are serially sectioned and juxtaposed to generate an interspersed pattern of non-adjacent component image sections.

Composite images of method 800 may be created from two or more component images which have been serially sectioned and the image sections from one image interspersed with another one or with two images as shown in FIGS. 22A-22D and 23A-23F.

If it is determined in step 827 that a single-image interactivity is desirable, the method proceeds to step 830, and a single-image algorithm is loaded. In step 835, the system offers the user a choice of images to select. After receiving a selection, the system proceeds to step 840. In step 840, a single-image interactivity is produced based on the single image selected.

Figure 23E:
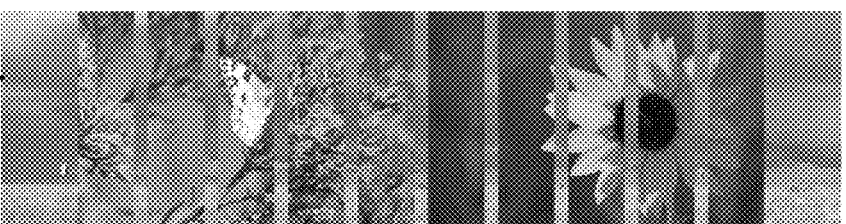
FIGS. 23E-23F show examples of different sectioning strategies, including interweaving a solid color background.
Figure 23F:
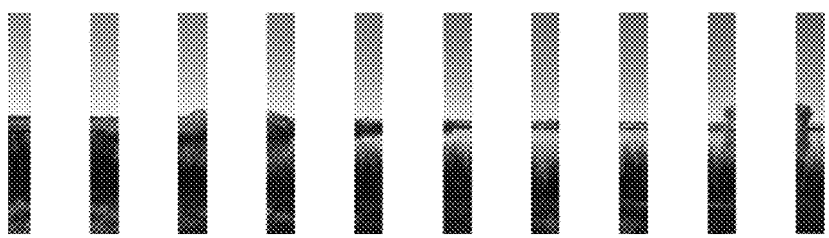

Returning to step 827, if in step 827 it is determined that the user would like to select multiple images (e.g., in FreePlay mode), then in step 845 (FIG. 8B) the user is offered multiple images to select from or is given access to the image library. If in step 827 it is determined that a protocol calls for multiple images (e.g., in Protocol mode), then in step 845 the system selects multiple images based on the protocol and/or the user is offered a selection of images that comply with the protocol. If in step 827 the system automatically determines that multiple images is most appropriate according to the user's skill level (e.g., in Challenge mode), then in step 845 the system automatically selects or suggests multiple images. In step 845, algorithms for creating multiple-image interactivities are retrieved. In step 850, Image #1 is selected, in step 855, Image #2 is selected, and in step 860, Image #3 is selected. Step 860 is only performed if the composite image is determined to be at least a three component image composite. In some embodiments, more than three images are selected. In some embodiments, two images are selected. In one embodiment, in composite image scenes at least one of the images (Image #1) may contain real-world content portrayed as a photograph, graphic, painted image, illustration or as a constructed image including a tangible prop or other type of physical and/or digital manipulative, while at least one other image (Images #2, #3 and/or #4) may contain content and be presented in a format similar to Image #1 or can consist of a solid color or mix of solid colors including: white, black or gray tones of varying percentages or other types of illustration (FIG. 23F).

The sectioning strategy may be uniform or variable for one or more of the images. The juxtaposition strategy may be sequential, non-sequential, may include partial or full masking (skipping) of one or more image sections, and/or use a solid color image giving the appearance of unfilled gaps between image sections. Sectioning strategies may be uniform for each of the component images between 1.5% and 50% and/or portray a mixed sectioning strategy, depending on the construct. Each component image may follow an independent sectioning strategy, and each component image may itself portray a mixed sectioning strategy as shown in FIGS. 22A-22D and FIGS. 23A-23F. The variation in sectioning strategy can contribute to the designated skill level for one or more of the platform's interactivities. In general, the thinner, and/or the smaller the image sections, the more challenging the interactivities. The thinner and/or smaller the image sections, the greater the demand on the user's cognitive abilities, and the greater the requirement placed on the user to focus their attention on the contiguities and/or other component elements of an image that provide visual cues in interpreting an image that are helpful for identifying parts of the whole. In one embodiment, the impact of the sectioning strategy, 10%, 12.5%, 20%, 25%, and 50% for example is adjusted with a weighted factor, reflecting the availability of image content cues and image details within the image sections for facilitating the user's analyses of the image set's content and the complexity level to solve the interactivities (FIG. 4C/Table 2). In one embodiment, a 20% sectioning strategy may lend itself to ease of use as compared to a 25% sectioning strategy and/or a 10% sectioning strategy because of the ease of access and/or hyphenation of content in more refined sectioning strategies within a sectioning strategy range, a "sweet spot", but which is further metered by the component images used and the complexity of the image set's content.

In one embodiment, a progressive reduction in the sectioning width, and/or an increase in the number of sections is conveyed to the user for all and/or part of the image. The change in sectioning may be used as part of a training protocol to convey attention-focusing skills development, through an increase or decrease in the sectioning. The increase or decrease in sectioning may be used, and the subsequent interactivities used, for one or more of the images in a composite image set, and/or individual images with associated interactivities, as can be with the use of images containing potential attractor/distractor elements.

In step 865, a composite image is generated from the images selected in step 850 and 855 and optionally step 860.

Figure 8B:
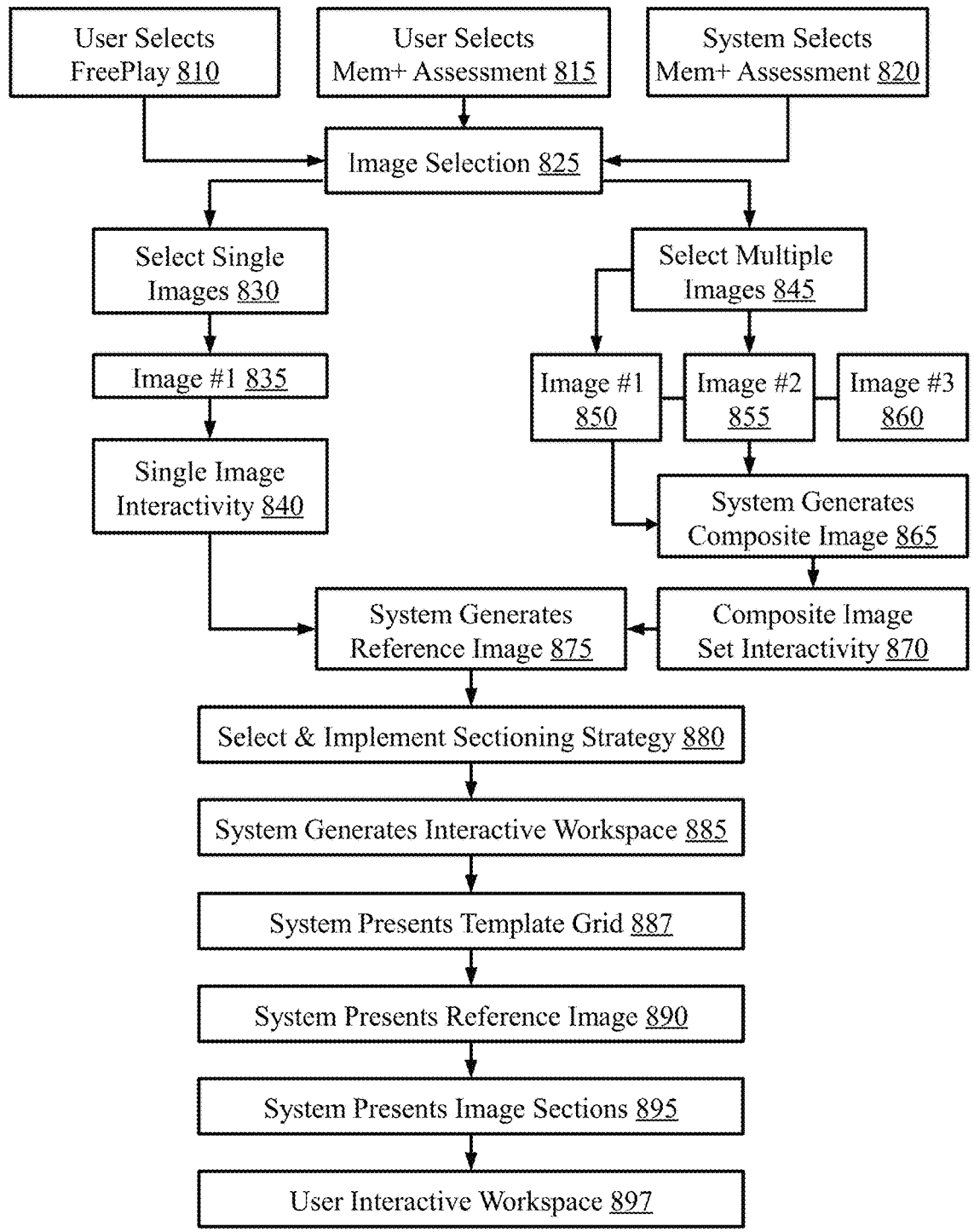

In step 870, a composite image set interactivity is produced using the composite image of FIG. 8B, step 865.

In step 870, based on the images selected in steps 850-860 and step 865, the system creates a user interactive workspace. In some embodiments, "user-interactive" means that at least one user-preference was incorporated into the workspace.

In step 875, optionally the system generates a reference image based on the image selected in steps 835 and/or the composite image generated in step 865, and the user may be provided with the reference image. The reference image may be presented in several modes: continuous, intermittent, preview, limited and/or on-demand display mode. The reference image may serve as the source of the visual cues where the user can match to, and/or work with, associated manipulatable elements related to the reference image towards working on and completing one or more tasks. The non-continuous display of a reference image for an interactivity and/or set of interactivities can increase the cognitive requirement for memory and attention, among other cognitive domains impacted directly or indirectly by the change in cognitive demand and related to the interactivity used. As described for the sectioning strategy, factors are applied to adjust the weighted values for each cognitive domain's representation and contribution to the multi-domain character for each interactivity (FIG. 4B-4E/Table 1-4). In one embodiment, the user is provided with a reference image by which to model the user's tasks for a subset of the platform's interactivities but with a variable engagement of multiple cognitive domains as compared to intermittent, preview, or on-demand use of reference images which can introduce additional memory and attention domain metrics.

In one embodiment, where the reference image is presented as a composite image set, the user's referencing of the image to perform associated tasks may provide for additional interactivity based on the composite image sets' Virtual View-Only interactive capacity. The view-only capacity may be based on cognitive engagement—a factor which is differentially weighted into the multi-domain character of a given interactivity and its contribution with a battery of interactivities, and the switch capacity of the composited image set (stable versus multi-stable). The additional image set interactions based on the user's referencing of the image set can be viewed as a value-added element for therapeutic and training goals. The additional interactions with the image set may be delivered via the multi-purpose interactive cognitive platform's presentation of a composite-type reference image to the user and the use of the reference image by the user while completing an interactivity task.

Tables 1-4 of FIGS. 4B-4E, respectively, are examples of weights used for scoring interactivities related to method 800. In an embodiment, reference images can be presented to users for a specified period of time and/or can be available throughout the interactivity session and/or previewed for the user prior to the start of the interactivity, and/or is available to the user on-demand, depending on the requirements of the treatment and/or training protocol.

In step 880, the system selects and implements a sectioning strategy, in step 885, the system selects or generates an interactive workspace using the sectioning strategy and the images chosen, which may still need to be populated with an image and/or images sections. In step 887, the system selects or generates a template grid. In step 890, the system presents the reference image. In step 895, the system presents the image sections. In step 897, the user interactive workspace is developed using the image or images selected and based on the interactivity and/or interactivity set. The interactive workspace is matched to the interactivity and/or interactivity set and/or sets for tracking speed and accuracy data, and mapping user movements.

In an embodiment, each of the steps of method 800 is a distinct step. In another embodiment, although depicted as distinct steps in FIG. 8A, step 810-897 may not be distinct steps. In other embodiments, method 800 may not have all of the above steps and/or may have other steps in addition to or instead of those listed above. The steps of method 800 may be performed in another order. Subsets of the steps listed above as part of method 800 may be used to form their own method. FIG. 8A and method 800*a* is essentially the same as FIG. 8B and method 800*b* (and may be implemented by interactivity builder 242) except that in steps 830-840 of method 800*b* of FIG. 8B are combined into steps 835 and 840 of FIG. 8A.

Figure 9:
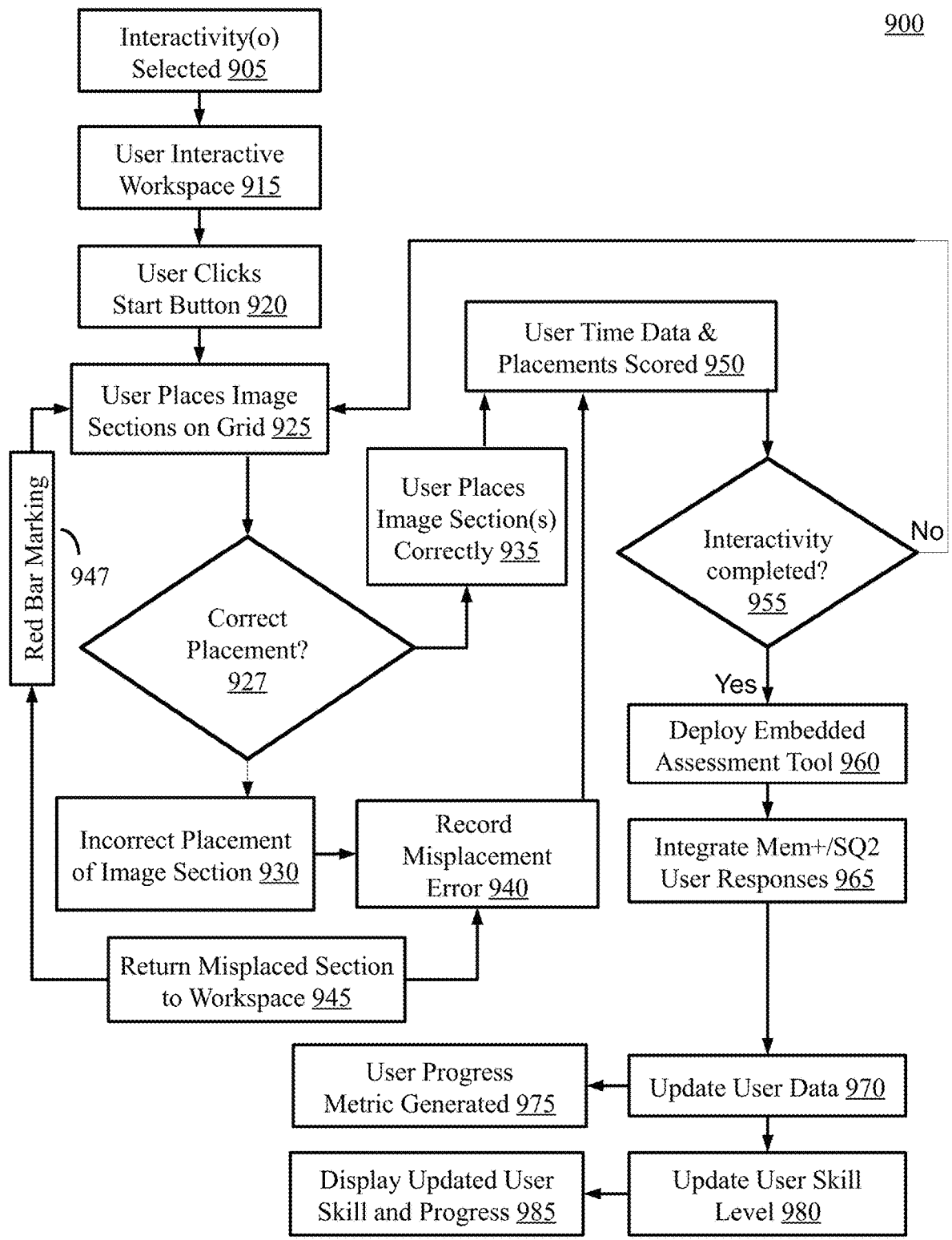
FIG. 9 is an example of a method of a user interacting with a multi-purpose interactive cognitive platform to generate a metric and/or update a user skill level.
Figure 10:
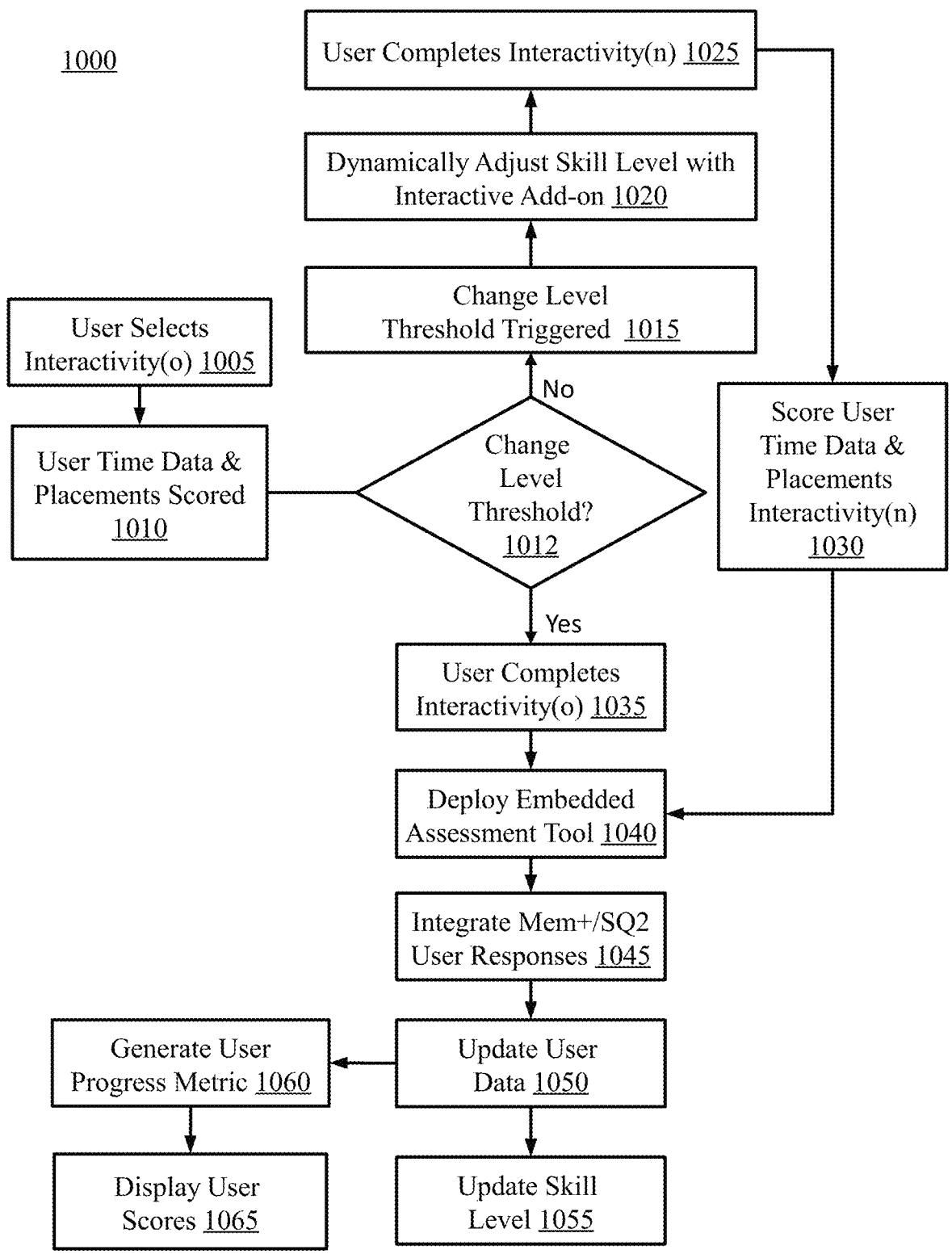
FIG. 10 is a second example of a method for interacting with a multi-purpose interactive cognitive platform by a user (see also FIG. 9).

FIGS. 9 and 10 provide embedded assessment tools which are part of the multi-purpose interactive cognitive platform through intra-activity Mem+ alpha assessments of speed and accuracy, and movement mapping; in post-activity Mem+ beta assessments; and, with the integration of integrated and/or third-party biometrics data and tools. The methods of FIGS. 9 and 10 may be implemented by assessment logic 234. A feature of the platform is the embedded aspect of the assessments across multiple cognitive domains, which are integrated with the interactivities. The embedded aspect of the assessment allows the cognitive assessments to include other metrics beyond intra-activity speed and accuracy measures and sub-measures of individual domain associated skills, but rather to look at cognition as a whole, at both skills and processes across multiple cognitive domains.

FIG. 9 is an example of a method 900 of a user interacting with a multi-purpose interactive cognitive platform to generate a metric and/or update a user skill level. Method 900 may be implemented by assessment logic 234.

In step 905, an interactivity (0) is selected by a healthcare worker or user. Interactivity (0) refers to an interactivity which has not yet been personalized to a user.

In step 915, a user interactive workspace is provided for the interactivity (0). In step 920, system 100 waits to receive input from the user, such as click on a start button. The user starts the interactivity (0) by first clicking the start button when he or she is ready (step 920) and then in step 925, system waits to receive a placement of an image section on a grid (step 925). Grids may be used in a Compose, Construct, Missing Pieces, and/or Extrapolate interactivity, for example. Grids may vary in size, and may be larger or smaller than a reference image. In step 927, a determination is made as to whether the piece has been placed correctly. If in step 927 it is determined that the piece was incorrectly placed, method 900 proceeds to step 930. If in step 927 it is determined that the piece was correctly placed, method 900 proceeds to step 935.

In step 930, if the system determines that the user incorrectly places one or more sections, an auto-alert element indicates the incorrect placement to the user. In an embodiment, in the all-edge design of image parts, the elimination of specific fitted shape restrictions makes all placements possible, whether or not the placement is correct. As such, users rely on alternative information including: color, content and contiguity cues and patterns to effect correct placements. In some embodiments, in the digital version of the platform, the user may be alerted to a misplacement with visual and auditory alerts, and/or kinesthetic feedback. Alternatively or additionally, vibratory indicators of correct and/or incorrect placements, can be used to provide proximity hints to the user. In some embodiments, as the user places an element incorrectly, the misplaced element can be automatically returned to the "active" interactivity space or game board area, and can be marked or tagged as having been tested and/or tried by the user. In some embodiments, a visual signal (e.g., a red bar) is placed above used pieces which have been incorrectly placed by the user. However, other graphical or sensory methods can be used to indicate incorrect placements. In an embodiment, the user is given the chance to correct the placement until the placement is correct (in another embodiment the user may be given a finite number of chances to correctly place a piece, such as between one and 30 chances to correctly place the section or sections on the grid) and/or within a specified time limit. In some embodiments, the user is given the option to change the skill level if the placement and/or interactivity is too difficult, and/or image sets too visually complex (e.g., if the user tries more than 5 times to correctly place the section on the grid and does not accomplish correct placement).

In addition to absolute errors, an error pattern can be discerned through movement mapping. In some embodiments, the interactivity will go on to the next interactivity or protocol step if the user cannot correct the placement after a present number of tries, such as between one and 10 tries, and/or within a specified period of time.

The alert system may be configured to allow the user to receive dynamic feedback to correct near-completed and/or actual mis-placements. The alert may be dispensed with to allow the user to complete the placement of all game pieces without feedback, and then the user's placements may be scored at the completion of the task. Depending on the protocol, the user may be given an opportunity to correct mis-placements for the purposes of achieving a better score, and/or for learning purposes about missed visual cues and cognitive skills development. For example, the user may be offered the option to select a second choice or a second-best choice option. A secondary digital interface such as a phone, tablet computer, or other type of smart device may also be used to scan or capture an image of the user's completed interactive task and results conveyed to the platform's assessment module for scoring purposes, and as such can be used with offline, non-device based interactivities.

After step 935, method 900 proceeds to step 950. After step 930, method 900 proceeds to step 940. In step 940, the misplacement error is recorded. In some embodiments, the number of times required for the user to correct the incorrect placement is also recorded. Tracking of user errors and categorization of error types, including repeated attempts of placements in the same location using the same image part provides insight into user strategy and decision-making (random versus targeted), and is informed by attention, memory and other cognitive considerations.

In optional step 945, the misplaced section is returned to the workspace (in an alternative embodiment, the misplaced section is left where it has been placed by the user, optionally with a visual indication that the placement is incorrect). After step 945, method 900 continues to optional step 947 and a red bar is displayed to indicate the misplacement of the piece. After step 940, 945, or 947, method 900 returns to step 925 to allow the user to choose another placement of a piece. After step 935, method 900 proceeds to step 950. Step 950 may receive input from step 940, if there was a misplacement of a piece prior to step 935.

In step 950, the user's time, speed and accuracy/placement data are scored. A time stamp may be recorded after the user clicks the start button (step 920) to record time information, after the user places an image section correctly (step 935), after the user completes the interactivity, and/or after a misplacement error (step 940) to provide numerous speed metrics including time per move and/or per placement. An increase in the amount of time to effect placements towards the end of a session, and/or an interactivity may be indicative of user fatigue, and the platform's interactivity sets adjusted, optimized and/or personalized to meet and reflect the user's current and future needs.

In step 955, a determination is made whether the user has completed interactivity (0). If the user has not completed the interactivity, method 900 returns to step 925, where the user selects another piece to place. If the user has completed the interactivity, method 900 proceeds to step 960, where the user selects another piece to place. The completion of the interactivity may occur when the image has been properly constructed, and/or pieces properly matched, and/or pieces properly placed on a grid, depending on the interactivity. The completion of the interactivity may occur when the system indicates that the user has completed the task, and/or after the user has spent more than a predetermined about of time with the interactivity and/or exceeded another limit such as time and/or errors.

In step 960, the Mem+ embedded assessment tools are deployed—the interactivity is assessed. The Mem+ embedded assessment tool may compute and/or recompute other test metrics, such as those in step 965 and the Word List Recall tests, based on input from the current interactivity.

In step 965, the Mem+/SQ2, a beta-type of assessment, may be integrated with the user's responses to the interactivity. Word List Recall assessments and SQ2-type questions are image-based evaluations, which may be integrated into and with the interactivities, allowing for a more sensitive and accurate assessment of the user's memory and attention performance, which can be metered to address a user's changing and evolving status and/or requirements across all cognitive domains.

The platform's Mem+ interactivity-embedded assessment tools therefore may include an evaluation of the number of correct/incorrect responses and/or the time taken to complete an interactive task. The platform's embedded assessment tools may include the pattern of errors together with the recall/delayed recall and extended delayed recall, and SQ2 responses. The data collected by the Mem+ assessment tools may provide a usable metric to help assess a user's cognitive capacity and/or cognitive status relative to baseline measures and other measurements. The data collected by the Mem+ assessment tools may be taken at different points in time and/or at defined intervals. The data collected by the assessment tools may be collected as part of a clinical and/or research protocol, and/or other comparative measures. Some other comparative analysis measures may include Big Data analyses of user data obtained from a sample pool and compared across user data, physical and physiological variables including: age, sex/gender, diagnosis, stress levels, EEG, education, professional positions, and/or potentially other contributing variables to develop reference data for comparing multiple user groups with and without cognitive issues.

The data collected by the assessment tools may contribute to the user profile, which may be used in building both point-in-time (cognitive profiles) and changes-over-time metrics (cognitive signatures) based on user data. The data collected by the assessment tools may contribute to large cohort analytics (Big Data). The data collected by the assessment tools may be integrated into and with third-party data. The data collected by the assessment tools may be used to inform the platform's evolution and in continuously improving models for product research and development to meet current and future user and/or cohort needs. The data collected by the assessment tools may be useful in developing predictive analytics benchmarks for a broad range of uses, including: diagnostics, treatment and cognitive change monitoring.

In step 970, the user data is updated based on the integration of Mem+ beta data and, in step 975, a user progress metric is generated. In step 980, based on the interactivity and analyses of the embedded assessment data, the user skill level is updated. In step 985, a display of the users speed and accuracy, skill level progress may be updated and/or sent to a remote location.

In an embodiment, each of the steps of method 900 is a distinct step. In another embodiment, although depicted as distinct steps in FIG. 9, step 905-980 may not be distinct steps. In other embodiments, method 900 may not have all of the above steps and/or may have other steps in addition to or instead of those listed above. The steps of method 900 may be performed in another order. Subsets of the steps listed above as part of method 900 may be used to form their own method.

FIG. 10 is a second example of a method for interacting with a multi-purpose interactive cognitive platform by a user 1000 (see also FIG. 9). FIG. 10 provides possibilities for what happens after a user selects an interactivity.

In step 1005, the user selects an interactivity (0).

In step 1010, the user time, data and placements are scored. After step 1010, optionally method 1000 proceeds to step 1012 where a determination is made whether there is a need to change the user's threshold level. For example, in step 1012, method 1000 may determine whether the user is a first time user (or should be treated as a first-time user for other reasons or should take interactivity (0) for other reasons), or not. If, in step 1012, if it is determined that threshold level should be changed and/or the user should not take interactivity (0), method 1000 proceeds to step 1015. If, in step 1012, it is determined that that user should take interactivity (0), method 1000 proceeds to step 1030. Optionally, the determination of whether the user should take interactivity (0) may be based on the scoring in step 1010. In other words, after step 1010 and/or 1012, the user may either complete the interactivity (in step 1035) or a change-level threshold may be triggered (in step 1015) based on the previous progress results by the user and/or the progression of the user's cognitive disorder. A change in the level threshold (step 1015) is a threshold at which a change is detected and the level is adjusted, via adjustment logic 236. In some embodiments, the change may be because as a user practices the types of interactivities provided, which is referred to as practice effects, and where the user may get better at the interactivities and as such may require a higher skill level.

After step 1015, method 1000 proceeds to step 1020. In step 1020, after the change level is triggered, the skill level is dynamically adjusted, via adjustment logic 236, by the system with an interactive added to the interactivities set.

Next, in step 1025, the user completes the new interactivity (n).

Next, in step 1030, the user time, speed and accuracy/placements data in the interactivity (n) are scored.

If after step 1010 or 1012, method 1000 proceeds to step 1035, then in step 1035, in other words, if the change level threshold is not triggered (e.g., if it is the first time the user is interacting with an interactivity), the user completes interactivity (0), not interactivity (n).

In step 1040, the embedded assessment tool is deployed after completion of either interactivity (0 or n), after either step 1030 or after 1025.

In step 1045, the Mem+/SQ2 user responses are integrated with the assessment of the interactivity. In an embodiment, Mem+/SQ2 are used as an example of a post-activity assessment (beta category assessment) as described in conjunction with FIG. 15.

In step 1050, the user data is updated, the skill level is then updated in step 1055, and/or the user progress is generated in step 1060. In step 1065, a display of the user's speed and accuracy, skill level progress may be updated and/or sent to a remote location.

In an embodiment, each of the steps of method 1000 is a distinct step. In another embodiment, although depicted as distinct steps in FIG. 10, step 1005-1060 may not be distinct steps. In other embodiments, method 1000 may not have all of the above steps and/or may have other steps in addition to or instead of those listed above. The steps of method 1000 may be performed in another order. Subsets of the steps listed above as part of method 1000 may be used to form their own method.

With reference to FIGS. 1-15, in some embodiments, two or more of the platform's components can be combined. For example, in a Stress module, a suggested sequence of interactivities may be provided to the user as part of an assessment. Alternatively or additionally, the user may elect to use the platform in a self-directed manner, accessing a user-defined module, which may allow the user to select the image sets, the interactivities, the skill level, and/or whether to use a timer. The user's interactivity statistics are analyzed, recorded, and stored, and the data statistics may be presented to the user to help inform platform-assisted recommendations and/or the user's own decisions. The platform may be integrated with additional devices, including tablets, phones, other touch-mediated devices, and/or equipment that allows for the monitoring of physiological metrics. Similarly, the platform can be integrated with add-ons for monitoring other biometrics. As a non-limiting example, the platform may be integrated with multi-channel EEG, single channel EEG, eye-tracking, a heart rate monitor, respiratory rate monitor, blood pressure monitor, galvanic skin response monitor, pupil dilation monitor, temperature monitor, and/or other spatial, temporal and/or frequency brain states monitoring as assessment tools.

FIGS. 11-15 provide methods for use of the platform by a professional to create a specific cognitive diagnostic or assessment (test), which may be implemented by protocol builder logic 240. In the platform, the term "professional user" may refer to a clinician, practitioner, a researcher, a healthcare worker, a platform administrator in the healthcare profession or other industry, including human resources, and/or a professional game maker or a gamer. The platform may be designed to allow for dynamic configurations and the assembly of the elements to generate personalized game boards, and interactivity batteries (interactivity sets), based on user preferences, and/or healthcare worker-based, and/or other professional user inputs. The system's dynamic configurations may be used for therapy and/or diagnostic and/or assessment or other professional purposes ("professional"). Configurations may be generated by system AI logic in evaluating a user's preferences and/or cognitive requirements.

Figure 11:
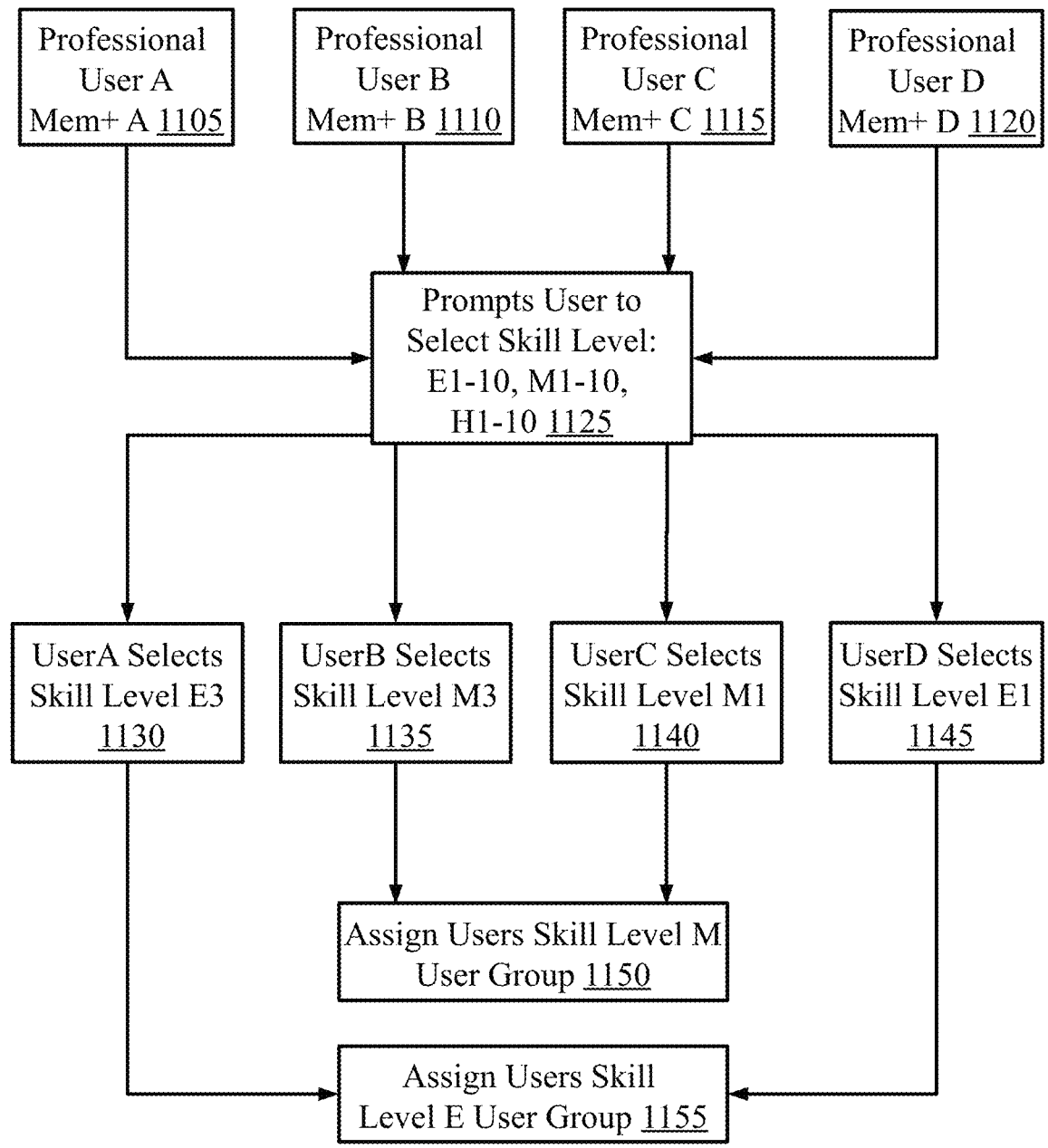
FIG. 11 is an example of a collaborative method in which professional users (e.g., healthcare workers) analyze data from users based on skill levels.

FIG. 11 shows a method 1100 for allowing professional users to build diagnostic, assessment, treatment, and training tools. Professional communities may be able to use a menu of choices and branched options to establish interactivity parameters towards building their own protocol configurations (protocol configuration builder), via protocol builder logic 240 and/or may opt to use a Standard Protocol Template and/or the template to meet their requirements as is and/or for building their own configurations. Configurations may be stored under a Protocol label and may be used to build a dynamic library of diagnostic, assessment, treatment and training tools to support cognitive well-being and skills training for people across the cognitive spectrum. FIG. 11 is an example of a collaborative method in which professional users (e.g., healthcare workers) may analyze data from users based on skill levels. The method in FIG. 11 may be used by a healthcare worker for treatment or diagnosis of a disease, or for understanding a diagnostic tool, producing an effective treatment, producing an effective diagnostic tool, producing an effective treatment tool, and/or for research into understanding brain, neuronal and neurocognitive processes for example. In some embodiments, the method may be used in combination with other treatments (to analyze the effectiveness of the combination of treatments) and/or with other diagnostic tools. FIG. 11 shows collaboration (e.g., via collaboration logic 238) between four professional users, but in other embodiments, collaboration may take place between any number of professional users from 2 to 100s or 1000s or more. Professional users may include, but are not limited to: healthcare workers, analysts, professional game makers, software developers, practitioners, and/or gamers. Professional users typically do not include patients or those that interact with interactivities for training, therapy, and/or testing themselves, but the collaborative space may provision for interactions between professional users and enrolled users in a trial or study where researchers can virtually interact with users and/or study participants for assessment purposes and/or remote monitoring.

View-only mode may also be referred to as Virtual View-only (VVO) mode. VVO mode is particularly useful for people where hands-on interactivities cannot be performed such as if the user has limited and/or no fine/gross motor control, and/or where the user does not have access to eye-control technology and/or the person has limited or no ability to communicate verbally, and/or where the user is engaged in a primary activity which requires the use of their hands. VVO allows the user to use other methods for approaching the interactivities which can be of cognitive benefit to them. For example, when looking at the image sets—whether using stable or multi-stable image sets—the user's mind is engaged in resolving the ambiguities, related to discerning figure and ground relationships, the perception of depth and in re-assembling the hyphenated image parts into a confluent image. The user's engagement associated with multi-stable images can be captured, tracked, and imaged using eye-tracking, fMRI, EEG/ERP and other physiological biometrics to capture user cognitive metrics. An EEG can be used to help detect potential problems associated with an activity. An EEG tracks and records brain wave patterns. Event Related Potentials (ERP) are measured with an EEG and other brain imaging tools. For example, the healthcare worker says "flower" and the eye tracking tools show eye movement to the flower region of an image set. If the healthcare worker then says "yellow flower," there is specific eye movement to a yellow flower which can be spatially distinguished from a red flower, for example. In some embodiments, a healthcare worker or multi-purpose interactive cognitive platform sourced audio commands can instruct the user to focus their attention on the ground-positioned image in a stable image set, or to maintain their attention on one of the images in a multi-stable image set. In some embodiments, to temporally and spatially refine eye-tracking signals, EEG/ERP signals (or fMRI or SPECT signals or other brain imaging tools) can be matched to image recognition. Further, the system can be used to discern the switch between the component images in a composite image set, for example, done with the user clicking a button and saying switch. This approach, however, lacks temporal accuracy and requires the user to actively engaged in the switch reporting process. The process can be refined by applying technology to demonstrate and characterize the switching phenomenon, which can be done because the platform integrates the use of both stable and multi-stable images, and transitional image sets where a multi-stable image can be transformed into a stable image and in the reverse sequence as well as by using a combination of biometrics and physiological monitoring tools to capture switch events.

In steps 1105-1120, professional users A-D create Mem+ assessment interactivities A-D. Mem+ assessment interactivities are discussed in detail in FIG. 6A. However, the Mem+ assessment interactivities may also include interactivities that can be done in virtual view-only mode (VVO) and/or in hands-free mode. VVO and hands-free modes are particularly useful for professional users who have patients with diseases where patients may no longer have the use of their extremities, cannot speak, and/or have difficulty with speaking or physical movements, including with temporary conditions such as following the administration of general anesthesia where recovery of cognitive functions can be temporarily slowed and/or in recovering from a stroke or traumatic brain injury, and/or for people with neuromuscular conditions such as Parkinson's disease and Amyotrophic Lateral Sclerosis, and/or for persons with locked-in syndrome, and/or those who are classified as minimally conscious but who may also benefit from cognitively stimulating interactivities. Under circumstances in which the patient is impaired, one approach to diagnosing the condition is to observe patterns of brain activity while performing an interactivity. An example of this is hemispatial neglect, also known as hemineglect, where users are essentially unaware of objects, actions or other types of information to one side of space—and which can be on the right or left. With the platform, the user's inability to work with activity spaces, or to place sections in regions spatially located on one side of an image, and/or not be able to reference part of an image such as in a Construct, Compose, and/or Match-type interactivity can be used as a diagnostic tool similar to the Clock Drawing Test. In some embodiments, parts of the patient's brain may be compensating for damaged parts of the brain and/or the patient's may also be trained as part of their working with and through the interactivities. In one embodiment, the user's switch ability can be evaluated because there are hierarchical relationships between contiguities which can be seen with different image combinations. In FIG. 23C, a 3-image composite, the component images have been re-grouped (1:2:3 versus 1:2 versus 2:3 versus 1:3) as shown in FIGS. 25B-25D. These figures demonstrate image-driven differences which are processed differently in terms of figure-ground positioning hierarchies. The figure-ground hierarchical shifts with different image combinations can be tracked by monitoring physiological and biometrics changes. Similarly, physiological and biometrics changes can be tracked when a user is presented with a multi-stable image set where a 3-image combination shown in FIG. 23A of component images (FIGS. 24A(1)-24A(3)) are re-grouped as multi-stable 2-image composites (FIGS. 24C and 24D), and which can be transformed into stable image sets (FIGS. 24E and 24F), respectively by removing the contiguities from one of the component images (FIG. 24A(1)).

With both stable and multi-stable composite image sets, the user no longer perceives just random parts, but rather parts of the whole, and/or the whole itself. Because of figure-ground hierarchical contiguity relationships, and the ability to stabilize and de-stabilize (i.e., manipulate) an image set's figure-ground characteristics, and known differences in switch rate characteristics as a function of age and neuropsychological conditions, the platform can be used to link interactivities and assessments, embedding the assessments within the interactivities using these types of enriched visual stimuli. For example, the user may be presented with a stable image set, and the user may be asked to describe what the user sees. The process of the user determining what the user sees is different when using a multi-stable image set where the user must concentrate (prevent attention shifting and ignore the flanking content) to describe each component image's content individually and which is described in the Dimensional Descriptor interactivity. The ability to identify image elements primarily draws on memory, attention and language domains, and the ability to resolve the image sets ambiguities requires the integrated use of multiple cognitive domains, including: executive function, attention and visual-spatial processes and skills.

The platform's hands-free mode is to be distinguished from the virtual view-only mode which is also hands-free but involves active engagement of the user with the use of an alternative user adaptive type of input devices or use of other assistive technologies such as eye-control, mouse cursor control, voice-activated controls, brain-computer interfaces, another type of intermediary device or tool for the device-based platform components, offline components, and/or hybrid-type components. The use case for hands-free modality can also be applied where the user is not impaired in terms of the user's manual dexterity, but where the user requires the use of their hands for other purposes or functions. A hands-free device can include Virtual Reality/Augmented Reality and/or mixed reality-training devices, such as pop-up displays on visors, helmets, glasses, and/or holographic projections. For some users, a Tangible User Interface (TUI) may be preferable to the graphical user interface (and/or the keyboard). Examples of a TUI prop can include a physical puzzle piece prop with or without other embedded sensors (grip strength, grasp, galvanic skin response, pulse, blood pressure), which may be equipped to detect and track motion using a digital touchscreen and/or other interactive surface.

In step 1125, the system prompts a professional user to select a skill level. In some embodiments, the skill level is determined by a mixture of the sectioning strategy, the number of images, interactivity mix, image content, and/or thresholds to evaluate a new category of users from a clinical research and/or training standpoint. In some embodiments, the skill level is chosen from E1-10 (Easy 1-10), M1-10 (Medium 1-10), or H1-10 (High 1-10), where each of E1, E2, E3 . . . E10 are different skill levels, each of M1, M2, M3 . . . M10 are different skill levels each of H1, H2, H3 . . . H10 are different skill levels, which are labeled sequentially according to increasing or decreasing degrees of difficulty. In some embodiments, a "1" is the easier level and a 10 is the highest level within a skill level bracket.

Adjusting complexity variables (e.g., via adjustment logic 236) adjusts the platform's skill levels, and combined with the "game is not the only assessment" approach where only speed and accuracy metrics are derived for a single cognitive domain or a narrow band of cognitive domains, the platform instead deploys an integrated multi-cognitive domain approach which gives the platform a powerful capacity and versatility to address a multiplicity of cognitive issues and/or learning and/or training situations for people across the cognitive spectrum. For example, complexity can be modulated by varying the number of interactive elements (game pieces), the image content, and the image type (e.g., including whether the type of images are photographs, artwork, line drawings, illustrations, color, halftone, and/or degraded) can be modulated to meet a user's needs and/or user groups' assessment, learning, remediation, and/or training needs. Similarly the number of images (2+) used in a composite and size of the elements can be modulated to meet a user's needs and/or user groups' assessment, learning, remediation, and/or training needs. The content character of the elements, such as whether there is a high or low amount of detail and color variability can be modulated to meet a user's needs and/or user groups' assessment, learning, remediation, and/or training needs. The on-demand, preview and use of a reference image to effect an interactivity's solution, and/or the use of alternate pattern references, such as partial placement of image sections can be modulated to meet a user's needs and/or user groups' assessment, learning, remediation, and/or training needs. The use of stable and/or multi-stable image sets can be modulated to meet a user's needs and/or user groups' assessment, learning, remediation, and/or training needs. The spatial assignment of the elements (whether the elements are grouped, random, or single elements) can be modulated to meet a user's needs and/or user groups' assessment, learning, remediation, and/or training needs. The rotation of image parts and sections can be modulated to meet a user's needs and/or user groups' assessment, learning, remediation, and/or training needs. The individual image sectioning strategy (such as: 1:2 (50%), 1:4 (25%), 1:6 (16.67%), 1:8 (12.5%), 1:10 (10%), 1:12 (8.3%), 1:15 (6.67%), 1:20 (5%), and/or higher/lower percentages) can be modulated to meet a user's needs and/or user groups' assessment, learning, remediation, and/or training needs. Whether the sectioning strategy from image to image and within an image is fixed, mixed, or a variable sectioning strategy can be modulated to meet a user's needs and/or user groups' assessment, learning, remediation, and/or training needs. The type of interactivity mix for both component/single images and/or composite image sets can be modulated to meet a user's needs, interests, and/or regionally-specific image content, and/or user groups' assessment, learning, remediation, and/or training needs. Whether hints are available, whether reference images are used, whether the interactivity components are timed/un-timed can be modulated to meet a user's needs and/or user groups' assessment, learning, remediation, and/or training needs. The time constraints (time-to-completion requirements), the AI adaptations and tolerance/threshold levels can be modulated to meet a user's needs and/or user groups' assessment, learning, remediation, and/or training needs. The word lists and number of words to be recalled as part of a Mem+ assessment protocol can be modulated to meet a user's needs and/or user groups' assessment, learning, remediation, and/or training needs. The SQ2 questions, the number of questions and level of difficulty, among other elements, can be modulated to meet a user's needs and/or user groups' assessment, learning, remediation, and/or training needs—all using a series of related image-based interactivities.

In steps 1130-1145, each User (A-D) selects a skill level. For a given interactivity, the size, and width of an image's sections, together with the image and/or image set's complexity can be varied to reflect a user's skill level and/or changes to their skill level, and/or abilities to make dynamic adjustments, via adjustment logic 236. The dynamic adjustments may be to interactivity boards and interactivity pieces in assessing and challenging cognitive function on a global cognition basis (multi-domain). Adjustments may be made with a particular focus on attention and memory, and/or with other cognitive domains, and to aid in evaluating the user's strategy and problem-solving abilities using the interactivities in terms of user process, solution finding, task completion, movement mapping, and follow-up assessments.

In step 1150, the system assigns the users of the same skill level (E, M, or H) to a user group. For example, in step 1150, User B and User C are put in the same group because User B and User C selected skill level M and in step 1155, User A and User D are put in the same group because User A and User D selected skill level E. In some embodiments, setting multiple users to the same group allows the professional users to better analyze the progress of a user by comparing that user to other users of the same skill level as a cohort. The professional user may also identify whether a user needs to be moved to another skill level based on this comparison or in other embodiments the system's AI logic 224 or via adjustment logic 236 may initiate recommendations or depending on the configuration automatically perform skill level or other adjustments to user interactions with the platform.

In an embodiment, each of the steps of method 1100 is a distinct step. In another embodiment, although depicted as distinct steps in FIG. 11, step 1105-1155 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

Figure 12:
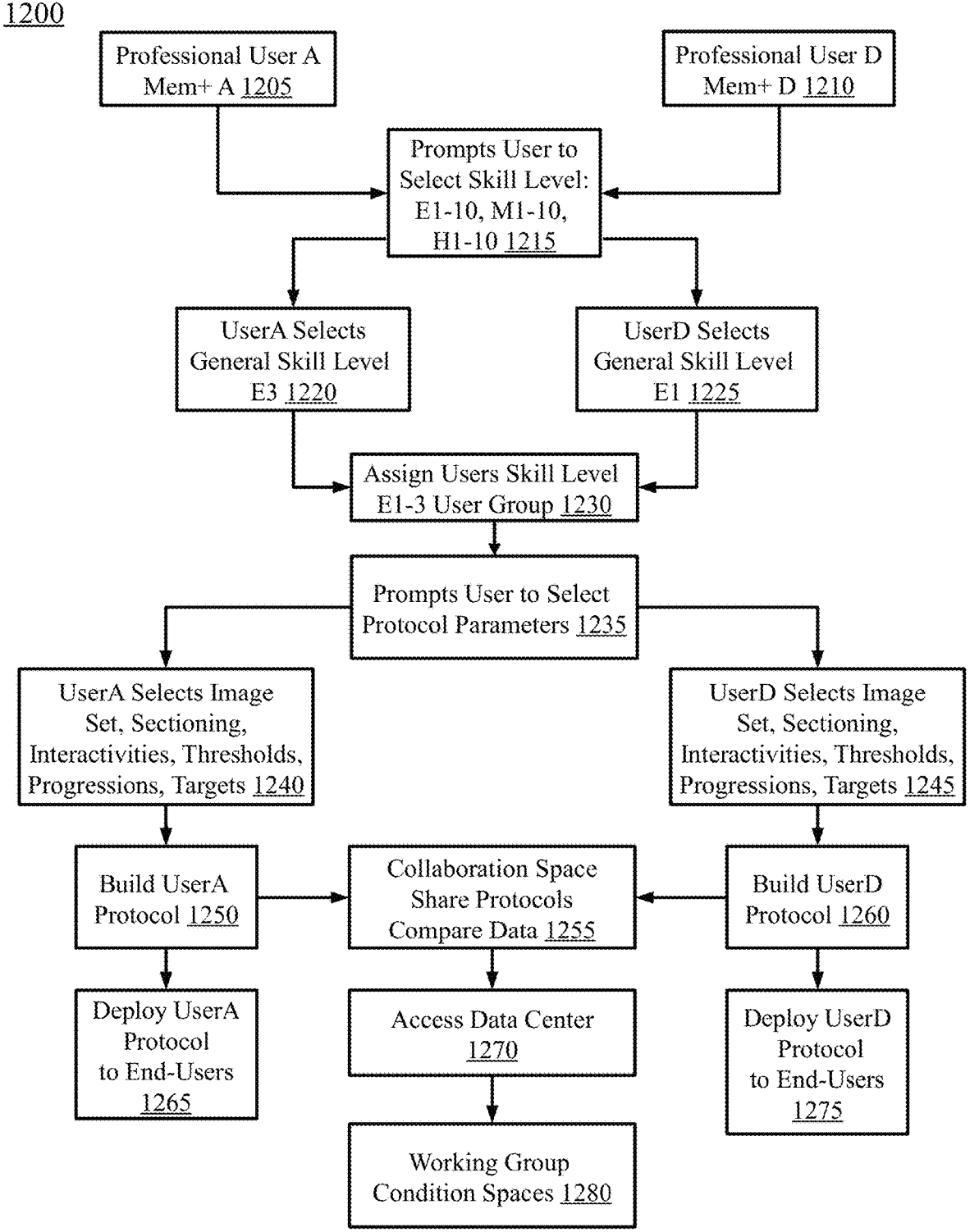
FIG. 12 is a second example of a collaborative method in which professional users (e.g., healthcare workers) analyze data from users based on skill levels (see also FIG. 11).

FIG. 12 is a second example of a collaborative method 1200 in which professional users (e.g., healthcare workers) analyze data from users based on skill levels 1200 (see also FIG. 12). In FIG. 12, professional User A and D are collaborating. Method 1200 may be performed by collaboration logic 238.

In steps 1205 and 1210, Professional User A and D choose a Mem+ assessment set of interactivities (A and D). In step 1215, the system prompts a user to select a skill level.

Next, in steps 1220 and 1225, User A selects general skill level E3, and User D selects general skill level E1.

Then, in step 1230, users that choose skill levels E1-3 are assigned a user group.

After step 1230, in step 1235, the system prompts the User to select protocol parameters, allowing that user to choose how long he or she wants the user to work on an assessment or image set with specific contiguity characteristics, how many interactivities the user may be tasked to do, for example.

In steps 1240 and 1245, User A and User D selects an image set, sectioning, interactivities, thresholds, progressions, targets, for example allowing User A and User D to create a personalized protocol that is still at skill level 1-3. The images and/or image sets can be presented to the user by the system according to a protocol and/or can be selected by the user. After steps 1240 and 1245, if another image set is needed (e.g., for another interactivity, method 1200 returns to step 1235. If no more image sets are needed, method 1200 proceeds to steps 1250 and 1260 (depending on the user).

In steps 1250 and 1260, the system builds a Mem+ assessment protocol based on the skill level and selections (in steps 1240 and 1245) for each of the users, User A and User D. Progressions refer to the sequence of interactivities. For example, staying with the "Construct" interactivity for two images where the user first uses 25% sectioning, then after reaching a threshold for changing skill level, the user may use a 20% sectioning (or the 25% sectioning but with a larger number of smaller image parts to use in Construct). After reaching another threshold for changing skill level, the user might use a 10% sectioning (or another sectioning with even smaller pieces). Each of the changes in sectioning may represent a significant skill level jump. The user may be presented with an option to downgrade (or upgrade the skill level) to another skill level (7.5% cuts, 5% cuts), as part of a change in skill level. Changing to three image composites, not just two images may also be part of a change in skill level. Changing the image set may also be part of a change in skill level. Progressions (or skill levels) can also define what comprises an Interactivities Set (such as Compose 25%; Construct 20%; Construct 10%; Missing Pieces 4×4 grid; MatchME! 25% cuts with half and quarter size pieces).

In step 1255, the Protocol developed for users A and D, in steps 1250 and 1260 are added to collaboration space, thereby allowing the Professional users A and D (and perhaps other Professional users) to share protocols and compare data for group E1-3. Also the protocols developed in steps 1250 and 1260 may be based on protocols previously shared in step 1255. Utilizing a collaborative format and forum for posting questions and information on a message board or with video conferencing, a professional configuration can be shared and re-purposed and/or modified by other Professional users for their applications without having to build a protocol from scratch. The original protocol configuration, developed by a Professional user, may remain unchanged, but other users may be provided with copies of the configuration for their individual use. The collaboration may share protocols for research. The platform may be a research platform for collaboration and sharing of protocols.

After steps 1250 and 1260, in steps 1265 and 1275, the protocols developed for User A and User D protocols are activated and/or deployed to the end-users. As determined by the administrator, a professionally developed configuration may be deployed to the end-user space. In some embodiments, the deployment of the Mem+ assessment interactivities to the end-user space results in an output of assessment data to the collaboration space to build the platform's analytics' capabilities providing a dynamic source of additional datasets.

After step 1255, in step 1270, the Professional users are granted access to the data center, and in then step 1280, the user may create working-group-condition-spaces. As determined by the administrator, a professionally developed configuration by voluntary agreement can be tested with different user groups in a modified evaluation of the configuration by target audiences. "Condition Spaces" can be defined as areas of collaboration for specific diseases. As specialists tend to think about cognition and the kinds of patients a clinician would be treating according to the disease being treated, and thus categorizing collaborative spaces according to the disease being treated can provide a useful, though limited, perspective on disease-based cognitive associations. In an embodiment, other "Spaces" can be defined based on other criteria such as a "Medication Space" defined by a cohort on the same medication protocol or testing a newly developed medication or other treatment protocol. Other "Spaces" can be defined based on collaboration needs.

In an embodiment, each of the steps of method 1200 is a distinct step. In another embodiment, although depicted as distinct steps in FIG. 12, step 1205-1680 may not be distinct steps. In other embodiments, method 1200 may not have all of the above steps and/or may have other steps in addition to or instead of those listed above. The steps of method 1200 may be performed in another order. Subsets of the steps listed above as part of method 1200 may be used to form their own method.

Figure 13:
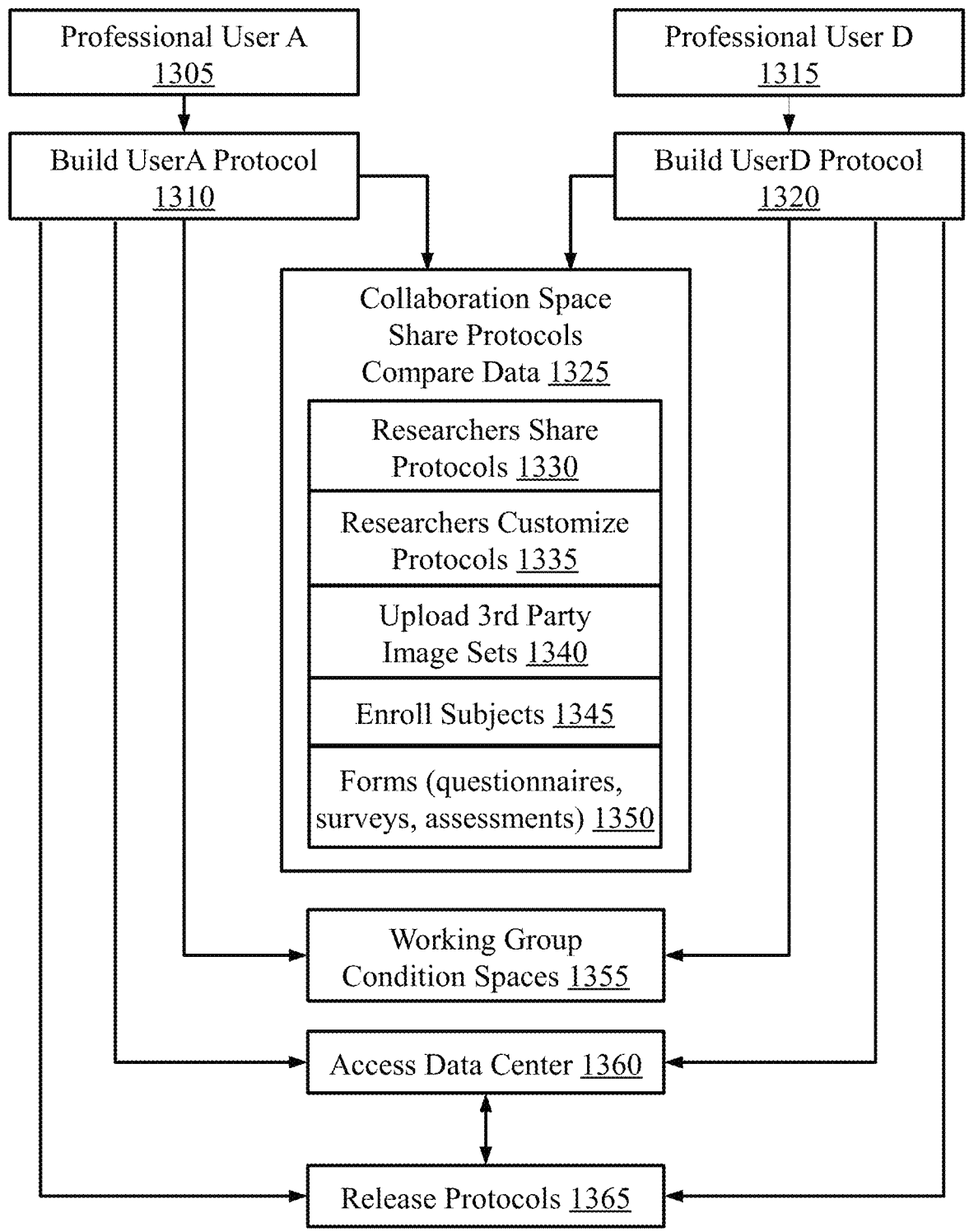
FIG. 13 is an example of a method that allows professional users to create a multi-purpose interactive cognitive platform for specific uses (e.g., tests, diagnoses, treatments of specific diseases) in a collaborative way.

FIG. 13 is an example of a method 1300 that allows professional users to configure a multi-purpose interactive cognitive platform (of system 100) for specific uses (e.g., assessments/tests, diagnostics, treatments of specific diseases) in a collaborative way, which may be implemented by collaboration logic 238 and protocol builder logic 240. The multi-purpose interactive cognitive platform can be produced using collaborative processes between Professional users.

In FIG. 13, two Professional users (A and D) are collaborating to produce a multi-purpose interactive cognitive platform for a joint study.

In step 1305 and 1315, Professional user A and D begin to build a protocol.

In step 1310 and 1320, protocols are produced for Users A and D.

In step 1325, a collaboration space is produced, via collaboration logic 238, for sharing protocols and comparing data and the protocols of user A and D may be entered into the collaboration space with anonymized patient data for privacy protection. Steps 1330-1350 are sub-steps of an embodiment of Step 1325. As discussed in FIG. 12, step 1255, in the collaboration space is a professional configuration which can be shared and re-purposed and/or modified by other Professional users for their applications. The original protocol configuration developed by a user remains unchanged and other users are provided with copies of a configuration for their use. The collaboration can be shared protocols for research purposes. Thus, the platform can be a platform for collaboration and sharing of protocols that are best suited for a specific patient, group of patients, type of patient, or other user group (see steps 1330-1350). In step 1330, clinicians can share protocols. In step 1335, clinicians can customize shared protocols. In optional step 1340, third party image sets are uploaded (if desired). The images and/or image sets may be presented to the user by the system according to a protocol and/or can be selected by the user (e.g., a professional user). In step 1345, subjects are enrolled. The subjects may be anyone who wants to participate in a customized protocol. In step 1350, forms (questionnaires, surveys, and assessments) are prepared, given to subjects, and included in the collaboration space. Protocol user statistics and associated data, including questionnaires and assessments are kept separate and in a research safe assigned to each professional developer who is conducting research studies so as to protect participants' identities and other privacy related data and considerations, including anonymization of shared user/patient records.

In step 1355, working-group-condition-spaces are identified. Working groups may include groups that are appropriate for specific collaborative protocols (e.g., patients with the same diagnosis, patients at the same skill levels, people who want to use the protocols for maintaining cognitive health, patients who need customized treatments, and/or those enrolled in a specific test protocol, for example).

In step 1360, a data center is accessed. The data center may contain the information about whether a user can access a specific protocol. Safeguards may ensure that only users that are authorized to access a particular protocol have access, which may help ensure that a protocol may not be accidentally provided to the wrong user. In at least the embodiment of method 1300, a user may be a professional collaborator.

In step 1365, final collaborative protocols are released to the collaboration space to be used by collaborators.

In some embodiments, steps 1325-1350 can be skipped and the Professional Users can immediately include their protocols within the working-group-condition-spaces. In some embodiments, steps 1325-1355 can be skipped and the Professional Users can immediately include their protocols in the data center (step 1360). In some embodiments, Professional users can immediately include their protocols for use in the platform (step 1365). Steps 1360 and 1365 may depend on one another, in that a protocol, based on data accessed in step 1360, may be stored and released in step 1365, which may generate more data to access, and which may lead to releasing a new protocol, which may be an improvement on the protocol previously released.

In an embodiment, each of the steps of method 1300 is a distinct step. In another embodiment, although depicted as distinct steps in FIG. 13, step 1305-1365 may not be distinct steps. In other embodiments, method 1300 may not have all of the above steps and/or may have other steps in addition to or instead of those listed above. The steps of method 1300 may be performed in another order. Subsets of the steps listed above as part of method 1300 may be used to form their own method.

Figure 14:
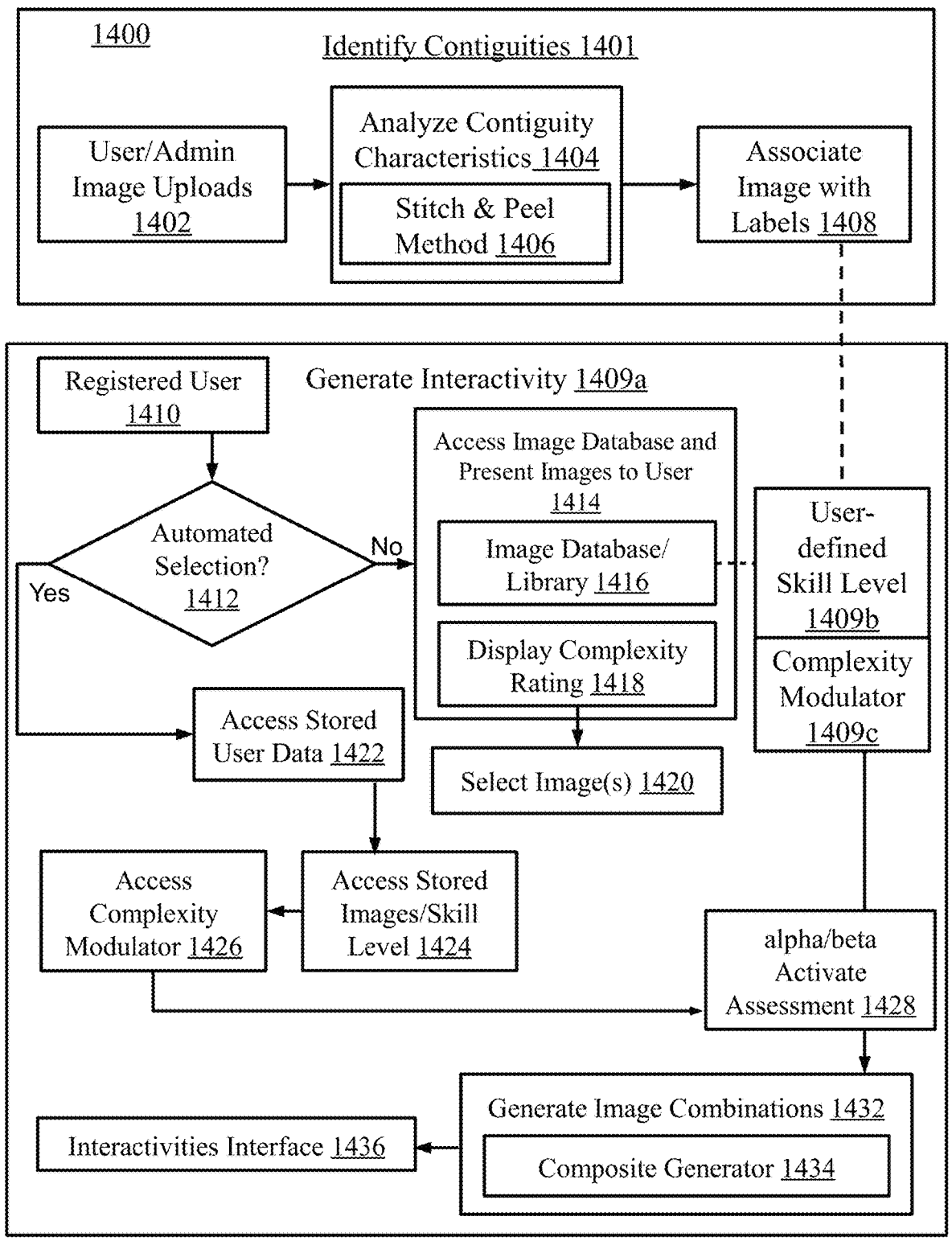
FIG. 14 is a flowchart showing an embodiment of a portion of cognitive interactivity platform for creating an interactivity.

FIG. 14 is a flowchart showing an embodiment of a method 1400 that is implemented on the multi-purpose interactive cognitive platform. A professional user can use the platform to treat, diagnose, and/or train cognitive processes across multiple cognitive domains; while non-professional users, i.e., patients or users interested in maintaining their cognitive health can use the platform. Method 1400 starts with step 1401, in which the characteristics of the images used are analyzed. Step 1401 does not need to be repeated each time the user wants to interact with an interactivity, but may need to be repeated every time a user (e.g., a clinician, someone who desires to improve their cognitive abilities, and/or a patient) would like to add an image to the platform library to personalize the experience. Platform 1400 includes a system and method for identifying contiguity characteristics in an image and a Mem+ Assessment tool. A user may interact with the platform online via a GUI or the Mem+ Assessment Interactivities auto-launch. The platform may also be run offline and include modules that can be used to capture speed and accuracy data. The platform may utilize the TUI hybrid model—a tactile prop—together with an active surface, such as a touchscreen, to effect digital data captures.

Step 1401 may include steps 1402-1408. In step 1402, the user/administrator (who may be a clinician or non-clinician)

uploads and analyzes one or more images, so that the image may be added to a library of images with or without user-supplied, regional, or other personalized content for use in the platform's interactivities.

After the user/administrator uploads one or more images in step 1402, then in step 1404, the platform analyzes contiguity characteristics of the unaltered image. As part of step 1404, the image characteristics are identified and/or quantified. Step 1404 may include determining the number of contiguities, the contiguity rating, regularity, the number of vertical disruptors, the linearity, span, distribution, and/or color block depth, for example. Step 1404 may include determining the content of images, which may be added as content tags. Step 1404 may include sub-step of 1406. In step 1406, the image is stitched and peeled to determine the image's contiguity characteristics.

In step 1408, the images are associated with descriptive information. For example, content tags (indication of the content of the image), complexity ratings, aesthetic value, contiguity, and/or switch capacity (which may have been determined in step 1404 and 1406) may be associated with the image After step 1408, the method proceeds to step 1409*a*. Alternatively, if the images have already been analyzed and associated with labels, the user may start with step 1409*a*. In step 1409*a*, the user may interact with one or more interactivities, during which time the user's activities may be monitored and analyzed, so that the interactivities presented to the user may be adjusted according to the user's needs and skill level, for example. Step 1409*a* includes steps 1409*b*-1436.

Step 1409*a* has two entry points, which are steps 1409*b* and 1410. Step 1409*b* may follow after step 1408. In other words, if step 1401 was implemented, the next step may be step 1409*b*. In step 1409*b*, the user may define what the user believes is their skill level. In step 1409*c*, based on the user's input about their skill level, the criteria are determined for selecting parameters of images for interactivities and/or interactivities. When the user enters step 1409*a*, via step 1409*b*, an administrator may be logged into the platform, and an administrator and/or the user may set up their own account. As an alternative to step 1409*b*, the user may enter step 1409*a* at step 1410, and at step 1410, the user logs into the platform.

In step 1410 (which is the second entry point to the platform), a registered user begins to use the multi-purpose interactive cognitive platform. If the user is not registered, the user may register at step 1410, which may include establishing an initial profile. After step 1410, in step 1412 a determination is made whether the user would like to manually select images for the interactivities or whether the user would like the platform to automatically select the images according to the user's needs as indicated by past assessments, user category norms and predictive analytics, and/or clinician input.

If, in step 1412, it is determined that the user wants to select their own images, method 1400 proceeds to step 1414. In step 1414, the image database may be accessed, and images available to the user are presented. In one embodiment, all the images of the database may be available to the user. In another embodiment, only images selected by a clinician for the user and/or previously selected by the user as images from which the user may be able to select. In another embodiment, the system may present a subset of images which best match a user's profile based on age, health status, education, geographic location and/or other parameters such as interests, hobbies or preferences.

Image Database 1416 is the database of images available to the user, which may be accessed during steps 1409*b* and/or 1414. Image Database 1416 may include a library of images, including user-supplied content, where the user can be either a professional user or an end-user patient or non-patient end-user, for example.

Step 1418 may be part of step 1414. In step 1418, the complexity of the images may be displayed to inform the user regarding which images they may wish to select.

Next, in step 1420, the user selects one or more images for one or more interactivities. As part of step 1420, the user may determine whether the user would like an interactivity with a single intact image or an interactivity that involves a multi-image composite. If the user decides they want an interactivity that uses a composite of multiple images, the user decides how many images will make up the composite and then selects that number of images.

Returning to step 1412, if the user decided to have the images automatically selected by the system, then the method proceeds from step 1412 to step 1422. In step 1422, the system accesses the user's data if the user is a returning user, or if relevant information is contained in the user's profile. In step 1424, the user's stored skill level and the image database is accessed. Then, in step 1426, the method activates a complexity modulator, which establishes criteria for selecting an image and set of interactivities based on the skill level and/or cognitive ability of the user.

After steps 1409*c*, 1420, or 1424 (or any time beforehand), the assessment activity 1428 is activated, so as to include the interactivity with the platform prior to actually interacting with the interactivities. The assessment may begin at any point prior to the start of the first interactivity, the Mem+ assessment may include a questionnaire of the user's habits and general health, as well as any recent changes to their health status, including diagnoses and/or changes in medication. In an embodiment, a full questionnaire is only used at registration, while a shorter questionnaire used prior to the start of an assessment-linked session. Questions may include, for example, "Did you sleep well?" "Have you eaten?" "Have there been any changes in your medication or health since the last time you answered these questions?" "How would you rate your alertness/attention on a scale of 1-5?" "Are you wearing your glasses?" For example, assessment 1428 may be activated as soon as the user logs in, sets up an account, and/or is logged in by a clinician.

After assessment 1428 is activated, in step 1430, an image set is selected (e.g., based on the user's skill level as determined in steps 1409*c* or 1426 or the user's selection of step 1420). Based on step 1430, in step 1432, a composite image is generated. Step 1432 may use a composite generator 1434 to combine 2 or more images into one composite image set which the user or clinician selected, or which the system automatically selected for the user. For example, composite generator 1434 generates 2 or 3 image combinations. The composite generator 1434 creates composites based on the skill level and selected images. The Composite Generator 1434 is a system and process where 2 or 3 images are serially sectioned and the image slices alternately juxtaposed.

In step 1436, an interactivity and/or interactivities set is created for the user based on the user's self-determined skill level, automatically determined skill level, input from a clinician, a group the user is a part of, and/or a preassigned interactivity protocol. The width of the sections may be varied with each image or be the same for both images or within the same image. In an embodiment, the range of sectioning is between 1.5%-50 percent. Some embodiments may include a slide bar for sectioning images 1.5%-50%. In other embodiments, the Composite Generator may also be used to develop a sectioned substrate where individual images may be printed on the substrate and/or for display on a TUI prop. In the substrate printed version, the blocks may then be combined to create a 2- or 3-image composite, for example, which may have a fixed width. The printed image sections may be used for the same interactivities using printed templates and image parts (game pieces). In other embodiments, the composite generator includes a Tangible User Interface (TUI) Prop, which may be used to interact with an active surface displaying a sectioned portion of an image. The prop may virtually "pick-up" digitally displayed image sections, so that the digitally displayed section can be manipulated as a physical, tactile entity in the TUI prop form.

In one embodiment, other types of tactile interactions may be accomplished using a three-dimensional printer (3-D printer) that prints three-dimensional objects, such as puzzle pieces having sensors, and/or bar coding on the puzzle pieces/interactivity pieces, so as to detect the user's placement of the puzzle pieces/interactivity pieces on an active surface. The width of the section can be varied and where the prop displays the section in whatever size it is, or is desired for use with the platform's interactivities.

In an embodiment, each of the steps of method 1400 is a distinct step. In another embodiment, although depicted as distinct steps in FIG. 14, step 1402-1436 may not be distinct steps. In other embodiments, method 1400 may not have all of the above steps and/or may have other steps in addition to or instead of those listed above. The steps of method 1400 may be performed in another order. Subsets of the steps listed above as part of method 1400 may be used to form their own method.

Figure 15:
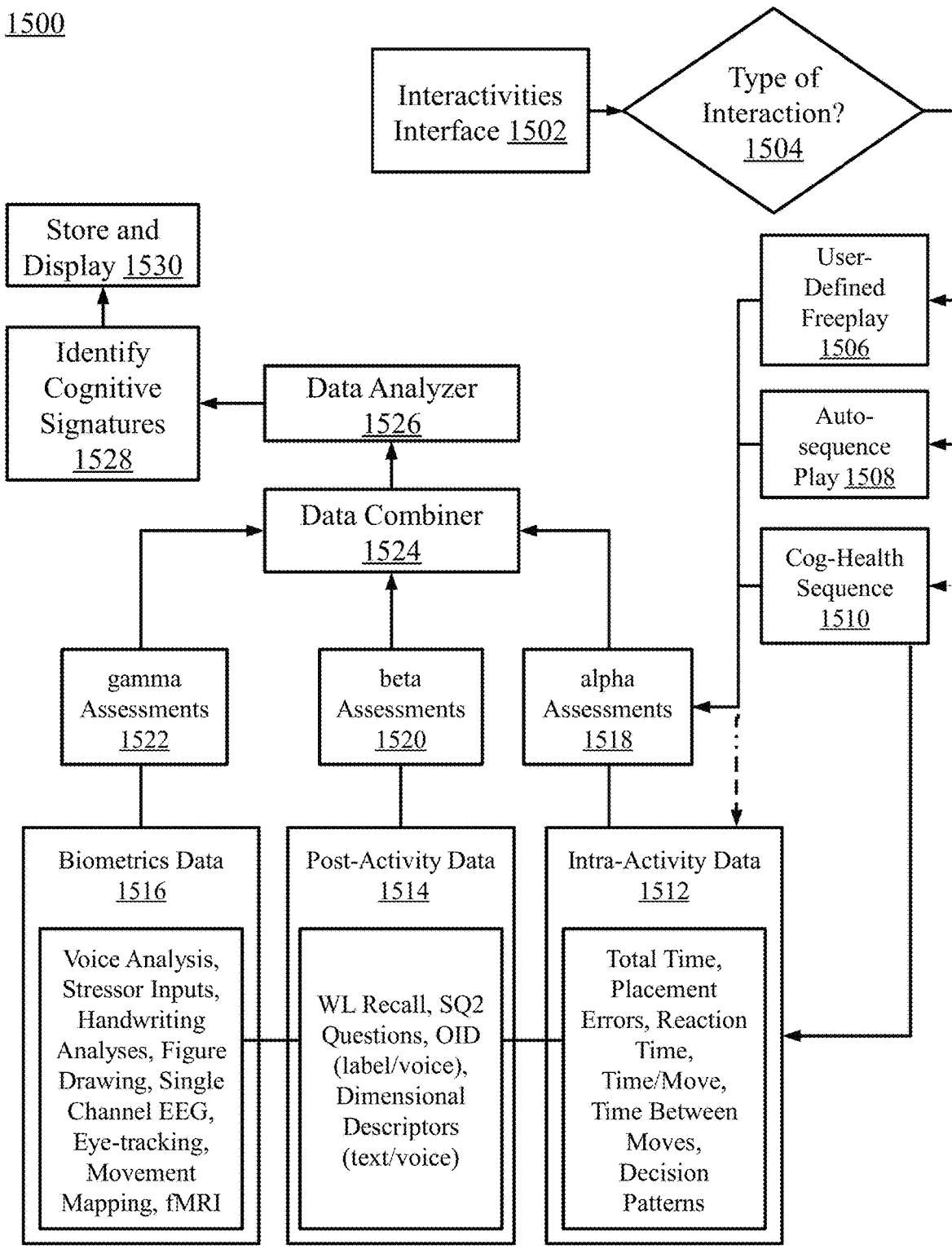
FIG. 15 shows a flowchart of a method of interacting with an interactivity to capture assessment data.

FIG. 15 shows a flowchart of a method 1500 of interacting with an interactivity. In step 1502, an interface for an interactivity is shown to the user. In step 1504, a determination is made of the type of interactivity to be presented to the user. For example, the user may be presented with a choice of interactivities, a clinician may choose an interactivity for the user, an automated choice may be made by the system, based on input information and/or assessment information indicating a type of interactivity which would be best for the user. The system may make recommendations to a clinician regarding the type of interactivity to use. The user may be part of a group and the type or interactivity may be based on the group that the user is part of, and/or a predefined protocol may be assigned to the user that has a pre-selected type of interactivity. For example, a determination may be made whether to present the user with a FreePlay mode option, and/or whether to present the user with an automated sequence of interactivities in which each interactivity is chosen for the user, and/or whether to present a cognitive health-related interactivity set in which each interactivity is selected for the purpose of diagnosing and/or treating a cognitive issue. If the FreePlay mode is presented to the user, the user may be allowed to choose each interactivity prior to interacting with the interactivity. If the interactivities are chosen for the user, the interactivities may be chosen for use in a pre-established protocol. While the FreePlay mode is defined by the user, the data captured through the platform's internal speed and accuracy measures can be used to detect changes in user behavior and responses over time, and as such can provide users with an early indicator of potential cognitive health issues warranting follow-up with a professional. Subjective, self-reporting of cognitive health changes is typically included in traditional patient assessments for cognitive health screenings. The platform, as such, can provide supportive data of cognitive changes which may be analyzed and attributed to a condition, change in medication, stress, or other effects, whether transient in nature, progressive, chronic, symptomatic or otherwise.

If it is determined in step 1504, to present the FreePlay mode to the user, method 1500 proceeds to step 1506, and in step 1506, the FreePlay mode begins.

If it is determined in step 1504, to present an automated sequence of interactivities to the user, method 1500 proceeds to step 1508, and in step 1508, the automated sequence of interactivities begins.

If it is determined in step 1504, to present a cognitive health mode to the user, method 1500 proceeds to step 1510, and in step 1510, the cognitive health interactivities begin. After step 1510, the method proceeds to step 1512, in which intra-activity data (or Mem+ alpha-type data and which can be designated by the term, $\alpha$) is collected while the user interacts with the interactivities. Optionally, step 1512 may be performed after steps 1506 and/or 1508. Collecting the intra-activity data may include recording the total time for an interactivity, recording the time between each move, recording the errors in placements of pieces, recording the time each move takes, recording the time between the end of a move and the start of the next move, and/or recording the time to the first move. Collecting the intra-activity data may include computing and/or recording the reaction time, average reaction time, and/or recording decision patterns through movement mapping analyses. Determination of the decision pattern may include the sequence in which the pieces are placed, the correct or incorrect placement based on color, placement order, or a spatial sequence, repeat error sequences and time between placements as behavioral metrics. As a further example of determining a decision pattern, the process may include determining the sequence in which the pieces were placed based on the location of the image part in the image, such as by placing first the pieces at the edges in the correct locations and then placing the other pieces in their correct locations. As a further example, a decision pattern may be informed by the content of the section to be placed in terms of saliency, color, uniqueness and/or image content details.

Next, in step 1514, post-activity data (or beta-type data and which can be designated by the term, $\beta$) is collected, which may include collecting data that relates to the interactivity and image sets after the interactivity is finished. For example, the user may be asked to recall a word list associated with the images used in the interactivity set, the user may be asked SQ2-type questions (e.g., what color was the flower, or the bird in the image looked most like which of the following birds). For example, the user may be asked to recall 5-7 objects they previously identified in an image, or to recall 7-10 items present or descriptive of the image they worked with in the interactivities. The input for the word list recall may be received, via text, clicking on a list of words or clicking on words which and/or by voice/verbal response, or other communications' devices and modalities. The user may be asked to differentially provide a description of only one of the images in a stable or multi-stable image set, such as a list of the objects in one of the images or to provide a scene caption, and which may be provided by keystroke, clicking, text, written, and/or voice recording, among other input options.

Next, in step 1516 biometrics data (or gamma-type data, and which can designated by the term, $\gamma$) may be collected (which optionally may be collected by a third party and integrated into the platform, and/or by using third party devices to collect data). For example, the biometrics data may include, an analysis of the user's voice, stressor inputs, and/or an analysis of the user's handwriting. To analyze the user's handwriting, user responses to some questions may be received, via a handwritten response (e.g., via a touch pad or electronic writing pad that sends signals to the platform, or where handwriting samples are scanned into the system. An analysis may be performed on the user's attempts to try to draw different types of figures. Collecting biometrics data may be include conducting a Single Channel EEG. For example, the single channel EEG may be performed while taking the assessment or while performing another assessment. Collecting biometrics data may include tracking eye movements while the user is performing the interactivity, mapping hand movements and/or tracking other body movements while the user is performing one or more of the interactivities or following engagement with the platform, image sets and/or the interactivities. Alternatively or additionally, any of the interactivities and/or any of the tasks of step 1516 may be performed while an fMRI or other type of imaging is performed, and/or combined with another type of movement and/or cognitive engagement and/or type of therapy and/or task.

After, or as part of, steps 1512-1516, the data is collected and analyzed by alpha assessments 1518, beta assessments 1520, and gamma assessments 1522. In other words, data related to user performance is obtained through Mem+ alpha assessments, through Mem+ beta assessments and through gamma assessments. The combined assessment data is then merged and analyzed.

Returning to step 1506 and 1508, after steps 1506 and 1508, the method proceeds to step 1518 for a Mem+ alpha assessment.

Next data combiner 1524 combines the data collected from the alpha assessments 1518, beta assessments 1520, and/or gamma assessments 1522 (data combiner 1524 is optional).

Then data analyzer 1526 analyzes the data from data combiner 1524 and/or from the alpha assessments 1518, beta assessments 1520, and/or gamma assessments 1522.

In step 1528, user profiles and signatures reflecting cognitive issues and/or cognitive strengths are identified. For example, the system may be used for assessment whether a user has unusually good cognitive skills in one or more cognitive domains, such as people with Asperger's with generally excellent visual spatial abilities; or people with William's Syndrome with generally poor depth perception abilities.

The use of content rich, real-world images (pictures), and other content-rich/dense visual stimuli allows for the development of image-cued word lists for recall assessments. There may be a threshold value for the density of objects in an image, and if the image has a higher density than the threshold the image is considered to be content rich. An image with a higher density of objects has a higher capacity for associating words with the image, allowing for a larger word list to be developed and associated with the image. Similarly, there may be a threshold for a score for whether or not an image is considered content rich. The score may be computed for any combination (e.g., a weighted sum) of the number of contiguous regions, the color density of the image, the number of edges in an image, and/or the total length of all the edges of the image summed together. The content rich images may engage a larger number of regions of the brain and/or a larger number of cognitive domains to a greater degree than simpler images, and therefore may be more therapeutic to the user. The word list for Mem+ assessments can be image-cued. For example, the word list may be derived from the images with which the user will perform interactivities for a period of time. The number of words which are image-cued can be varied as can the number of words used in the memory recall assessment for immediate, delayed and extended recall assessments. In one embodiment, greater than 30% of the words in a word list are image-cued. For example, a person can be tasked to remember 5 words, 3 of which are image-cued, or the user may be tasked to remember 5 words where all 5 are image-cued. Similarly, the user may be tasked to remember 7-10 words, where none, all, or only a portion of the words to be recalled, are image-cued.

The stored user images are accessed based on the user's stored skill level. User data that is stored allows the user to pick up where the user left off in a previous session. In FreePlay mode, the user can continue with the same process or change options (change skill level, images, or interactivities). In training mode, to advance skill levels, other parameters can be changed. If thresholds are not met (e.g., number of tasks completed within a specified time; increase in the number of errors, total time increase), then game logic might offer a downgrade, encouragement, or a hint for solving the interactivity. Additionally or alternatively, if thresholds are not met, the platform automatically adjusts the skill level slightly to support continued use at the higher skill level/complexity, but at the skill level's lower end rather than at the middle or higher end of a given skill level. For example, if the Skill Level is measured as follows: Difficult (Diff) can be broken into Diff0, Diff1, Diff2, ... Diff(n), where Diff(n) where "n" might be 10. If a user hits all thresholds for Diff(10) then the user advances similarly within the Difficulty level with additional and more complex tasks, higher thresholds to be met and other complexity modulation adjustments which can be made and added to the platform's interactivities' base to meet evolving user and/or group requirements. If the difficulty level is Easy a similar design can be used for E0 where the levels are E0.1 ... E0(n) between E0 and E1. Being able to change/modulate the difficulty and complexity allows for more refined screenings, assessments and for tracking positive and/or negative changes in cognitive health status over time (see FIGS. 4B-4E for an example of how to change the weights used for scoring when changing the difficulty of the interactivity). In some embodiments, the platform can adjust the complexity level with changes to sectioning, color and image content, number of pieces, and size of the pieces. In one example, a person is given three puzzle sections for a given image and is tasked with reconstructing the whole image using the 3 pieces. Another person, with a slightly better or similar cognitive status might be given the same image, but with four pieces and be tasked with constructing the image using pieces of the same width but where there is now a mixture of 2-whole sections (2-W) and 1 section which has been divided in half (2-H). The two users may initially be given the puzzle sections for construction, and then be tasked with constructing the image. The progression might continue on the same day, or another day in another session. The progression may continue with a simple training exercise (which also serves as an assessment) where the user is still working with a 3-image puzzle but the sections to be matched are now 1 whole section and 2 sections which are each divided into halved parts (or quarter parts). For example, fewer parts, larger parts could be used to establish complexity levels below E0 (←|E0|); while more puzzle parts and smaller puzzle parts could be used to establish complexity levels above E0 (|E0|→with a designation of 0.1 through 0.9 for example and, which can be summarized in terms of complexity modulation as follows: ←|E0|→.

The collection of Mem+ alpha, beta and gamma data ($\alpha\beta\gamma$) in the $\alpha\beta\gamma$ Mem+ assessment data combiner collection and analyzer in step 1524 and 1526 is implemented, respectively. Once activated the $\alpha\beta\gamma$ Mem+ data module can capture and analyze data from interactivities, including: intra-activity Word List Recall (T=0'); Delayed Recall (T=5'); intra-activity Speed and Accuracy, including: Placement Error; Time/Move; Time between Moves, and post-activity Word List Extended Delay Recall (T=10-15') (tap/text/voice), SQ2 Questions (spatial, quantitative, qualitative)(text/voice); Object Dimensional Descriptors (tap/text/voice); DescribeIT! (tap/text/voice); ObjectID/OIDm (tap/label/voice), and utilize embedded API or 3rd Party tools for voice analysis, handwriting analysis, stressors, eye tracking, single channel EEG, fMRI and other biometrics.

Mem+ alpha is assessed during the interactivities. Speed and accuracy measures, individual time records of time taken per move, time between moves, and movement mapping of users decisions in arriving at interactivity solutions may be recorded during game play. Placement Error Repeats and other patterns may also be recorded. The word list recalls (T=0', 5' and 15'), together with other post-activity assessments are used to acquire Mem+ beta data and which together with Mem+ alpha and/or with or without 3rd party Apps are combined to develop a user's Cognitive Profile (which represents point-in-time measures) and their Signatures (which may be measured over a time period).

Mem+ gamma data can be used to further refine Cognitive Profiles and Signatures. Third-party applications may be integrated into the platform, which can also be factored throughout the user's engagement with the interactivities or with biometrics' data collected separate from the platform. Third party applications may include: single/multi-channel EEG, eye tracking, and physiological and stress level measures (HR, RR, BP, skin galvanic response, pupil dilation), among others which may evolve over time and/or within a session.

The metrics from third party applications (e.g., from the gamma assessment), together with intra-activity 1512 and post-activity 1514 Mem+ assessments (e.g., the alpha and beta assessments, respectively) may be used to develop Cognitive Profiles and Signatures (e.g., which provide more comprehensive point-in-time and changes-over-time insights into the user's cognitive status).

If the Cognitive Health Sequence 1510 is used, the user may choose for themselves and/or the Mem+ $\alpha\beta$ assessment option can be activated for them by the system.

Mem+ $\alpha$ assessment data related to the interactivities collects speed and accuracy data as a default and is correlated to the use mode (Freeplay 1506, Challenge, Protocol (e.g., auto Sequence play 1508), and Cognitive Health 1510, for example).

A registered user may elect to review a detailed analysis of data at the end of a session and/or with each interactivity. The Mem+ data collector and/or other data collectors may collect data as part of the interactivities. The data may include the $\alpha$ Mem+ or $\alpha\beta$ or $\alpha\beta(\gamma)$ data, for example. Data is captured continuously. Data from $\alpha\beta$ is captured before, during and after the interactivities. Additional alpha and beta data is collected during and after at least in terms of WL Recall, Dimensional Descriptors, Object ID/Object ID Memory, and SQ2 for speed of response and accuracy measures. In general, for those interactivities which require a user to respond verbally or with other input, the assessment may be characterized as beta, and/or if there is a break in the interactivity, except as noted above.

The $\alpha\beta\gamma$ data is analyzed from each interactivity and across interactivities within a given session and/or across multiple sessions within a given week and/or across multiple weeks for a therapeutic and/or training protocol. For a training protocol, the results of $\alpha\beta\gamma$ (intra-activity, post-activity, and biometrics data, if available) can be used to determine if the user has reached thresholds for advancement in the complexity level to another skill level. Those complexity level changes could include, but are not limited to, changing the sectioning strategy, changing the size of pieces to be matched or constructed, and/or increasing the color complexity and/or content number of objects in an image. For example, a bird on a branch with uniform color in the background can be less complicated than a bison on the road with the mountains in the background, and a speed limit road sign. For baseline assessment purposes, age and health normative data can be collected for a given set of interactivities, using the same images, at a given skill level. Using normative references, other assessment scales for high and low "outliers" can be developed individually and across a spectrum for cognition as a whole, giving the platform the ability to scale skill levels based on user needs. Spectrum outlier ends might be represented by healthy, superior athletes and great thinkers with superior creative and/or critical skills; and, at the opposite end conditions based outliers on a cognitive degradation scale (e.g., end-stage Alzheimer's disease and/or other dementias). In some embodiments, there would be other scales where a skill may be superior in one group of cognitive-domain related skills and/or processes (i.e., visual-spatial for users with Asperger's syndrome, for example) but where other domain-based skills and processes can show deficits (see FIG. 4C for an example of how to adjust the weights for scoring, based on age and the degree to which Alzheimer's has set in). In some embodiments, for a person with Williams' syndrome visual spatial and depth perception can be compromised to greater/lesser extents but verbal language and reasoning can be excellent, and where both enhanced skills and deficits can operate across a spectrum. The system can be used to identify "glocal" markers which demonstrate global cognitive engagement (skills and processes) together with domain-referenced skills (local). Identifying glocal markers can be used to inform the development of a high-impact product group which can authentically tap into associative cognitive networks across multiple domains, assessing, reinforcing and/or improving on existing skills and processes, while at the same time identifying and/or addressing deficiencies—a streamlined, sensitive glocal assessment and/or interventional strategy.

The $\alpha\beta(\gamma)$ data is analyzed and used to generate the user's Cognitive Profile and which is added towards building the user's Cognitive Signature. The Profile and Signature are stored and can be displayed to a registered user where data is collected and stored.

Next, in step 1530, the results of the analysis and assessments are stored and displayed. Optionally, in step 1530, a display of the user's speed and accuracy, and skill level progress may be updated and/or sent to a remote location. Optionally, if one or more of the user's metrics change by more than a threshold amount, an alert may be sent to a caregiver, medical professional, and/or the user, according to privacy settings.

In an embodiment, each of the steps of method 1500 is a distinct step. In another embodiment, although depicted as distinct steps in FIG. 15, step 1502-1532 may not be distinct steps. In other embodiments, method 1500 may not have all of the above steps and/or may have other steps in addition to or instead of those listed above. The steps of method 1500 may be performed in another order. Subsets of the steps listed above as part of method 1500 may be used to form their own method.

Figure 16:
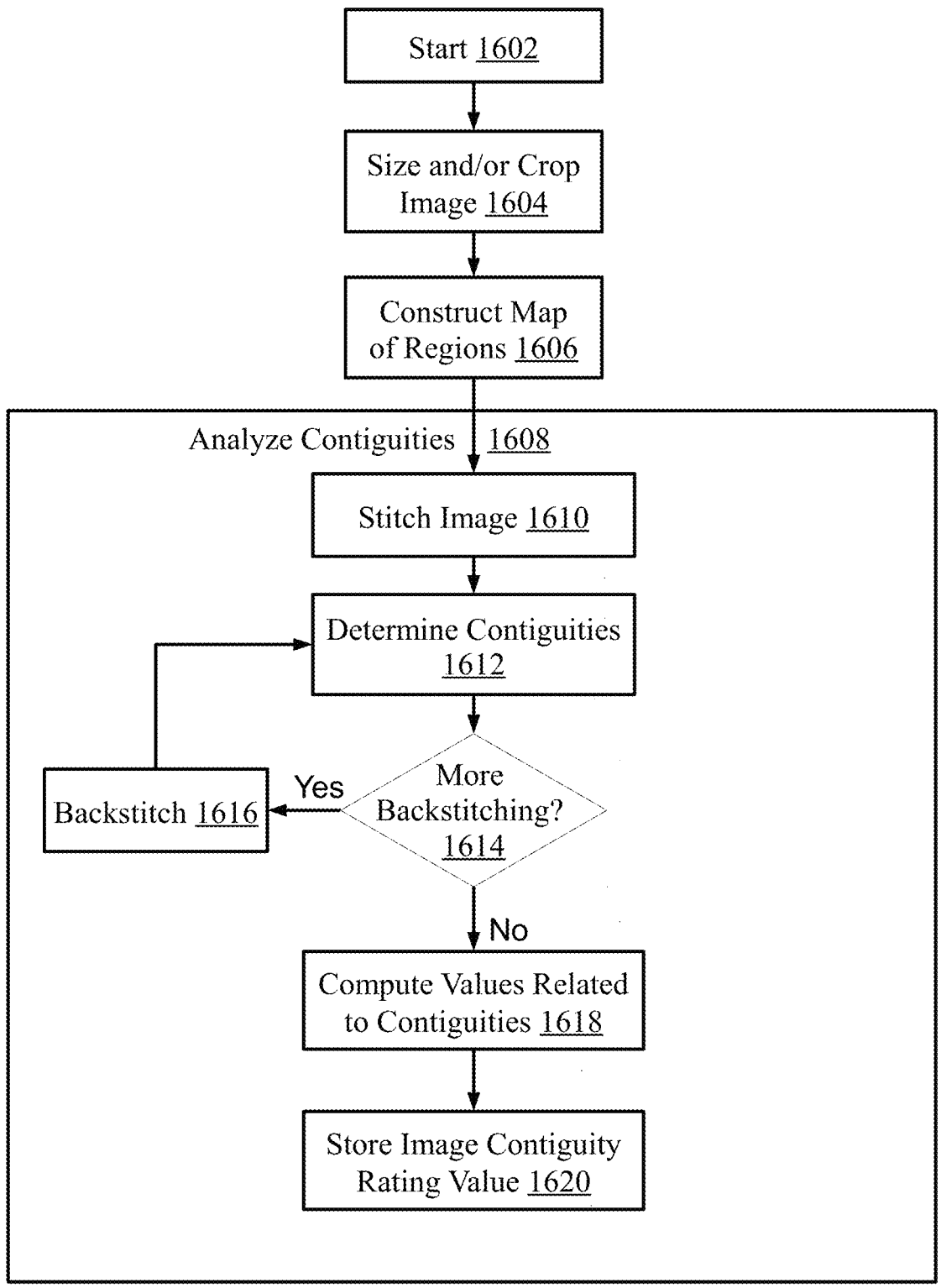
FIG. 16 shows an example of a flowchart for performing a contiguity analysis of an image for a multi-purpose interactive cognitive platform.

FIG. 16 shows an example of a flowchart 1600 for performing a contiguity analysis of an image for use in generating composites used in multi-purpose interactive cognitive platforms. In step 1602, method 1600 starts. For example, in step 1602, one or more images are received, retrieved, captured, taken, and/or formed, via processor system 102 and/or communication interface 112.

In step 1604, the image may be sized and cropped (step 1604 is optional), via processor 112 and/or sizing and cropping logic 228. In other words, the image may be enlarged or reduced and/or edges may be removed by processor 112 and/or sizing and cropping logic 228. In at least one embodiment, machine system 101 may be configured to size and crop the image to a predetermined size. The cropping may remove portions of the image that are not wanted, or edges of the image that cause the image to be too large for generating the composite image, and to centralize dominant contiguities and color blocks.

In step 1606, a quadrant map and an image grid map are generated, via region/grid generator 214. In at least one embodiment, machine system 101, via region/grid generator 214, may generate a quadrant map, which can equally divide the image into quadrants spanning the entire area of the image (or into another number of regions, such as halves, thirds, fifths, sixths, eighths, for example. In at least one embodiment, the quadrants can be arranged along a Cartesian coordinate system including an X-axis and a Y-axis, in which the center of the Cartesian coordinate system can be predetermined according to predetermined parameters, such as position of dominant content, color blocks, and/or the like. The dominant contiguity may be content that occupies a majority of the image and/or spans across more of the width of an image, and/or that occupies a greater portion of the image than other identified content. For example, a single contiguity that extends horizontally across a larger segment of the image than all other color blocks or line-type contiguities may be the dominant contiguity. In other embodiments, other coordinate systems may be used, such as polar coordinates, hyperbolic coordinates, elliptical coordinates, for example.

In at least one embodiment, machine system 101, via region/grid generator 214, may be configured to generate the image grid map. The image grid map can be generated, for example, by designating the Cartesian coordinate system to the image designating numerical coordinates of the image. In at least one embodiment, the numerical coordinates can be pixel locations of the image or can be used to construct quadrants or some other predetermined areas of the image. The coordinates generated by region/grid generator 214 may be the pixel coordinates or may be the pixel coordinate plus (or minus) an additive constant and multiplied (or divided) by a scaling factor. In at least one embodiment, machine system 101, via region/grid generator 214, is configured to generate a measurement area within the image grid map. The measurement area may be designated as a predetermined area of the image grid map in which the contiguity characteristics may be identified. In at least one embodiment, the measurement area enables identification of objects in the image.

In step 1608, the contiguities of the image are analyzed, via contiguity logic 208. In at least one embodiment, machine system 101, via contiguity logic 208, is configured to analyze the image to identify contiguities in the image. In at least one embodiment, the contiguity of the image can include contiguity lines, e.g. the edges that separate different regions of the image according to color differences between the areas, color combinations, and/or the like. The identification of the contiguities may be performed by identifying edges and/or regions having a uniform coloring and/or brightness (within a predetermined threshold). In at least one embodiment, the contiguities can enable a viewer of the image to identify objects, backgrounds, foregrounds, or the like in the image. The contiguities may appear in different locations within the image according to the visual content of the image, image set, or image scene comprised of at least one image. Optionally, the contiguities are identified, via contiguity logic 208, prior to performing any of the sub-steps of step 1608. Contiguity logic 208 may call edge identification logic 210 and/or thresholding logic 226 to assist in identifying contiguities.

In step 1610, one or more images are stitched, via stitching logic 202, by removing one or more parts of the image. Optionally, the parts removed may be rectangular sections stretching from the top edge of the image to the bottom edge of the image. For example, the middle third of the image may be removed. Optionally, the part to be analyzed may be a rectangular section spanning across a portion of the width of an image, and for example the middle third of the image segment may be removed.

In step 1612, the contiguities of the stitched image are identified and/or analyzed, by contiguity logic 208. Contiguity logic 208 may call on stitching logic 202 to facilitate identifying contiguities. The stitching may further facilitate determining contiguities (that were not previously identified) and determining objects that interfere with the contiguity, breaking up the contiguities. Color blocks that have similar color but different colors may create object interference—interference that makes it difficult to distinguish the border between two or more objects. Stitching and peeling (via stitching logic 202 and/or contiguity logic 208) may facilitate identifying two separate contiguities and/or separate objects despite the object interference and may help bracket the location of a border between two color regions and/or two objects. In at least one embodiment, the stitch analysis may include masking and progressively peeling portions of the image to enable analyzing a reduced portion of the image to enable defining contiguity characteristics, e.g. contiguity lines, horizon lines, interfaces breaking up the lines, linearities, continuities, regularities, object locations, and figure-ground relationships, for example. The steps for continuity, linearity, and stitching and peeling are discussed further below.

In step 1614, a determination is made whether predetermined criteria are met indicating to backstitch the image. For example, in an embodiment, a determination may be made whether the image has been backstitched and, if the image has not been backstitched, whether the image should be backstitched. In another embodiment, the user may enter input that indicates whether to backstitch the image, and if it is determined that the input indicates that the user wants the backstitching to be performed, then it is determined that the backstitching is desired. If it is desired to backstitch, the method proceeds to step 1616. In step 1616 the image is backstitched. Optionally, each time step 1616 is performed a fraction of the image that was previously removed (or masked) is put back into the image (or unmasked). After step 1616, the method returns to step 1612, where the backstitched image is analyzed (e.g., for its contiguity characteristics). Steps 1612, 1614, and 1616 may be performed multiple times, until all of the backstitching desired is performed.

In at least one embodiment, machine system 101, can be configured to perform the serial backstitch to an image, set of images, or a scene within an image. The serial backstitch may compress the contiguity edge analysis by arranging in an adjacent manner the non-adjacent sections of an image. The serial backstitch can be configured to compress the image on which the contiguity and/or edge analysis is performed by bringing together non-adjacent sections of the image, in effect temporarily folding space within the image.

Returning to step 1614, if all the backstitching needed has been performed, the method proceeds to step 1618. In step 1618, the computations of the multiple implementations of step 1616 are combined. For example, the values representing the contiguity characteristics that were determined in each backstitch are averaged by the total number backstitching steps 1616 were performed. The backstitching and evaluation of contiguities is discussed further below.

In step 1620, an image contiguity rating ("CR") value (ambiguity value, or juxtaposition value) is stored in association with the image. In this specification, the terms juxtaposition value and contiguity rating value and ambiguity value are used interchangeably. Throughout this specification, either term may be substituted for the other term to obtain different embodiments. The locations of the contiguities are also stored in association with the data, for further analysis of the image. In at least one embodiment, machine system 101 can be configured to store the image CR value and in assigning a complexity value to the image. The image CR value can include a rating that enables machine system 101 to determine image compatibility for use in generating the composite images of a specified type, for example, stable or multi-stable. Composite images may be a combination of multiple images. For example, two or more images may be interwoven with one another to form a composite image. The image CR value may be based on multiple parameters, such as the definiteness of the contiguity in the image, the number of contiguities identified in the image, the spatial distribution of the contiguities, the width of the contiguities, the color composition of the contiguities, and/or the angularity of the contiguity. The definiteness of the contiguities may be how much contrast exists between the contiguity and surrounding regions. The angularity of the contiguity may be the angle at which contiguity is oriented. A larger angle between the horizontal axis and the contiguity may detract from the contiguity's characteristics and therefore lower the CR, in a convention in which a higher CR value represents one or more contiguities with a higher distinctiveness of individual contiguities, when viewed in isolation of the other contiguities.

Figure 17:
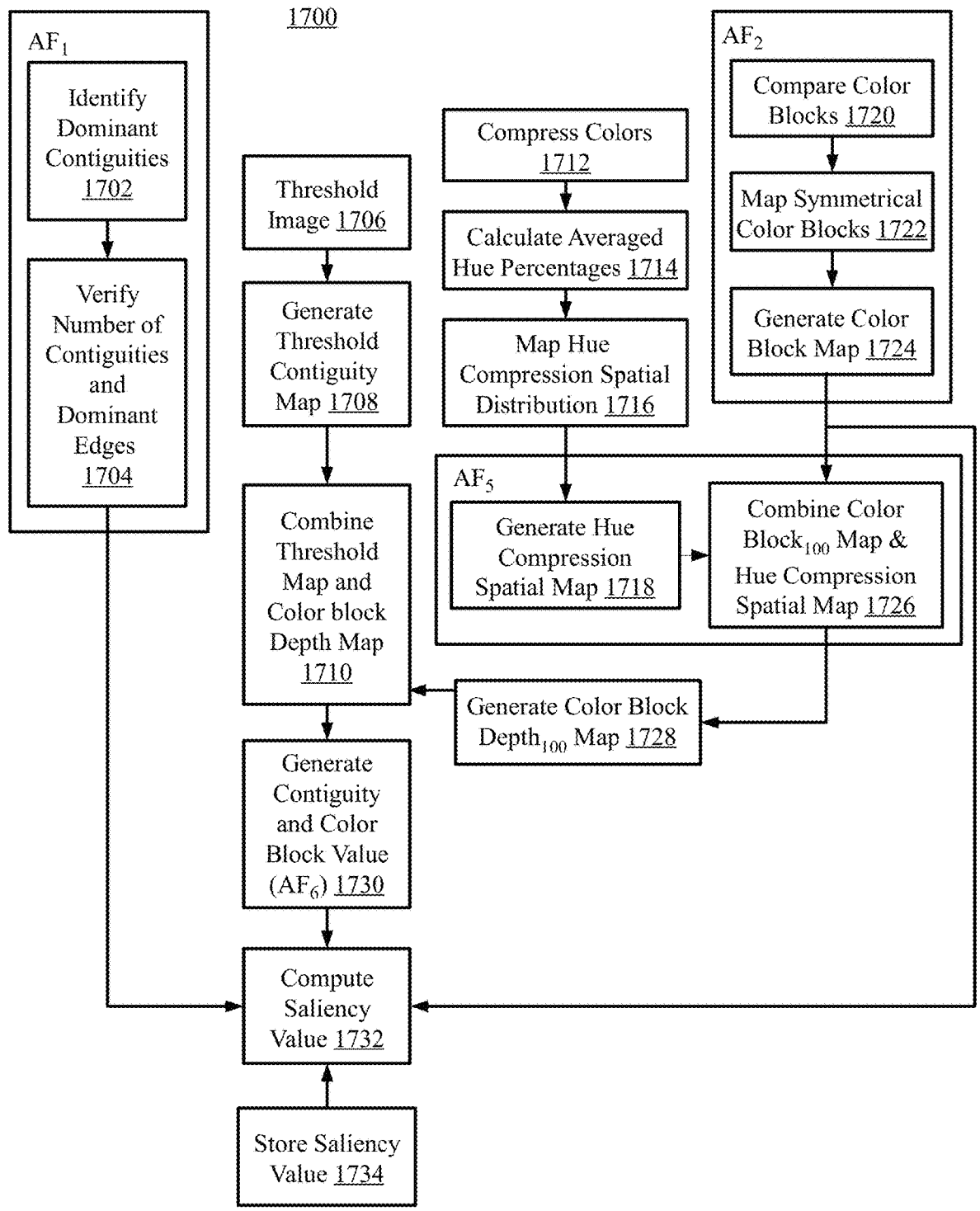
FIG. 17 shows an example of flowchart of an embodiment of a method for computing parameters associated with contiguities and/or contiguity lines for a multi-purpose interactive cognitive platform.

FIG. 17 schematically illustrates a method 1700 for generating a contiguity rating value and other related parameters for use in multi-purpose interactive cognitive platforms. In step 1702, dominant contiguities are identified by edge identification logic 210. In at least one embodiment, machine system 101 is configured to identify dominant contiguities. The dominant contiguities can be identified, for example, implementing Sobel filters to the image, or another edge identification method, and then using the edges to determine the size and distinctiveness of each contiguity. The dominant contiguities can be determined by the edges of the image as well as the color blocks in the image. For example, each contiguity may be assigned a score. In an embodiment, a contiguity that includes a dominant edge is a dominant contiguity. Dominant edges are dominant contiguities, but not all dominant contiguities may be dominant edges as a contiguity can also be a color block.

Continuing with the description of step 1702, in step 1702, the total number of contiguities and dominant edges are also identified in the image. In an embodiment, a dominant edge is an edge that extends across at least a majority of the image. In an embodiment, a dominant edge is an edge that is longer than the majority of other edges. In an embodiment, a dominant edge is an edge that is longer than the majority of edges and extends more horizontally than vertically, and/or extends diagonally. In an embodiment, a dominant edge-type contiguity would extend horizontally across 75% or more of the image. In at least one embodiment, machine system 101 is configured to verify the total number of contiguities, which include the dominant edges in the image, which may be in any direction. The dominant edge can be determined by performing a corner and border identification of the image and identifying edges between color blocks that are above a predetermined contrast and/or threshold level. A dominant edge can have a CR value between 0.75-2.25 (FIG. 19B). In at least one embodiment, the dominant edge/contiguity is the edge/contiguity that is used for making measurements, and which contributes to the image's switch capacity. Optionally, a dominant edge has a contrast between adjacent regions that is above a predetermined threshold. For example, in an embodiment, a dominant edge has a contrast of at least 8:1, at least 10:1, at least 20:1, or at least 100:1.

In step 1704 thresholding is performed by threshold logic 226. Thresholding logic 226 may form a binary image by setting pixels of the original image above the threshold to white (or black) and the pixels below the threshold being set to black (white). The threshold may be for brightness, a particular color, and/or hue. In at least one embodiment, machine system 101, by thresholding logic 226, may be configured to apply a threshold filter function to the image. The threshold filter function of thresholding logic 226 may aid in partitioning the image into foreground and background parts. The thresholding of thresholding logic 226 may be based on a particular reduction of the colors in the image. The reduction of the color in the image may be performed by representing a color that is not in the color palette of the machine that made the image with the closest color in the palette and/or a dithering pattern of the close colors. The threshold filter function of thresholding logic 226 may generate a binary image of the image to enable edge recognition or detection between the foreground, the background, and/or objects in the image, for example. The terms recognition and detection are used in interchangeably throughout the specification. Throughout this specification, each may be substituted for the other to obtain different embodiments. The threshold filter function may include computing, by thresholding logic 226, a histogram, and clustering the colors into bins and setting the threshold, so as to operate between two clusters of bins. Thresholding logic 226 may choose the threshold based on color, hue, or brightness level. The threshold may be a value (representing a color, hue, or brightness level) that divides between colors, hues, and/or brightness levels that are associated with different levels of entropy. For example, perhaps pixels having a brightness above 200 are associated with regions having more entropy than those below the threshold and so the binary image is formed with the threshold set at a brightness of 200. The threshold of thresholding logic 226 may be set based on an object attribute. For example, pixels that are known to be associated with a particular attribute or interest (e.g., an object of interest) tend to have a particular color or brightness and so the threshold may be set and a color or brightness above or below that particular color. The threshold of thresholding logic 226 may be based on spatial filtering. For example, certain regions of the image may be removed from the image, prior to setting the threshold. In at least one embodiment, a multi-level thresholding filter can be implemented by thresholding logic 226 to designate a separate threshold for each of the red, green, and blue components of the image, which can then be combined, for example. Alternatively, multiple brightness thresholds may be set by thresholding logic 226 to produce multiple binary images.

In step 1706, thresholding logic 226 may generate a threshold-spatial map (which may be referred to as a T-spatial map). The threshold spatial map stores the locations (e.g., the pixel coordinates of each pixel of the original image that has a value above a threshold and/or each pixel of the original image that has a pixel value below a threshold may be stored as the T-spatial map). In at least one embodiment, machine system 101 can be configured to generate, by thresholding logic 226, the T-spatial map, for example, by implementing a threshold filter to the image. The application of the T-spatial map to an image helps define edges, contiguities, and dominant contiguities. The line in the image that divides between regions of the image having the pixels that is above and below the threshold may be and/or may be related to edges, contiguity lines, and dominant contiguities in the image. Similarly, the regions having pixels of one of the two types, may be contiguities or may be parts of contiguities (depending on the size and shape of the region, whether the region is identified as being part of a larger region and/or other characteristics of the region).

In step 1712, color hues are compressed, by color map logic 212. The compression of the colors may involve, for each pixel determining which of a predetermined number of colors the pixel of the original image is closest. In at least one embodiment, machine system 101 can be configured to compress the color hues. The color hue compression may reduce the colors in the image to a predetermined number of colors, for example, to a number of colors that is within a range of 2-6 colors, for example.

In step 1714, the averaged hue percentages are computed, by color map logic 212. For example, for each of the predetermined colors the percentage of the total number of pixels in the image that are binned with (closest to) one of the predetermined colors. Thus, if one of the colors (e.g., red) has 2500 pixels associated with that color and the image has 1096×1096 pixels, then there are 2500*100%/(1096× 1096)=0.2% red pixels. In at least one embodiment, machine system 101 can be configured to calculate, via color map logic 212, the averaged hue percentages. Optionally, a map is constructed having the pixel locations (e.g., pixel coordinates) of each color. The averaged hue percentages of the colors may be identified in the image locations.

In step 1716, the hue compression ("HC") spatial distribution is mapped by the color map logic 212. In at least one embodiment, machine system 101 may be configured, by the color map logic 212, to map the hue compression spatial distribution. In other words, the probability of a pixel having a particular color being in a particular region is computed (e.g., as the percentage of the pixels in a particular region having that color). The HC spatial distribution can be correlated to location according to a higher-order probability distribution and/or correlation between the pixels of the image and the location of the colors in the image. The higher order probability refers to other information that may skew the probability distribution. For example, perhaps, as a result of binning the pixels, it is known that 30% of the pixels are blue. Perhaps, as a result of user input, prior images, a category to which the image belongs (or other information), it is expected that the image includes a region in the upper half of the image representing the sky. Because of this expectation, based on prior images, there is a 90% chance of a blue pixel being located in the upper half of the image and only a 10% chance that a blue pixel is located the lower half of the image. Then for this image, there is a 27% chance that pixels in the upper half of the image are blue and 3% chance that pixels in the lower half are blue. The likelihood of a particular pixel being a particular color, depending on where the pixel is in the image, may be affected by the context, saliencies, and a knowledge reference matching pixel distribution (that is, based on prior distributions of the pixels of prior similar images).

In step 1718, a hue compression spatial map may be generated by color map logic 212. In at least one embodiment, machine system 101 can be configured to generate the hue compression spatial map. The hue compression spatial map provides a mapping of the colors provided through the hue compression. As part of step 1718, color map logic 212 may compute the locations of color blocks (each color block has the color of the average of the color of the block or the hue with the most pixels in its bin). Optionally, each block of a grid is overlaid on the image and is assigned its average color as the color of that block, by color map logic 212.

In step 1722, color blocks are compared to one another, by color map logic 212. In at least one embodiment, machine system 101 can be configured, by color map 212, to compare the color blocks, which may determine different color blocks in the image and may determine similarities and dissimilarities within and across the image grid map. Regions of color blocks (where each region is a group of adjacent blocks of the same color) may be compared according to different quadrants in the image grid. The comparing of the color blocks may be in order to determine the different values. For example, in a black and white image, the color block comparison can differentiate between colors having a binary value of zero for white color blocks and a binary value of one for black color blocks. In a second example, the image may include color blocks such as green and blue, where each color is represented by a distinct value, which enables comparing the color blocks within the image grid map.

In step 1724, symmetrically placed color blocks may be mapped by color map logic 212. In at least one embodiment, machine system 101, by color map logic 212, may map color blocks that have a symmetrical shape. Machine system 101, by color map logic 212, may determine that the color blocks are symmetrical according to the pixel location or the location within the grid of the color block pixels on the image grid map and may evaluate the asymmetry of a color block, by color map logic 212. In at least one embodiment, the number of grid boxes of the color block on the image grid map may be compared, by color map logic 212, to determine the edges of a region having adjacent block of the same color, to determine whether the region of having a group of color blocks of the same color is symmetric, across and within the region of the color blocks of the same color. The number of grid boxes of the color block on the image grid map may be compared, by color map logic 212, to color block depth$_{ST}$ (CBD$_{ST}$) data that is symmetrical or shows symmetrical color characteristics, such as blue hues in a region of sky. The "ST" in the subscript of the term "color block" stands for the word "stitch," as in the stitched image and the number "ST" indicates the percentage of the total image that remains after the stitching. For example, color block depth of 67 means a color block value performed in an image that was stitched by removing ⅓ of the image leaving ⅔ of the image and the value assigned, according to rules described in FIG. 19D. The shape of the region of blocks having the same color may be indicative of an underlying contiguity and may place limits on the size and shape of the underlying contiguity. Using the bins, the color block depth may be computed. The image is divided into four blocks, where each block is a quadrant of the image. For each quadrant, the color with the most pixels in that color's bin is determined, and that is the "color mode" for the block. The "color mode" of a block is the color—of the 2-6 colors into which the image is mapped that occurs most often in that block. If all four quadrants have the same color mode, the color block depth is one. If two adjacent blocks have one color mode and the other two adjacent blocks have another color mode, the color block depth is 0.75. If two adjacent blocks have one color mode, and the other two blocks have each have a color mode different from one another and different from the first two blocks, the value is 0.5. If two nonadjacent blocks have one color mode and the other two nonadjacent blocks have another color mode, then the color block depth is 0.5. If all quadrants have different color block modes, the color block depth has a value of zero. If two nonadjacent blocks have one color mode and the other two blocks each have a color mode that is different from one another and different from the first two blocks, the color block depth is zero. Each quadrant may be further subdivided into quadrants and a color block depth may be computed for each quadrant. The color block depth may be computed for different degrees of the stitched or back-stitched image.

In step 1726, a color block depth 100 (CBD$_{100}$) map is generated by color map logic 212. In at least one embodiment, machine system 101 can be configured to generate the CBD$_{100}$ map. The image may be divided into a predetermined number of blocks. Quadrants that can be defined as positive and negative values arranged on the Cartesian coordinate system or with a numerical label, Q1, Q2, Q3 and Q4. The number of color block patterns identified by machine system 101, in each quadrant, relative to other quadrants in the image can provide a relational analysis of different color portions of the image, the distribution of the color portions, and/or the symmetry of the color portions. The distribution of color portions can be mapped onto the grid of the map to generate the CBD$_{100}$ map. The nuanced differences are regions which are subjected to further analysis. As quadrants are drilled down into sub-quadrants (and sub-sub-Qs), CB differences become more evident. The CB difference may allow for, and may be used to, identify IEs and VDs (FIGS. 19C-19D). Each quadrant may be analyzed individually, and any quadrant that has features that correspond to something of interest may be further divided into quadrants (or other sectors) and analyzed individually and each sub-quadrant, having features corresponding something of interest may be further subdivided and analyzed individually. The process of identifying sectors having features corresponding to something of interest and then further subdividing those sectors may be continued until there are too few pixels in the sectors with which to make further analyses (e.g., when each sector only has one pixel).

The values for CBD$_{100}$ are based on the rules which will be described, below, in FIG. 19D-19E. The color block map of the original intact image and the various stitched images may be compared and the characteristics of the image derived from the color maps from each stitch may be averaged.

In step 1726, the hue compression spatial map and CBD$_{100}$ map are combined (e.g., integrated or superimposed on one another, so that one map appears foreground and the other map appears as background). In at least one embodiment, machine system 101 combines the hue compression spatial map and the CBD$_{100}$ map. The hue compression spatial map generated from the threshold function may be aligned with the CBD$_{100}$ map to provide a unified map for recognizing the necessary edges for designating the contiguities in the image based on the color composition. The combined hue compression spatial map and CBD$_{100}$ map may be used to maintain the embedded color information of the image.

In step 1728, a CBD$_{100}$ is generated in at least one embodiment, machine system 101 can be configured to generate the CBD$_{100}$, which is the compo sited map including the overlaid information obtained by aligning the hue compression spatial map and the CBD$_{100}$ map.

In step 1710, the T-spatial map and the CBD$_{100}$ are combined. In at least one embodiment, machine system 101 can be configured to combine (e.g., integrate) the T-spatial map and the CBD$_{100}$.

In step 1704, a contiguity number (or value) is generated by contiguity logic 208. Color block data and spatial data may also be generated by contiguity logic 208, as part of step 1730. In at least one embodiment, as part of step 1732, machine system 101 may generate the contiguity number, the color blocks, and the spatial data. The contiguity number may be the number of contiguities designated in the image based on predetermined parameters (e.g., based on predetermined thresholds for threshold maps and predetermined number of stitches and peels, are predetermined set of bins of hue, and predetermined grid, and block size for the blocks of the regions of color blocks having the same color), FIG. 19E.

In step 1732, an image saliency value is generated. In at least one embodiment, machine system 101 can be configured to generate the image saliency value. The image saliency value provides a unique quality for a group of pixels or for a single pixel relative to surrounding pixels and the rest of the image, and enables easier analysis of the image. In one embodiment, the saliency is represented by a combination of ambiguity factors including: contiguity number (AF$_1$), number of color blocks (AF$_2$), color block depth 100 (AF$_5$), and the spatial color contiguity (AF$_6$) comparison as described in FIG. 19B. Regions where color or brightness differences may be present are identified by the differences in the distribution and the number contiguities and color blocks in an image.

The image saliency value sets a contour for extracting information from the image to enable edge detection, e.g. each pixel in a region that is similar with respect to a predetermined characteristic or computed property, such as color, intensity, texture or the like. In other words, since the saliency value is an indication of whether a particular region is of interest, if the saliency value crosses a particular threshold value, the region may be further analyzed to determine characteristics of sub-regions with the region of interest. (The saliency value is an indication of whether a particular region is of interest, as a result of having a different color, brightness, texture, and/or other characteristics than neighboring regions). In this specification, the words brightness and intensity are interchangeable, either may be substituted for the other wherever they occur to obtain different embodiments.

In step 1734, the saliency value is stored in image database 110 and/or passed on to other methods that make use of the saliency. The saliency score is a sum of a subset of the ambiguity factors. The saliency score may be referred to as a type of ambiguity value. The image saliency value, which is a measure of internal contrast, contributes to the dominance of a subset of image characteristics defined in part or whole by continuous and/or a contiguous group of color blocks of recognized elements and their corresponding juxtapositions (or Contiguity Rating—CR values), or as defined by the shape of the group of color blocks. As will be discussed further below, the ambiguity value is given by $Ambi_{SAL} = \Sigma(AF_1 + AF_2 + AF_5 + AF_6)$.

$AF_1$, $AF_2$, $AF_5$, and $AF_6$ are discussed further below, and the steps of FIG. 17A that compute each ambiguity factor is indicated in FIG. 17. In an embodiment, if $Ambi_{SAL} < 5.5$, the images contains a significant number of poorly defined distractions—no clear attention focus, save for the contiguities present in the image. Images in this category can be used to focus on nuanced details as an attractor and/or distractor element. If $Ambi_{SAL}$ is between 5.5-14 then there is a balanced color blocking (a potential indication of symmetry and non-disrupted contiguity and color blocks) and contiguity/edge sharpness (an optimal range for looking at details in an image and/or for focusing on a particular object or element in the image). If $Ambi_{SAL} > 14$, the image contains a significant number of discontinuous contiguities, little or no color symmetry, and/or the objects may be disrupted; in other words there are many unlike parts of an image to look at. Images in this category can be used to focus users on nuanced details as attractor and/or distractor elements.

FIGS. 18A-19E provide methods for performing contiguity analyses for use in multi-purpose interactive cognitive platforms and rules which can be applied. Images can be analyzed using manual and/or automated methods to derive Ambiguity and Aesthetic values based on one or more dominant image contiguities. Contiguity analysis can be conducted for both online and offline components of the platform as the images can be printed from digital files. The digital files can be used by the platform and/or transferred to a medium or a substrate such as paper, metal, and wood. Data based on a manual analysis of contiguity characteristics can be entered manually into the digital platform or may be entered using a hybrid system of manually entering data using a series of prompted fields with a stylus or other marking device. The data may attached to the image and used to calculate Ambiguity, Aesthetic and Compositing Factor values for each image (and Saliency values as a subset of Ambiguity Factors ($AF_1$, $AF_2$, $AF_5$, $AF_6$). The automation of the process facilitates deriving the Compositing Factor for combining images to generate 2- and 3-image composited images. Deriving the compositing factor may be performed as part of the multi-purpose interactive cognitive platform. If the compositing factor is used with offline components, or to integrate user-supplied images, the compositing factor may be used in assigning skill levels to images and image sets which can be added to the library.

Figure 18A:
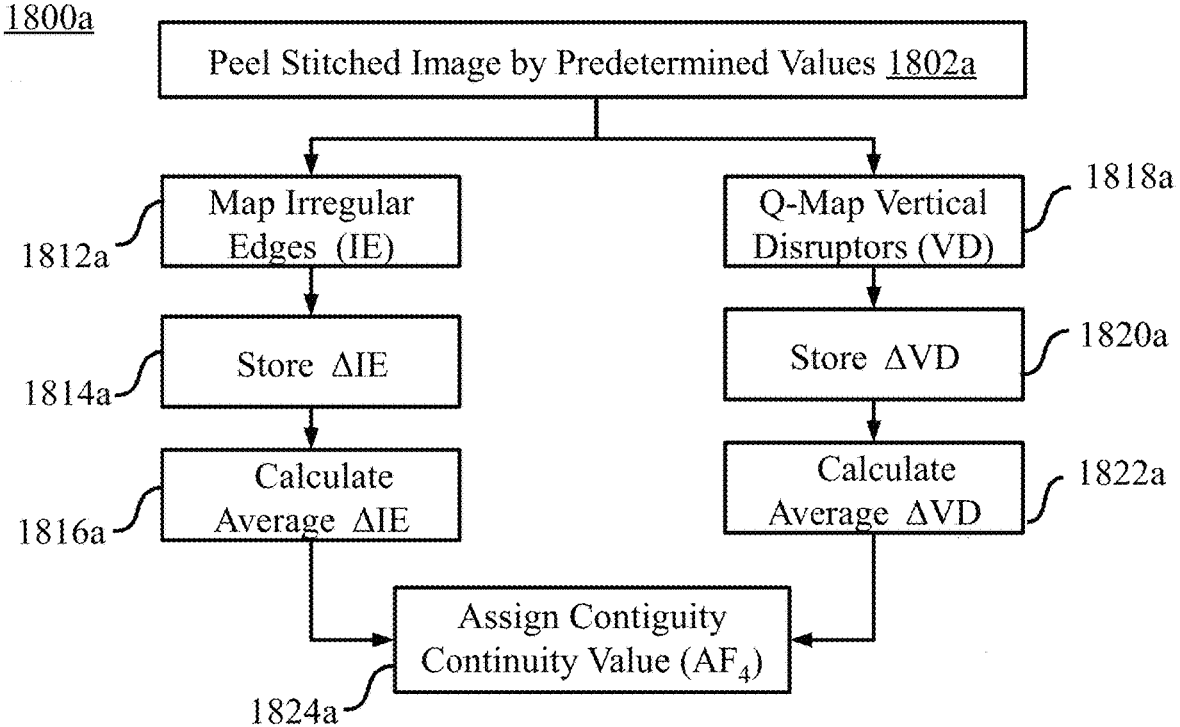
FIGS. 18A and 18B show an example of a flowchart of a method of computing contiguity continuity and contiguity linearity values using a stitched image for a multi-purpose interactive cognitive platform.

FIG. 18A schematically illustrates a method 1800a of peeling, according to at least one embodiment for use in multi-purpose interactive cognitive platforms. In step 1802a, peeling operations are performed at predetermined values, such as predetermined percentages of stitching and/or peeling. In at least one embodiment, machine system 101 can be configured to peel a first section (e.g., a first 30% of the image), and then a second section at the predetermined values (a second 30% of the image). Alternatively, the different percentage could be used, such as 25% or 10%.

In step 1812a, irregular edges (IE) are mapped. In step 1812a, a map of irregular edges is computed. The map may be based on the regions (e.g., quadrants and blocks of the quadrants) of the region map, and the map for each region may be computed. In at least one embodiment, machine system 101 can be configured to map the irregular edges, which can be edges that include shapes, contrast hue, and/or color difference with the surrounding areas. The edge irregularity may be computed by computing differences between edge parameters, such as the differences in the angle, contrast, brightness, color, and hue of the edge. Differences between edge irregularities of different degrees of stitching/peeling and/or thresholding may also be computed.

Using the original image and the stitched image, deviations off the X-axis relative to the dominant contiguity may be evaluated setting up a grid to define the Intrusion Area, which is the area that the vertical intrusion (disruptor) intrudes into an area above (and/or optionally below) the dominant contiguity. The vertical disruption by a Vertical Disruptor (VD) can be in the contiguity and may be objects of interest, and the fact that a region is a vertical disruptor may be used as one factor of multiple factors that indicate that a region is part of an object of interest and/or that the object may be a foreground object. If the suspected IE extends beyond one or more adjacent grid boxes, extends along the X-axis for 3 or more grid boxes (which for example may be 0.1 inch to ⅛th inch when the image is viewed in the size that the image will be printed or presented), then the intrusion is evaluated as a Vertical Disruptor. In addition, if the suspected IE fills one or more grid boxes, fills more than 20% of the height of a contiguity, and/or extends beyond the boundaries of one or more grid boxes, then the intrusion is evaluated as a Vertical Disruptor. All Vertical Disruptors are irregular edges. However, irregular edges are not necessarily Vertical Disruptors.

In an embodiment, in step 1812a, the irregular edges that are not Vertical Disruptors are mapped. The area of the VD may be approximated by the height and width of the boxes that encompass the VD. In measuring a VD, the size of the grid boxes should be chosen so that the area of the Vertical Disruptor is at least 40% of the area arrived at by using area of the boxes that encompass the VD. Alternatively, the width and height of the boxes that fit within the Vertical Disruptor may be used as an approximation of the area of the VD, and the sizes of the boxes should be chosen such that the area of the boxes should that fit within the VD is at least 40% of the area of the VD. The area of the intrusion may be computed in other ways (such as by counting the number of pixels used to represent the intrusion divided by the number of pixels in the region that intrusion intrudes into).

In another embodiment, a vertical disruption larger than a predetermined threshold divides a region into different parts. Additionally, or alternatively, the horizontal disruptions may also divide a region into parts. Additionally, or alternatively, disruptions in other directions may also divide a region into parts. In an embodiment, a disruption is more than 50% of the distance from a first edge to a second edge facing the first edge. For example, a vertical edge that is 50% of the distance from the top edge to the bottom edge of the region divides a region into parts. In other embodiments, the ratio of the length of the disruption to the distance between the opposite facing edges (e.g., between the top and the bottom edge) may be a different percentage, such as 15%, 25%, 75% or 80%.

In step 1814*a*, the edge irregularities and optionally the differences in edge irregularities are stored.

In step 1816*a*, the average position and/or contour of the irregular edges are calculated. In at least one embodiment, machine system 101 can be configured to calculate the average irregular edges. The average position and/or contour of the irregular edges may be computed by averaging the differences in the edge irregularities (e.g., including one value of no difference corresponding to the baseline value itself), and then adding the average values of the position to the baseline values (of the location and contour of the irregular edges) of the contiguities.

In step 1818*a*, vertical disruptors in the contiguity and/or contiguity lines are mapped. In step 1818*a*, a map of vertical disruptors is computed as a baseline computation of the position and other parameters (e.g., the contrast or degree of disruption) of the vertical disruptor. In at least one embodiment, machine system 101 may be configured to map the vertical disruptors. The vertical disruptors may be objects or elements identified in the image that extend into a vertical plane from a horizontal line, e.g., from a contiguity. Vertical disruptors are horizontal features that disrupt contiguity lines and/or contiguities. The map may be based on the regions (quadrants) of the region map, and a map for each region may be computed. In at least one embodiment, machine system 101 can be configured to map the vertical disruptors. Differences between the vertical disruptors of different degrees of stitching/peeling and/or thresholding may also be computed.

In step 1820*a*, the vertical disruptors and optionally the differences in the positions of the vertical disruptors are stored.

In step 1822*a*, an average vertical disruptor may be calculated by averaging the differences in the vertical disruptor (e.g., including one value of no difference corresponding to the baseline value itself) and then adding the average of the differences to the baseline values of the vertical disruptor, and/or the spatial separation between multiple VDs stored. In at least one embodiment, machine system 101 can be configured to calculate the average width span, height, and/or density (co-localization) of the vertical disruptors.

In step 1824*a*, a contiguity continuity value (CV) is computed (e.g., based on steps 1816*a* and 1822*a*). In at least one embodiment, machine system 101 can be configured to assign the contiguity continuity value, which is the value assigned to the contiguity and represents the degree to which there are disruptions in the contiguity across the X-axis, e.g., where the X-axis is the horizontal plain of the image. For example, the contiguity continuity value can have a value within a range of −1.0 to 1.0. The contiguity continuity value may be assigned according to the values obtained for the vertical disruptors and irregular edges. For example, where the contiguity extends across the image within a range of 75 to 100 percent, a contiguity value range of 1 may be assigned. Where the contiguity line extends across the image width within a range of 50 to 75 percent, a value of 0 may be assigned. Where contiguity extends across the image within a range of 0 and 50 percent, or the contiguity is zero, a value of −1 may be assigned. In alternative embodiments, other values and methods of computing the contiguity continuity may be used. For example, the percentage of the width of the image that the contiguity extends (or the percentage of the width of the image that the contiguity extends minus 50%) may be used as the contiguity continuity value (so that the contiguity continuity value is a continuous variable) and as defined in the rules table of FIG. 19C.

Figure 18B:
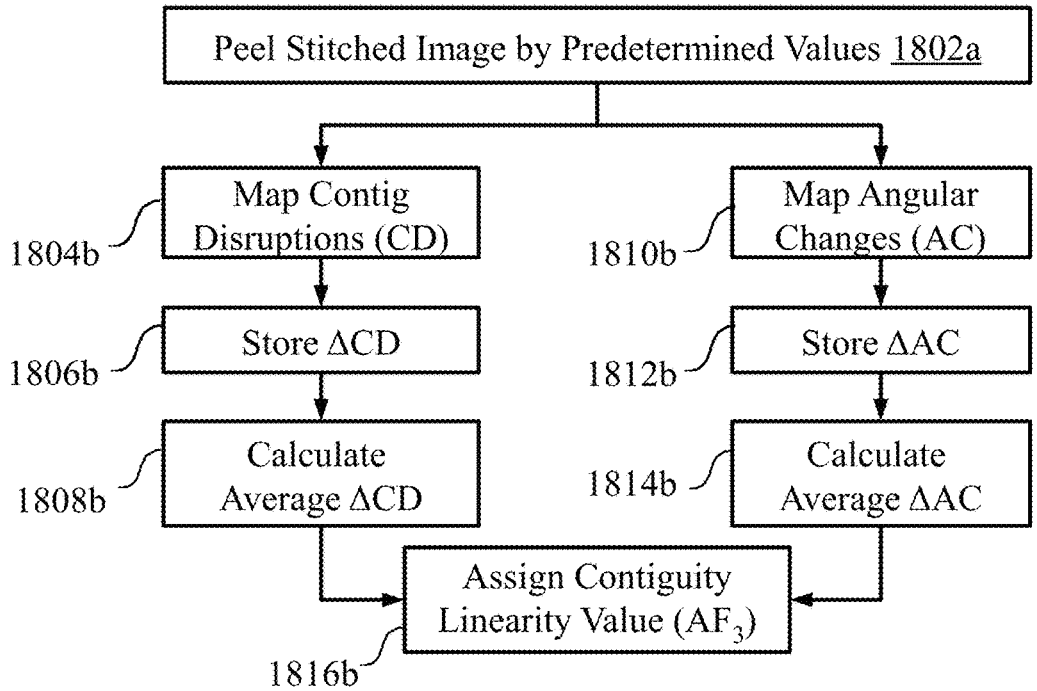

The method of FIG. 18B is part of the method of FIG. 18A. Step 1802*a* of FIGS. 18A and 18B may be the same step.

In step 1804*b*, the position and shape (and optionally other parameters) of the contiguity disruptions (CD) are mapped to establish a baseline of the shape, dimensions, and/or position of the disruptions. Contiguity disruptions are breaks or partial breaks into a contiguity. For example, a region in which the width of the contiguity is less than the adjacent regions (e.g., by more than 10% or 15%) may be considered a contiguity disruption (in other embodiments other criteria and/or percentages may be used for determining a contiguity disruption). Note that the terminology used here the length of contiguity extends generally along the horizontal axis or at an acute angle with the horizontal axis of the image, and the width of the contiguity extends along the vertical axis of the image or at an acute angle to the vertical axis of the image. In at least one embodiment, machine system 101 can be configured to map the contiguity disruptions. The contiguity disruptions are mapped to enable machine system 101 to locate the contiguity disruptions in the image, e.g. where there are objects or portions of the image that disrupt the contiguity in the image. The map may be based on the regions (quadrants) of the region map, and map for each region may be computed. In at least one embodiment, machine system 101 can be configured to map the contiguity disruptions, which may also include vertical disruptions in contiguities or contiguity lines. Optionally, differences—resulting from different degrees of stitching/peeling and/or thresholding—in one or more contiguity's, linearity, and/or continuity may also be computed and compared.

In step 1806*b*, the contiguity disruptors and optionally the differences in contiguity disruptions are stored.

In step 1808*b*, an average contiguity disruption is computed, by averaging the differences in the contiguity disruption (e.g., including one value of no difference corresponding to the baseline value itself) and then adding the average of the differences to the baseline values of the contiguity disruption. In at least one embodiment, machine system 101 can be configured to calculate the average contiguity disruption.

In step 1810*b*, angular changes (AC) in the contiguity and/or contiguity lines are mapped, to establish baseline values. In at least one embodiment, machine system 101 can be configured to map angular change of the contiguity line. The angular change (AC) can be the angle at which the contiguity in the image relative to an X-axis (a horizontal axis), e.g., horizontal plain of the image. The map may be based on the regions (quadrants) of the region map, and map for each region may be computed. Optionally, difference between angular changes in contiguities of different degrees of stitching/peeling and/or thresholding may also be computed. In step 1812*b*, the angular changes and optionally the differences in angular changes are stored.

In step 1814*b*, an average angular change (AC) is calculated, by averaging the differences in the angular change (e.g., including one value of no difference corresponding to the baseline value itself) and then adding the average of the differences to the baseline values of the angular change. In at least one embodiment, machine system 101 may be configured to calculate the average angular change. The average angular change can be the average angular change of the dominant contiguity, another designated contiguity or all contiguities in the image.

In step 1816*b*, a contiguity linearity value is computed, which may be based on steps 1808*b* and 1814*b*. In at least one embodiment, machine system 101 can be configured to assign the contiguity linearity value, which is the value assigned to the contiguity for a deviation of the X-axis, e.g., horizontal plain of the image. For example, in an embodiment, the contiguity linearity value can have a value within a range of −1.0 to 1.0 and is derived from the average contiguity changes (Step 1808*b*) and angular changes (Step 1816*b*) using measurement boxes, which may be computed in steps 406 (FIG. 4) and/or step 606 (FIG. 6) of Ser. No. 16/427,305. The measurement boxes (or regions of other shapes) may be boxes formed by the grid. The contiguity disruptor and angular change may be computed for each region (in steps 1804*b* and 1810*b*). Then, the values of each region for the contiguity disruptor and angular change may be averaged over the entire images in steps 1808*b* and 1814*b*, and then the two averages (the contiguity disruptor and angular change) may be used to compute the contiguity linearity in step 1816*b*. Although in FIGS. 18A and 18B average values are computed by computing a baseline value and then averaging the differences of subsequent measurements taken at different degrees of stitching and/or thresholding, in other embodiments, the average values may be computed in other ways. For example, the average values may be obtained by re-measuring the edge irregularities, the vertical disruptors, the contiguity continuity, and/or the contiguity linearity, and averaging the entire measurement.

In an embodiment, each of the steps of methods 1800*a* and 1800*b* is a distinct step. In another embodiment, although depicted as distinct steps in FIGS. 18A and 18B, step 1802*a*-1816*b* may not be distinct steps. In other embodiments, methods 1800*a* and 1800*b* may not have all of the above steps and/or may have other steps in addition to or instead of those listed above. The steps of methods 1800*a* and 1800*b* may be performed in another order. Subsets of the steps listed above as part of methods 1800*a* and 1800*b* may be used to form their own method.

FIG. 19 provides a method 1900 for analyzing the content of images. Sub-library images can contain regional content and/or culturally-appropriate content, and/or images designed to meet a particular cognitive protocol for a subset of users with particular cognitive requirements. Images and image sets can be selected by the system as part of a protocol and/or treatment schema, and/or to assess the user's cognitive status. Alternatively or additionally, in the case of a registered user, image sets and interactivity gameboards containing images and image sets can be user-defined (e.g., personalized), based on a set of rules designed to match user interests and preferences to the user's skill level and/or a desired treatment regimen at a point in time. User activities can be stored so as to retrieve user data. The retrieved user data may allow for the completion of a saved interactive and/or may be used for the regimen to progress from the prior activities and/or level activities already completed to the next activities and/or level according to the user's training and/or therapeutic protocol, and/or pre-defined skill level threshold achievement.

In step 1910, an image is uploaded or scanned by a user, healthcare worker or platform administrator. The image can be an image selected by a user to be part of that user's personalized cognitive assessment/test, game, or interactivity. The user may find the image by searching the internet, or the user may choose a personal image from a photograph, for example, in the user's library. In some embodiments, the user is a healthcare worker who is preparing a multi-purpose interactive cognitive platform configuration to be used for diagnosis, treatment, or research. The healthcare worker may choose the image or images that are appropriate for a particular patient or group of patients. The image or images chosen may be referred to as an image of interest or images of interest. For example nature scenes, urban scenes and/or a mixture of the two as per user interest, preferences and/or protocol requirements.

In step 1920, the image of interest in this embodiment is sized and/or cropped to a predetermined size automatically (based on previous input or rule) or may be sized and cropped by a user. The cropping may remove portions of the image or the portions of the image that are not wanted, or edges of the image that cause the image to be too large for generating the composite image, and/or to centralize dominant contiguities and color blocks in the image or in a portion of an image or other salient features. The cropping and/or sizing may be performed in a manner that achieves a desired value for a parameter, such as the contiguity rating and/or saliency value.

In step 1930, each image in the library is tagged with descriptive elements. The descriptive elements can define the image's action, content, and/or color. Each image can also be tagged with an optional text display box that identifies image content. To address users that speak a language other than English for example, alternative text labeling in the user's native or preferred language can be included to maximize the value of the interactivity for specific cognitive interventions, language remediation, and/or training purposes. The platform may include a language pack to accommodate multiple language capabilities. Additionally, interactivities that do not include a language domain assessment can be handled in a language agnostic way.

The image may be tagged with descriptors with optional human input. In some embodiments, once the image of choice is tagged with descriptors, the image is stored in association with its data in the library (in step 1980). The tagged descriptors may include a robust collection or library of descriptive terms. Optionally, once the tags are inputted in one language, an AI-based system may optionally be used to generate companion language sets with image descriptors, optionally without administrative/human input.

In step 1940 the contiguity analysis is performed. Each image in the library is ranked according to its complexity based on content complexity and contiguity characteristics among other factors. The impact of contiguities can be seen using a sunflower field example where the field fills the entire frame versus an image where a part of the sky is visible creating a more traditional horizon-type contiguity. The horizontal contiguity can be viewed as an interface (of field:sky) with an identifiable demarcation in both content and color distribution, which simplifies and facilitates interpreting the image. The identification of the demarcation as in the interface between the sky and ground may be based on the user's personal knowledge and experience.

Complexity is at least in part a function of the content, the spatial relationship of the content, and the presence or absence of one or more contiguities. For example, an image containing a single yellow flower with a brown center framed in a single color background would be ranked as less visually complex then a field of flowers. The lower complexity ranking of the single flower is because the single flower has a stronger contiguity than the field of flowers without a horizon. However, the single flower may have a weaker contiguity compared to a field of flowers with a horizon-type interface (providing hierarchical relationships to figure-ground positioning of image content based on the image's contiguity characteristics) and compared to contiguity characteristics of the field of flowers with a horizon that is combined with other images in generating composite image sets. A hierarchical example of contiguity relationships is shown in the 3-image composite of FIG. 23C and the re-distribution of the component images into 2-image composites of FIGS. 25A-25C).

As part of the contiguity analysis 1940, in addition to assigned attributes, each image in the library is analyzed and assigned aesthetic and ambiguity values based on a subset of image characteristics. In addition, a second value, a Compositing Factor may be derived in part from the aesthetic and ambiguity values (see FIG. 19B). The Compositing Factor characterizes a combination of images and may be related to combining an image with one or more other images, based on a subset of image characteristics. The ambiguity value is also known as the Complexity Rating (CR) and may be based on contiguity characteristics of at least one dominant contiguity and/or contiguous region that can contribute to the ambiguity and/or aesthetic scoring. The CR value can also be derived for a multiplicity of contiguities contained in a single image, based on the potential positive and/or negative impact of the contiguities in a composite image. The relative negative or positive contribution to the CR value depends on contiguity characteristics, including: content coherence, context, color composition, and spatial separation.

In steps 1950, 1960 and 1970, the CR value, the Aesthetic value, and the Compositing Factor ($CF_{CR}$) are stored in association with other information about the image.

In step 1980, the image of choice and the data associated with the image of choice are stored in a library. In some embodiments, the library may be specific to a user, a healthcare worker, a condition/disease type, a research protocol, training protocol, or a testing protocol. In some embodiments, once the image of choice is provided with a CR value, the image is stored in association with data in the library, in step 1980. In some embodiments, once the image of choice is provided with an aesthetic value, the image is stored in association with data in the library, in step 1980.

The image library can obtain source materials from image databases and stock photo distributors, artists, which can include: individual photographers, photography groups, painters, illustrators, graphic artists, and other artists, including end-user supplied image content. Image uploads from specific user groups and/or individuals, including research and clinical administrators, may be integrated into user-specific interactivities. Alternatively or additionally, licensed images from other third party vendors may be uploaded to system 100, including archives and content providers to meet specific use cases and/or user requirements. The use of library images may be tracked internally for inclusion in any of the hands-on, hands-free, and/or view-only interactivities, including manipulatives as well as printed material as environmental enrichments. The tracking also serves to minimize duplication of content and/or near-content with the use of similar and/or related images and/or associated Word Lists used for assessments. The component image tracking system can be used for tracking usage and any remunerations owed to the contributing artist based on prior arrangements and agreements.

In an embodiment, each of the steps of method 1900 is a distinct step. In another embodiment, although depicted as distinct steps in FIG. 19A, step 1910-1980 may not be distinct steps. In other embodiments, method 1900 may not have all of the above steps and/or may have other steps in addition to or instead of those listed above. The steps of method 1900 may be performed in another order. Subsets of the steps listed above as part of method 1900 may be used to form their own method.

FIGS. 19B-19E show tables of rules and values that summarize some computations that may be performed to identify and/or characterize contiguities. Referring to FIG. 19B, the prominence and number of contiguities may be represented by a contiguity rating value (CR also referred to as the Ambi Value or juxtaposition value), which may be computed based on the formula, $CR = \Sigma(AF_1 + AF_2 + AF_3 + AF_4 + AF_5 + AF_6)/n$ (where n=6), where $AF_1$, $AF_2$, $AF_3$, $AF_4$, $AF_5$, $AF_6$ are ambiguity factors (AF). In other embodiments, there may be other factors and/or one or more of $AF_1$, $AF_2$, $AF_3$, $AF_4$, $AF_5$, $AF_6$ may be divided into multiple factors, while one or more others of $AF_1$, $AF_2$, $AF_3$, $AF_4$, $AF_5$, and $AF_6$ may be left out thereby changing the value of n.

As indicated in FIG. 19B, $AF_1$ is a contiguity number which is determined by detecting edges, using an edge detection technique and/or threshold techniques edge detection technique and/or other types of filters, which produce a binary image based on a threshold that determines which of two values a pixel is assigned.

Contiguity Count Total ($AF_1$) is the average of the count of contiguities based on a variety of methods of counting contiguities. For example, a number of different threshold images may be produced for a variety of intact or different stitched images (which may be stitched differently). For example, the threshold values for the image measured at a starting point of 127 value (for example) and then at 160 (for example) for standard images, where the color may be represented by pixels values of 0 to 255, for example, and for each image and stitched image the number of contiguities are counted. The number of contiguities may also be separately computed from the edges generated by an edge detection technique, such as a Sobel filter. A variety of color map images may be generated for a variety of different stitches, and the contiguities for each image may be counted. The total number of contiguities can be counted for each variation of the image and the method of counting contiguities are averaged.

More than just two thresholds may be computed. For an image using the thresholds of 127 and 160, $$\text{Averaged Contiguity Count}_{T127} = (\text{Parts}_{T127b} + \text{Parts}_{T127w})/2,$$

$$\text{Averaged Contiguity Count}_{T160} = (\text{Parts}_{T160b} + \text{Parts}_{T160w})/2,$$

where $\text{Parts}_{T127b}$ and $\text{Parts}_{T160b}$ are the number of parts of the image, that after thresholding have an average pixel value of black, and where $\text{Parts}_{T127w}$ and $\text{Parts}_{T160w}$ are the number of parts of the image that after thresholding have an average pixel value of white, and the subscripts "T127" and "T160" represent the threshold used for generating the threshold map. Each part may be a continuous region of a set of contiguous pixels of the same pixel value after thresholding. In an embodiment, one may count the number of black and white regions across the width of the image to arrive at the number of parts (e.g., along the central horizontal axis of the image or a long a line that is halfway between the top and the bottom the image).

$$\text{Contiguity Count Total } (AF_1) = (\text{Averaged Contiguity Count}_{T127} + \text{Averaged Contiguity Count}_{T160})/2.$$

$AF_2$ is the color block. Color blocks may be determined based on a sequential color extraction using a reduced, fixed number of colors (e.g., 2-6) from which color images may be based. Color blocks are a kind of contiguity. $AF_2$-CB defines the distribution of color. A color block may extend in any direction. A color block may be formed by a concentration or density of similar colors representing an object or region across a continuum or continuous region in both the horizontal and vertical directions. An example of a color block is the sky. Even in a stitched image, the sky can be blue, albeit of similar or different hues, across the width of an image. The image may be divided into regions (e.g., quadrants and sub-quadrants) and dominant color or colors are determined for each region. Color blocking allows for the identification and analysis of the colors in an image. Color blocking allows for an analysis of the colors in an image, the distribution of the color, symmetry of color blocks, and the identification of breaks in the block may be determined, indicating the presence of one or more vertical disruptors and/or other objects. The interruptions in color confluency can disrupt the color block's saliency, and/or create new regions of saliency, and/or facilitate identifying what the color block is. In an embodiment of the color blocking process, the image is progressively reduced to a smaller number of colors (e.g., less than 8, less than 7, less than 6, less than 5, less than 4, less than 3). During color reduction, the pixels may be grouped into bins of a histogram according to which color bin color value of the pixel is closest (e.g., if the image is reduced to the colors having color pixel values 100 and 200, then a pixel with a color value of 75 would be place in the bin for the color 100). A color extraction is performed on each color-reduced image to determine the number of pixels in each color bin. The values are averaged to arrive at the $AF_2$ value. In one embodiment, up to six color blocks can be identified and used for the calculation, depending on the number of colors and their percentage of contribution to the image.

For example, for a 3-color reduction the formula for the $AF_2$ is $CB.c_{\bar{x}}(AF_2)=(CB.c2+CB.c3)/3$. More generally, the formula for $AF_2$ is $$CB.c_{\bar{x}}(AF_2)=(CB.c2+CB.c3+\ldots CB.c(n))/n$$

(where n is the number of colors which are in the image, and which is an integer number having a value selected from the numbers, 2-6). In the above formula CB.c2 is the number of regions of contiguous pixels of one color identified after a reduction to two colors. CB.c3 is number of regions of contiguous pixels of the same color identified after a reduction to three colors, and CB.c(n) is the number of regions of contiguous pixels of the same color identified after a reduction to n colors.

$AF_3$, is contiguity linearity ($C_{linearity}$) for a contiguity using a stitched image. $AF_3$ may be computed from $C_{linearity}=C_A+C_D$, where $C_A$ is a value that represents an average of the degree to which the angle of the contiguity changes (e.g., the angularity) across the contiguity, and $C_D$ is average the number of breaks in the contiguity. $C_D$ also represents a value that reflects how disrupted the contiguity is, as measured using the stitched image. For example, in an embodiment, $C_D$ may have one of two values, which are 0 and −0.25, where $C_D$ is assigned the value of zero if the contiguity spans more than 75% of the width, and $C_D$ is assigned a value of −0.25 if the contiguity spans less than 75% of the width.

The contiguity angle may be computed from $$C_A=(L2C_x+R2C_x)/2,$$

where L2C is the angle made by a line connecting the center of the contiguity to the point where the contiguity intersects the left side of the image, and R2C is the angle made by a line connecting the center of the contiguity to the point where the contiguity intersects the right side of the image R2C is the line that best approximates the angle made by the right side of the contiguity whether or not the contiguity intersects the right side of the image. L2C is angle made by the line that best approximates the angle made by the left side of the contiguity whether or not the contiguity intersects the left side of the image.

Some rules for determining linearity according to at least one embodiment are as follows. The values in the following discussion are based on the angle of the dominant contiguity and, the distance off the X-axis (the horizontal axis). The measured angles are computed and averaged. The measured angles are further distilled with rules, so that images which differ significantly in terms of content can be still be grouped and categorized according to their angular complexity. However, having the angularity data for each stitch and peel image additionally allows for the extraction of other information.

A value of zero is assigned if the contiguity disruption is a straight edge, extending across more than 75% of the image width and if the averaged angular difference of a single baseline point is less than 5°.

A value of 0.15 is assigned to the linearity if the average angular difference is between 5° to 30°. A value of 0.25 is assigned to the linearity if the average angle difference is between 30° to 45°. A value of 0.75 is assigned to the linearity if the average angle difference is greater than 45° and if the contiguity extends across the image as a diagonal. A value of −0.15 is assigned to the contiguity if the contiguity is disrupted and/or non-linear (or irregular). A value of −1.0 is assigned to images without a defined contiguity or without an object-based contiguity. For example, if the only contiguity is the sky, that contiguity has a linearity of −1.0.

In at least one embodiment a solid block of color is not viewed as a horizon contiguity with linearity. If there is a horizon type of contiguity, the value of the horizon contiguity is different than −1, but in this embodiment, as a color block the sky has no linearity, per se, as defined by angles or disruptions since there are no disruptions in the sky's continuity.

In an alternative embodiment, the absolute value of the sine of the average angle (or the square of the sine of the average angle) may be used for linearity for contiguities with no disruptions.

$AF_4$ is the contiguity continuity value ($C_{continuity}$) for a contiguity using a stitched image. $AF_4$ is computed from $C_{continuity}=C_{VD}+C_{IE}$, where $C_{VD}$ is a value representing the average of the span (e.g., average of the total width of all) of the vertical disruptors (VD) per contiguity, and $C_{IE}$ is an average of the span of irregular edges (IE) of a contiguity. Some examples of VDs are a tree, a grove of trees, or a house on an otherwise continuous contiguity. Each VD has a height and can extend from the contiguity to the top edge of the image or to points in between. The irregular edges refer to what can be likened to an uneven surface—a rocky shoreline, or a city landscape which forms an irregularly edged (uneven, bumpy) contiguity by virtue of the color block of sky above and the continuity of the buildings across some or all the horizon.

The Contiguity Continuity Rules for assigning values to images with Vertical Disruptors and/or Irregular Edges are summarized in FIG. 19C. The Continuity Rules are: if an image has at least one contiguity which is continuous across the entire width of the image (75-100%+/−3%), then assign a value of 1.0. If the contiguity is continuous across 50-75%+/−3% of the image, then 0; if less than 50% or if contiguity number is 0, then assign a value of −1.0. If there is/are a vertical disruptor extending more than 5% but less than 30%, individually or if combined, up from an otherwise linear and continuous contiguity but which has additional complex contiguities, then assign a value of 0.5. If there are 2-3 VD that are spatially separated, then a value of 0.5 is assigned to the VD. If the vertical disruptors individually extend in the vertical direction less than 20% of the distance to the top of the image from an otherwise linear contiguity then the VD is assigned a value of 0.5.

If there are multiple vertical distractors present in the image (trees in the foreground), then assign a value of −1.0. Optionally one can use progressive decrements to identify variations/objects off the X-axis and their return to an established baseline across the entire image. If there are multiple irregular edges on one or more contiguities or if there is a single contiguity without a color block greater than 30% of the image's height above the IE, then assign a value of −0.25. Assign A value of −0.15 is assigned to a single contiguity with a poorly defined edge which may be interrupted across the width of the image, be irregular, or have vertical disruptions, but which is adjacent to at least one continuous color block or a color block greater than 30%.

For Irregular Edges, a poorly defined edge is a contiguity which is irregular, and/or which has multiple vertical disruptions throughout its width and/or clustered in regions. From a quantitative standpoint, a poorly defined edge would be an edge having multiple Vertical Disruptors present along the entire length of the contiguity, disrupting the horizon interface and/or where less than 30% of the contiguity's interface has a discernible color block above the disrupted portion of the contiguity. The percentage of disruption may also be defined by a series of grid tools to evaluate how much space a VD occupies and the color block above and around it.

The $C_{VD}$ is computed using the above contiguity rules (FIG. 19C).

Note that the formula below is used to determine where a VD meets the criteria for the rules. The formula accounts for multiple vertical disruptions. For example, for a farmhouse on the prairie with a silo, windmill, barn, and house in otherwise open space, each of the elements would represent a VD which would be analyzed according to each VD's contribution to the overall VD impact to disrupting the contiguity's continuity, because the individual VDs are considered to define the VD relative to one another. The space between VDs from a width perspective, and the height parameter for the image, as defined by the contiguity's Y-location are part of what defines a VD.

To compute the $C_{VD}$, the Sub-area$_{dc}$ is the area above the dominant contiguity. The distance between vertical distractors is measured. The ratio of the area of the first vertical distractor to the subarea (e.g. quadrant) in which the first vertical distractor is in is computed according to the formula:

$$C_{VD.a1} = \text{Vertical Distractor}_{area1} = (VD1_{Q1w})(VD1_{Q1h})/\text{Sub-area}_{dc}$$

VDmQ$_{nw}$ is the width of vertical disruptor m of quadrant n and VDmQ$_{nh}$ is the height of the vertical distractor m of quadrant n. For example, VD1$_{Q1w}$ is the width of vertical disruptors of quadrant 1 and VD1$_{Q1h}$ is the height of the vertical distractors of quadrant 1. The subarea is the area above the contiguity, and each $C_{VD}$ is the percentage of the area above the contiguity that is occupied by the vertical distractor. The above continuity rules are applied to the first vertical distractor based on the area $C_{VD.a1}$, and where quadrants are used to divide an image into parts for targeted analyses of specific areas of an image.

The ratio of the area of the second vertical distractor to the subarea (e.g. quadrant) in which the second vertical distractor is in is computed according to the formula $$C_{VD.a2} = \text{Vertical Distractor area } 2 = (VD2_{Q2w})(VD2_{Q2h})/\text{Sub-area}_{dc}$$

The continuity rules of FIG. 19C, are applied to the first vertical distractor and to the ratio of the area of the second vertical distractor to the subarea containing the second vertical distractor, $C_{VD.a2}$. The process applied to VD1 and VD2 is repeated for each vertical distractor $C_{VD}$. In an embodiment, for Irregular Edges, there is only one definition for a vertical disruptor, which is based on the width of the irregularity. As noted previously, all VDs are irregular edges, but not all irregular edges are VDs. For example, the trees of a grove of trees are VDs; the grass or flowers of a field with flowers or grass form an IE or part of an IE with a sky interface above the field; but where tall sunflowers along a rocky shoreline would be viewed as VDs, a rocky shoreline can be viewed as an IE.

$C_{IE}$ describes irregular edges as part of computing the contiguity's continuity according to the following rule: If there are multiple irregular edges present on one or more contiguities; or, if a single contiguity is present but without a vertically adjacent color block with an area greater than 30% of the image above the contiguity, then assign a value of −0.25. A value of −0.15 is assigned if there is only a single contiguity with a poorly defined edge, but which is adjacent to at least one continuous color block, or has a vertically adjacent color block with an area greater than 30% of the image, above the contiguity.

Referring to FIGS. 19B and 19D, AF$_5$, is the color block depth 100, which defines the color block distribution (see steps 1724 and 1726, above). The assignment of a value follows a set of rules described in FIG. 19D using a quadrant-based analysis of the color distribution in the image. The FIG. 19D rules table applies to both AF$_5$-Color Block Depth 100 (CBD$_{100}$) and CBD$_{ST}$, for the stitched image.

Referring to FIGS. 19B and 19E, AF$_6$ is the spatial color-contiguity value, which compares the contiguity number to the color block number. To obtain a value for AF$_6$, the value obtained for AF$_2$ (Color Block) may be compared to AF$_1$ (number of contiguities present in the image), and are summarized in the table in FIG. 19E as follows. If AF$_1$ is equal to AF$_2$, then assign a value of 0; if AF$_1$ is greater than AF$_2$, then assign a value of 1; if AF$_1$ is less than AF$_2$, unless the contiguity number is equal to 0, then assign a value of 2; and, if AF$_1$=0 then assign a value of −1.

Figure 20A:
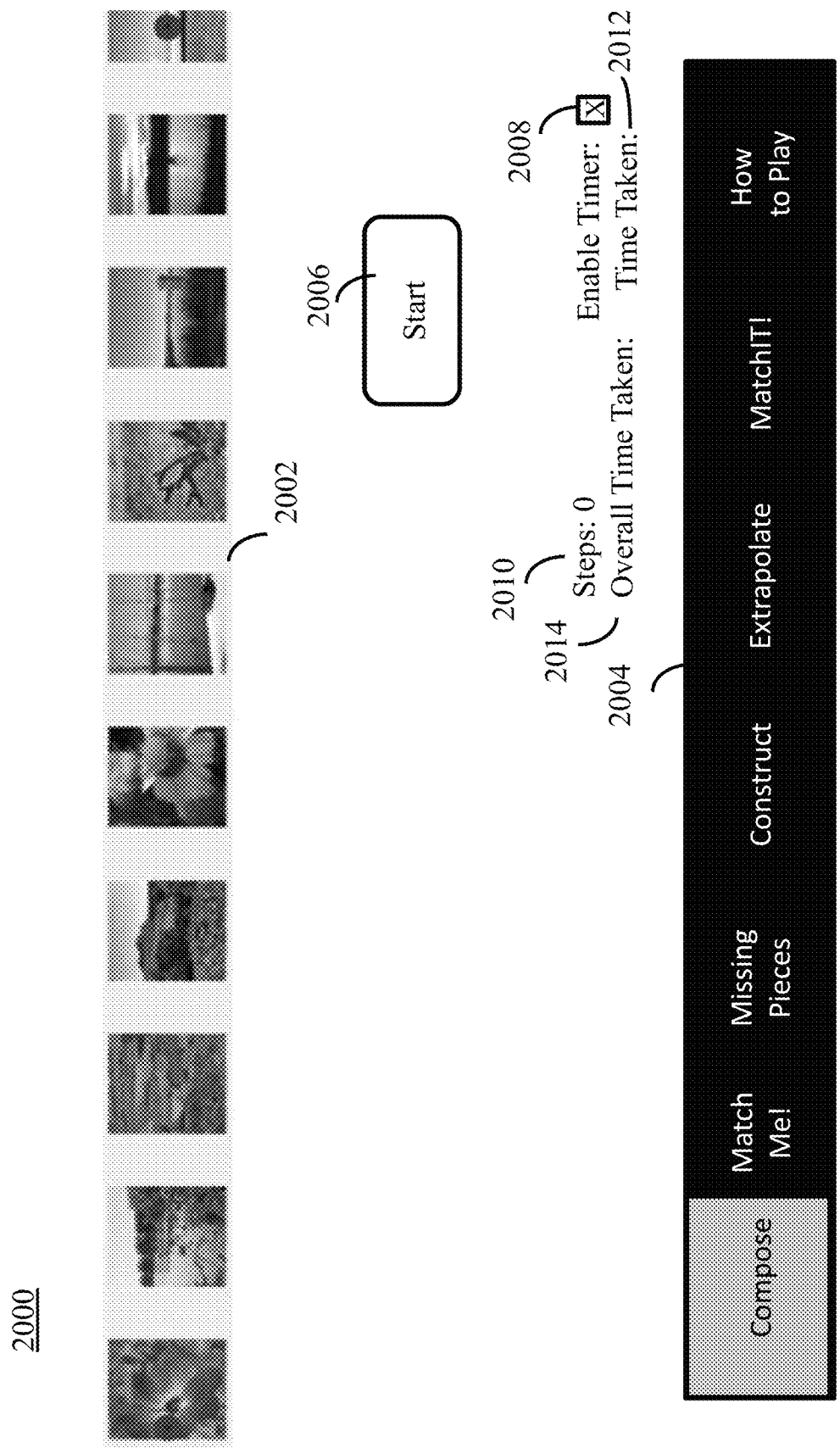

FIG. 20A illustrates a screenshot of a Freeplay Navigation 2000, which may include scrolling image library 2002, navigation bar 2004, start button 2006, timer toggle 2008, Number of Steps 2010, Time Taken 2012, and/or overall time taken 2014.

Navigation 2000 is an example of a page that a user may use for selecting an interactivity and images for the interactivity. Scrolling image library 2002 is a library of images through which the user may scroll, which may be part of interactivity interface 229. Once the user finds a desired image or images, the user may select that image or images (e.g., by clicking on the image). Navigation bar 2004 may be used to select a desired interactivity. In an embodiment of FIG. 20A, Navigation bar 2004 may display, and the user may select from a Compose interactivity, Missing Pieces interactivity, MatchMe! interactivity, a Construct interactivity, Extrapolate interactivity and a how-to play button. Alternatively or additionally, the menu bar (or other navigation tool) may have links for other interactivities options. In the example of FIG. 20A, the Construct interactivity, Extrapolate interactivity, and MatchIT! interactivity use a composite image; while the Compose interactivity, Missing Pieces interactivity, and MatchMe! interactivity use a single non-compo sited image Start button 2006, when activated, may initiate an interactivity. Timer toggle 2008, when activated may change whether there is a timer that is on while the user interacts with the interactivity. Number of Steps 2010 may record and display the number of steps the user takes to complete the interactivity. Time Taken 2012 may indicate completion of the time taken for one interactivity, whereas overall time taken 2014 may indicate the total time for completing all the interactivities.

FIG. 20B(1) shows pieces 2016, work area 2018, reference figure 2020, and/or sectioning selector 2022. Pieces 2016 are parts of an image that may have been jumbled, which the user is tasked with reassembling. Work area 2018 is the location where the user supposed to place the pieces. Reference figure 2020 is an image that the user may refer to determine where in work area 2018 to place 2016 image sections which can be referred to as a holding area. Reference figure 2020 may be the figure that user is tasked with reassembling. Sectioning selector 2022 is a set of choices that the user may select to choose the sectioning strategy of the interactivity. In FIG. 20B(1), the user has selected a sectioning strategy that uses 4 pieces. In an embodiment, FIG. 20B(1) and FIG. 20B(2) each show the same image, but with different sectioning strategies for the Compose interactivity. FIG. 20B(1) is sectioned into pieces that each are 25% of the image, and FIG. 20B(2) is sectioned into pieces that each are 12.5% of the image. Each of FIGS. 20B(1) and 20B(2) have a different grid size corresponding to the dimensions of and shape of the pieces. In each of FIGS. 20B(1) and 20B(2) the user selects an image piece (e.g., with a cursor), and drags and drops the piece to the grid space where the user wants to place the selected piece. If the user places the piece in the correct grid space, the piece stays in place, and optionally an audio feedback in provided indicating that the piece was correctly placed, such as with a click. If the user places the piece in an incorrect grid space, the user may receive feedback indicating that the placement is incorrect. The feedback may be audio. Optionally, the piece may move back to its original location in the holding pen rather than staying in place, and/or may be indicated with a visual cue of an incorrect placement.

Figure 20C:
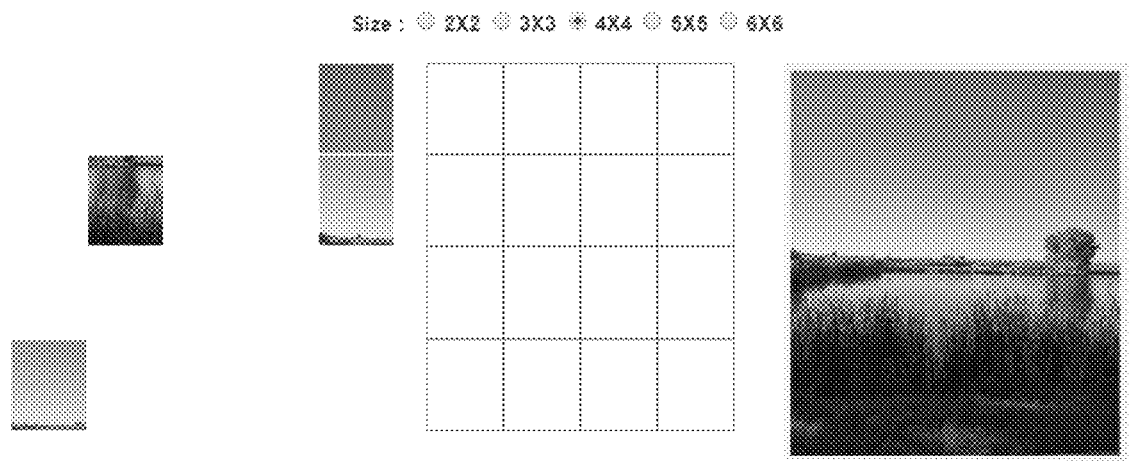

FIG. 20C shows a missing pieces interactivity, in which in addition to the sectioning being variable, the number of pieces that the user interacts with is a fraction of the total number of pieces of the interactivity. In the example of FIG. 20C, the user has chosen a 4×4 grid, dividing the image into 16 sections, and the user has chosen to locate only 4 of the pieces.

Figure 20D:
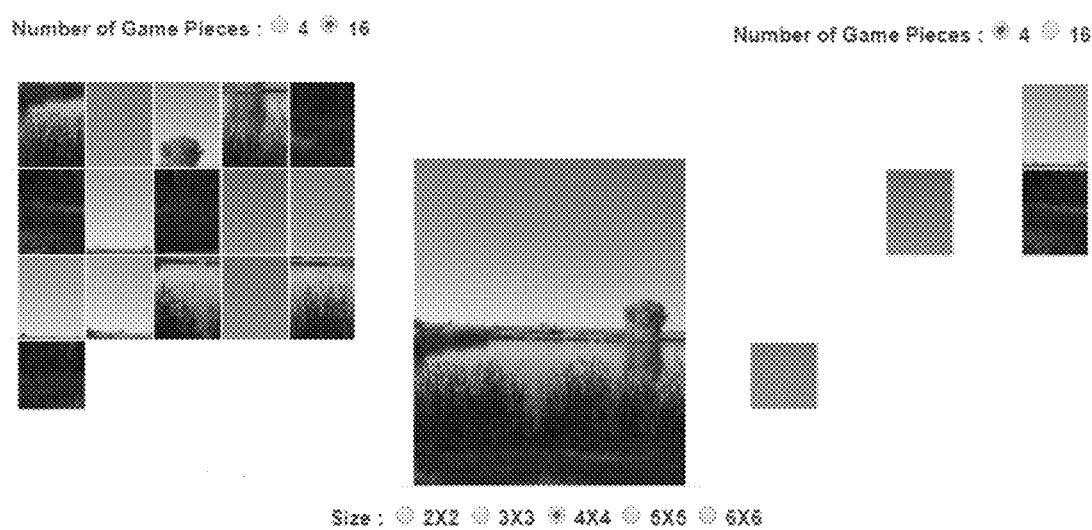

FIG. 20D shows an example of a MatchMe! Interactivity, which has a variable and adjustable size and number of pieces for the interactivity. In FIG. 20D, the user may place the pieces directly on the reference image, instead of on an empty gird. In the left panel, the user has selected to divide the image into a 4×4 grid (16 rectangles), and to match 16 of the 16 pieces to the correct location of the reference image. In the right-most panel, the user has selected to match 4 of the 16 pieces.

Figure 20E:
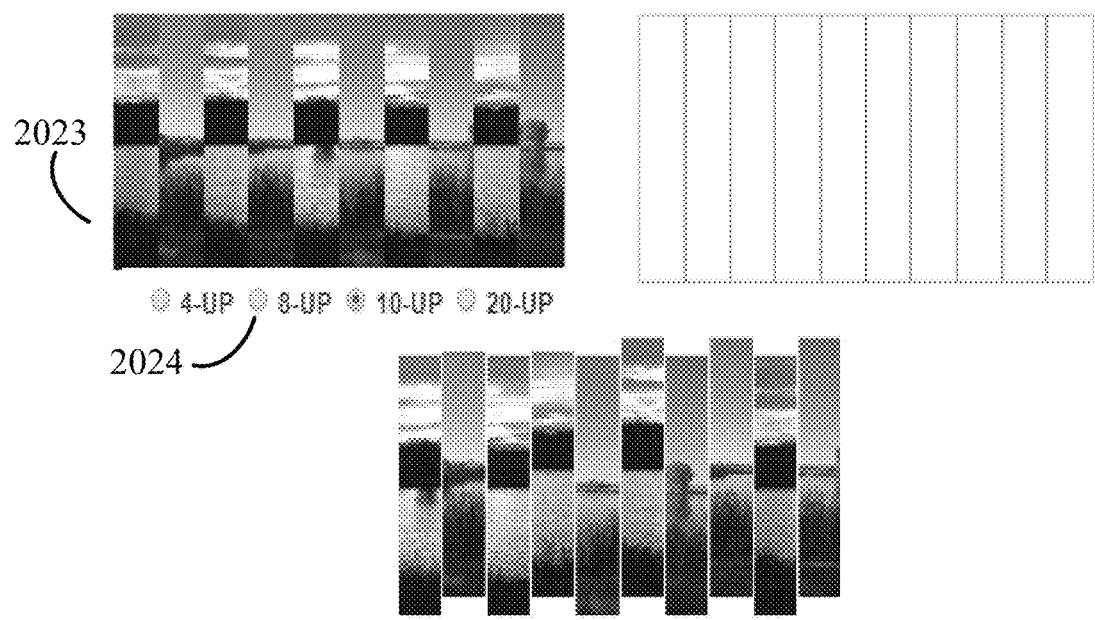

FIG. 20E shows a Composite Construct Interactivity with grid, and a selection tool, 2024 for choosing different sectioning strategies with corresponding different sized grids and number of sections. In FIG. 20E, the user is tasked with sorting the jumbled image sections and constructing the image by referring to a reference image. In one embodiment, the reference image may be previewed and then hidden from the user. In one embodiment, the user may not be presented with a reference image and is tasked with solving the pattern through trial and error problem-solving.

Figure 20F:
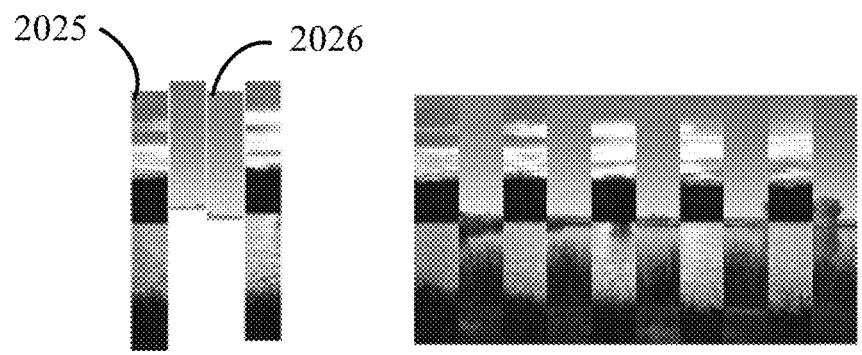

FIG. 20F shows a MatchIT! Interactivity. The pieces include full section pieces 2025 and half section pieces 2026 for matching to a composite reference image.

Figure 20G:
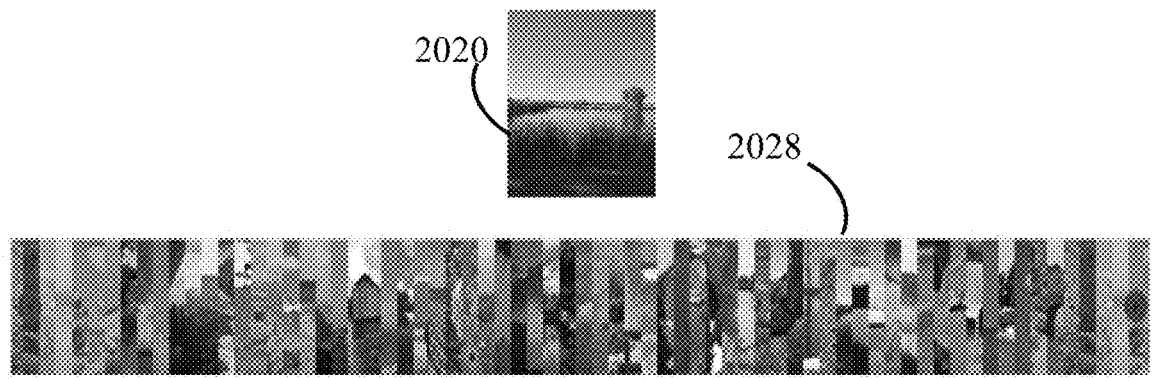

FIG. 20G is a Banner MatchMe! and/or MatchIT! interactivity. In an embodiment, a banner interactivity has many game pieces. In an embodiment, a banner interactivity may be an interactivity where single image sections are grouped together. In an example of FIG. 20G, the banner is comprised of image sections with 50 or more pieces from 50 different images. The user is tasked with scanning the banner for sections (for example, 2028) which can be matched to one or more of the component images (2020) or to composite reference images (2023).

In some embodiments, the multi-purpose interactive cognitive platform graphical user interface (GUI) components may include: a digital application, an expandable image library, categories of interactivities or a pre-defined battery of interactivities (for example, Jumble-Sort, Compose, Missing Pieces, MatchMe!) which may be applied to individual images and to 2-image composites or multi-image composites (for example, Jumble-Sort, Construct, MatchIT!, Extrapolate, Dimensional Descriptors at fixed or variable sectioning strategies and/or complexity levels. The percent (%) sectioning strategy (that is the percentage of the total image that each sectioned part is) may be varied, which may affect the number and size of the playing pieces. In an embodiment, a timer can be toggled and hidden. In an embodiment, user interactivity statistics (alpha-type speed and accuracy assessments) may be displayed. User gameplay statistics may include the time taken for each move, the time taken for each group of moves, reaction time (time to first move), average reaction time, the total time taken to complete the interactive, and/or number of errors. User gameplay statistics stored as part of the user statistics and are incorporated into built cognitive profiles and cognitive signatures for registered users.

In an embodiment, a protocol may be set up so as to be taken in a unit of 12-sessions, in which the user performs 2 sessions per week with fixed interactivities and image sets, at the easy level, for example.

In another embodiment, the platform may include an Auto-Sequence Play. The Auto-Sequence mode may be a set of interactivities based on user progress through a pre-defined sequence of increasing complexity, in which the user completes tasks with a countdown clock and proceeds through the pre-set threshold progressions. The platform may include a Cognitive Health Sequence, which may be similar to sequenced play, but with an embedded Mem+ assessment (Remedial, Easy, Medium, Hard levels, for example) with additional scales, and/or to include the use of an optional visible timer. The platform may include specialty modules. The specialty modules may be a subset of interactivities and related assessments. For example, one specialty module may be a Stroke Recovery module, which may include an interface and configuration personalized for those who have suffered a stroke, and therefore may include Virtual View-only and/or Auto-run modes combined with a progression to hands-on interactivities. The Stroke Recovery module may implement a progression from VVO to Hands-on modalities as users recover/regain language and/or fine/gross motor abilities.

In some embodiments, there may be alternative presentation modes. In one presentation mode, there may be a user-specific registration and back-end user data stored, Language pack which has an association between words and elements in images in multiple languages, a Linguistic library which has a list of synonyms, including slang for use in Word List recalls, and/or an expanded image library which excludes a subset of images based on color, content, and/or context, based on user preferences, limitations and/or protocol requirements. The expanded library may include a number of images that are potentially searchable based on content tags, User-supplied images, semi-automated contiguity analysis, image descriptors tagging, and/or image usage statistics to eliminate potential bias in user selection and to avoid over-use/frequent use of the same images across all users and user groups.

In some embodiments, user statistics may include a movement mapper (that maps movement of the user as the user interacts with the interactivity). The interface for the user statistics may have saved data linked to the user, a Slide bar to adjust a percentage of the sectioning, and a link for unequal sectioning of the different images. For example, the size of the section of image 1 may be different than the size of the sections of image 2, which in-turn may be may be different from the size of the sections of Image 3. The presentation may include a tool for converting a 2-image composite image (e.g., which may have strips of two images interleaved with one another) to a 3-image composite image (e.g., by adding a strip of the third image between a strip of image 1 and a strip of image 2 and/or before image 1 and/or after image 2). The presentation may include increased and/or decreased size of the composite image for use as the reference image. The presentation may include a modified Navigation menu. The presentation may include an option for fixing or changing the size/change of an image changing the content of an image, a feature for pausing the Game pause, and Piece rotations, zoom in and out features, among other presentation features.

Figures 21A, 21B:
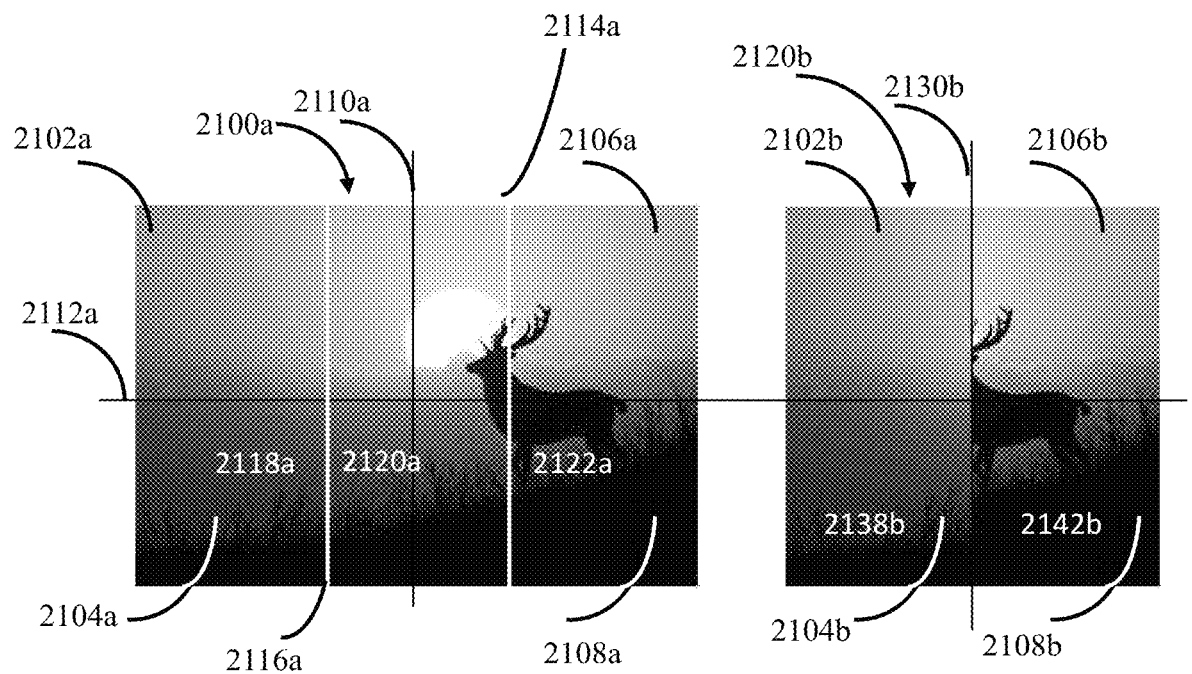
FIGS. 21A-21C show an example of the application of quadrant-based measures, FIGS. 21A and B show a stitch-based analysis of an image
Figure 21C:
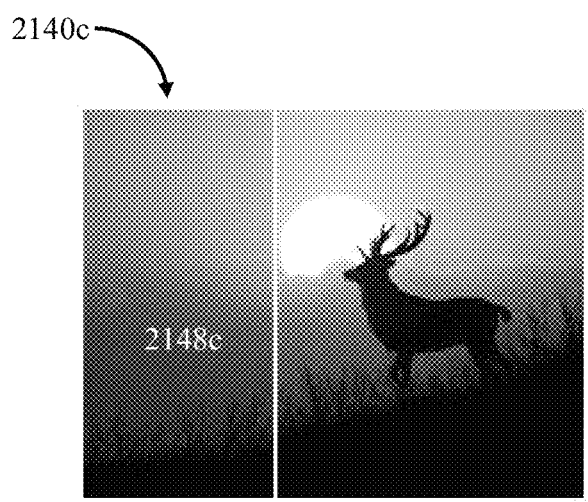

FIGS. 21A and 21B show the application of a stitch and peel, according to at least one embodiment. FIGS. 21A and 21B show two versions of an image of a buck, which includes image 2100a which is the full image prior to being stitched, and image 2120b which is the same image as image 2100a after being stitched.

In at least one embodiment, image 2100a (FIG. 21A) are divided into predefined sections, e.g., a first section, a second section, and a third section. For example, white lines 2114a and 2116a divide image 2100a into three horizontal strips, each horizontal strip is about ⅓ of the full image.

In FIG. 21B, the first section can be shifted from being adjacent to a second area to being adjacent to be a third area, so that the first section can mask the second section, thereby removing the second section (which in one embodiment may be ⅓ or 33% of the image) from the resulting image. For example, in image 2120b shown in FIG. 21B, line 2130b is in the location where line 2114a has been moved to in the process of removing the middle section of image 2100a. The locations of line 2130b is also the location were line 2114a was located in FIG. 21A, So that in image 2120b, lines 2114a, 2116a and 2130b are all in the same location as a result of removing the middle section of image 2100a. The first section can be peeled at another predetermined value, for example, at twenty percent, as represented by image 2140c (FIG. 21C) in which the central 25% of the image is removed); alternatively other amounts (e.g., 6.26%, of the total image, 12.5%, of the total image, 18.75% of the total image, for example) and by FIG. 21C a peel where part of 2100a is revealed. Different aspects of the contiguities and the images, as a whole are emphasized, and by averaging the characteristics of the different stitched versions of the same image of the images 2120a and 2120b features that may be missed by looking at the image and/or in identifying changes in an image scene, including a sequence of images such as video content, as a whole may be found or by looking at any one given stitch, or through multiple stitch and peels. In other embodiments, the stitching and peeling may be done in a different way than what is depicted in FIGS. 21A-21C). For example, a different percentage of the image may be masked than the percentages which are put back. For example, 90%, 80%, 60%, 40%, or 20% of the image may initially be masked, but where each stitch may put back only 10% of the amount removed, 15% of the amount removed, 20% of the amount removed, 25% of the amount removed 33% of the amount removed, or 50% of the amount removed until the original image and the positions of its sections are restored. For example, in the first stitch 15% of the amount removed may be returned, and in the second stitch 55% of the amount removed may be returned, and as a result of the first and second stitch is to return a total of 15%+55%=70% to focus on different aspects of interest in the image. The stitch also has the added benefit of condensing image content across an image, such that similar areas, and/or areas of change and/or differences across an image can be more quickly and easily identified.

Image 2120b (FIG. 21B) shows a stitch of a first image 2100a (FIG. 21A), according to at least one embodiment. The first image 2100a (FIG. 21A) is divided into four quadrants, e.g., first quadrant 2102a, second quadrant 2104a, third quadrant 2106a, and fourth quadrant 2108a. The four quadrants are defined by horizontal line 2112 and vertical line 2110 (FIG. 21A).

In stitched image 2120b (FIG. 21B) the quadrants overlap to produce first stitch quadrant 2102b, second stitch quadrant 2106b, third stitch quadrant 2104b and fourth stitch quadrant 2108b. The stitched image 2120b can enable determining that the color blocks between the quadrants, and which of the quadrants are symmetrical and/or different and asymmetrical. By bringing together two areas of the image that are not actually juxtaposed, machine system 101 can more easily provide an indication of a disruption in the color block or the presence of an object (e.g., a vertical distractor) in the image. In 2120b, the stitched image of figure 2100a, the vertical axis 2110a is replaced with vertical axis 2130b, while the horizontal axis 2112a is the same.

In FIGS. 21A and 21B, the disruption at the seam may be less than the disruption of the foreground, which facilitates automatically identifying a contiguity which spans continuously or is split across the image (similar to the way the mind is able to piece together the horizon and distinguish the background from the foreground).

FIG. 21C is an example of a partial peel, 2140c. Panel 2148c is the same as panels 2118a and 2138b. However, panel 2148c has not been moved to the right a full ⅓ of the image, but has just been moved ⅙ of the full image and revealing all of panel 2122a but only part of panel 2120a.

Figure 22A:
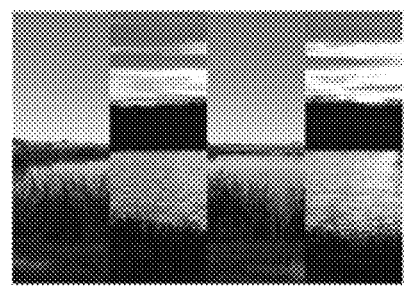
FIGS. 22A-22D shows examples of various sectioning strategies in 2-image composites.
Figure 22B:
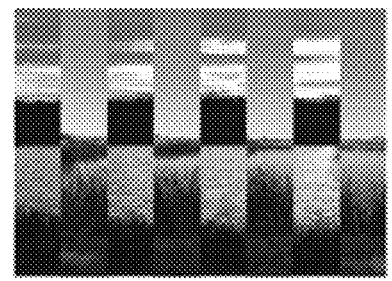
Figure 22C:
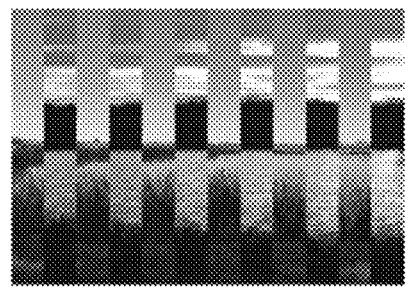
Figure 22D:
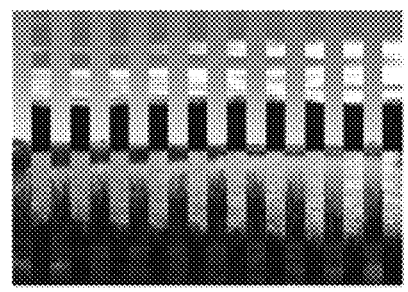

FIGS. 22A-22D show four examples of 2-image composites, comprised of the same component images, but each composite is sectioned differently: 50% for each image (FIG. 22A), 25% for each image (FIG. 22B); 16.67% for each image (FIG. 22C); and 10% for each image (FIG. 22D).

FIGS. 23A-23D show four examples of composite images, each comprised of three images, and how the presence of contiguities in one or more of the images affects the stability of the image in the ground position at any point in time. FIGS. 23A and 23B are multi-stable image sets, whereas FIGS. 23C and 23D are stable or fixed, i.e. the image in the ground position remains in the ground position and does not switch with the other component images in the image set. FIG. 23E shows a variable sectioning strategy, where two of the images in a three-image composite have the same sectioning strategy and a third image shows a mixed sectioning strategy. This type of sectioning strategy establishes mixed figure-ground relationships across the composite, while also facilitating the identification of image parts. In FIG. 23F, a single image is sectioned into parts, and the parts are separated by a solid white background which in other image sets can be occupied by sections from a second and/or third image FIGS. 23A-23F provide examples of how composite image sets may embed multiple Gestalt principles such as figure-ground, completion, and continuation, and which engage top-down cognition processes and bottom-up sensory processing as the user virtually reassembles the spatially separated image parts of the image in the ground position back into the original image from its parts, and as figure-ground dynamics are established in the constructed image sets.

FIG. 23A shows a composite image with a bird on a tree limb as one image, a frozen lake with a crack in the ice and shadow diagonally extending across the surface as another image, and a foggy lake scene with surrounding trees against the sky as the third image. The full composite image of the bird on a branch when used as one component image of a 3-image composite, shows how the contiguity "strength", contiguity position relative to the viewer's horizontal and vertical gaze position in the composite can affect which of the three images is seen to occupy the ground position, i.e. which image is pushed to the ground position at any point in time. Since all three images have contiguities, depending on where the user is looking, one of the images will be perceived as occupying the ground position at any one point in time. The sectioning aspect is not trivial and in many ways counter-intuitive. The greater the number of the sections (up to a point), the smaller the intervening sections which serve as disruptors and the greater the confluency capacity of the ground image, i.e., the easier it will be for the mind to reassemble the ground image, but which is mediated by the hierarchical relationship between the contiguities in each of the component images and the complexity of each image's content.

In FIG. 23A, each of the component images have reasonably distinct contiguities, namely the tree limb in the first image, the shadow on the frozen lake in the second image, and the interface between the water and the sky, combined with the sky and water color block size and coherency in the third image. Consequently, FIG. 23A is multi-stable, because each of the images has a contiguity. Each image's contiguities also extends across the width of the image, and are spatially separated to allow for switching to occur between all three images to greater and lesser degrees of ease.

FIG. 23B shows the top of a deer with antlers, a lake scene with clear skies, and a field with a cloudy sky. In FIG. 23B, the antlers and the top of the body of the deer form an object-type contiguity comprised of a single object against a relatively uniform color block (the field). In the second image of the composite, the interface between the ground and the cloudy sky, and in the third image, the interfaces between shoreline, lake and sky, each presents the user with contiguities, and which makes the image set multi-stable. One noteworthy aspect of the composite image of FIG. 23B is that in the middle to upper right of the composite image, the water in the lake and sky interface are dominant, but which become less salient on the left portion of the composite. Towards the middle left, however, the deer's antlers, which are framed against the field, allow that portion of the image to assume the ground position. Finally, the field-cloudy sky image can become the ground image when the bottom 10-20% of the image becomes the focal point of the user's attention or interest.

Thus, ground positioning is dynamic based on contiguity dominance and where the user's attention is focused. In FIGS. 23A and 23B, each image comprising the image set has at least one contiguity. The three contiguities are of different weights/saliency and are spatially separated in both horizontal and vertical spaces—giving the grouping of images switch characteristics as a multi-stable image set. The switch characteristic occurs because the mind is processing, trying to resolve the ambiguities in the image set, and tries to apply order and sense to the visual input using available patterns and knowledge. As such, the mind predicts what comes next, inferring based on information it has available such as color, content, context and the visual cues imparted by the contiguities. These visual cues are derived from but also inform the Gestalt principles of continuation, completion and closure to fill in the gaps, or in this case serve to guide the user in following the visual cues, ignoring the distractions (flanking content, gaps and/or blank spaces) in reassembling the image in the ground position, a dynamic process which depends on where the viewer is focusing their attention and/or interest. Contiguities may also be formed by large regions of the same or similar texture and/or coloring (e.g., the sky, a body of water, field behind the deer) as noted previously in the discussion of color blocks.

FIG. 23C shows two different floral scenes, one against a sky and the other without a clear distinction, and an image of mountains against a strong sky background. In this combination of images, only the image of the mountains against the sky has distinct contiguities, and so the image is stable with the component image of the mountains seen as being in the ground position, fixed in the ground position, i.e. stable in the ground position.

Similarly, FIG. 23D which shows a snakeskin, raccoon tracks in the sand, and a bird walking along a railing against a background of water only has one image with distinct contiguity. In this case, only the image of the bird on the railing has distinct contiguities, and so FIG. 23D is also stable where the image in the ground position is fixed, i.e., a stable perception (a stable percept). The virtual reassembly of the image in the ground position is a facilitated process. In a multi-stable image set, maintaining ground positioning for one of the images places a higher cognitive demand on the user as they attempt to hold one of the images in the ground position, or when the switching occurs with the reassembly in turn of each of the other component images in an image set. Consciously, the user must focus their attention, ignoring the distracting flanking content in order to prevent a perceptual switch from occurring, if that is the intention of an attention-training protocol. For FIGS. 23C and 23D, reconstructing the component images which occupy the figure position may require a higher degree of cognition, if it can be accomplished at all, since only one of the three images has a contiguity uniting the component parts of that image. The additional difference between FIGS. 23C and 23D is the ease of identifying what the component images are, the parts of the whole. In FIG. 23C the floral content is clearly discernible and recognizable, whereas in FIG. 23D, the snakeskin and raccoon tracks have a more abstract quality, making their identification more difficult and the image set more ambiguous overall and on a relative scale in comparing the two image sets' visual content. Both are still stable, but their complexity differs and, as such, the interactivity skill levels using these image sets would also differ.

Figure 24B:
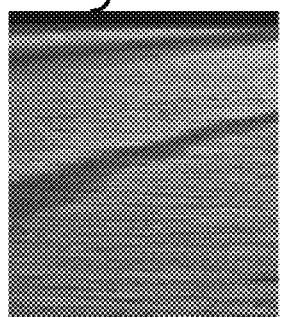
FIG. 24B is a composite image composed of three images, images 24A(1)-A(3).
Figure 24B:
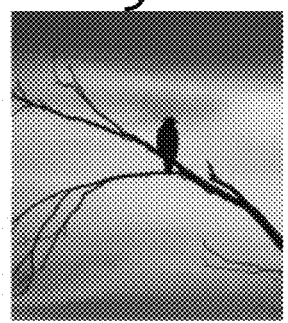
Figure 24B:
Figure 24B:
Figure 24B:
Figure 24C:
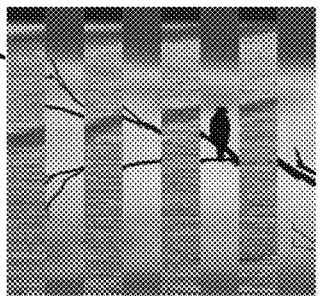
FIGS. 24C and 24D show multi-stable composite images each made from two of the images 24A(1)-24A(3).
Figure 24D:
Figure 24E:
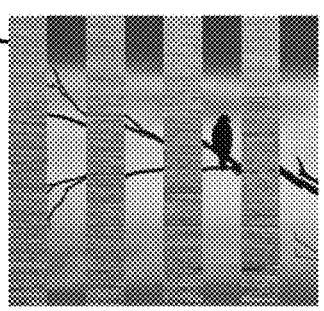
FIGS. 24E and 24F show stable composite images each made from two of the images FIGS. 24A(1)-24A(3), but with contiguities removed from the component image of FIG. 24A(1), thereby stabilizing the figure-ground relationship between the images.
Figure 24F:
Figure 25C:
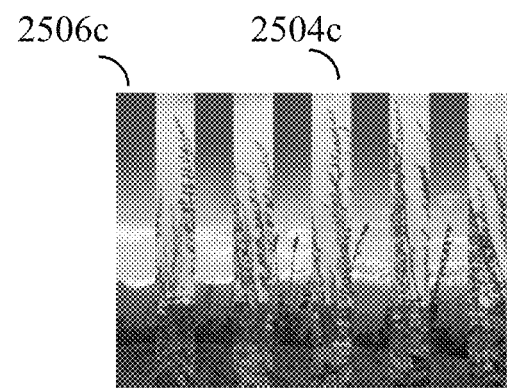
Figure 25D:
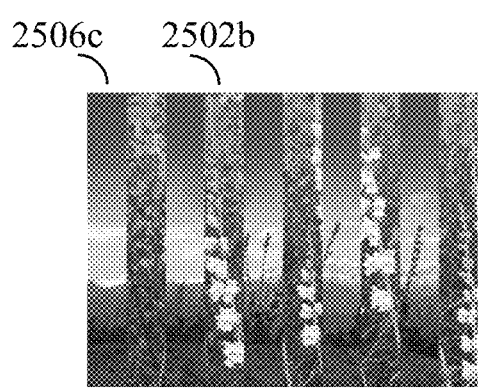

FIGS. 24A(1)-24A(3) show examples of the component images used to create the complete three-image composite of FIG. 23A, partial 3-image composite of FIG. 24B, and the derived 2-image composites FIGS. 24C and 24D, and the-modified 2-image composite images in which the contiguities are removed from one of the images to change the switch characteristics of the composite image (FIGS. 24E and 24F). FIG. 24A(1) is a first component image 2402 used for making the composite images of FIGS. 24B-24F. FIG. 24A(2) is a second component image 2404 used for making the composite images of FIGS. 24B, 24C, and 24E. FIG. 24A(3) is a third component image 2406 used for making the composite images of FIGS. 24B, 24D, and 24F. FIGS. 24C and 24E are the same, except that the contiguities that were present in component image 2402 (and which are present in FIG. 24C) have been removed from FIG. 24E. Similarly, FIGS. 24D and 24F are the same except that the contiguities that were present in component image 2402 (and that are present in FIG. 24D) have been removed from FIG. 24F.

FIGS. 24E and 24F show the effect of removing contiguities from component images of the composite image sets of FIG. 24C and FIG. 24D. Specifically, FIGS. 24B-24D are multi-stable as a result of the contiguities of the component images 2402-2406 (and one can relatively easily observe a switch between the component images in the ground positions and which image is in the figure positions between the two component images). By contrast, FIGS. 24E and 24F are stable as a result of the removal of the contiguities from component image 2402 which stabilizes the image set and precludes switching between the image in the ground position and the image in the figure position. FIGS. 24E and 24F are stable. In other words, the multi-stable nature of an image set can be manipulated and changed to a stable configuration by selectively removing one or more contributing contiguities which otherwise positively enables the image set's switch capacity. The shifting between switch (multi-stable) and non-switch (stable) and back to switch-capable image sets can be incorporated as part of a training protocol (and/or a testing and/or therapeutic protocol). Shifting between switch and non-switch and back to switch may be used to affect one or more cognitive domains, including the translation of response times from changes in processing speed attributable to switch speed rates for attention focusing and in object recognition tasks.

FIGS. 25A-D have been described previously and are used to demonstrate contiguity hierarchical and dominance relationships between images.

Alternatives and Extensions

In one embodiment of the platform, the images and/or image sets are gamified to generate manipulatable game pieces which the user uses in the various interactivities. Unlike many traditional types of puzzling interactivities, game pieces, e.g., manipulatable elements generated for, by, and/or used with the platform do not contain fitted-shaped edges with fit specificity. Rather, manipulatable elements are produced with only straight edges on each of its sides. Since all of the manipulatable elements potentially fit together with one another, the user is required to rely on visual and cognitive cues such as: image content, patterns, horizon lines/contiguities, color contiguity coherency as well as user knowledge and experience in identifying parts and reassembling puzzle pieces and/or other actions for engaging in other interactive manipulations.

In one embodiment using offline non-digital manipulatives, the sectioned puzzle pieces can be manufactured with a magnetic bud inserted into the sides of the image sections. Placing the magnetic buds (or sensors) in the puzzle pieces may create kinesthetic awareness of the image sections top-bottom orientation to provide immediate feedback on the placement attempt relative to interactivities using a single image composition and/or a composite. For people with pacemakers or other implanted devices, where proximity to magnets can be problematic, as well as with other users, but where tracking of the user's performance is desired, the platform may include a hybrid electronic game board incorporating a TUI prop as described previously. The TUI prop may include a timer element and/or may be programmed based on the image sets using a QR-type barcoding reader, and/or other type of sensor that can identify individual game pieces/image sections. The TUI prop may include a sensor that detect the completed image and/or image set, and provide data on speed and accuracy. The TUI prop may evaluate proper placements and map user decision-making movements, based on the sensor input (e.g., indicating that the user has finished placing a piece and/or finished an interactivity), and may include other sensors for measuring grip strength and other useful physiological and behavioral biometrics. In one embodiment, the digital game board interface, i.e., an active surface, may include embedded sensors lights and/or other visual and/or auditory cues to indicate proper as well as improper placement of individual pieces.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application of, or technical improvement over, technologies found in the marketplace, or to enable others of ordinary skill in the art to understand the embodiments disclosed herein.

The platform allows users to engage in the interactivities in a self-directed fashion as well as facilitated, group play and competitive play. The diverse modalities of self-directed, facilitated and group interactions is possible in part because of the nature of the interactivities, where turns can be taken, but also because the interactivities do not have to be time-dependent even though a timer may run in the background but which does not have to be visible to the user. The timer can also be used to limit a person's placement time during group play, where every turn is given a specified amount of time in which to complete a given turn/placement. Each of these variations is possible because interactivities are not time constrained and/or the solution or task completion does not have to be time-dependent.

These options give the multi-purpose interactive cognitive platform significant advantages over other cognitive platforms; specifically, for group and facilitated interactions. Group interactions can provide workforce partners with an opportunity for competition and team building on a larger scale looking at time to complete a series of tasks. The second type of group interaction can provide groups of individuals with opportunities for socialization as each can take a turn or work cooperatively to arrive at a solution as part of a group interactivity.

Facilitated-type interactions can also be overseen by a therapist during a treatment session and/or be provided by family and/or a caregiver and also can serve as a means of socialization, including direct engagement and also providing conversation prompts. The facilitated interaction may also be used to support cognitive training and/or treatment according to a set of protocols. Self-directed interactivities can be applied to the platform's multiple modes, including: Challenge, FreePlay, and Protocol mode or other modalities—where the latter describes defined professional protocols developed for diagnostic, assessment, treatment, and training purposes. A general Development mode description can be applied to the process of creating one or more interactivities by any non-professional and/or professional user for the purpose of supporting cognitive health and order performance enhancement skills training.

In one embodiment, the platform can be used for training purposes in Volume Information Processing mode and used in conjunction with a memory and/or attention assessment. In the Volume Information Processing mode or in any interactive mode, the user may be provided with sections extracted from an image and the user is then tasked to identify scenes or objects the user has observed in the task, identify color, and identify the scenes of the object's spatial position within the image. Another interactive can be the presentation of multiple image sections from 5 or more images, and then tasking the user to identify parts of the whole from the collection of images in a Sorting and/or MatchMe!-Banner type interactivity (see FIG. 20G). In one embodiment of a banner activity, image slices are extracted from multiple images. For example, 5 or 10 or 25 or 50 or 100 different images and arranged in a single banner and/or multiple banners where the single image slices are juxtaposed next to one another in a jumbled mix which can be randomized and/or directed according to the user's requirements and the interactivity. The user can be tasked to select from the banner one or more slices which match a reference image or multiple reference images. In an embodiment, multiple image slices from a single image can be distributed to multiple banners and the user is tasked with collecting all of the image's parts changing the MCD contributions of the various domains to enhance visual-spatial, attention and executive functions contributions within the interactivity.

In one embodiment, the platform can be configured to include an additional variable based on the presentation mode and the additional variable can be used to build skill level differences based on how the individual game pieces/ interactive elements are presented to the user. The differences in the building of a skill level can be in how the individual game pieces/interactive elements are presented to the user, and may include the presentation of all game pieces at the same time, where the user is then required to sort through the sections. In an alternative presentation format, the user may be tasked with working with a composite image set, and where the sections from only one of the component images are presented to the user for placement, and in being given only a section from one of multiple images of a composite image set can be used to vary the complexity of the skill level for the Jumble-Sort interactivity. Alternatively or additionally, the complexity of the skill level may be varied at the start of any of the interactivities where one or more game pieces can be presented to the user as whole sections and/or parts of a whole section as half, quarter and eighth-sized pieces, for example.

In one embodiment, the composite image sets can be used in a virtual view-only (VVO) mode and presented to the user as a kind of slideshow with and/or without interactivity sequences as a mini-movie or video clip, which can depict the manipulation of image sections in the platform's puzzle-type interactivities. The presentation mode may also include the component images as intact images and/or as a sequence which can show the construction and/or deconstruction of one or more composite image sets from its component images and a deconstruction interactivity back to its component images from the composite, respectively. The presentation mode may also label image objects and elements to support language recovery such as may be needed following a stroke, traumatic brain injury, concussion and/or with minimally conscious patients who may benefit from cognitively-stimulating activities. The slideshow-styled presentation can be viewed on a digital device, including: computer, tablet, phone, TV, monitor/screen, IoT device, and/or other type of smart device and deployed at specific intervals and/or to fill patient-therapist downtime. Parts of the component image or images can also include text labels placed on image elements, as noted above. Text labels can be configured as part of a multi-language pack to make the platform user-friendly to non-native English speakers and/or to people who have developed language challenges associated with cognitive changes.

In one embodiment, a user may use the platform in an offline mode using view-only images in a printed format and/or may use the platform through a digital device mode. The platform allows the user to change modes at different points in time to use a different platform module or component. The platform's offline interactivities, device-based interoperability, overlapping component images, and composite image sets allow for the translation of data from one device to another, from one mode to another, from one subset of interactivities to another, and to develop a battery of related interactivities with multiple cognitive domain characteristics. The transfer may occur throughout and/or at any time during the user's engagement with the platform and its components for diagnostic, assessment, treatment, rehabilitation, maintenance and skills advancement purposes adjusting to the user's requirements and changes in their cognitive status across multiple user environments, including in the absence of digital devices and/or where digital electronics cannot be used.

The versatility of being able to switch devices and modalities represents a significant advance over other platforms, which are generally relegated to either an offline interactive or a device-based interactive, but with little or no crossover between the two modalities. Prior platforms may be at best focused on using relatively simple stimuli with siloed impact on the user's skills and individual cognitive domains. Further, many platforms are based on the use of neuropsychological assessments or are derivative from assessments which were not initially designed or developed as treatments, and/or were developed at a time when tools available for measuring and detecting multi-cognitive domain interactions of processes and skills were not available and/or were not sensitive enough to detect subtle differences. As such, one or more embodiments of system 100 represents a paradigm shift in developing sensitive diagnostic and assessment protocols towards identifying cognitive biomarkers and implementing effective treatment protocols as well as learning modalities to advance user skills in one or more areas and capabilities.

The platform is particularly well-suited to people who are recovering from a condition which impacts their cognition within a limited time frame and where functional recovery is possible. The platform has particular applications for people who with early interventions within a system which is responsive to their changing needs in terms of linguistic challenges, fine motor control, limited mobility, and/or need for facilitated use can translate to skills and process recovery to greater and lesser extents, depending on the individual circumstances. The functional requirements of users either individually, and/or together in-part or in their entirety, can be affected over time through both natural healing/recovery processes and/or interventional impacts with transitions to a different functional capacity and/or other types of improvements, which can be accommodated by the platform's multi-domain and multi-modal capabilities.

In some embodiments, the platform can have applications for people following stroke, Traumatic Brain Injury (TBI), stress, Anxiety, Depression, Mild Cognitive Impairment (MCI), Alzheimer's disease and other dementias, Bipolar Disorder, Schizophrenia, as well as other conditions such as Multiple Sclerosis, Parkinson's disease, Cardiovascular (CV) issues, Type II Diabetes, Attention Deficit Hyperactivity Disorder (ADHD)/Attention Deficit Disorder (ADD), and Autism Spectrum Disorder. In an embodiment, the platform may assess and/or score memory, visual-spatial, executive function, language, attention and/or sensorimotor skills and processes. The platform can be used with people as inpatients and/or outpatients in rehabilitation settings, in long-term care facilities, and/or in at-home settings where limited mobility and/or downtime between therapies and therapist interactions may occur, and where self-directed interactions and/or auto-launched, view-only mode type of interaction can provide an interventional therapy and/or supplemental or adjunct treatment modality earlier in, and/or throughout the recovery process.

In one embodiment using a TUI prop, the face of the prop can convey an image segment on its surface. When the TUI prop is brought into proximity of another TUI and/or separate electronic game board, and/or interfaces with a computer, tablet, and/or other smart device, the selected image is "transferred" onto the game board/screen. The TUI prop can then display another game piece using an automated process or on-demand process initiated by the user, instructing the TUI prop to display the next game piece. The sequence can be random and/or placement can be facilitated by presenting the user with sections from only one of the component images for directed placements, and/or in a mixed grouping from two or more images.

With a mixed grouping whether using a TUI hybrid system, offline components or the device-based modality, the platform can provide the user with a Jumble-Sort interactivity, which can include an assessment of the user's strategy in sorting and/or with subsequent placement of the image parts. The Jumble-Sort interactivity can be varied in complexity with the number and size of the pieces to be sorted, which may aid in assessing the user's strategy. The Jumble-Sort interactive can be applied to component images in the composites and/or to composited image sets where two or more sectioned images are mixed together and the user is tasked to separate the image sections into groups belonging to Image #1, Image #2, and/or Image #3. In one embodiment of the Jumble-Sort interactivity, the system presents the user with a mixed grouping of one or more images, which can include both horizontally and vertically sections pieces of the same and/or of different images, and which may use a variable sectioning strategy, and which may also include distractor pieces which are not part of and cannot be matched to the image set. The user is then tasked with separating not only between the images but to separate these according to their sectioning strategy, and/or those which do not belong to the set/grouping.

The Jumble-Sort interactivity can be used as a stand-alone interactivity or be combined with another interactivity such as Compose or Construct. The Jumble-Sort interactive, whether used as a stand-alone interactivity or in combination with another interactivity, can be scored accordingly for correct and incorrect sorting, time, and strategy, though the user may not need to be made aware of the timed aspect of the task.

The user can be provided with a reference image and/or be tasked with using other visual cues embedded in the images themselves, including: color, content, and context to inform user decisions and/or be provided with a textual description of the target image and/or audio clues, and/or be provided with clues and rules to direct sorting and/or placement of image parts, akin to the Wisconsin Card Sorting Task.

The user's ability to complete a Jumble-Sort task (which may include sorting according to a set of rules) may serve as an index of cognitive change as measured over time and the user's ability to perform the Jumble-Sort task using multiple metrics for set-shifting and cognitive flexibility by measuring speed and accuracy according to the number of pieces, size of the pieces, image complexity, and sectioning strategy. Similarly, other interactive tasks such as a Compose (single images) and Construct (composite image sets) interactivities can serve as an index of cognitive change in being able to discern color and contiguity patterns, i.e. mismatched placements. The user can be presented with incorrectly composed component images and or composited image sets, such as through the Mutation interactivity and who is then tasked with fixing and/or identifying the incorrect placements as described previously. In addition, changes in the user's ability to complete tasks, the error rate, and speed of completing a task and speed sub-measures may also indicate a change in cognitive ability. In addition, other assessment components, such as whether the user is using individual images and/or composite images, can serve as an index of cognitive change. These measures of cognitive change can be used as a baseline and/or as a change metric. In one embodiment, a user's ability to perform interactivities can improve or regress, and/or fluctuate between progressions and regressions within a span of time. The changes in the user's ability to perform a task can regress from being able to complete tasks using composite images and component image sections, to not being able to sort individual component image sections along a spectrum of interactivities and/or other regressions and/or progressions.

Similarly, other users may have a starting point or baseline where the user is capable of performing single image tasks, such as composing single image interactivities using sections, to not being able to assemble single image sections into a coherent image, with or without the use of a reference image, and vice a versa with an improvement and/or progression in skill and process abilities. The placement of an individual along a cognitive capacity spectrum can also be assessed by changing the number and size of the sections. In one embodiment, the same image can be used but during an assessment that same image is sectioned differently, varying the number and/or size of the "game" pieces/elements used in the interactivities.

In monitoring a user's progression and/or regression within a skill level or between skills levels, the platform uses a multiplicity of embedded measures and which can be used to signal a change in the user's cognitive profile and corresponding changes in the level of interactivity for rehabilitation, treatment and/or skills development and/or learning purposes. The internal measures combined with external inputs can provide a cogent data stream reflecting multiple cognitive domain-driven interactivities which can enhance our understanding of a user's cognitive status and improve change tracking tools and capabilities. The platform can also integrate third party sensors and third party data to provide both general and context-referenced biometrics captured during Mem+ assessment interactivities to derive an enhanced cognitive profile. Third party data might include medical/health tracking and monitoring tools for diet, exercise, sleep patterns, medication and medication changes, physiological biometrics (heart rate, respiratory rate, blood pressure) and other data collected and/or aggregated over time which can impact cognitive health and well-being.

Metric-based changes which may be related to changes in cognitive status can include: consistent/inconsistent time to complete tasks across multiple sessions; an increase/decrease in reaction times, an increase/decrease in the amount of time it takes for the user to complete a task; change in a metric and/or sub-metric for one or more tasks; an increase/decrease in the number of misplacements; increase/decrease in the use of the reference image for on-demand display; Mem+ associated verbal responses (Word List Recalls and SQ2); deliberate/erratic screen movements; response to altered sectioning strategy trials; response to altered sizes of to-be-placed image parts; and/or, change in the number of pieces the user works with and/or the presentation, e.g., all at once or just one or more at a time; integration of other device data such as derived from a mobile phone tracking gait, other movements and other inputs such as forgotten password/passcode, increase in the number of misspelled words or consistent and repeated keystroke errors or keystroke sequences; changes in health status, prescription drug intake, food intake and sleep status; changes in handwriting, change in gaze and/or eye tracking across a composite image set; eye-tracking combined with ERP and EEG analysis, and/or fMRI data for sustained attention and engagement assessments; body language cues, increase in frustration, and/or changes in mood as well as subjective reporting by the user and/or family and/or caregivers. Some of the user-provided information is collected as part of a pre-session questionnaire when the user is prompted to fill out and can be used with the platform in any of its modes, and can be provided by the user through self-reporting, and/or by a caregiver and/or healthcare worker.

When a user presents with changes in one or more factors with measured impacts on their cognitive status and/or skill acquisition abilities and/or learning capacity, the platform can adjust the user's skill level and evaluate how the user adapts to the new interactive regimen and/or protocol. Changes can include moving a user to a more advanced skill level and/or to a lower skill level, and/or switch to an alternate interactivity, and/or introduce an assessment protocol towards improving training and/or treatment efficacy. Detection of significant changes in cognitive status can be linked to an alert system to advise the user and/or family, and/or caregiver and/or professional medical and healthcare personnel (primary care physician, nurse, visiting nurse, occupational therapist and/or researcher and/or clinical team) where passive and/or active remote monitoring of cognitive health status can be of benefit to the user and/or aid in the collection of data for monitoring protocol and/or treatment efficacy.

In one embodiment, the invention's assessments use a combination of user data for conducting both "point in time" and "changes over time" analyses for building Cognitive Profiles and Cognitive Signatures, respectively. Additional analyses can gather data from multiple user groups in order to help define and identify potential biomarkers for further study. A biomarker for a given user group can be used to facilitate diagnoses and implement interventions earlier in a disease process. The identification of non-invasive, cognitive biomarkers can potentially be used with and/or be derived from the platform, and/or be used in conjunction with other biomarker identification methods such as Big Data analyses. The identification of cognitive biomarkers may be used in conjunction with the platform to assess the user's cognitive status as well as with other devices capable of measuring physiological and neuropsychological inputs, and/or devices and tools for capturing data. As such, the platform can operate as a diagnostic tool and/or an assessment tool, and/or treatment tool and/or training tool to identify and monitor change and/or in an interventional treatment modality.

In some embodiments, audio recordings regardless of whether these are obtained from self-directed and/or facilitated assessments can be subjected to additional analyses and compiled as part of Big Data analyses of multiple users, and/or used to analyze biometrics' changes of the individual user over time using audio recordings of the user's voice. Voice change indicators, vocal indicators can provide insight into changes in the user's cognitive status as reflected in nuanced changes in vocal prosody. Indicators of changes in cognitive ability may also manifested in other communications, physical, physiological and/or behavioral changes such as handwriting and posture for example. For example, the system may monitor for changes in vocal prosody by monitoring for changes in acoustic features of the user's speech associated with assessments which can capture verbal responses (for example, Word List Recall, Object ID and Dimensional Descriptors). The system may monitor for changes in lexical, syntactic, and/or semantic content of signals. The system may monitor for changes in the user's fundamental frequency, pitch, intensity, timing, speech rate, rhythm, and/or patterning in normal conversation. The system may monitor for changes in jitter, shimmer (cycle-to-cycle variation in frequency and intensity) and/or energy distribution among formants (the resonance bands that determine the phonetic quality vowel sounds). Additionally or alternatively, the system may monitor for changes in cepstral features for representing transduced human voice and/or music signals to detect changes in pitch including intensity which may change with age, condition and user frailty and reflected in their communications.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A method comprising:
sending, by a machine, one or more interactivities to a user, the one or more interactivities including at least one image, the one or more interactivities including at least requesting image input, the image input including at least a manipulation of an image element associated with the at least one image, the machine including at least a processor system having one or more processors and a memory system;

receiving, at the machine, the image input from the user; and assessing the image input from the user, by the machine, and based on the assessment determining a score that is indicative of cognitive status of the user;

wherein the one or more interactivities include at least an interactivity in which a user is presented with one or more elements of the at least one image, the at least one image being composed of one or more images, and the user is asked to identify information of the at least one image indicative of whether a figure-ground relationship is perceived.

2. The method of claim 1, further comprising adjusting an interactivity of the one or more interactivities, as the user is engaged with a platform using the method, during the interactivity of the one or more interactivities in which the image input was received.

3. The method of claim 1, wherein the assessing is based on information gathered during a session including one or more interactivities, where information is gathered prior to the one or more interactivities, when no interactivity is running.

4. The method of claim 1, wherein the assessing is based on information gathered during one or more interactivities.

5. The method of claim 1, wherein the assessing is based on information gathered during multiple sessions of the user.

6. The method of claim 1, wherein the assessing is based on information gathered from multiple users.

7. The method of claim 1, wherein the assessing is based on at least physiological data or biometrics data.

8. The method of claim 1, further comprising receiving input from multiple clinicians related to an interactivity protocol and creating an interactivity protocol based on the input from the multiple clinicians.

9. The method of claim 1, further comprising creating an interactivity based on assessing user interactions with the interactivity created using a composite of two or more interleaved images of the multi-image set.

10. The method of claim 1, the assessing including at least an assessment based on a word list associated with a composite of two or more images, at multiple time points.

11. The method of claim 1, wherein the one or more interactivities include an interactivity in which a user is presented with parts of the at least one image and asked to reconstruct a single image, the single image being composed of one or more images.

12. The method of claim 1, wherein the one or more interactivities include at least an interactivity in which a user is presented with the at least one image, and the at least one image is composed of one or more images; the at least one image having a missing par and the user is asked to fill in the missing part of the at least one image.

13. The method of claim 1, wherein the one or more interactivities include at least an interactivity in which a user is offered a range of activities that the user may choose from.

14. The method of claim 1,
wherein the one or more interactivities include at least an interactivity in which a user is presented with an image of the at least one image and asked to identify parts of the image that was presented;
where the image that was presented is a composite image of multiple component images, in which parts of each component image are mixed with parts of others of the component images.

15. The method of claim 1, the assessment being based on a decision pattern.

16. The method of claim 1, the assessment being based on error analysis in placements of elements of the at least one image, when reconstructing, matching or identifying at least a portion of the at least one image.

17. The method of claim 1, the assessment being based on reaction time.

18. The method of claim 1, wherein the one or more interactivities include at least one interactivity from which multiple scores are derived which include at least a first score for a first domain of cognition and a second score for a second domain of cognition.

19. A method comprising:
sending, by a machine, one or more interactivities to a user, the one or more interactivities including at least one image, the one or more interactivities including at least requesting image input, the image input including at least a manipulation of an image element associated with the at least one image, the machine including at least a processor system having one or more processors and a memory system;
receiving, at the machine, the image input from the user; and
assessing the image input from the user, by the machine, and based on the assessment determining a score that is indicative of cognitive status of the user;
wherein the one or more interactivities include at least an interactivity in which the user is presented with a composite image set and is asked to identify aspects of the composite image indicative of whether there is a perception of dimensions that is based on a figure-ground relationship.

20. A method comprising:
sending, by a machine, one or more interactivities to a user, the one or more interactivities including at least one image, the one or more interactivities including at least requesting image input, the image input including at least a manipulation of an image element associated with the at least one image, the machine including at least a processor system having one or more processors and a memory system;
receiving, at the machine, the image input from the user; and
assessing the image input from the user, by the machine, and based on the assessment determining a score that is indicative of cognitive status of the user;
determining, by a machine, one or more contiguities of an image, the contiguity being a group of picture elements that are adjacent to one another the group of picture elements form an image element that extends at least as much horizontally as vertically and that extends horizontally across most the image;
determining, by the processor system, a value that represents characteristics of the one or more contiguities that are in the image; and
determining, by the machine, which images to include in an interactivity based on the value associated with aspects of the contiguities and a skill level of the user.

21. A method comprising:
sending, by a machine, one or more interactivities to a user, the one or more interactivities including at least one image, the one or more interactivities including at least requesting image input, the image input including at least a manipulation of an image element associated with the at least one image, the machine including at least a processor system having one or more processors and a memory system;

receiving, at the machine, the image input from the user; and assessing the image input from the user, by the machine, and based on the assessment determining a score that is indicative of cognitive status of the user;

the image input being received via a tangible user interface (TUI).

22. The method of claim 21, the tangible user interface comprising physical pieces having portions of the at least one image.

23. The method of claim 21, the tangible user interface comprising physical props.

24. The method of claim 21, the tangible user interface comprising individual image manipulatives, the individual image manipulatives have portions of the image on a substrate, the individual image manipulatives being sections that fit together, and that can be separated and combined together in different ways.

25. A system comprising:

a processor system having one or more processors, and a memory system, the memory system storing one or more machine instructions, which when implemented, causes the system to implement a method including at least, sending, by the system, one or more interactivities to a user, the one or more interactivities including at least one image, the one or more interactivities including at least requesting image input, the image input including at least a manipulation of an image element associated with the at least one image;

receiving, at the system, the image input from the user; and assessing the image input of the user by the system, and based on the assessment determining a score or scores that are indicative of cognitive abilities of the user;

wherein the one or more interactivities include at least an interactivity in which a user is presented with a composite image set and is asked to identify aspects of a composite image indicative of whether the user perceives a figure-ground relationship, the composite image being based on the composite image set.

26. The system of claim 25, the method further comprising adjusting an interactivity of the one or more interactivities, as the user is engaged with a platform using the method, during a session in which the assessment occurred.

27. The system of claim 25, wherein the assessing is based on information gathered during a session including one or more interactivities, where information is gathered prior to the one or more interactivities, when no interactivity is running.

28. The system of claim 25, wherein the assessing is based on information gathered during one or more interactivities.

29. The system of claim 25, wherein the assessing is based on information gathered during multiple sessions of the user.

30. The system of claim 25, wherein the assessing is based on information gathered from multiple users.

31. The system of claim 25, wherein the assessing is based on at least physiological data or biometrics data.

32. The system of claim 25, the method further comprising receiving input from multiple clinicians related to an interactivity protocol and creating an interactivity protocol based on the input from the multiple clinicians.

33. The system of claim 25, the method, further comprising creating an interactivity based on the assessing, the interactivity created including at least a composite of two or more interleaved images of at least one multi-image set.

34. The system of claim 25, the assessing including at least an assessment based on a word list associated with a composite of two or more images, at multiple time points.

35. The system of claim 25, wherein the one or more interactivities include at least an interactivity in which a user is presented with parts of an image and asked to reconstruct a single image, the single image being composed of one or more images.

36. The system of claim 25, wherein the one or more interactivities include at least an interactivity in which a user is presented with an image that is composed of one or more images; the image, that is composed of one or more images, having a missing part and the user is asked to fill in the missing part of the image.

37. The system of claim 25, wherein the one or more interactivities include at least an interactivity in which a user is offered a range of activities that the user may choose from.

38. The system of claim 25, wherein the one or more interactivities include at least an interactivity in which a user is presented with an image and asked to identify parts of the image;

where the image is a composite image of multiple component images, in which parts of each image are mixed with parts of other images.

39. The system of claim 25, the assessment being based on a decision pattern.

40. The system of claim 25, the assessment being based on error analysis in placements of elements of an image when reconstructing, matching, or identifying at least a portion of an image.

41. The system of claim 25, the assessment being based on reaction time.

42. The system of claim 25, wherein the one or more interactivities include at least one interactivity from which multiple scores are derived which include at least a first score for a first domain of cognition and a second score for a second domain of cognition.

43. The system of claim 25, wherein the one or more interactivities include at least an interactivity in which a user is presented with the at least one image, and the at least one image is composed of one or more images; the interactivity including at least requesting the user to match a piece of the at least one image with at least another part of the at least one image.

44. A system comprising:

a processor system having one or more processors, and a memory system, the memory system storing one or more machine instructions, which when implemented, causes the system to implement a method including at least, sending, by a machine, one or more interactivities to a user, the one or more interactivities including at least one image, the one or more interactivities including at least requesting image input, the image input including at least a manipulation of an image element associated with the at least one image, the machine including at least a processor system having one or more processors and a memory system;

receiving, at the machine, the image input from the user; and assessing the image input of the user by the machine, and based on the assessment determining a score that is indicative of a cognitive status of the user;

the image input being received via a tangible user interface (TUI).

45. The system of claim 44, the tangible user interface including at least a sensor for sensing the user's grip strength.

46. The system of claim 44, the tangible user interface including at least a sensor for sensing the user's grasp.

47. The system of claim 44, the tangible user interface including at least a sensor for sensing the user's galvanic skin response.

48. The system of claim 44, the tangible user interface including at least a sensor for sensing the user's pulse.

49. The system of claim 44, the tangible user interface including at least a sensor for sensing the user's blood pressure.

50. The system of claim 44, the tangible user interface including one or more sensors for sensing behavioral biometric input.

51. The system of claim 44, the tangible user interface including one or more sensors for tracking user movements.

52. The system of claim 44, the tangible user interface including at least a headset that produces an augmented reality image.

53. The system of claim 44, the tangible user interface including at least a headset having a display that produces a virtual reality image.

* * * * *